US011613567B2

(12) United States Patent
Magliery et al.

(10) Patent No.: US 11,613,567 B2
(45) Date of Patent: Mar. 28, 2023

(54) MODULATORS OF NOTCH SIGNALING AND METHODS OF USE THEREOF

(71) Applicant: Ohio State Innovation Foundation, Columbus, OH (US)

(72) Inventors: Thomas J. Magliery, Columbus, OH (US); Mikhail M. Dikov, Dublin, OH (US); David Carbone, Hilliard, OH (US); Nicholas Long, Columbus, OH (US); Brandon Sullivan, Gahanna, OH (US); Elena Tchekneva, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/496,163

(22) PCT Filed: Mar. 26, 2018

(86) PCT No.: PCT/US2018/024343
§ 371 (c)(1),
(2) Date: Sep. 20, 2019

(87) PCT Pub. No.: WO2018/176034
PCT Pub. Date: Sep. 27, 2018

(65) Prior Publication Data

US 2020/0277354 A1 Sep. 3, 2020

Related U.S. Application Data

(60) Provisional application No. 62/476,616, filed on Mar. 24, 2017.

(51) Int. Cl.
*A61K 38/00* (2006.01)
*C07K 14/705* (2006.01)
*A61P 37/06* (2006.01)
*A61P 35/00* (2006.01)

(52) U.S. Cl.
CPC ........ *C07K 14/70596* (2013.01); *A61P 35/00* (2018.01); *A61P 37/06* (2018.01); *A61K 38/00* (2013.01)

(58) Field of Classification Search
CPC .... C07K 14/70596; A61P 37/06; A61P 35/00; A61K 38/00
See application file for complete search history.

(56) References Cited

U.S. PATENT DOCUMENTS

| | | | | |
|---|---|---|---|---|
| 2003/0096432 A1* | 5/2003 | Jakobsen | ............. | G01N 33/566 436/518 |
| 2005/0220886 A1 | 10/2005 | Bodmer et al. | | |
| 2005/0261477 A1* | 11/2005 | Champion | ............. | C07H 21/04 530/350 |
| 2014/0286955 A1* | 9/2014 | Aifantis | ............. | A61K 39/3955 424/139.1 |

FOREIGN PATENT DOCUMENTS

WO 2015/047062 A1 4/2015

OTHER PUBLICATIONS

Klose et al. Soluble Notch ligand and receptor peptides act antagonistically during angiogenesis. 2015. Cardiovascular Research (2015) 107, 153-163 (Year: 2015).*

Mollen et al. Moving Breast Cancer Therapy up a Notch. 2018. Front. Oncol., 2018, vol. 8: 518 (Year: 2018).*

Yuan et al. Notch signaling: An emerging therapeutic target for cancer treatment. 2015. Cancer Letters 369 (2015) 20-27 (Year: 2015).*

Rizzo et al. Rational targeting of Notch signaling in cancer. 2008. Oncogene (2008) 27, 5124-5131 (Year: 2008).*

Robert Peter Gale "Overview of Cancer Therapy," last modified Aug. 2018, In Merck Manual Consumer Version, accessed on May 8, 2020 at <https://www.merckmanuals.com/professional/hematology-and-oncology/principles-of-cancer-therapy/overview-of-cancer-therapy> (Year: 2018).*

Robert Peter Gale "Cancer Treatment Principles," last modified Aug. 2018, In Merck Manual Consumer Version, accessed on May 8, 2020 at <https://www.merckmanuals.com/home/cancer/prevention-and-treatment-of-cancer/cancer-treatment-principles>. (Year: 2018).*

What is Cancer? National cancer Institute, accessed on May 8, 2020 <https://www.cancer.gov/about-cancer/understanding/what-is-cancer> (Year: 2020).*

Cancer prevention overview, (PDQ®) Patient Version. National cancer Institute, accessed on May 8, 2020 <https://www.cancer.gov/about-cancer/causes-prevention/patient-prevention-overview-pdq> (Year: 2020).*

Medical news today. Accessed May 2020, at <https://www.medicalnewstoday.com/articles/322700> (Year: 2018).*

Molecular Cell Biology—NCBI Bookshelf. Accessed Jul. 2020 at <https://www.ncbi.nlm.nih.gov/books/NBK21607/> (Year: 2020).*

International Search Report and Written Opinion issued by the International Searching Authority (ISA/US) in PCT Application No. PCT/US2018/024343 dated Aug. 8, 2019. 12 pages.

Adams, A.B., M.A. Williams, T.R. Jones, N. Shirasugi, M.M. Durham, S.M. Kaech, E.J. Wherry, T. Onami, J.G. Lanier, K.E. Kokko, T.C. Pearson, R. Ahmed, and C.P. Larsen (2003) "Heterologous immunity provides a potent barrier to transplantation tolerance," J Clin Invest. 111, 1887-95.

Alam, M.S., Y. Maekawa, A. Kitamura, K. Tanigaki, T. Yoshimoto, K. Kishihara, and K. Yasutomo (2010) "Notch signaling drives IL-22 secretion in CD4+ T cells by stimulating the aryl hydrocarbon receptor," Proceedings of the National Academy of Sciences of the United States of America. 107, 5943-8.

(Continued)

*Primary Examiner* — Aradhana Sasan
*Assistant Examiner* — Mercy H Sabila
(74) *Attorney, Agent, or Firm* — Meunier Carlin & Curfman LLC

(57) ABSTRACT

Described herein are Notch-modulating peptides (including monomers and multimers) capable of increasing or decreasing an immune response in a subject, compositions comprising the peptides, and methods of use thereof.

18 Claims, 34 Drawing Sheets

Specification includes a Sequence Listing.

(56) References Cited

OTHER PUBLICATIONS

Altschul, Stephen F., et al. "Gapped BLAST and PSI-BLAST: a new generation of protein database search programs." Nucleic acids research 25.17 (1997): 3389-3402.
Altschul, Stephen F., et al. "Basic local alignment search tool." Journal of molecular biology 215.3 (1990): 403-410.
Amsen D, Blander JM, Lee GR, Tanigaki K, Honjo T, Flavell RA. Instruction of distinct CD4 T helper cell fates by different notch ligands on antigen-presenting cells. Cell 2004; 117: 515-26.
Amsen, D., A. Antov, and R.A. Flavell (2009) "The different faces of Notch in T-helper-cell differentiation," Nature reviews. Immunology. 9, 116-24.
Amsen, D., A. Antov, D. Jankovic, A. Sher, F. Radtke, A. Souabni, M. Busslinger, B. McCright, T. Gridley, and R.A. Flavell (2007) "Direct regulation of Gata3 expression determines the T helper differentiation potential of Notch," Immunity. 27, 89-99.
Amsen, D., C. Helbig, and R.A. Backer (2015) "Notch in T Cell Differentiation: All Things Considered," Trends in immunology. 36, 802-14.
Amsen, D., R.A. Backer, and C. Helbig (2013) "Decisions on the road to memory," Advances in experimental medicine and biology. 785, 107-20.
Andrawes, M.B., X. Xu, H. Liu, S.B. Ficarro, J.A. Marte, J.C. Aster, and S.C. Blacklow (2013) "Intrinsic selectivity of Notch 1 for Delta-like 4 over Delta-like 1," J Biol Chem. 288, 25477-89.
Artavanis-Tsakonas, S., M.D. Rand, and R.J. Lake (1999) "Notch signaling: cell fate control and signal integration in development," Science. 284, 770-6.
Atochina-Vasserman EN, et al., "Aquaporin 11 insufficiency modulates kidney susceptibility to oxidative stress." American journal of physiology Renal physiology. 2013;304:F1295-1307.
Auderset F, Schuster S, Coutaz M, et al. Redundant Notch1 and Notch2 signaling is necessary for IFNgamma secretion by T helper 1 cells during infection with Leishmania major. PLoS pathogens 2012; 8: e1002560.
Auderset F, Schuster S, Fasnacht N, et al. Notch signaling regulates follicular helper T cell differentiation. J Immunol 2013; 191: 2344-50.
Ayasoufi, K., H. Yu, R. Fan, X. Wang, J. Williams, and A. Valujskikh (2013) "Pretransplant antithymocyte globulin has increased efficacy in controlling donor-reactive memory T cells in mice," Am J Transplant. 13, 589-99.
Ayasoufi, K., R. Fan, R.L. Fairchild, and A. Valujskikh (2016) "CD4 T Cell Help via B Cells Is Required for Lymphopenia-Induced CDS T Cell Proliferation," J Immunol. 196, 3180-90.
Backer, Ronald A., et al. "A central role for Notch in effector CD8+ T cell differentiation." Nature immunology 15.12 (2014): 1143.
Bailis W, Yashiro-Ohtani Y, Fang TC, et al. Notch simultaneously orchestrates multiple helper T cell programs independently of cytokine signals. Immunity 2013; 39: 148-59.
Bettelli, E., Y. Carrier, W. Gao, T. Korn, T.B. Strom, M. Oukka, H.L. Weiner, and V.K. Kuchroo (2006) "Reciprocal developmental pathways for the generation of pathogenic effector TH 17 and regulatory T cells," Nature. 441, 235-8.
Biktasova, Asel K., et al. "Multivalent forms of the Notch ligand DLL-1 enhance antitumor T-cell immunity in lung cancer and improve efficacy of EGFR-targeted therapy." Cancer research 75.22 (2015): 4728-4741.
Bingaman, A.W. and D.L. Farber (2004) "Memory T cells in transplantation: generation, function, and potential role in rejection," Am J Transplant. 4, 846-52.
Boshart, Michael, et al. "A very strong enhancer is located upstream of an immediate early gene of human cytomegalovirus." cell 41.2 (1985): 521-530.
Bray, Sarah J. "Notch signalling: a simple pathway becomes complex." Nature reviews Molecular cell biology 7.9 (2006): 678.
Brook, M.O., K.J. Wood, and N.D. Jones (2006) "The impact of memory T cells on rejection and the induction of tolerance," Transplantation. 82, 1-9.
Brooker R, Hozumi K, Lewis J. Notch ligands with contrasting functions: Jagged1 and Delta1 in the mouse inner ear. Development 2006; 133: 1277-86.
Beaucage, S. L., and Marvin H. Caruthers. "Deoxynucleoside phosphoramidites—a new class of key intermediates for deoxypolynucleotide synthesis." Tetrahedron Letters 22.20 (1981): 1859-1862.
Cahill EF, Tobin LM, Carty F, Mahon BP, English K. Jagged-1 is required for the expansion of CD4+ CD25+ FoxP3+ regulatory T cells and tolerogenic dendritic cells by murine mesenchymal stromal cells. Stem cell research & therapy 2015; 6: 19.
Campbell, D.J. and M.A. Koch (2011) "Phenotypical and functional specialization of FOXP3+regulatory T cells," Nature reviews. Immunology. 11, 119-30.
Charbonnier, L.M., S. Wang, P. Georgiev, E. Sefik, and T.A. Chatila (2015) "Control of peripheral tolerance by regulatory T cell-intrinsic Notch signaling," Nature immunology. 16, 1162-73.
Chen JQ, Xiu QY, Shen C, Yan ZM, et al. Immunotherapy of spontaneous metastatic lung cancer with tumor antigen-pulsed, interleukin-12 gene-modified dendritic cells. Chinese Journal of Caner Research 15(3):182-188, 2003.
Chen, Y., P.S. Heeger, and A. Valujskikh (2004) "In vivo helper functions of alloreactive memory CD4+ T cells remain intact despite donor-specific transfusion and anti-CD40 ligand therapy," J Immunol. 172, 5456-66.
Chillakuri, C.R., D. Sheppard, M.X. Hagan, L.R. Holt, F. Abbott, S. Liang, R. Kopan, P.A. Handford, and S.M. Lea (2013) "Structural analysis uncovers lipid-binding properties of Notch ligands," Cell Rep. 5, 861-7.
Chung, J., L.V. Riella, and I. Maillard (2016) "Targeting the Notch pathway to prevent rejection," Am J Transplant, 3079.
Cordle, J., S. Johnson, J.Z. Tay, P. Roversi, M.B. Wilkin, B.H. de Madrid, H. Shimizu, S. Jensen, P. Whiteman, B. Jin, C. Redfield, M. Baron, S.M. Lea, and P.A. Handford (2008) "A conserved face of the Jagged/Serrate DSL domain is involved in Notch trans-activation and cis-inhibition," Nat Struct Mo/ Biol. 15, 849-57.
D'Souza B, Meloty-Kapella L, Weinmaster G. Canonical and non-canonical Notch Tigands. Current topics in developmental biology 2010; 92: 73-129.
Durani, V., B.J. Sullivan, and T.J. Magliery (2012) "Simplifying protein expression with ligation-free, traceless and tag-switching plasmids," Protein ExprPurif. 85, 9-17.
Elyaman, W., R. Bassil, E.M. Bradshaw, W. Orent, Y. Lahoud, B. Zhu, F. Radtke, H. Yagita, and S.J. Khoury (2012) "Notch receptors and Smad3 signaling cooperate in the induction of interleukin-9-producing T cells," Immunity. 36, 623-34.
Fairhead, Michael, and Mark Howarth. "Site-specific biotinylation of purified proteins using BirA." Site-Specific Protein Labeling. Humana Press, New York, NY, 2015. 171-184.
Fiúza, Ulla-Maj, and Alfonso Martinez Arias. "Cell and molecular biology of Notch." Journal of Endocrinology 194.3 (2007): 459-474.
Gabrilovich, et al., (1999) "Antibodies to vascular endothelial growth factor enhance the efficacy of cancer immunotherapy by improving endogenous dendritic cell function," Clinical cancer research: an official journal of the American Association for Cancer Research. 5, 2963-70.
Gopisetty, A., P. Bhattacharya, C. Haddad, J.C. Bruno, Jr., C. Vasu, L. Miele, and B.S. Prabhakar (2013) "OX40L/Jagged1 cosignaling by GM-CSF-induced bone marrow-derived dendritic cells is required for the expansion of functional regulatory T cells," Journal of immunology. 190, 5516-25.
Gorbacheva, V., K. Ayasoufi, R. Fan, W.M. Baldwin, 3rd, and A. Valujskikh (2015) "B cell activating factor (BAFF) and a proliferation indu ing ligand (April) mediate CD40-independent help by memory CD4 Tcells," Am J Transplant. 15, 346-57.
Gorbacheva, V., R. Fan, R.L. Fairchild, I. Baldwin, W. M., and A. Valujskikh (2016) "Memory CD4 T cells induce antibody mediated rejection of renal allografts" J Am Soc Nephrol 27: 3299-3307.
Gorbacheva, V., R. Fan, X. Wang, W.M. Baldwin, 3rd, R.L. Fairchild, and A. Valujskikh (2015) "IFNgamma production by memory helper T cells is required for CD40-independent alloantibody responses," J Immunol. 194, 1347-56.

(56) References Cited

OTHER PUBLICATIONS

Gridley, T. "Notch signaling in vascular development and physiology." Development. Aug. 2007;134(15):2709-18. Epub Jul. 4, 2007.
Hambleton, S., N.V. Valeyev, A. Muranyi, V. Knott, J.M. Werner, A.J. McMichael, P.A. Handford, and A.K. Downing (2004) "Structural and functional properties of the human notch-1 ligand binding region," Structure. 12, 2173-83.
Hayashi, Y., N. Ishimaru, R. Arakaki, S. Tsukumo, H. Fukui, K. Kishihara, H. Shiota, and K. Yasutomo (2004) "Effective treatment of a mouse model of Sjogren's syndrome with eyedrop administration of antiCD4 monoclonal antibody," Arthritis and rheumatism. 50, 2903-10.
Heinzel K, Benz C, Martins VC, Haidl ID, Bleul CC. Bone marrow-derived hemopoietic precursors commit to the T cell lineage only after arrival in the thymic microenvironment. J Immunol 2007; 178: 858-68.
Heinzel, K., C. Benz, and C.C. Bleul (2007) "A silent chemokine receptor regulates steady-state leukocyte homing in vivo," Proceedings of the National Academy of Sciences of the United States of America. 104, 8421-6.
Helbig, C., R. Gentek, R.A. Backer, Y. de Souza, I.A. Derks, E. Eldering, K. Wagner, D. Jankovic, T. Gridley, P.O. Moerland, R.A. Flavell, and D. Amsen (2012) "Notch controls the magnitude of T helper cell responses by promoting cellular longevity," Proceedings of the National Academy of Sciences of the United States of America. 109, 9041-6.
Henikoff, Steven, and Jorja G. Henikoff. "Amino acid substitution matrices from protein blocks." Proceedings of the National Academy of Sciences 89.22 (1992): 10915-10919.
Hozumi K, Negishi N, Suzuki D, et al. Delta-like 1 is necessary for the generation of marginal zone B cells but not T cells in vivo. Nat Immunol 2004; 5: 638-44.
Huang Y, Lin L, Shanker A, et al. Resuscitating cancer immunosurveillance: selective stimulation of DLL1-Notch signaling in T cells rescues T-cell function and inhibits tumor growth. Cancer Res 2011; 71: 6122-31.
Huang, Y., X. Chen, M.M. Dikov, S.V. Novitskiy, C.A. Mosse, L. Yang, and D.P. Carbone (2007) "Distinct roles of VEGFR-1 and VEGFR-2 in the aberrant hematopoiesis associated with elevated levels of VEGF," Blood. 110, 624-31.
Josefowicz, S.Z., L.F. Lu, and A.Y. Rudensky (2012) "Regulatory T cells: mechanisms of differentiation and function," Annu Rev Immunol. 30, 531-64.
Kared H, Adle-Biassette H, Fois E, et al. Jagged2-expressing hematopoietic progenitors promote regulatory T cell expansion in the periphery through notch signaling. Immunity 2006; 25: 823-34.
Karlin and Altschul (1993) Proc. Natl. Acad. Sci. USA 90:5873-5787.
Kassner, N., M. Krueger, H. Yagita, A. Dzionek, A. Hutloff, R. Kroczek, A. Scheffold, and S. Rutz (2010) "Cutting edge: Plasmacytoid dendritic cells induce IL-10 production in T cells via the Delta-like-4/Notch axis," Journal of immunology. 184, 550-4.
Keerthivasan, S., R. Suleiman, R. Lawlor, J. Roderick, T. Bates, L. Minter, J. Anguita, I. Juncadella, B.J. Nickoloff, I.C. Le Poole, L. Miele, and B.A. Osborne (2011) "Notch signaling regulates mouse and human Th17 differentiation," Journal of immunology. 187, 692-701.
Kershaw, N.J., N.L. Church, M.D. Griffin, C.S. Luo, T.E. Adams, and A.W. Burgess (2015) "Notch ligand delta-likel: X-ray crystal structure and binding affinity," Biochem J. 468, 159-66.
Klose, R., C. Berger, I. Moll, M.G. Adam, F. Schwarz, K. Mohr, H.G. Augustin, and A. Fischer (2015) "Soluble Notch ligand and receptor peptides act antagonistically during angiogenesis," Cardiovasc Res. 107, 153-63.
Kopan, R. and M.X. Ilagan (2009) "The canonical Notch signaling pathway: unfolding the activation mechanism," Ce//. 137, 216-33.
Krawczyk C, Pearce E, Borjian A, Young S, Mahbuba R. Regulation of dendritic cell function by Notch receptors and ligands. J Immunol 2012; 188. Abstract.
Krawczyk, C.M., J. Sun, and E.J. Pearce (2008) "Th2 differentiation is unaffected by Jagged2 expression on dendritic cells," Journal of immunology. 180, 7931-7.
Ladi E, Nichols JT, Ge W, et al. The divergent DSL ligand Dll3 does not activate Notch signaling but cell autonomously attenuates signaling induced by other DSL Tigands. J Cell Biol 2005; 170: 983-92.
Laky K, Evans S, Perez-Diez A, Fowlkes BJ. Notch signaling regulates antigen sensitivity of naive CD4+ T cells by tuning co-stimulation. Immunity 2015; 42: 80-94.
Lee, C.T., S. Wu, I.F. Ciernik, H. Chen, S. Nadaf-Rahrov, D. Gabrilovich, and D.P. Carbone (1997) "Genetic immunotherapy of established tumors with adenovirus-murine granulocyte-macrophage colonystimulating factor," Human gene therapy. 8, 187-93.
Lin, Y., W. Chen, J. Li, G. Yan, C. Li, N. Jin, J. Chen, C. Gao, P. Ma, S. Xu, and Z. Qi (2015) "Overexpression of Jagged-1 combined with blockade of CD40 pathway prolongs allograft survival," Immunology and cell biology. 93, 213-7.
Liotta F, Frosali F, Querci V, et al. Human immature myeloid dendritic cells trigger a TH2-polarizing program via Jagged-1/Notch interaction. J Allergy Clin Immunol 2008; 121: 1000-5 e8.
Luca, V.C., K.M. Jude, N.W. Pierce, M.V. Nachury, S. Fischer, and K.C. Garcia (2015) "Structural biology. Structural basis for Notch1 engagement of Delta-like 4," Science. 347, 847-53.
Mace TA, Shakya R, Pitarresi JR, et al. IL-6 and PD-L1 antibody blockade combination therapy reduces tumour progression in murine models of pancreatic cancer. Gut 2018; 67: 320-32.
Maekawa Y, Tsukumo S, Chiba S, et al. Delta1-Notch3 interactions bias the functional differentiation of activated CD4+ T cells. Immunity 2003; 19: 549-59.
Maekawa, Y., C. Ishifune, S. Tsukumo, K. Hozumi, H. Yagita, and K. Yasutomo (2015) "Notch controls the survival of memory CD4+ T cells by regulating glucose uptake," Nat Med. 21, 55-61.
Magee, C.N. and L.V. Riella (2016) "Notch and its ligands in alloimmunity and rejection," CurrOpin Organ Transplant. 21, 15-21.
Mandelboim O, Bar-Haim E, Vadai E, Fridkin M, Eisenbach L. Identification of shared tumor-associated antigen peptides between two spontaneous lung carcinomas. J Immunol 1997; 159: 6030-6.
Matsushita S, Higashi T. Human Th17 cell clones and natural immune responses. Allergology international : official journal of the Japanese Society of Allergology 2008; 57: 135-40.
Mayhew, Mark, et al. "Ligand requirements for Ca2+ binding to EGF-like domains." Protein Engineering, Design and Selection 5.6 (1992): 489-494.
Miyajima, M., C.M. Chase, A. Alessandrini, E.A. Farkash, P. Della Pelle, G. Benichou, J.A. Graham, J.C. Madsen, P.S. Russell, and R.B. Colvin (2011) "Early acceptance of renal allografts in mice is dependent on foxp3(+) cells," Am J Pathol. 178, 1635-45.
Mochizuki K, He S, Zhang Y. Notch and inflammatory T-cell response: new developments and challenges. Immunotherapy 2011; 3: 1353-66.
Takebe, Yutaka, et al. "SR alpha promoter: an efficient and versatile mammalian cDNA expression system composed of the simian virus 40 early promoter and the R-U5 segment of human T-cell leukemia virus type 1 long terminal repeat." Molecular and cellular biology 8.1 (1988): 466-472.
Mukherjee S, Schaller MA, Neupane R, Kunkel SL, Lukacs NW. Regulation of T cell activation by Notch ligand, DLL4, promotes IL-17 production and Rorc activation. J Immunol 2009; 182: 7381-8.
Novitskiy SV, Ryzhov S, Zaynagetdinov R, et al. Adenosine receptors in regulation of dendritic cell differentiation and function. Blood 2008; 112: 1822-31.
Novitskiy, S.V., (2010) "Antivascular endothelial growth factor treatment in combination with chemotherapy delays hematopoietic recovery due to decreased proliferation of bone marrow hematopoietic progenitor cells," Journal of thoracic oncology: official publication of the International Association for the Study of Lung Cancer. 5, 1410-5.
Okamoto, M., K. Takeda, A. Joetham, H. Ohnishi, H. Matsuda, C.H. Swasey, B.J. Swanson, K. Yasutomo, A. Dakhama, and E.W. Gelfand (200S) "Essential role of Notch signaling in effector

(56) References Cited

OTHER PUBLICATIONS memory CDS+ T cell-mediated airway hyperresponsiveness and inflammation," J Exp Med. 205, 1087-97.
Ong, C.T., J.R. Sedy, K.M. Murphy, and R. Kopan (2008) "Notch and presenilin regulate cellular expansion and cytokine secretion but cannot instruct Th1/Th2 fate acquisition," PloS one. 3, e2823.
Osborne BA, Minter LM. Notch signalling during peripheral T-cell activation and differentiation. Nat Rev Immunol 2007; 7: 64-75.
Palaga, T., L. Miele, T.E. Golde, and B.A. Osborne (2003) "TCR-mediated Notch signaling regulates proliferation and IFN-gamma production in peripheral T cells," Journal of immunology. 171, 3019-24.
Parks, A.L., J.R. Stout, S.B. Shepard, K.M. Klueg, A.A. Dos Santos, T.R. Parody, M. Vaskova, and M.A. Muskavitch (2006) "Structure-function analysis of delta trafficking, receptor binding and signaling in *Drosophila*," Genetics. 174, 1947-61.
Pintar, A., C. Guarnaccia, S. Dhir, and S. Pongor (2009) "Exon 6 of human JAG1 encodes a conserved structural unit," BMC Struct Biol. 9, 43.
Politi, K., M.F. Zakowski, P.O. Fan, E.A. Schonfeld, W. Pao, and H.E. Varmus (2006) "Lung adenocarcinomas induced in mice by mutant EGF receptors found in human lung cancers respond to a tyrosine kinase inhibitor or to down-regulation of the receptors," Genes & development. 20, 1496-510.
O'hare, K., C. Benoist, and R. Breathnach. "Transformation of mouse fibroblasts to methotrexate resistance by a recombinant plasmid expressing a prokaryotic dihydrofolate reductase." Proceedings of the National Academy of Sciences 78.3 (1981): 1527-1531.
Rabant, M., V. Gorbacheva, R. Fan, H. Yu, and A. Valujskikh (2013) "CD40-independent help by memory CD4 T cells induces pathogenic alloantibody but does not lead to long-lasting humeral immunity," Am J Transplant. 13, 2831-41.
Radtke F, Fasnacht N, Macdonald HR. Notch signaling in the immune system. Immunity 2010; 32: 14-27.
Radtke, F., H.R. MacDonald, and F. Tacchini-Cottier (2013) "Regulation of innate and adaptive immunity by Notch," Nature reviews. Immunology. 13, 427-37.
Rakhra, K., P. Bachireddy, T. Zabuawala, R. Zeiser, L. Xu, A. Kopelman, A.C. Fan, Q. Yang, L. Braunstein, E. Crosby, S. Ryeom, and D.W. Felsher (2010) "CD4(+) T cells contribute to the remodeling of the microenvironment required for sustained tumor regression upon oncogene inactivation," Cancer cell. 18, 485-98.
Rebay, I., R.J. Fleming, R.G. Fehon, L. Cherbas, P. Cherbas, and S. Artavanis-Tsakonas (1991) "Specific EGF repeats of Notch mediate interactions with Delta and Serrate: implications for Notch as a multifunctional receptor," Cell. 67, 687-99.
Regales, L., M.N. Balak, Y. Gong, K. Politi, A. Sawai, C. Le, J.A. Koutcher, D.B. Solit, N. Rosen, M.F. Zakowski, and W. Pao (2007) "Development of new mouse lung tumor models expressing EGFR T790M mutants associated with clinical resistance to kinase inhibitors," PloS one. 2, e810.
Riella LV, Yang J, Chock S, et al. Jagged2-signaling promotes IL-6-dependent transplant rejection. Eur J Immunol 2013; 43: 1449-58.
Rutz, S., B. Mordmuller, S. Sakano, and A. Scheffold (2005) "Notch ligands Delta-like1, Delta-like4 and Jagged1 differentially regulate activation of peripheral T helper cells," European journal of immunology. 35, 2443-51.
Ryzhov, S., S.V. Novitskiy, R. Zaynagetdinov, A.E. Goldstein, D.P. Carbone, I. Biaggioni, M.M. Dikov, and I. Feoktistov (2008) "Host A(2B) adenosine receptors promote carcinoma growth," Neoplasia. 10, 987-95.
Samon, J.B., A. Champhekar, L.M. Minter, J.C. Telfer, L. Miele, A. Fauq, P. Das, T.E. Golde, and B.A. Osborne (2008) "Notch1 and TGFbeta1 cooperatively regulate Foxp3 expression and the maintenance of peripheral regulatory T cells," Blood. 112, 1813-21.
Sauma D, Espejo P, Ramirez A, Fierro A, Rosemblatt M, Bono MR. Differential Yegulation of Notch ligands in dendritic cells upon interaction with T helper cells. Scand J Immunol 2011; 74: 62-70.
Sauma D, Ramirez A, Alvarez K, Rosemblatt M, Bono MR. Notch signalling regulates cytokine production by CD8+ and CD4+ T cells. Scand J Immunol 2012; 75: 389-400.
Schenk, A.O., T. Nozaki, M. Rabant, A. Valujskikh, and R.L. Fairchild (200S) "Donor-reactive CDS memory T cells infiltrate cardiac allografts within 24-h posttransplant in naive recipients," Am J Transplant. 8, 1652-61.
Shin-Ya, M., 0. Mazda, C. Tsuchihara, H. Hirai, J. Imanishi, and M. Takeuchi (2003) "Interleukin-2 abolishes myeloid cell accumulation induced by Lewis lung carcinoma," Journal of interferon & cytokine research: the official journal of the International Society for Interferon and Cytokine Research. 23, 631-8.
Sicard, A., T.W. Phares, H. Yu, R. Fan, W.M. Baldwin, 3rd, R.L. Fairchild, and A. Valujskikh (2012) "The spleen is the major source of antidonor antibody-secreting cells in murine heart allograft recipients," Am J Transplant. 12, 170S-19.
Sierra RA, Thevenot P, Raber PL, et al. Rescue of notch-1 signaling in antigen-specific CD8+ T cells overcomes tumor-induced T-cell suppression and enhances immunotherapy in cancer. Cancer immunology research 2014; 2: 800-11.
Sierra RA, Trillo-Tinoco J, Mohamed E, et al. Anti-Jagged Immunotherapy Inhibits MDSCs and Overcomes Tumor-Induced Tolerance. Cancer Res 2017; 77: 5628-38.
Skokos D, Nussenzweig MC. CD8—DCs induce TL-12-independent Th1 differentiation through Delta 4 Notch-like ligand in response to bacterial LPS. J Exp Med 2007; 204: 1525-31.
Sugimoto K, Maekawa Y, Kitamura A, et al. Notch2 signaling is required for potent antitumor immunity in vivo. J Immunol 2010; 184: 4673-8.
Sun, J., C.J. Krawczyk, and E.J. Pearce (2008) "Suppression of Th2 cell development by Notch ligands Delta1 and Delta4," Journal of immunology. 180, 1655-61.
Tanigaki K, Tsuji M, Yamamoto N, et al. Regulation of alphabeta/gammadelta T cell lineage commitment and peripheral T cell responses by Notch/RBP-J signaling. Immunity 2004; 20: 611-22.
Taylor, P., H. Takeuchi, D. Sheppard, C. Chillakuri, S.M. Lea, R.S. Haltiwanger, and P.A. Handford (2014) "Fringe-mediated extension of 0-linked fucose in the ligand-binding region of Notch1 increases binding to mammalian Notch ligands," Proceedings of the National Academy of Sciences of the United States of America. 111, 7290-5.
Thounaojam MC, Dudimah DF, Pellom ST, Jr., et al. Bortezomib enhances expression of effector molecules in anti-tumor CD8+ T lymphocytes by promoting Notch-nuclear factor-kappaB crosstalk. Qncotarget 2015; 6: 32439-55.
Matteucci, et al., J. Am. Chem. Soc., 103:3185 (1981).
Tran, I.T., A.R. Sandy, A.J. Carulli, C. Ebens, J. Chung, G.T. Shan, V. Radojcic, A. Friedman, T. Gridley, A. Shelton, P. Reddy, L.C. Samuelson, M. Yan, C.W. Siebel, and I. Maillard (2013) "Blockade of individual Notch ligands and receptors controls graft-versus-host disease," The Journal of clinical investigation. 123, 1590-604.
Tsukumo, S. and K. Yasutomo (2004) "Notch governing mature T cell differentiation," Journal of immunology. 173, 7109-13.
Valujskikh, A. and X.C. Li (2007) "Frontiers in nephrology: T cell memory as a barrier to transplant tolerance," J Am Soc Nephrol. 18, 2252-61.
Valujskikh, A., 0. Lantz, S. Celli, P. Matzinger, and P.S. Heeger (2002) "Cross-primed CDS(+) T cells mediate graft rejection via a distinct effector pathway," Nat Immunol. 3, 844-51.
Vigouroux S, Yvon E, Wagner HJ, et al. Induction of antigen-specific regulatory T cells following overexpression of a Notch ligand by human B lymphocytes. J Virol 2003; 77: 10872-80.
Wang Y, Xing F, Ye S, et al. Jagged-1 signaling suppresses the IL-6 and TGF-beta treatment-induced Th17 cell differentiation via the reduction of RORgammat/IL-17A/IL-17F/IL-23a/IL-12rb1. Scientific reports 2015; 5: 8234.
Whiteman, P., C. Redfield, and P.A. Handford (2014) "Bacterial expression and in vitro refolding of limited fragments of the Notch receptor and its ligands," Methods Mo! Biol. 1187, 193-208.
Xiong Y, Lingrel JB, Wuthrich M, et al. Transcription Factor KLF2 in Dendritic Cells Downregulates Th2 Programming via the HIF-1alpha/Jagged2/Notch Axis. mBio 2016; 7(3):e00436-16.
Xu J, Krebs LT, Gridley T. Generation of mice with a conditional null allele of the Jagged2 gene. Genesis 2010; 48: 390-3.

(56) References Cited

OTHER PUBLICATIONS

Xu, A., L. Lei, and K.D. Irvine (2005) "Regions of Drosophila Notch that contribute to ligand binding and the modulatory influence of Fringe," J Biol Chem. 280, 30158-65.
Yamamoto, S., K.L. Schulze, and H.J. Bellen (2014) "Introduction to Notch signaling," Methods Mo/ Biol. 1187, 1-14.
Yuan JS, Kousis PC, Suliman S, Visan I, Guidos CJ. Functions of notch signaling in the immune system: consensus and controversies. Annu Rev Immunol 2010; 28: 343-65.
Yvon ES, Vigouroux S, Rousseau RF, et al. Overexpression of the Notch ligand, Jagged-1, induces alloantigen-specific human regulatory T cells. Blood 2003; 102: 3815-21.
Zhang, Q., Y. Chen, R.L. Fairchild, P.S. Heeger, and A. Valujskikh (2006) "Lymphoid sequestration of alloreactive memory CD4 T cells promotes cardiac allograft survival," J Immunol. 176, 770-7.
International Preliminary Report on Patentability issued for Application No. PCT/US2018/024343 dated Oct. 3, 2019.

* cited by examiner

SEQUENCE LISTING

<160> NUMBER OF SEQ ID NOS: 157

<210> SEQ ID NO 1
<211> LENGTH: 352
<212> TYPE: PRT
<213> ORGANISM: Artificial Sequence
<220> FEATURE:
<223> OTHER INFORMATION: synthetic construct

<400> SEQUENCE: 1

Met Lys Tyr Leu Leu Pro Thr Ala Ala Ala Gly Leu Leu Leu Leu Ala

-continued

```
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe
    50                  55                  60

Thr Cys Gly Glu Arg Gly Glu Lys Val Cys Asn Pro Gly Trp Lys Gly
65                  70                  75                  80

Pro Tyr Cys Thr Glu Pro Ile Cys Leu Pro Gly Cys Asp Glu Gln His
                85                  90                  95

Gly Phe Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Asp Leu Asn Tyr Cys Thr His His Lys Pro Cys
145                 150                 155                 160

Lys Asn Gly Ala Thr Cys Thr Asn Thr Gly Gln Gly Ser Tyr Thr Cys
                165                 170                 175

Ser Cys Arg Pro Gly Tyr Thr Gly Ala Thr Cys Glu Leu Gly Ser Ser
            180                 185                 190

Gly Ser Ser Gly Phe Val Cys Asp Glu His Tyr Tyr Gly Glu Gly Cys
        195                 200                 205

Ser Val Phe Cys Arg Pro Arg Asp Asp Ala Phe Gly His Phe Thr Cys
    210                 215                 220

Gly Glu Arg Gly Glu Lys Val Cys Asn Pro Gly Trp Lys Gly Pro Tyr
225                 230                 235                 240

Cys Thr Glu Pro Ile Cys Leu Pro Gly Cys Asp Glu Gln His Gly Phe
                245                 250                 255

Cys Asp Lys Pro Gly Glu Cys Lys Cys Arg Val Gly Trp Gln Gly Arg
            260                 265                 270

Tyr Cys Asp Glu Cys Ile Arg Tyr Pro Gly Cys Leu His Gly Thr Cys
        275                 280                 285

Gln Gln Pro Trp Gln Cys Asn Cys Gln Glu Gly Trp Gly Gly Leu Phe
    290                 295                 300

Cys Asn Gln Asp Leu Asn Tyr Cys Thr His His Lys Pro Cys Lys Asn
305                 310                 315                 320

Gly Ala Thr Cys Thr Asn Thr Gly Gln Gly Ser Tyr Thr Cys Ser Cys
                325                 330                 335

Arg Pro Gly Tyr Thr Gly Ala Thr Cys Glu Leu Gly Ser Ser Gly Cys
            340                 345                 350
```

<210> SEQ ID NO 2
<211> LENGTH: 329
<212> TYPE: PRT
<213> ORGANISM: Artificial Sequence
<220> FEATURE:
<223> OTHER INFORMATION: synthetic construct

<400> SEQUENCE: 2

```
His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
```

```
            20                  25                  30

Pro Arg Asp Asp Ala Phe Gly His Phe Thr Cys Gly Glu Arg Gly Glu
        35                  40                  45

Lys Val Cys Asn Pro Gly Trp Lys Gly Pro Tyr Cys Thr Glu Pro Ile
    50                  55                  60

Cys Leu Pro Gly Cys Asp Glu Gln His Gly Phe Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Asp Leu
        115                 120                 125

Asn Tyr Cys Thr His His Lys Pro Cys Lys Asn Gly Ala Thr Cys Thr
    130                 135                 140

Asn Thr Gly Gln Gly Ser Tyr Thr Cys Ser Cys Arg Pro Gly Tyr Thr
145                 150                 155                 160

Gly Ala Thr Cys Glu Leu Gly Ser Ser Gly Ser Ser Gly Phe Val Cys
                165                 170                 175

Asp Glu His Tyr Tyr Gly Glu Gly Cys Ser Val Phe Cys Arg Pro Arg
            180                 185                 190

Asp Asp Ala Phe Gly His Phe Thr Cys Gly Glu Arg Gly Glu Lys Val
        195                 200                 205

Cys Asn Pro Gly Trp Lys Gly Pro Tyr Cys Thr Glu Pro Ile Cys Leu
    210                 215                 220

Pro Gly Cys Asp Glu Gln His Gly Phe Cys Asp Lys Pro Gly Glu Cys
225                 230                 235                 240

Lys Cys Arg Val Gly Trp Gln Gly Arg Tyr Cys Asp Glu Cys Ile Arg
                245                 250                 255

Tyr Pro Gly Cys Leu His Gly Thr Cys Gln Gln Pro Trp Gln Cys Asn
            260                 265                 270

Cys Gln Glu Gly Trp Gly Gly Leu Phe Cys Asn Gln Asp Leu Asn Tyr
        275                 280                 285

Cys Thr His His Lys Pro Cys Lys Asn Gly Ala Thr Cys Thr Asn Thr
    290                 295                 300

Gly Gln Gly Ser Tyr Thr Cys Ser Cys Arg Pro Gly Tyr Thr Gly Ala
305                 310                 315                 320

Thr Cys Glu Leu Gly Ser Ser Gly Cys
                325


<210> SEQ ID NO 3
<211> LENGTH: 272
<212> TYPE: PRT
<213> ORGANISM: Artificial Sequence
<220> FEATURE:
<223> OTHER INFORMATION: synthetic construct

<400> SEQUENCE: 3

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe
```

```
    50                  55                  60

Thr Cys Gly Glu Arg Gly Glu Lys Val Cys Asn Pro Gly Trp Lys Gly
65                  70                  75                  80

Pro Tyr Cys Thr Glu Pro Ile Cys Leu Pro Gly Cys Asp Glu Gln His
                85                  90                  95

Gly Phe Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Gly Ser Ser Gly Ser Ser Gly Phe Val Cys Asp
145                 150                 155                 160

Glu His Tyr Tyr Gly Glu Gly Cys Ser Val Phe Cys Arg Pro Arg Asp
                165                 170                 175

Asp Ala Phe Gly His Phe Thr Cys Gly Glu Arg Gly Glu Lys Val Cys
            180                 185                 190

Asn Pro Gly Trp Lys Gly Pro Tyr Cys Thr Glu Pro Ile Cys Leu Pro
        195                 200                 205

Gly Cys Asp Glu Gln His Gly Phe Cys Asp Lys Pro Gly Glu Cys Lys
    210                 215                 220

Cys Arg Val Gly Trp Gln Gly Arg Tyr Cys Asp Glu Cys Ile Arg Tyr
225                 230                 235                 240

Pro Gly Cys Leu His Gly Thr Cys Gln Gln Pro Trp Gln Cys Asn Cys
                245                 250                 255

Gln Glu Gly Trp Gly Gly Leu Phe Cys Asn Gln Gly Ser Ser Gly Cys
            260                 265                 270


<210> SEQ ID NO 4
<211> LENGTH: 249
<212> TYPE: PRT
<213> ORGANISM: Artificial Sequence
<220> FEATURE:
<223> OTHER INFORMATION: synthetic construct

<400> SEQUENCE: 4

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Glu Arg Gly Glu
        35                  40                  45

Lys Val Cys Asn Pro Gly Trp Lys Gly Pro Tyr Cys Thr Glu Pro Ile
    50                  55                  60

Cys Leu Pro Gly Cys Asp Glu Gln His Gly Phe Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Gly Ser
        115                 120                 125

Ser Gly Ser Ser Gly Phe Val Cys Asp Glu His Tyr Tyr Gly Glu Gly
    130                 135                 140

Cys Ser Val Phe Cys Arg Pro Arg Asp Asp Ala Phe Gly His Phe Thr
```

```
145                 150                 155                 160

Cys Gly Glu Arg Gly Glu Lys Val Cys Asn Pro Gly Trp Lys Gly Pro
                165                 170                 175

Tyr Cys Thr Glu Pro Ile Cys Leu Pro Gly Cys Asp Glu Gln His Gly
            180                 185                 190

Phe Cys Asp Lys Pro Gly Glu Cys Lys Cys Arg Val Gly Trp Gln Gly
        195                 200                 205

Arg Tyr Cys Asp Glu Cys Ile Arg Tyr Pro Gly Cys Leu His Gly Thr
    210                 215                 220

Cys Gln Gln Pro Trp Gln Cys Asn Cys Gln Glu Gly Trp Gly Gly Leu
225                 230                 235                 240

Phe Cys Asn Gln Gly Ser Ser Gly Cys
                245


<210> SEQ ID NO 5
<211> LENGTH: 347
<212> TYPE: PRT
<213> ORGANISM: Artificial Sequence
<220> FEATURE:
<223> OTHER INFORMATION: synthetic construct

<400> SEQUENCE: 5

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe
    50                  55                  60

Thr Cys Gly Glu Arg Gly Glu Lys Val Cys Asn Pro Gly Trp Lys Gly
65                  70                  75                  80

Pro Tyr Cys Thr Glu Pro Ile Cys Leu Pro Gly Cys Asp Glu Gln His
                85                  90                  95

Gly Phe Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Asp Leu Asn Tyr Cys Thr His His Lys Pro Cys
145                 150                 155                 160

Lys Asn Gly Ala Thr Cys Thr Asn Thr Gly Gln Gly Ser Tyr Thr Cys
                165                 170                 175

Ser Cys Arg Pro Gly Tyr Thr Gly Ala Thr Cys Glu Leu Gly Ser Ser
            180                 185                 190

Gly Ser Ser Gly Phe Val Cys Asp Glu His Tyr Tyr Gly Glu Gly Cys
        195                 200                 205

Ser Val Phe Cys Arg Pro Arg Asp Asp Ala Phe Gly His Phe Thr Cys
    210                 215                 220

Gly Glu Arg Gly Glu Lys Val Cys Asn Pro Gly Trp Lys Gly Pro Tyr
225                 230                 235                 240

Cys Thr Glu Pro Ile Cys Leu Pro Gly Cys Asp Glu Gln His Gly Phe
                245                 250                 255

Cys Asp Lys Pro Gly Glu Cys Lys Cys Arg Val Gly Trp Gln Gly Arg
```

```
            260                 265                 270

Tyr Cys Asp Glu Cys Ile Arg Tyr Pro Gly Cys Leu His Gly Thr Cys
        275                 280                 285

Gln Gln Pro Trp Gln Cys Asn Cys Gln Glu Gly Trp Gly Gly Leu Phe
    290                 295                 300

Cys Asn Gln Asp Leu Asn Tyr Cys Thr His His Lys Pro Cys Lys Asn
305                 310                 315                 320

Gly Ala Thr Cys Thr Asn Thr Gly Gln Gly Ser Tyr Thr Cys Ser Cys
                325                 330                 335

Arg Pro Gly Tyr Thr Gly Ala Thr Cys Glu Leu
            340                 345


<210> SEQ ID NO 6
<211> LENGTH: 324
<212> TYPE: PRT
<213> ORGANISM: Artificial Sequence
<220> FEATURE:
<223> OTHER INFORMATION: synthetic construct

<400> SEQUENCE: 6

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Glu Arg Gly Glu
        35                  40                  45

Lys Val Cys Asn Pro Gly Trp Lys Gly Pro Tyr Cys Thr Glu Pro Ile
    50                  55                  60

Cys Leu Pro Gly Cys Asp Glu Gln His Gly Phe Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Asp Leu
        115                 120                 125

Asn Tyr Cys Thr His His Lys Pro Cys Lys Asn Gly Ala Thr Cys Thr
    130                 135                 140

Asn Thr Gly Gln Gly Ser Tyr Thr Cys Ser Cys Arg Pro Gly Tyr Thr
145                 150                 155                 160

Gly Ala Thr Cys Glu Leu Gly Ser Ser Gly Ser Ser Gly Phe Val Cys
                165                 170                 175

Asp Glu His Tyr Tyr Gly Glu Gly Cys Ser Val Phe Cys Arg Pro Arg
            180                 185                 190

Asp Asp Ala Phe Gly His Phe Thr Cys Gly Glu Arg Gly Glu Lys Val
        195                 200                 205

Cys Asn Pro Gly Trp Lys Gly Pro Tyr Cys Thr Glu Pro Ile Cys Leu
    210                 215                 220

Pro Gly Cys Asp Glu Gln His Gly Phe Cys Asp Lys Pro Gly Glu Cys
225                 230                 235                 240

Lys Cys Arg Val Gly Trp Gln Gly Arg Tyr Cys Asp Glu Cys Ile Arg
                245                 250                 255

Tyr Pro Gly Cys Leu His Gly Thr Cys Gln Gln Pro Trp Gln Cys Asn
            260                 265                 270

Cys Gln Glu Gly Trp Gly Gly Leu Phe Cys Asn Gln Asp Leu Asn Tyr
```

-continued

```
        275                 280                 285

Cys Thr His His Lys Pro Cys Lys Asn Gly Ala Thr Cys Thr Asn Thr
    290                 295                 300

Gly Gln Gly Ser Tyr Thr Cys Ser Cys Arg Pro Gly Tyr Thr Gly Ala
305                 310                 315                 320

Thr Cys Glu Leu


<210> SEQ ID NO 7
<211> LENGTH: 267
<212> TYPE: PRT
<213> ORGANISM: Artificial Sequence
<220> FEATURE:
<223> OTHER INFORMATION: synthetic construct

<400> SEQUENCE: 7

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe
    50                  55                  60

Thr Cys Gly Glu Arg Gly Glu Lys Val Cys Asn Pro Gly Trp Lys Gly
65                  70                  75                  80

Pro Tyr Cys Thr Glu Pro Ile Cys Leu Pro Gly Cys Asp Glu Gln His
                85                  90                  95

Gly Phe Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Gly Ser Ser Gly Ser Ser Gly Phe Val Cys Asp
145                 150                 155                 160

Glu His Tyr Tyr Gly Glu Gly Cys Ser Val Phe Cys Arg Pro Arg Asp
                165                 170                 175

Asp Ala Phe Gly His Phe Thr Cys Gly Glu Arg Gly Glu Lys Val Cys
            180                 185                 190

Asn Pro Gly Trp Lys Gly Pro Tyr Cys Thr Glu Pro Ile Cys Leu Pro
        195                 200                 205

Gly Cys Asp Glu Gln His Gly Phe Cys Asp Lys Pro Gly Glu Cys Lys
    210                 215                 220

Cys Arg Val Gly Trp Gln Gly Arg Tyr Cys Asp Glu Cys Ile Arg Tyr
225                 230                 235                 240

Pro Gly Cys Leu His Gly Thr Cys Gln Gln Pro Trp Gln Cys Asn Cys
                245                 250                 255

Gln Glu Gly Trp Gly Gly Leu Phe Cys Asn Gln
            260                 265


<210> SEQ ID NO 8
<211> LENGTH: 244
<212> TYPE: PRT
<213> ORGANISM: Artificial Sequence
<220> FEATURE:
<223> OTHER INFORMATION: synthetic construct
```

<400> SEQUENCE: 8

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Glu Arg Gly Glu
        35                  40                  45

Lys Val Cys Asn Pro Gly Trp Lys Gly Pro Tyr Cys Thr Glu Pro Ile
    50                  55                  60

Cys Leu Pro Gly Cys Asp Glu Gln His Gly Phe Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Gly Ser
        115                 120                 125

Ser Gly Ser Ser Gly Phe Val Cys Asp Glu His Tyr Tyr Gly Glu Gly
    130                 135                 140

Cys Ser Val Phe Cys Arg Pro Arg Asp Asp Ala Phe Gly His Phe Thr
145                 150                 155                 160

Cys Gly Glu Arg Gly Glu Lys Val Cys Asn Pro Gly Trp Lys Gly Pro
                165                 170                 175

Tyr Cys Thr Glu Pro Ile Cys Leu Pro Gly Cys Asp Glu Gln His Gly
            180                 185                 190

Phe Cys Asp Lys Pro Gly Glu Cys Lys Cys Arg Val Gly Trp Gln Gly
        195                 200                 205

Arg Tyr Cys Asp Glu Cys Ile Arg Tyr Pro Gly Cys Leu His Gly Thr
    210                 215                 220

Cys Gln Gln Pro Trp Gln Cys Asn Cys Gln Glu Gly Trp Gly Gly Leu
225                 230                 235                 240

Phe Cys Asn Gln

<210> SEQ ID NO 9
<211> LENGTH: 194
<212> TYPE: PRT
<213> ORGANISM: Artificial Sequence
<220> FEATURE:
<223> OTHER INFORMATION: synthetic construct

<400> SEQUENCE: 9

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe
    50                  55                  60

Thr Cys Gly Glu Arg Gly Glu Lys Val Cys Asn Pro Gly Trp Lys Gly
65                  70                  75                  80

Pro Tyr Cys Thr Glu Pro Ile Cys Leu Pro Gly Cys Asp Glu Gln His
                85                  90                  95

Gly Phe Cys Asp Lys Pro Gly Glu Cys Lys Cys Arg Val Gly Trp Gln
            100                 105                 110

```
Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Asp Leu Asn Tyr Cys Thr His His Lys Pro Cys
145                 150                 155                 160

Lys Asn Gly Ala Thr Cys Thr Asn Thr Gly Gln Gly Ser Tyr Thr Cys
                165                 170                 175

Ser Cys Arg Pro Gly Tyr Thr Gly Ala Thr Cys Glu Leu Gly Ser Ser
            180                 185                 190

Gly Cys


<210> SEQ ID NO 10
<211> LENGTH: 171
<212> TYPE: PRT
<213> ORGANISM: Artificial Sequence
<220> FEATURE:
<223> OTHER INFORMATION: synthetic construct

<400> SEQUENCE: 10

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Glu Arg Gly Glu
        35                  40                  45

Lys Val Cys Asn Pro Gly Trp Lys Gly Pro Tyr Cys Thr Glu Pro Ile
    50                  55                  60

Cys Leu Pro Gly Cys Asp Glu Gln His Gly Phe Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Asp Leu
        115                 120                 125

Asn Tyr Cys Thr His His Lys Pro Cys Lys Asn Gly Ala Thr Cys Thr
    130                 135                 140

Asn Thr Gly Gln Gly Ser Tyr Thr Cys Ser Cys Arg Pro Gly Tyr Thr
145                 150                 155                 160

Gly Ala Thr Cys Glu Leu Gly Ser Ser Gly Cys
                165                 170


<210> SEQ ID NO 11
<211> LENGTH: 154
<212> TYPE: PRT
<213> ORGANISM: Artificial Sequence
<220> FEATURE:
<223> OTHER INFORMATION: synthetic construct

<400> SEQUENCE: 11

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45
```

Gly Cys Ser Val Phe Cys Arg Pro Arg Asp Asp Ala Phe Gly His Phe
    50                  55                  60

Thr Cys Gly Glu Arg Gly Glu Lys Val Cys Asn Pro Gly Trp Lys Gly
65                  70                  75                  80

Pro Tyr Cys Thr Glu Pro Ile Cys Leu Pro Gly Cys Asp Glu Gln His
                85                  90                  95

Gly Phe Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Gly Ser Ser Gly Cys
145                 150

<210> SEQ ID NO 12
<211> LENGTH: 131
<212> TYPE: PRT
<213> ORGANISM: Artificial Sequence
<220> FEATURE:
<223> OTHER INFORMATION: synthetic construct

<400> SEQUENCE: 12

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Glu Arg Gly Glu
        35                  40                  45

Lys Val Cys Asn Pro Gly Trp Lys Gly Pro Tyr Cys Thr Glu Pro Ile
    50                  55                  60

Cys Leu Pro Gly Cys Asp Glu Gln His Gly Phe Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Gly Ser
        115                 120                 125

Ser Gly Cys
    130

<210> SEQ ID NO 13
<211> LENGTH: 189
<212> TYPE: PRT
<213> ORGANISM: Artificial Sequence
<220> FEATURE:
<223> OTHER INFORMATION: synthetic construct

<400> SEQUENCE: 13

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe

```
    50                  55                  60

Thr Cys Gly Glu Arg Gly Glu Lys Val Cys Asn Pro Gly Trp Lys Gly
65                  70                  75                  80

Pro Tyr Cys Thr Glu Pro Ile Cys Leu Pro Gly Cys Asp Glu Gln His
                85                  90                  95

Gly Phe Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Asp Leu Asn Tyr Cys Thr His His Lys Pro Cys
145                 150                 155                 160

Lys Asn Gly Ala Thr Cys Thr Asn Thr Gly Gln Gly Ser Tyr Thr Cys
                165                 170                 175

Ser Cys Arg Pro Gly Tyr Thr Gly Ala Thr Cys Glu Leu
            180                 185


<210> SEQ ID NO 14
<211> LENGTH: 166
<212> TYPE: PRT
<213> ORGANISM: Artificial Sequence
<220> FEATURE:
<223> OTHER INFORMATION: synthetic construct

<400> SEQUENCE: 14

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Glu Arg Gly Glu
        35                  40                  45

Lys Val Cys Asn Pro Gly Trp Lys Gly Pro Tyr Cys Thr Glu Pro Ile
    50                  55                  60

Cys Leu Pro Gly Cys Asp Glu Gln His Gly Phe Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Asp Leu
        115                 120                 125

Asn Tyr Cys Thr His His Lys Pro Cys Lys Asn Gly Ala Thr Cys Thr
    130                 135                 140

Asn Thr Gly Gln Gly Ser Tyr Thr Cys Ser Cys Arg Pro Gly Tyr Thr
145                 150                 155                 160

Gly Ala Thr Cys Glu Leu
                165


<210> SEQ ID NO 15
<211> LENGTH: 149
<212> TYPE: PRT
<213> ORGANISM: Artificial Sequence
<220> FEATURE:
<223> OTHER INFORMATION: synthetic construct

<400> SEQUENCE: 15
```

Met Lys Tyr Leu Leu Pro Thr Ala Ala Ala Gly Leu Leu Leu Leu Ala
1 5 10 15

Ala Gln Pro Ala Met Ala Ala His His His His His His Gly Gly Glu
20 25 30

Asn Leu Tyr Phe Gln Gly Phe Val Cys Asp Glu His Tyr Tyr Gly Glu
35 40 45

Gly Cys Ser Val Phe Cys Arg Pro Arg Asp Asp Ala Phe Gly His Phe
50 55 60

Thr Cys Gly Glu Arg Gly Glu Lys Val Cys Asn Pro Gly Trp Lys Gly
65 70 75 80

Pro Tyr Cys Thr Glu Pro Ile Cys Leu Pro Gly Cys Asp Glu Gln His
85 90 95

Gly Phe Cys Asp Lys Pro Gly Glu Cys Lys Cys Arg Val Gly Trp Gln
100 105 110

Gly Arg Tyr Cys Asp Glu Cys Ile Arg Tyr Pro Gly Cys Leu His Gly
115 120 125

Thr Cys Gln Gln Pro Trp Gln Cys Asn Cys Gln Glu Gly Trp Gly Gly
130 135 140

Leu Phe Cys Asn Gln
145

<210> SEQ ID NO 16
<211> LENGTH: 126
<212> TYPE: PRT
<213> ORGANISM: Artificial Sequence
<220> FEATURE:
<223> OTHER INFORMATION: synthetic construct

<400> SEQUENCE: 16

His His His His His His Gly Gly Glu Asn Leu Tyr Phe Gln Gly Phe
1 5 10 15

Val Cys Asp Glu His Tyr Tyr Gly Glu Gly Cys Ser Val Phe Cys Arg
20 25 30

Pro Arg Asp Asp Ala Phe Gly His Phe Thr Cys Gly Glu Arg Gly Glu
35 40 45

Lys Val Cys Asn Pro Gly Trp Lys Gly Pro Tyr Cys Thr Glu Pro Ile
50 55 60

Cys Leu Pro Gly Cys Asp Glu Gln His Gly Phe Cys Asp Lys Pro Gly
65 70 75 80

Glu Cys Lys Cys Arg Val Gly Trp Gln Gly Arg Tyr Cys Asp Glu Cys
85 90 95

Ile Arg Tyr Pro Gly Cys Leu His Gly Thr Cys Gln Gln Pro Trp Gln
100 105 110

Cys Asn Cys Gln Glu Gly Trp Gly Gly Leu Phe Cys Asn Gln
115 120 125

<210> SEQ ID NO 17
<211> LENGTH: 348
<212> TYPE: PRT
<213> ORGANISM: Artificial Sequence
<220> FEATURE:
<223> OTHER INFORMATION: synthetic construct

<400> SEQUENCE: 17

Met Lys Tyr Leu Leu Pro Thr Ala Ala Ala Gly Leu Leu Leu Leu Ala
1 5 10 15

Ala Gln Pro Ala Met Ala Ala His His His His His His Gly Gly Glu
20 25 30

```
Asn Leu Tyr Phe Gln Gly Gln Val Trp Ser Ser Gly Val Phe Glu Leu
        35                  40                  45

Lys Leu Gln Glu Phe Val Asn Lys Lys Gly Leu Leu Gly Asn Arg Asn
    50                  55                  60

Cys Cys Arg Gly Gly Ala Gly Pro Pro Pro Cys Ala Cys Arg Thr Phe
65                  70                  75                  80

Phe Arg Val Cys Leu Lys His Tyr Gln Ala Ser Val Ser Pro Glu Pro
                85                  90                  95

Pro Cys Thr Tyr Gly Ser Ala Val Thr Pro Val Leu Gly Val Asp Ser
            100                 105                 110

Phe Ser Leu Pro Asp Gly Gly Gly Ala Asp Ser Ala Phe Ser Asn Pro
        115                 120                 125

Ile Arg Phe Pro Phe Gly Phe Thr Trp Pro Gly Thr Phe Ser Leu Ile
    130                 135                 140

Ile Glu Ala Leu His Thr Asp Ser Pro Asp Asp Leu Ala Thr Glu Asn
145                 150                 155                 160

Pro Glu Arg Leu Ile Ser Arg Leu Ala Thr Gln Arg His Leu Thr Val
                165                 170                 175

Gly Glu Glu Trp Ser Gln Asp Leu His Ser Ser Gly Arg Thr Asp Leu
            180                 185                 190

Lys Tyr Ser Tyr Arg Phe Val Cys Asp Glu His Tyr Tyr Gly Glu Gly
        195                 200                 205

Cys Ser Val Phe Cys Arg Pro Arg Asp Asp Ala Phe Gly His Phe Thr
    210                 215                 220

Cys Gly Glu Arg Gly Glu Lys Val Cys Asn Pro Gly Trp Lys Gly Pro
225                 230                 235                 240

Tyr Cys Thr Glu Pro Ile Cys Leu Pro Gly Cys Asp Glu Gln His Gly
                245                 250                 255

Phe Cys Asp Lys Pro Gly Glu Cys Lys Cys Arg Val Gly Trp Gln Gly
            260                 265                 270

Arg Tyr Cys Asp Glu Cys Ile Arg Tyr Pro Gly Cys Leu His Gly Thr
        275                 280                 285

Cys Gln Gln Pro Trp Gln Cys Asn Cys Gln Glu Gly Trp Gly Gly Leu
    290                 295                 300

Phe Cys Asn Gln Asp Leu Asn Tyr Cys Thr His His Lys Pro Cys Lys
305                 310                 315                 320

Asn Gly Ala Thr Cys Thr Asn Thr Gly Gln Gly Ser Tyr Thr Cys Ser
                325                 330                 335

Cys Arg Pro Gly Tyr Thr Gly Ala Thr Cys Glu Leu
            340                 345
```

```
<210> SEQ ID NO 18
<211> LENGTH: 325
<212> TYPE: PRT
<213> ORGANISM: Artificial Sequence
<220> FEATURE:
<223> OTHER INFORMATION: synthetic construct

<400> SEQUENCE: 18

His His His His His His Gly Gly Glu Asn Leu Tyr Phe Gln Gly Gln
1               5                   10                  15

Val Trp Ser Ser Gly Val Phe Glu Leu Lys Leu Gln Glu Phe Val Asn
            20                  25                  30

Lys Lys Gly Leu Leu Gly Asn Arg Asn Cys Cys Arg Gly Gly Ala Gly
        35                  40                  45
```

```
Pro Pro Pro Cys Ala Cys Arg Thr Phe Phe Arg Val Cys Leu Lys His
    50                  55                  60

Tyr Gln Ala Ser Val Ser Pro Glu Pro Pro Cys Thr Tyr Gly Ser Ala
65                  70                  75                  80

Val Thr Pro Val Leu Gly Val Asp Ser Phe Ser Leu Pro Asp Gly Gly
                85                  90                  95

Gly Ala Asp Ser Ala Phe Ser Asn Pro Ile Arg Phe Pro Phe Gly Phe
            100                 105                 110

Thr Trp Pro Gly Thr Phe Ser Leu Ile Ile Glu Ala Leu His Thr Asp
        115                 120                 125

Ser Pro Asp Asp Leu Ala Thr Glu Asn Pro Glu Arg Leu Ile Ser Arg
    130                 135                 140

Leu Ala Thr Gln Arg His Leu Thr Val Gly Glu Glu Trp Ser Gln Asp
145                 150                 155                 160

Leu His Ser Ser Gly Arg Thr Asp Leu Lys Tyr Ser Tyr Arg Phe Val
                165                 170                 175

Cys Asp Glu His Tyr Tyr Gly Glu Gly Cys Ser Val Phe Cys Arg Pro
            180                 185                 190

Arg Asp Asp Ala Phe Gly His Phe Thr Cys Gly Glu Arg Gly Glu Lys
        195                 200                 205

Val Cys Asn Pro Gly Trp Lys Gly Pro Tyr Cys Thr Glu Pro Ile Cys
    210                 215                 220

Leu Pro Gly Cys Asp Glu Gln His Gly Phe Cys Asp Lys Pro Gly Glu
225                 230                 235                 240

Cys Lys Cys Arg Val Gly Trp Gln Gly Arg Tyr Cys Asp Glu Cys Ile
                245                 250                 255

Arg Tyr Pro Gly Cys Leu His Gly Thr Cys Gln Gln Pro Trp Gln Cys
            260                 265                 270

Asn Cys Gln Glu Gly Trp Gly Gly Leu Phe Cys Asn Gln Asp Leu Asn
        275                 280                 285

Tyr Cys Thr His His Lys Pro Cys Lys Asn Gly Ala Thr Cys Thr Asn
    290                 295                 300

Thr Gly Gln Gly Ser Tyr Thr Cys Ser Cys Arg Pro Gly Tyr Thr Gly
305                 310                 315                 320

Ala Thr Cys Glu Leu
                325


<210> SEQ ID NO 19
<211> LENGTH: 307
<212> TYPE: PRT
<213> ORGANISM: Artificial Sequence
<220> FEATURE:
<223> OTHER INFORMATION: synthetic construct

<400> SEQUENCE: 19

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Gln Val Trp Ser Ser Gly Val Phe Glu Leu
        35                  40                  45

Lys Leu Gln Glu Phe Val Asn Lys Lys Gly Leu Leu Gly Asn Arg Asn
    50                  55                  60

Cys Cys Arg Gly Gly Ala Gly Pro Pro Pro Cys Ala Cys Arg Thr Phe
65                  70                  75                  80
```

```
Phe Arg Val Cys Leu Lys His Tyr Gln Ala Ser Val Ser Pro Glu Pro
                85                  90                  95

Pro Cys Thr Tyr Gly Ser Ala Val Thr Pro Val Leu Gly Val Asp Ser
            100                 105                 110

Phe Ser Leu Pro Asp Gly Gly Gly Ala Asp Ser Ala Phe Ser Asn Pro
        115                 120                 125

Ile Arg Phe Pro Phe Gly Phe Thr Trp Pro Gly Thr Phe Ser Leu Ile
    130                 135                 140

Ile Glu Ala Leu His Thr Asp Ser Pro Asp Asp Leu Ala Thr Glu Asn
145                 150                 155                 160

Pro Glu Arg Leu Ile Ser Arg Leu Ala Thr Gln Arg His Leu Thr Val
                165                 170                 175

Gly Glu Glu Trp Ser Gln Asp Leu His Ser Ser Gly Arg Thr Asp Leu
            180                 185                 190

Lys Tyr Ser Tyr Arg Phe Val Cys Asp Glu His Tyr Tyr Gly Glu Gly
        195                 200                 205

Cys Ser Val Phe Cys Arg Pro Arg Asp Asp Ala Phe Gly His Phe Thr
    210                 215                 220

Cys Gly Glu Arg Gly Glu Lys Val Cys Asn Pro Gly Trp Lys Gly Pro
225                 230                 235                 240

Tyr Cys Thr Glu Pro Ile Cys Leu Pro Gly Cys Asp Glu Gln His Gly
                245                 250                 255

Phe Cys Asp Lys Pro Gly Glu Cys Lys Cys Arg Val Gly Trp Gln Gly
            260                 265                 270

Arg Tyr Cys Asp Glu Cys Ile Arg Tyr Pro Gly Cys Leu His Gly Thr
        275                 280                 285

Cys Gln Gln Pro Trp Gln Cys Asn Cys Gln Glu Gly Trp Gly Gly Leu
    290                 295                 300

Phe Cys Asn
305


<210> SEQ ID NO 20
<211> LENGTH: 284
<212> TYPE: PRT
<213> ORGANISM: Artificial Sequence
<220> FEATURE:
<223> OTHER INFORMATION: synthetic construct

<400> SEQUENCE: 20

His His His His His His Gly Gly Glu Asn Leu Tyr Phe Gln Gly Gln
1               5                   10                  15

Val Trp Ser Ser Gly Val Phe Glu Leu Lys Leu Gln Glu Phe Val Asn
            20                  25                  30

Lys Lys Gly Leu Leu Gly Asn Arg Asn Cys Cys Arg Gly Gly Ala Gly
        35                  40                  45

Pro Pro Pro Cys Ala Cys Arg Thr Phe Phe Arg Val Cys Leu Lys His
    50                  55                  60

Tyr Gln Ala Ser Val Ser Pro Glu Pro Pro Cys Thr Tyr Gly Ser Ala
65                  70                  75                  80

Val Thr Pro Val Leu Gly Val Asp Ser Phe Ser Leu Pro Asp Gly Gly
                85                  90                  95

Gly Ala Asp Ser Ala Phe Ser Asn Pro Ile Arg Phe Pro Phe Gly Phe
            100                 105                 110

Thr Trp Pro Gly Thr Phe Ser Leu Ile Ile Glu Ala Leu His Thr Asp
        115                 120                 125
```

-continued

Ser Pro Asp Asp Leu Ala Thr Glu Asn Pro Glu Arg Leu Ile Ser Arg
130 135 140

Leu Ala Thr Gln Arg His Leu Thr Val Gly Glu Glu Trp Ser Gln Asp
145 150 155 160

Leu His Ser Ser Gly Arg Thr Asp Leu Lys Tyr Ser Tyr Arg Phe Val
165 170 175

Cys Asp Glu His Tyr Tyr Gly Glu Gly Cys Ser Val Phe Cys Arg Pro
180 185 190

Arg Asp Asp Ala Phe Gly His Phe Thr Cys Gly Glu Arg Gly Glu Lys
195 200 205

Val Cys Asn Pro Gly Trp Lys Gly Pro Tyr Cys Thr Glu Pro Ile Cys
210 215 220

Leu Pro Gly Cys Asp Glu Gln His Gly Phe Cys Asp Lys Pro Gly Glu
225 230 235 240

Cys Lys Cys Arg Val Gly Trp Gln Gly Arg Tyr Cys Asp Glu Cys Ile
245 250 255

Arg Tyr Pro Gly Cys Leu His Gly Thr Cys Gln Gln Pro Trp Gln Cys
260 265 270

Asn Cys Gln Glu Gly Trp Gly Gly Leu Phe Cys Asn
275 280

<210> SEQ ID NO 21
<211> LENGTH: 352
<212> TYPE: PRT
<213> ORGANISM: Artificial Sequence
<220> FEATURE:
<223> OTHER INFORMATION: synthetic construct

<400> SEQUENCE: 21

Met Lys Tyr Leu Leu Pro Thr Ala Ala Ala Gly Leu Leu Leu Leu Ala
1 5 10 15

Ala Gln Pro Ala Met Ala Ala His His His His His His Gly Gly Glu
20 25 30

Asn Leu Tyr Phe Gln Gly Phe Val Cys Asp Glu His Tyr Tyr Gly Glu
35 40 45

Gly Cys Ser Val Phe Cys Arg Pro Arg Asp Asp Ala Phe Gly His Phe
50 55 60

Thr Cys Gly Asp Arg Gly Glu Lys Met Cys Asp Pro Gly Trp Lys Gly
65 70 75 80

Gln Tyr Cys Thr Asp Pro Ile Cys Leu Pro Gly Cys Asp Asp Gln His
85 90 95

Gly Tyr Cys Asp Lys Pro Gly Glu Cys Lys Cys Arg Val Gly Trp Gln
100 105 110

Gly Arg Tyr Cys Asp Glu Cys Ile Arg Tyr Pro Gly Cys Leu His Gly
115 120 125

Thr Cys Gln Gln Pro Trp Gln Cys Asn Cys Gln Glu Gly Trp Gly Gly
130 135 140

Leu Phe Cys Asn Gln Asp Leu Asn Tyr Cys Thr His His Lys Pro Cys
145 150 155 160

Arg Asn Gly Ala Thr Cys Thr Asn Thr Gly Gln Gly Ser Tyr Thr Cys
165 170 175

Ser Cys Arg Pro Gly Tyr Thr Gly Ala Asn Cys Glu Leu Gly Ser Ser
180 185 190

Gly Ser Ser Gly Phe Val Cys Asp Glu His Tyr Tyr Gly Glu Gly Cys
195 200 205

```
Ser Val Phe Cys Arg Pro Arg Asp Asp Ala Phe Gly His Phe Thr Cys
    210                 215                 220

Gly Asp Arg Gly Glu Lys Met Cys Asp Pro Gly Trp Lys Gly Gln Tyr
225                 230                 235                 240

Cys Thr Asp Pro Ile Cys Leu Pro Gly Cys Asp Asp Gln His Gly Tyr
                245                 250                 255

Cys Asp Lys Pro Gly Glu Cys Lys Cys Arg Val Gly Trp Gln Gly Arg
            260                 265                 270

Tyr Cys Asp Glu Cys Ile Arg Tyr Pro Gly Cys Leu His Gly Thr Cys
        275                 280                 285

Gln Gln Pro Trp Gln Cys Asn Cys Gln Glu Gly Trp Gly Gly Leu Phe
    290                 295                 300

Cys Asn Gln Asp Leu Asn Tyr Cys Thr His His Lys Pro Cys Arg Asn
305                 310                 315                 320

Gly Ala Thr Cys Thr Asn Thr Gly Gln Gly Ser Tyr Thr Cys Ser Cys
                325                 330                 335

Arg Pro Gly Tyr Thr Gly Ala Asn Cys Glu Leu Gly Ser Ser Gly Cys
            340                 345                 350


<210> SEQ ID NO 22
<211> LENGTH: 329
<212> TYPE: PRT
<213> ORGANISM: Artificial Sequence
<220> FEATURE:
<223> OTHER INFORMATION: synthetic construct

<400> SEQUENCE: 22

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Asp Arg Gly Glu
        35                  40                  45

Lys Met Cys Asp Pro Gly Trp Lys Gly Gln Tyr Cys Thr Asp Pro Ile
    50                  55                  60

Cys Leu Pro Gly Cys Asp Asp Gln His Gly Tyr Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Asp Leu
        115                 120                 125

Asn Tyr Cys Thr His His Lys Pro Cys Arg Asn Gly Ala Thr Cys Thr
    130                 135                 140

Asn Thr Gly Gln Gly Ser Tyr Thr Cys Ser Cys Arg Pro Gly Tyr Thr
145                 150                 155                 160

Gly Ala Asn Cys Glu Leu Gly Ser Ser Gly Ser Ser Gly Phe Val Cys
                165                 170                 175

Asp Glu His Tyr Tyr Gly Glu Gly Cys Ser Val Phe Cys Arg Pro Arg
            180                 185                 190

Asp Asp Ala Phe Gly His Phe Thr Cys Gly Asp Arg Gly Glu Lys Met
        195                 200                 205

Cys Asp Pro Gly Trp Lys Gly Gln Tyr Cys Thr Asp Pro Ile Cys Leu
    210                 215                 220
```

```
Pro Gly Cys Asp Asp Gln His Gly Tyr Cys Asp Lys Pro Gly Glu Cys
225                 230                 235                 240

Lys Cys Arg Val Gly Trp Gln Gly Arg Tyr Cys Asp Glu Cys Ile Arg
                245                 250                 255

Tyr Pro Gly Cys Leu His Gly Thr Cys Gln Gln Pro Trp Gln Cys Asn
            260                 265                 270

Cys Gln Glu Gly Trp Gly Gly Leu Phe Cys Asn Gln Asp Leu Asn Tyr
        275                 280                 285

Cys Thr His His Lys Pro Cys Arg Asn Gly Ala Thr Cys Thr Asn Thr
    290                 295                 300

Gly Gln Gly Ser Tyr Thr Cys Ser Cys Arg Pro Gly Tyr Thr Gly Ala
305                 310                 315                 320

Asn Cys Glu Leu Gly Ser Ser Gly Cys
                325
```

<210> SEQ ID NO 23
<211> LENGTH: 272
<212> TYPE: PRT
<213> ORGANISM: Artificial Sequence
<220> FEATURE:
<223> OTHER INFORMATION: synthetic construct

<400> SEQUENCE: 23

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe
    50                  55                  60

Thr Cys Gly Asp Arg Gly Glu Lys Met Cys Asp Pro Gly Trp Lys Gly
65                  70                  75                  80

Gln Tyr Cys Thr Asp Pro Ile Cys Leu Pro Gly Cys Asp Asp Gln His
                85                  90                  95

Gly Tyr Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Gly Ser Ser Gly Ser Ser Gly Phe Val Cys Asp
145                 150                 155                 160

Glu His Tyr Tyr Gly Glu Gly Cys Ser Val Phe Cys Arg Pro Arg Asp
                165                 170                 175

Asp Ala Phe Gly His Phe Thr Cys Gly Asp Arg Gly Glu Lys Met Cys
            180                 185                 190

Asp Pro Gly Trp Lys Gly Gln Tyr Cys Thr Asp Pro Ile Cys Leu Pro
        195                 200                 205

Gly Cys Asp Asp Gln His Gly Tyr Cys Asp Lys Pro Gly Glu Cys Lys
    210                 215                 220

Cys Arg Val Gly Trp Gln Gly Arg Tyr Cys Asp Glu Cys Ile Arg Tyr
225                 230                 235                 240

Pro Gly Cys Leu His Gly Thr Cys Gln Gln Pro Trp Gln Cys Asn Cys
                245                 250                 255
```

```
Gln Glu Gly Trp Gly Gly Leu Phe Cys Asn Gln Gly Ser Ser Gly Cys
            260                 265                 270


<210> SEQ ID NO 24
<211> LENGTH: 249
<212> TYPE: PRT
<213> ORGANISM: Artificial Sequence
<220> FEATURE:
<223> OTHER INFORMATION: synthetic construct

<400> SEQUENCE: 24

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Asp Arg Gly Glu
        35                  40                  45

Lys Met Cys Asp Pro Gly Trp Lys Gly Gln Tyr Cys Thr Asp Pro Ile
    50                  55                  60

Cys Leu Pro Gly Cys Asp Asp Gln His Gly Tyr Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Gly Ser
        115                 120                 125

Ser Gly Ser Ser Gly Phe Val Cys Asp Glu His Tyr Tyr Gly Glu Gly
    130                 135                 140

Cys Ser Val Phe Cys Arg Pro Arg Asp Asp Ala Phe Gly His Phe Thr
145                 150                 155                 160

Cys Gly Asp Arg Gly Glu Lys Met Cys Asp Pro Gly Trp Lys Gly Gln
                165                 170                 175

Tyr Cys Thr Asp Pro Ile Cys Leu Pro Gly Cys Asp Asp Gln His Gly
            180                 185                 190

Tyr Cys Asp Lys Pro Gly Glu Cys Lys Cys Arg Val Gly Trp Gln Gly
        195                 200                 205

Arg Tyr Cys Asp Glu Cys Ile Arg Tyr Pro Gly Cys Leu His Gly Thr
    210                 215                 220

Cys Gln Gln Pro Trp Gln Cys Asn Cys Gln Glu Gly Trp Gly Gly Leu
225                 230                 235                 240

Phe Cys Asn Gln Gly Ser Ser Gly Cys
                245


<210> SEQ ID NO 25
<211> LENGTH: 347
<212> TYPE: PRT
<213> ORGANISM: Artificial Sequence
<220> FEATURE:
<223> OTHER INFORMATION: synthetic construct

<400> SEQUENCE: 25

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
```

```
        35                  40                  45

Gly Cys Ser Val Phe Cys Arg Pro Arg Asp Asp Ala Phe Gly His Phe
    50                  55                  60

Thr Cys Gly Asp Arg Gly Glu Lys Met Cys Asp Pro Gly Trp Lys Gly
65                  70                  75                  80

Gln Tyr Cys Thr Asp Pro Ile Cys Leu Pro Gly Cys Asp Asp Gln His
                85                  90                  95

Gly Tyr Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Asp Leu Asn Tyr Cys Thr His His Lys Pro Cys
145                 150                 155                 160

Arg Asn Gly Ala Thr Cys Thr Asn Thr Gly Gln Gly Ser Tyr Thr Cys
                165                 170                 175

Ser Cys Arg Pro Gly Tyr Thr Gly Ala Asn Cys Glu Leu Gly Ser Ser
            180                 185                 190

Gly Ser Ser Gly Phe Val Cys Asp Glu His Tyr Tyr Gly Glu Gly Cys
        195                 200                 205

Ser Val Phe Cys Arg Pro Arg Asp Asp Ala Phe Gly His Phe Thr Cys
    210                 215                 220

Gly Asp Arg Gly Glu Lys Met Cys Asp Pro Gly Trp Lys Gly Gln Tyr
225                 230                 235                 240

Cys Thr Asp Pro Ile Cys Leu Pro Gly Cys Asp Asp Gln His Gly Tyr
                245                 250                 255

Cys Asp Lys Pro Gly Glu Cys Lys Cys Arg Val Gly Trp Gln Gly Arg
            260                 265                 270

Tyr Cys Asp Glu Cys Ile Arg Tyr Pro Gly Cys Leu His Gly Thr Cys
        275                 280                 285

Gln Gln Pro Trp Gln Cys Asn Cys Gln Glu Gly Trp Gly Gly Leu Phe
    290                 295                 300

Cys Asn Gln Asp Leu Asn Tyr Cys Thr His His Lys Pro Cys Arg Asn
305                 310                 315                 320

Gly Ala Thr Cys Thr Asn Thr Gly Gln Gly Ser Tyr Thr Cys Ser Cys
                325                 330                 335

Arg Pro Gly Tyr Thr Gly Ala Asn Cys Glu Leu
            340                 345
```

<210> SEQ ID NO 26
<211> LENGTH: 324
<212> TYPE: PRT
<213> ORGANISM: Artificial Sequence
<220> FEATURE:
<223> OTHER INFORMATION: synthetic construct

<400> SEQUENCE: 26

```
His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Asp Arg Gly Glu
        35                  40                  45

Lys Met Cys Asp Pro Gly Trp Lys Gly Gln Tyr Cys Thr Asp Pro Ile
```

```
    50                  55                  60

Cys Leu Pro Gly Cys Asp Asp Gln His Gly Tyr Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Asp Leu
        115                 120                 125

Asn Tyr Cys Thr His His Lys Pro Cys Arg Asn Gly Ala Thr Cys Thr
    130                 135                 140

Asn Thr Gly Gln Gly Ser Tyr Thr Cys Ser Cys Arg Pro Gly Tyr Thr
145                 150                 155                 160

Gly Ala Asn Cys Glu Leu Gly Ser Ser Gly Ser Ser Gly Phe Val Cys
                165                 170                 175

Asp Glu His Tyr Tyr Gly Glu Gly Cys Ser Val Phe Cys Arg Pro Arg
            180                 185                 190

Asp Asp Ala Phe Gly His Phe Thr Cys Gly Asp Arg Gly Glu Lys Met
        195                 200                 205

Cys Asp Pro Gly Trp Lys Gly Gln Tyr Cys Thr Asp Pro Ile Cys Leu
    210                 215                 220

Pro Gly Cys Asp Asp Gln His Gly Tyr Cys Asp Lys Pro Gly Glu Cys
225                 230                 235                 240

Lys Cys Arg Val Gly Trp Gln Gly Arg Tyr Cys Asp Glu Cys Ile Arg
                245                 250                 255

Tyr Pro Gly Cys Leu His Gly Thr Cys Gln Gln Pro Trp Gln Cys Asn
            260                 265                 270

Cys Gln Glu Gly Trp Gly Gly Leu Phe Cys Asn Gln Asp Leu Asn Tyr
        275                 280                 285

Cys Thr His His Lys Pro Cys Arg Asn Gly Ala Thr Cys Thr Asn Thr
    290                 295                 300

Gly Gln Gly Ser Tyr Thr Cys Ser Cys Arg Pro Gly Tyr Thr Gly Ala
305                 310                 315                 320

Asn Cys Glu Leu


<210> SEQ ID NO 27
<211> LENGTH: 267
<212> TYPE: PRT
<213> ORGANISM: Artificial Sequence
<220> FEATURE:
<223> OTHER INFORMATION: synthetic construct

<400> SEQUENCE: 27

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe
    50                  55                  60

Thr Cys Gly Asp Arg Gly Glu Lys Met Cys Asp Pro Gly Trp Lys Gly
65                  70                  75                  80

Gln Tyr Cys Thr Asp Pro Ile Cys Leu Pro Gly Cys Asp Asp Gln His
                85                  90                  95
```

```
Gly Tyr Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Gly Ser Ser Gly Ser Ser Gly Phe Val Cys Asp
145                 150                 155                 160

Glu His Tyr Tyr Gly Glu Gly Cys Ser Val Phe Cys Arg Pro Arg Asp
                165                 170                 175

Asp Ala Phe Gly His Phe Thr Cys Gly Asp Arg Gly Glu Lys Met Cys
            180                 185                 190

Asp Pro Gly Trp Lys Gly Gln Tyr Cys Thr Asp Pro Ile Cys Leu Pro
        195                 200                 205

Gly Cys Asp Asp Gln His Gly Tyr Cys Asp Lys Pro Gly Glu Cys Lys
    210                 215                 220

Cys Arg Val Gly Trp Gln Gly Arg Tyr Cys Asp Glu Cys Ile Arg Tyr
225                 230                 235                 240

Pro Gly Cys Leu His Gly Thr Cys Gln Gln Pro Trp Gln Cys Asn Cys
                245                 250                 255

Gln Glu Gly Trp Gly Gly Leu Phe Cys Asn Gln
            260                 265


<210> SEQ ID NO 28
<211> LENGTH: 244
<212> TYPE: PRT
<213> ORGANISM: Artificial Sequence
<220> FEATURE:
<223> OTHER INFORMATION: synthetic construct

<400> SEQUENCE: 28

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Asp Arg Gly Glu
        35                  40                  45

Lys Met Cys Asp Pro Gly Trp Lys Gly Gln Tyr Cys Thr Asp Pro Ile
    50                  55                  60

Cys Leu Pro Gly Cys Asp Asp Gln His Gly Tyr Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Gly Ser
        115                 120                 125

Ser Gly Ser Ser Gly Phe Val Cys Asp Glu His Tyr Tyr Gly Glu Gly
    130                 135                 140

Cys Ser Val Phe Cys Arg Pro Arg Asp Asp Ala Phe Gly His Phe Thr
145                 150                 155                 160

Cys Gly Asp Arg Gly Glu Lys Met Cys Asp Pro Gly Trp Lys Gly Gln
                165                 170                 175

Tyr Cys Thr Asp Pro Ile Cys Leu Pro Gly Cys Asp Asp Gln His Gly
            180                 185                 190
```

```
Tyr Cys Asp Lys Pro Gly Glu Cys Lys Cys Arg Val Gly Trp Gln Gly
        195                 200                 205

Arg Tyr Cys Asp Glu Cys Ile Arg Tyr Pro Gly Cys Leu His Gly Thr
    210                 215                 220

Cys Gln Gln Pro Trp Gln Cys Asn Cys Gln Glu Gly Trp Gly Gly Leu
225                 230                 235                 240

Phe Cys Asn Gln


<210> SEQ ID NO 29
<211> LENGTH: 194
<212> TYPE: PRT
<213> ORGANISM: Artificial Sequence
<220> FEATURE:
<223> OTHER INFORMATION: synthetic construct

<400> SEQUENCE: 29

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe
    50                  55                  60

Thr Cys Gly Asp Arg Gly Glu Lys Met Cys Asp Pro Gly Trp Lys Gly
65                  70                  75                  80

Gln Tyr Cys Thr Asp Pro Ile Cys Leu Pro Gly Cys Asp Asp Gln His
                85                  90                  95

Gly Tyr Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Asp Leu Asn Tyr Cys Thr His His Lys Pro Cys
145                 150                 155                 160

Arg Asn Gly Ala Thr Cys Thr Asn Thr Gly Gln Gly Ser Tyr Thr Cys
                165                 170                 175

Ser Cys Arg Pro Gly Tyr Thr Gly Ala Asn Cys Glu Leu Gly Ser Ser
            180                 185                 190

Gly Cys


<210> SEQ ID NO 30
<211> LENGTH: 171
<212> TYPE: PRT
<213> ORGANISM: Artificial Sequence
<220> FEATURE:
<223> OTHER INFORMATION: synthetic construct

<400> SEQUENCE: 30

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Asp Arg Gly Glu
        35                  40                  45
```

-continued

```
Lys Met Cys Asp Pro Gly Trp Lys Gly Gln Tyr Cys Thr Asp Pro Ile
    50                  55                  60

Cys Leu Pro Gly Cys Asp Asp Gln His Gly Tyr Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Asp Leu
        115                 120                 125

Asn Tyr Cys Thr His His Lys Pro Cys Arg Asn Gly Ala Thr Cys Thr
    130                 135                 140

Asn Thr Gly Gln Gly Ser Tyr Thr Cys Ser Cys Arg Pro Gly Tyr Thr
145                 150                 155                 160

Gly Ala Asn Cys Glu Leu Gly Ser Ser Gly Cys
                165                 170


<210> SEQ ID NO 31
<211> LENGTH: 154
<212> TYPE: PRT
<213> ORGANISM: Artificial Sequence
<220> FEATURE:
<223> OTHER INFORMATION: synthetic construct

<400> SEQUENCE: 31

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe
    50                  55                  60

Thr Cys Gly Asp Arg Gly Glu Lys Met Cys Asp Pro Gly Trp Lys Gly
65                  70                  75                  80

Gln Tyr Cys Thr Asp Pro Ile Cys Leu Pro Gly Cys Asp Asp Gln His
                85                  90                  95

Gly Tyr Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Gly Ser Ser Gly Cys
145                 150


<210> SEQ ID NO 32
<211> LENGTH: 131
<212> TYPE: PRT
<213> ORGANISM: Artificial Sequence
<220> FEATURE:
<223> OTHER INFORMATION: synthetic construct

<400> SEQUENCE: 32

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30
```

```
Pro Arg Asp Asp Ala Phe Gly His Phe Thr Cys Gly Asp Arg Gly Glu
        35                  40                  45

Lys Met Cys Asp Pro Gly Trp Lys Gly Gln Tyr Cys Thr Asp Pro Ile
    50                  55                  60

Cys Leu Pro Gly Cys Asp Asp Gln His Gly Tyr Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Gly Ser
        115                 120                 125

Ser Gly Cys
    130
```

<210> SEQ ID NO 33
<211> LENGTH: 189
<212> TYPE: PRT
<213> ORGANISM: Artificial Sequence
<220> FEATURE:
<223> OTHER INFORMATION: synthetic construct

<400> SEQUENCE: 33

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe
    50                  55                  60

Thr Cys Gly Asp Arg Gly Glu Lys Met Cys Asp Pro Gly Trp Lys Gly
65                  70                  75                  80

Gln Tyr Cys Thr Asp Pro Ile Cys Leu Pro Gly Cys Asp Asp Gln His
                85                  90                  95

Gly Tyr Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln Asp Leu Asn Tyr Cys Thr His His Lys Pro Cys
145                 150                 155                 160

Arg Asn Gly Ala Thr Cys Thr Asn Thr Gly Gln Gly Ser Tyr Thr Cys
                165                 170                 175

Ser Cys Arg Pro Gly Tyr Thr Gly Ala Asn Cys Glu Leu
            180                 185
```

<210> SEQ ID NO 34
<211> LENGTH: 166
<212> TYPE: PRT
<213> ORGANISM: Artificial Sequence
<220> FEATURE:
<223> OTHER INFORMATION: synthetic construct

<400> SEQUENCE: 34

```
His His His His His His Gly Gly Glu Asn Leu Tyr Phe Gln Gly Phe
```

-continued

```
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Asp Arg Gly Glu
        35                  40                  45

Lys Met Cys Asp Pro Gly Trp Lys Gly Gln Tyr Cys Thr Asp Pro Ile
    50                  55                  60

Cys Leu Pro Gly Cys Asp Asp Gln His Gly Tyr Cys Asp Lys Pro Gly
65                  70                  75                  80

Glu Cys Lys Cys Arg Val Gly Trp Gln Gly Arg Tyr Cys Asp Glu Cys
                85                  90                  95

Ile Arg Tyr Pro Gly Cys Leu His Gly Thr Cys Gln Gln Pro Trp Gln
            100                 105                 110

Cys Asn Cys Gln Glu Gly Trp Gly Gly Leu Phe Cys Asn Gln Asp Leu
        115                 120                 125

Asn Tyr Cys Thr His His Lys Pro Cys Arg Asn Gly Ala Thr Cys Thr
    130                 135                 140

Asn Thr Gly Gln Gly Ser Tyr Thr Cys Ser Cys Arg Pro Gly Tyr Thr
145                 150                 155                 160

Gly Ala Asn Cys Glu Leu
                165


<210> SEQ ID NO 35
<211> LENGTH: 149
<212> TYPE: PRT
<213> ORGANISM: Artificial Sequence
<220> FEATURE:
<223> OTHER INFORMATION: synthetic construct

<400> SEQUENCE: 35

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Phe Val Cys Asp Glu His Tyr Tyr Gly Glu
        35                  40                  45

Gly Cys Ser Val Phe Cys Arg Pro Arg Asp Asp Ala Phe Gly His Phe
    50                  55                  60

Thr Cys Gly Asp Arg Gly Glu Lys Met Cys Asp Pro Gly Trp Lys Gly
65                  70                  75                  80

Gln Tyr Cys Thr Asp Pro Ile Cys Leu Pro Gly Cys Asp Asp Gln His
                85                  90                  95

Gly Tyr Cys Asp Lys Pro Gly Glu Cys Lys Cys Arg Val Gly Trp Gln
            100                 105                 110

Gly Arg Tyr Cys Asp Glu Cys Ile Arg Tyr Pro Gly Cys Leu His Gly
        115                 120                 125

Thr Cys Gln Gln Pro Trp Gln Cys Asn Cys Gln Glu Gly Trp Gly Gly
    130                 135                 140

Leu Phe Cys Asn Gln
145


<210> SEQ ID NO 36
<211> LENGTH: 126
<212> TYPE: PRT
<213> ORGANISM: Artificial Sequence
<220> FEATURE:
<223> OTHER INFORMATION: synthetic construct
```

<400> SEQUENCE: 36

His His His His His His Gly Gly Glu Asn Leu Tyr Phe Gln Gly Phe
1 5 10 15

Val Cys Asp Glu His Tyr Tyr Gly Glu Gly Cys Ser Val Phe Cys Arg
20 25 30

Pro Arg Asp Asp Ala Phe Gly His Phe Thr Cys Gly Asp Arg Gly Glu
35 40 45

Lys Met Cys Asp Pro Gly Trp Lys Gly Gln Tyr Cys Thr Asp Pro Ile
50 55 60

Cys Leu Pro Gly Cys Asp Asp Gln His Gly Tyr Cys Asp Lys Pro Gly
65 70 75 80

Glu Cys Lys Cys Arg Val Gly Trp Gln Gly Arg Tyr Cys Asp Glu Cys
85 90 95

Ile Arg Tyr Pro Gly Cys Leu His Gly Thr Cys Gln Gln Pro Trp Gln
100 105 110

Cys Asn Cys Gln Glu Gly Trp Gly Gly Leu Phe Cys Asn Gln
115 120 125

<210> SEQ ID NO 37
<211> LENGTH: 347
<212> TYPE: PRT
<213> ORGANISM: Artificial Sequence
<220> FEATURE:
<223> OTHER INFORMATION: synthetic construct

<400> SEQUENCE: 37

Met Lys Tyr Leu Leu Pro Thr Ala Ala Ala Gly Leu Leu Leu Leu Ala
1 5 10 15

Ala Gln Pro Ala Met Ala Ala His His His His His His Gly Gly Glu
20 25 30

Asn Leu Tyr Phe Gln Gly Gln Val Trp Ser Ser Gly Val Phe Glu Leu
35 40 45

Lys Leu Gln Glu Phe Val Asn Lys Lys Gly Leu Leu Gly Asn Arg Asn
50 55 60

Cys Cys Arg Gly Gly Ser Gly Pro Pro Cys Ala Cys Arg Thr Phe Phe
65 70 75 80

Arg Val Cys Leu Lys His Tyr Gln Ala Ser Val Ser Pro Glu Pro Pro
85 90 95

Cys Thr Tyr Gly Ser Ala Val Thr Pro Val Leu Gly Val Asp Ser Phe
100 105 110

Ser Leu Pro Asp Gly Ala Gly Ile Asp Pro Ala Phe Ser Asn Pro Ile
115 120 125

Arg Phe Pro Phe Gly Phe Thr Trp Pro Gly Thr Phe Ser Leu Ile Ile
130 135 140

Glu Ala Leu His Thr Asp Ser Pro Asp Asp Leu Ala Thr Glu Asn Pro
145 150 155 160

Glu Arg Leu Ile Ser Arg Leu Thr Thr Gln Arg His Leu Thr Val Gly
165 170 175

Glu Glu Trp Ser Gln Asp Leu His Ser Ser Gly Arg Thr Asp Leu Arg
180 185 190

Tyr Ser Tyr Arg Phe Val Cys Asp Glu His Tyr Tyr Gly Glu Gly Cys
195 200 205

Ser Val Phe Cys Arg Pro Arg Asp Asp Ala Phe Gly His Phe Thr Cys
210 215 220

```
Gly Asp Arg Gly Glu Lys Met Cys Asp Pro Gly Trp Lys Gly Gln Tyr
225                 230                 235                 240

Cys Thr Asp Pro Ile Cys Leu Pro Gly Cys Asp Asp Gln His Gly Tyr
                245                 250                 255

Cys Asp Lys Pro Gly Glu Cys Lys Cys Arg Val Gly Trp Gln Gly Arg
            260                 265                 270

Tyr Cys Asp Glu Cys Ile Arg Tyr Pro Gly Cys Leu His Gly Thr Cys
        275                 280                 285

Gln Gln Pro Trp Gln Cys Asn Cys Gln Glu Gly Trp Gly Gly Leu Phe
    290                 295                 300

Cys Asn Gln Asp Leu Asn Tyr Cys Thr His His Lys Pro Cys Arg Asn
305                 310                 315                 320

Gly Ala Thr Cys Thr Asn Thr Gly Gln Gly Ser Tyr Thr Cys Ser Cys
                325                 330                 335

Arg Pro Gly Tyr Thr Gly Ala Asn Cys Glu Leu
            340                 345


<210> SEQ ID NO 38
<211> LENGTH: 324
<212> TYPE: PRT
<213> ORGANISM: Artificial Sequence
<220> FEATURE:
<223> OTHER INFORMATION: synthetic construct

<400> SEQUENCE: 38

His His His His His His Gly Gly Glu Asn Leu Tyr Phe Gln Gly Gln
1               5                   10                  15

Val Trp Ser Ser Gly Val Phe Glu Leu Lys Leu Gln Glu Phe Val Asn
            20                  25                  30

Lys Lys Gly Leu Leu Gly Asn Arg Asn Cys Cys Arg Gly Gly Ser Gly
        35                  40                  45

Pro Pro Cys Ala Cys Arg Thr Phe Phe Arg Val Cys Leu Lys His Tyr
    50                  55                  60

Gln Ala Ser Val Ser Pro Glu Pro Pro Cys Thr Tyr Gly Ser Ala Val
65                  70                  75                  80

Thr Pro Val Leu Gly Val Asp Ser Phe Ser Leu Pro Asp Gly Ala Gly
                85                  90                  95

Ile Asp Pro Ala Phe Ser Asn Pro Ile Arg Phe Pro Phe Gly Phe Thr
            100                 105                 110

Trp Pro Gly Thr Phe Ser Leu Ile Ile Glu Ala Leu His Thr Asp Ser
        115                 120                 125

Pro Asp Asp Leu Ala Thr Glu Asn Pro Glu Arg Leu Ile Ser Arg Leu
    130                 135                 140

Thr Thr Gln Arg His Leu Thr Val Gly Glu Glu Trp Ser Gln Asp Leu
145                 150                 155                 160

His Ser Ser Gly Arg Thr Asp Leu Arg Tyr Ser Tyr Arg Phe Val Cys
                165                 170                 175

Asp Glu His Tyr Tyr Gly Glu Gly Cys Ser Val Phe Cys Arg Pro Arg
            180                 185                 190

Asp Asp Ala Phe Gly His Phe Thr Cys Gly Asp Arg Gly Glu Lys Met
        195                 200                 205

Cys Asp Pro Gly Trp Lys Gly Gln Tyr Cys Thr Asp Pro Ile Cys Leu
    210                 215                 220

Pro Gly Cys Asp Asp Gln His Gly Tyr Cys Asp Lys Pro Gly Glu Cys
225                 230                 235                 240
```

-continued

```
Lys Cys Arg Val Gly Trp Gln Gly Arg Tyr Cys Asp Glu Cys Ile Arg
                245                 250                 255

Tyr Pro Gly Cys Leu His Gly Thr Cys Gln Gln Pro Trp Gln Cys Asn
            260                 265                 270

Cys Gln Glu Gly Trp Gly Gly Leu Phe Cys Asn Gln Asp Leu Asn Tyr
        275                 280                 285

Cys Thr His His Lys Pro Cys Arg Asn Gly Ala Thr Cys Thr Asn Thr
    290                 295                 300

Gly Gln Gly Ser Tyr Thr Cys Ser Cys Arg Pro Gly Tyr Thr Gly Ala
305                 310                 315                 320

Asn Cys Glu Leu


<210> SEQ ID NO 39
<211> LENGTH: 306
<212> TYPE: PRT
<213> ORGANISM: Artificial Sequence
<220> FEATURE:
<223> OTHER INFORMATION: synthetic construct

<400> SEQUENCE: 39

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Gln Val Trp Ser Ser Gly Val Phe Glu Leu
        35                  40                  45

Lys Leu Gln Glu Phe Val Asn Lys Lys Gly Leu Leu Gly Asn Arg Asn
    50                  55                  60

Cys Cys Arg Gly Gly Ser Gly Pro Pro Cys Ala Cys Arg Thr Phe Phe
65                  70                  75                  80

Arg Val Cys Leu Lys His Tyr Gln Ala Ser Val Ser Pro Glu Pro Pro
                85                  90                  95

Cys Thr Tyr Gly Ser Ala Val Thr Pro Val Leu Gly Val Asp Ser Phe
            100                 105                 110

Ser Leu Pro Asp Gly Ala Gly Ile Asp Pro Ala Phe Ser Asn Pro Ile
        115                 120                 125

Arg Phe Pro Phe Gly Phe Thr Trp Pro Gly Thr Phe Ser Leu Ile Ile
    130                 135                 140

Glu Ala Leu His Thr Asp Ser Pro Asp Asp Leu Ala Thr Glu Asn Pro
145                 150                 155                 160

Glu Arg Leu Ile Ser Arg Leu Thr Thr Gln Arg His Leu Thr Val Gly
                165                 170                 175

Glu Glu Trp Ser Gln Asp Leu His Ser Ser Gly Arg Thr Asp Leu Arg
            180                 185                 190

Tyr Ser Tyr Arg Phe Val Cys Asp Glu His Tyr Tyr Gly Glu Gly Cys
        195                 200                 205

Ser Val Phe Cys Arg Pro Arg Asp Asp Ala Phe Gly His Phe Thr Cys
    210                 215                 220

Gly Asp Arg Gly Glu Lys Met Cys Asp Pro Gly Trp Lys Gly Gln Tyr
225                 230                 235                 240

Cys Thr Asp Pro Ile Cys Leu Pro Gly Cys Asp Asp Gln His Gly Tyr
                245                 250                 255

Cys Asp Lys Pro Gly Glu Cys Lys Cys Arg Val Gly Trp Gln Gly Arg
            260                 265                 270

Tyr Cys Asp Glu Cys Ile Arg Tyr Pro Gly Cys Leu His Gly Thr Cys
```

```
        275                 280                 285

Gln Gln Pro Trp Gln Cys Asn Cys Gln Glu Gly Trp Gly Gly Leu Phe
    290                 295                 300

Cys Asn
305
```

<210> SEQ ID NO 40
<211> LENGTH: 283
<212> TYPE: PRT
<213> ORGANISM: Artificial Sequence
<220> FEATURE:
<223> OTHER INFORMATION: synthetic construct

<400> SEQUENCE: 40

```
His His His His His His Gly Gly Glu Asn Leu Tyr Phe Gln Gly Gln
1               5                   10                  15

Val Trp Ser Ser Gly Val Phe Glu Leu Lys Leu Gln Glu Phe Val Asn
            20                  25                  30

Lys Lys Gly Leu Leu Gly Asn Arg Asn Cys Cys Arg Gly Gly Ser Gly
        35                  40                  45

Pro Pro Cys Ala Cys Arg Thr Phe Phe Arg Val Cys Leu Lys His Tyr
    50                  55                  60

Gln Ala Ser Val Ser Pro Glu Pro Pro Cys Thr Tyr Gly Ser Ala Val
65                  70                  75                  80

Thr Pro Val Leu Gly Val Asp Ser Phe Ser Leu Pro Asp Gly Ala Gly
                85                  90                  95

Ile Asp Pro Ala Phe Ser Asn Pro Ile Arg Phe Pro Phe Gly Phe Thr
            100                 105                 110

Trp Pro Gly Thr Phe Ser Leu Ile Ile Glu Ala Leu His Thr Asp Ser
        115                 120                 125

Pro Asp Asp Leu Ala Thr Glu Asn Pro Glu Arg Leu Ile Ser Arg Leu
    130                 135                 140

Thr Thr Gln Arg His Leu Thr Val Gly Glu Glu Trp Ser Gln Asp Leu
145                 150                 155                 160

His Ser Ser Gly Arg Thr Asp Leu Arg Tyr Ser Tyr Arg Phe Val Cys
                165                 170                 175

Asp Glu His Tyr Tyr Gly Glu Gly Cys Ser Val Phe Cys Arg Pro Arg
            180                 185                 190

Asp Asp Ala Phe Gly His Phe Thr Cys Gly Asp Arg Gly Glu Lys Met
        195                 200                 205

Cys Asp Pro Gly Trp Lys Gly Gln Tyr Cys Thr Asp Pro Ile Cys Leu
    210                 215                 220

Pro Gly Cys Asp Asp Gln His Gly Tyr Cys Asp Lys Pro Gly Glu Cys
225                 230                 235                 240

Lys Cys Arg Val Gly Trp Gln Gly Arg Tyr Cys Asp Glu Cys Ile Arg
                245                 250                 255

Tyr Pro Gly Cys Leu His Gly Thr Cys Gln Gln Pro Trp Gln Cys Asn
            260                 265                 270

Cys Gln Glu Gly Trp Gly Gly Leu Phe Cys Asn
        275                 280
```

<210> SEQ ID NO 41
<211> LENGTH: 485
<212> TYPE: PRT
<213> ORGANISM: Artificial Sequence
<220> FEATURE:
<223> OTHER INFORMATION: synthetic construct

<400> SEQUENCE: 41

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Glu
        35                  40                  45

Arg Gly Glu Lys Val Cys Asn Pro Gly Trp Lys Gly Pro Tyr Cys Thr
    50                  55                  60

Glu Pro Ile Cys Leu Pro Gly Cys Asp Glu Gln His Gly Phe Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Asp Leu Asn Tyr Cys Thr His His Lys Pro Cys Lys Asn Gly Ala
    130                 135                 140

Thr Cys Thr Asn Thr Gly Gln Gly Ser Tyr Thr Cys Ser Cys Arg Pro
145                 150                 155                 160

Gly Tyr Thr Gly Ala Thr Cys Glu Leu Gly Ser Ser Gly Ser Ser Gly
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ser Ser Gly Ser Ser Gly Phe Val
                325                 330                 335

Cys Asp Glu His Tyr Tyr Gly Glu Gly Cys Ser Val Phe Cys Arg Pro
            340                 345                 350

Arg Asp Asp Ala Phe Gly His Phe Thr Cys Gly Glu Arg Gly Glu Lys
        355                 360                 365

Val Cys Asn Pro Gly Trp Lys Gly Pro Tyr Cys Thr Glu Pro Ile Cys
    370                 375                 380

Leu Pro Gly Cys Asp Glu Gln His Gly Phe Cys Asp Lys Pro Gly Glu
385                 390                 395                 400

Cys Lys Cys Arg Val Gly Trp Gln Gly Arg Tyr Cys Asp Glu Cys Ile

```
                405                 410                 415

Arg Tyr Pro Gly Cys Leu His Gly Thr Cys Gln Gln Pro Trp Gln Cys
            420                 425                 430

Asn Cys Gln Glu Gly Trp Gly Gly Leu Phe Cys Asn Gln Asp Leu Asn
        435                 440                 445

Tyr Cys Thr His His Lys Pro Cys Lys Asn Gly Ala Thr Cys Thr Asn
    450                 455                 460

Thr Gly Gln Gly Ser Tyr Thr Cys Ser Cys Arg Pro Gly Tyr Thr Gly
465                 470                 475                 480

Ala Thr Cys Glu Leu
                485


<210> SEQ ID NO 42
<211> LENGTH: 643
<212> TYPE: PRT
<213> ORGANISM: Artificial Sequence
<220> FEATURE:
<223> OTHER INFORMATION: synthetic construct

<400> SEQUENCE: 42

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Glu
        35                  40                  45

Arg Gly Glu Lys Val Cys Asn Pro Gly Trp Lys Gly Pro Tyr Cys Thr
    50                  55                  60

Glu Pro Ile Cys Leu Pro Gly Cys Asp Glu Gln His Gly Phe Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Asp Leu Asn Tyr Cys Thr His His Lys Pro Cys Lys Asn Gly Ala
    130                 135                 140

Thr Cys Thr Asn Thr Gly Gln Gly Ser Tyr Thr Cys Ser Cys Arg Pro
145                 150                 155                 160

Gly Tyr Thr Gly Ala Thr Cys Glu Leu Gly Ser Ser Gly Ser Ser Gly
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
```

-continued

```
        275                 280                 285

Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ser Ser Gly Ser Ser Gly Phe Val
                325                 330                 335

Cys Asp Glu His Tyr Tyr Gly Glu Gly Cys Ser Val Phe Cys Arg Pro
            340                 345                 350

Arg Asp Asp Ala Phe Gly His Phe Thr Cys Gly Glu Arg Gly Glu Lys
        355                 360                 365

Val Cys Asn Pro Gly Trp Lys Gly Pro Tyr Cys Thr Glu Pro Ile Cys
    370                 375                 380

Leu Pro Gly Cys Asp Glu Gln His Gly Phe Cys Asp Lys Pro Gly Glu
385                 390                 395                 400

Cys Lys Cys Arg Val Gly Trp Gln Gly Arg Tyr Cys Asp Glu Cys Ile
                405                 410                 415

Arg Tyr Pro Gly Cys Leu His Gly Thr Cys Gln Gln Pro Trp Gln Cys
            420                 425                 430

Asn Cys Gln Glu Gly Trp Gly Gly Leu Phe Cys Asn Gln Asp Leu Asn
        435                 440                 445

Tyr Cys Thr His His Lys Pro Cys Lys Asn Gly Ala Thr Cys Thr Asn
    450                 455                 460

Thr Gly Gln Gly Ser Tyr Thr Cys Ser Cys Arg Pro Gly Tyr Thr Gly
465                 470                 475                 480

Ala Thr Cys Glu Leu Gly Ser Ser Gly Ser Ser Gly Phe Val Cys Asp
                485                 490                 495

Glu His Tyr Tyr Gly Glu Gly Cys Ser Val Phe Cys Arg Pro Arg Asp
            500                 505                 510

Asp Ala Phe Gly His Phe Thr Cys Gly Glu Arg Gly Glu Lys Val Cys
        515                 520                 525

Asn Pro Gly Trp Lys Gly Pro Tyr Cys Thr Glu Pro Ile Cys Leu Pro
    530                 535                 540

Gly Cys Asp Glu Gln His Gly Phe Cys Asp Lys Pro Gly Glu Cys Lys
545                 550                 555                 560

Cys Arg Val Gly Trp Gln Gly Arg Tyr Cys Asp Glu Cys Ile Arg Tyr
                565                 570                 575

Pro Gly Cys Leu His Gly Thr Cys Gln Gln Pro Trp Gln Cys Asn Cys
            580                 585                 590

Gln Glu Gly Trp Gly Gly Leu Phe Cys Asn Gln Asp Leu Asn Tyr Cys
        595                 600                 605

Thr His His Lys Pro Cys Lys Asn Gly Ala Thr Cys Thr Asn Thr Gly
    610                 615                 620

Gln Gly Ser Tyr Thr Cys Ser Cys Arg Pro Gly Tyr Thr Gly Ala Thr
625                 630                 635                 640

Cys Glu Leu
```

<210> SEQ ID NO 43
<211> LENGTH: 801
<212> TYPE: PRT
<213> ORGANISM: Artificial Sequence
<220> FEATURE:
<223> OTHER INFORMATION: synthetic construct

<400> SEQUENCE: 43

-continued

```
Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Glu
        35                  40                  45

Arg Gly Glu Lys Val Cys Asn Pro Gly Trp Lys Gly Pro Tyr Cys Thr
    50                  55                  60

Glu Pro Ile Cys Leu Pro Gly Cys Asp Glu Gln His Gly Phe Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Asp Leu Asn Tyr Cys Thr His His Lys Pro Cys Lys Asn Gly Ala
    130                 135                 140

Thr Cys Thr Asn Thr Gly Gln Gly Ser Tyr Thr Cys Ser Cys Arg Pro
145                 150                 155                 160

Gly Tyr Thr Gly Ala Thr Cys Glu Leu Gly Ser Ser Gly Ser Ser Gly
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ser Ser Gly Ser Ser Gly Phe Val
                325                 330                 335

Cys Asp Glu His Tyr Tyr Gly Glu Gly Cys Ser Val Phe Cys Arg Pro
            340                 345                 350

Arg Asp Asp Ala Phe Gly His Phe Thr Cys Gly Glu Arg Gly Glu Lys
        355                 360                 365

Val Cys Asn Pro Gly Trp Lys Gly Pro Tyr Cys Thr Glu Pro Ile Cys
    370                 375                 380

Leu Pro Gly Cys Asp Glu Gln His Gly Phe Cys Asp Lys Pro Gly Glu
385                 390                 395                 400

Cys Lys Cys Arg Val Gly Trp Gln Gly Arg Tyr Cys Asp Glu Cys Ile
                405                 410                 415
```

```
Arg Tyr Pro Gly Cys Leu His Gly Thr Cys Gln Gln Pro Trp Gln Cys
            420                 425                 430

Asn Cys Gln Glu Gly Trp Gly Gly Leu Phe Cys Asn Gln Asp Leu Asn
        435                 440                 445

Tyr Cys Thr His His Lys Pro Cys Lys Asn Gly Ala Thr Cys Thr Asn
    450                 455                 460

Thr Gly Gln Gly Ser Tyr Thr Cys Ser Cys Arg Pro Gly Tyr Thr Gly
465                 470                 475                 480

Ala Thr Cys Glu Leu Gly Ser Ser Gly Ser Ser Gly Phe Val Cys Asp
                485                 490                 495

Glu His Tyr Tyr Gly Glu Gly Cys Ser Val Phe Cys Arg Pro Arg Asp
            500                 505                 510

Asp Ala Phe Gly His Phe Thr Cys Gly Glu Arg Gly Glu Lys Val Cys
        515                 520                 525

Asn Pro Gly Trp Lys Gly Pro Tyr Cys Thr Glu Pro Ile Cys Leu Pro
    530                 535                 540

Gly Cys Asp Glu Gln His Gly Phe Cys Asp Lys Pro Gly Glu Cys Lys
545                 550                 555                 560

Cys Arg Val Gly Trp Gln Gly Arg Tyr Cys Asp Glu Cys Ile Arg Tyr
                565                 570                 575

Pro Gly Cys Leu His Gly Thr Cys Gln Gln Pro Trp Gln Cys Asn Cys
            580                 585                 590

Gln Glu Gly Trp Gly Gly Leu Phe Cys Asn Gln Asp Leu Asn Tyr Cys
        595                 600                 605

Thr His His Lys Pro Cys Lys Asn Gly Ala Thr Cys Thr Asn Thr Gly
    610                 615                 620

Gln Gly Ser Tyr Thr Cys Ser Cys Arg Pro Gly Tyr Thr Gly Ala Thr
625                 630                 635                 640

Cys Glu Leu Gly Ser Ser Gly Ser Ser Gly Phe Val Cys Asp Glu His
                645                 650                 655

Tyr Tyr Gly Glu Gly Cys Ser Val Phe Cys Arg Pro Arg Asp Asp Ala
            660                 665                 670

Phe Gly His Phe Thr Cys Gly Glu Arg Gly Glu Lys Val Cys Asn Pro
        675                 680                 685

Gly Trp Lys Gly Pro Tyr Cys Thr Glu Pro Ile Cys Leu Pro Gly Cys
    690                 695                 700

Asp Glu Gln His Gly Phe Cys Asp Lys Pro Gly Glu Cys Lys Cys Arg
705                 710                 715                 720

Val Gly Trp Gln Gly Arg Tyr Cys Asp Glu Cys Ile Arg Tyr Pro Gly
                725                 730                 735

Cys Leu His Gly Thr Cys Gln Gln Pro Trp Gln Cys Asn Cys Gln Glu
            740                 745                 750

Gly Trp Gly Gly Leu Phe Cys Asn Gln Asp Leu Asn Tyr Cys Thr His
        755                 760                 765

His Lys Pro Cys Lys Asn Gly Ala Thr Cys Thr Asn Thr Gly Gln Gly
    770                 775                 780

Ser Tyr Thr Cys Ser Cys Arg Pro Gly Tyr Thr Gly Ala Thr Cys Glu
785                 790                 795                 800

Leu
```

<210> SEQ ID NO 44
<211> LENGTH: 365
<212> TYPE: PRT
<213> ORGANISM: Artificial Sequence
<220> FEATURE:
<223> OTHER INFORMATION: synthetic construct

<400> SEQUENCE: 44

```
Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
            260                 265                 270

Arg Asp Asp Ala Phe Gly His Phe Thr Cys Gly Asp Arg Gly Glu Lys
        275                 280                 285

Met Cys Asp Pro Gly Trp Lys Gly Gln Tyr Cys Thr Asp Pro Ile Cys
    290                 295                 300

Leu Pro Gly Cys Asp Asp Gln His Gly Tyr Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350

Asn Cys Gln Glu Gly Trp Gly Gly Leu Phe Cys Asn Gln
        355                 360                 365
```

<210> SEQ ID NO 45
<211> LENGTH: 483
<212> TYPE: PRT
<213> ORGANISM: Artificial Sequence
<220> FEATURE:
<223> OTHER INFORMATION: synthetic construct

<400> SEQUENCE: 45

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
            260                 265                 270

Arg Asp Asp Ala Phe Gly His Phe Thr Cys Gly Asp Arg Gly Glu Lys
        275                 280                 285

Met Cys Asp Pro Gly Trp Lys Gly Gln Tyr Cys Thr Asp Pro Ile Cys
    290                 295                 300

Leu Pro Gly Cys Asp Asp Gln His Gly Tyr Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350

Asn Cys Gln Glu Gly Trp Gly Gly Leu Phe Cys Asn Gln Gly Ser Ser
        355                 360                 365

Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

```
Gly Asp Arg Gly Glu Lys Met Cys Asp Pro Gly Trp Lys Gly Gln Tyr
                405                 410                 415

Cys Thr Asp Pro Ile Cys Leu Pro Gly Cys Asp Asp Gln His Gly Tyr
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
    450                 455                 460

Gln Gln Pro Trp Gln Cys Asn Cys Gln Glu Gly Trp Gly Gly Leu Phe
465                 470                 475                 480

Cys Asn Gln


<210> SEQ ID NO 46
<211> LENGTH: 601
<212> TYPE: PRT
<213> ORGANISM: Artificial Sequence
<220> FEATURE:
<223> OTHER INFORMATION: synthetic construct

<400> SEQUENCE: 46

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
            260                 265                 270
```

```
Arg Asp Asp Ala Phe Gly His Phe Thr Cys Gly Asp Arg Gly Glu Lys
        275                 280                 285

Met Cys Asp Pro Gly Trp Lys Gly Gln Tyr Cys Thr Asp Pro Ile Cys
    290                 295                 300

Leu Pro Gly Cys Asp Asp Gln His Gly Tyr Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350

Asn Cys Gln Glu Gly Trp Gly Gly Leu Phe Cys Asn Gln Gly Ser Ser
        355                 360                 365

Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

Gly Asp Arg Gly Glu Lys Met Cys Asp Pro Gly Trp Lys Gly Gln Tyr
                405                 410                 415

Cys Thr Asp Pro Ile Cys Leu Pro Gly Cys Asp Asp Gln His Gly Tyr
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
    450                 455                 460

Gln Gln Pro Trp Gln Cys Asn Cys Gln Glu Gly Trp Gly Gly Leu Phe
465                 470                 475                 480

Cys Asn Gln Gly Ser Ser Gly Ser Ser Gly Phe Val Cys Asp Glu His
                485                 490                 495

Tyr Tyr Gly Glu Gly Cys Ser Val Phe Cys Arg Pro Arg Asp Asp Ala
            500                 505                 510

Phe Gly His Phe Thr Cys Gly Asp Arg Gly Glu Lys Met Cys Asp Pro
        515                 520                 525

Gly Trp Lys Gly Gln Tyr Cys Thr Asp Pro Ile Cys Leu Pro Gly Cys
    530                 535                 540

Asp Asp Gln His Gly Tyr Cys Asp Lys Pro Gly Glu Cys Lys Cys Arg
545                 550                 555                 560

Val Gly Trp Gln Gly Arg Tyr Cys Asp Glu Cys Ile Arg Tyr Pro Gly
                565                 570                 575

Cys Leu His Gly Thr Cys Gln Gln Pro Trp Gln Cys Asn Cys Gln Glu
            580                 585                 590

Gly Trp Gly Gly Leu Phe Cys Asn Gln
        595                 600
```

<210> SEQ ID NO 47
<211> LENGTH: 719
<212> TYPE: PRT
<213> ORGANISM: Artificial Sequence
<220> FEATURE:
<223> OTHER INFORMATION: synthetic construct

<400> SEQUENCE: 47

```
Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30
```

-continued

```
Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
            260                 265                 270

Arg Asp Asp Ala Phe Gly His Phe Thr Cys Gly Asp Arg Gly Glu Lys
        275                 280                 285

Met Cys Asp Pro Gly Trp Lys Gly Gln Tyr Cys Thr Asp Pro Ile Cys
    290                 295                 300

Leu Pro Gly Cys Asp Asp Gln His Gly Tyr Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350

Asn Cys Gln Glu Gly Trp Gly Gly Leu Phe Cys Asn Gln Gly Ser Ser
        355                 360                 365

Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

Gly Asp Arg Gly Glu Lys Met Cys Asp Pro Gly Trp Lys Gly Gln Tyr
                405                 410                 415

Cys Thr Asp Pro Ile Cys Leu Pro Gly Cys Asp Asp Gln His Gly Tyr
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
```

-continued

```
    450                 455                 460

Gln Gln Pro Trp Gln Cys Asn Cys Gln Glu Gly Trp Gly Gly Leu Phe
465                 470                 475                 480

Cys Asn Gln Gly Ser Ser Gly Ser Ser Gly Phe Val Cys Asp Glu His
                485                 490                 495

Tyr Tyr Gly Glu Gly Cys Ser Val Phe Cys Arg Pro Arg Asp Asp Ala
            500                 505                 510

Phe Gly His Phe Thr Cys Gly Asp Arg Gly Glu Lys Met Cys Asp Pro
        515                 520                 525

Gly Trp Lys Gly Gln Tyr Cys Thr Asp Pro Ile Cys Leu Pro Gly Cys
    530                 535                 540

Asp Asp Gln His Gly Tyr Cys Asp Lys Pro Gly Glu Cys Lys Cys Arg
545                 550                 555                 560

Val Gly Trp Gln Gly Arg Tyr Cys Asp Glu Cys Ile Arg Tyr Pro Gly
                565                 570                 575

Cys Leu His Gly Thr Cys Gln Gln Pro Trp Gln Cys Asn Cys Gln Glu
            580                 585                 590

Gly Trp Gly Gly Leu Phe Cys Asn Gln Gly Ser Ser Gly Ser Ser Gly
        595                 600                 605

Phe Val Cys Asp Glu His Tyr Tyr Gly Glu Gly Cys Ser Val Phe Cys
    610                 615                 620

Arg Pro Arg Asp Asp Ala Phe Gly His Phe Thr Cys Gly Asp Arg Gly
625                 630                 635                 640

Glu Lys Met Cys Asp Pro Gly Trp Lys Gly Gln Tyr Cys Thr Asp Pro
                645                 650                 655

Ile Cys Leu Pro Gly Cys Asp Asp Gln His Gly Tyr Cys Asp Lys Pro
            660                 665                 670

Gly Glu Cys Lys Cys Arg Val Gly Trp Gln Gly Arg Tyr Cys Asp Glu
        675                 680                 685

Cys Ile Arg Tyr Pro Gly Cys Leu His Gly Thr Cys Gln Gln Pro Trp
    690                 695                 700

Gln Cys Asn Cys Gln Glu Gly Trp Gly Gly Leu Phe Cys Asn Gln
705                 710                 715


<210> SEQ ID NO 48
<211> LENGTH: 837
<212> TYPE: PRT
<213> ORGANISM: Artificial Sequence
<220> FEATURE:
<223> OTHER INFORMATION: synthetic construct

<400> SEQUENCE: 48

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
```

-continued

```
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
            260                 265                 270

Arg Asp Asp Ala Phe Gly His Phe Thr Cys Gly Asp Arg Gly Glu Lys
        275                 280                 285

Met Cys Asp Pro Gly Trp Lys Gly Gln Tyr Cys Thr Asp Pro Ile Cys
    290                 295                 300

Leu Pro Gly Cys Asp Asp Gln His Gly Tyr Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350

Asn Cys Gln Glu Gly Trp Gly Gly Leu Phe Cys Asn Gln Gly Ser Ser
        355                 360                 365

Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

Gly Asp Arg Gly Glu Lys Met Cys Asp Pro Gly Trp Lys Gly Gln Tyr
                405                 410                 415

Cys Thr Asp Pro Ile Cys Leu Pro Gly Cys Asp Asp Gln His Gly Tyr
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
    450                 455                 460

Gln Gln Pro Trp Gln Cys Asn Cys Gln Glu Gly Trp Gly Gly Leu Phe
465                 470                 475                 480

Cys Asn Gln Gly Ser Ser Gly Ser Ser Gly Phe Val Cys Asp Glu His
                485                 490                 495

Tyr Tyr Gly Glu Gly Cys Ser Val Phe Cys Arg Pro Arg Asp Asp Ala
            500                 505                 510

Phe Gly His Phe Thr Cys Gly Asp Arg Gly Glu Lys Met Cys Asp Pro
        515                 520                 525
```

```
Gly Trp Lys Gly Gln Tyr Cys Thr Asp Pro Ile Cys Leu Pro Gly Cys
    530                 535                 540

Asp Asp Gln His Gly Tyr Cys Asp Lys Pro Gly Glu Cys Lys Cys Arg
545                 550                 555                 560

Val Gly Trp Gln Gly Arg Tyr Cys Asp Glu Cys Ile Arg Tyr Pro Gly
                565                 570                 575

Cys Leu His Gly Thr Cys Gln Gln Pro Trp Gln Cys Asn Cys Gln Glu
            580                 585                 590

Gly Trp Gly Gly Leu Phe Cys Asn Gln Gly Ser Ser Gly Ser Ser Gly
        595                 600                 605

Phe Val Cys Asp Glu His Tyr Tyr Gly Glu Gly Cys Ser Val Phe Cys
    610                 615                 620

Arg Pro Arg Asp Asp Ala Phe Gly His Phe Thr Cys Gly Asp Arg Gly
625                 630                 635                 640

Glu Lys Met Cys Asp Pro Gly Trp Lys Gly Gln Tyr Cys Thr Asp Pro
                645                 650                 655

Ile Cys Leu Pro Gly Cys Asp Asp Gln His Gly Tyr Cys Asp Lys Pro
            660                 665                 670

Gly Glu Cys Lys Cys Arg Val Gly Trp Gln Gly Arg Tyr Cys Asp Glu
        675                 680                 685

Cys Ile Arg Tyr Pro Gly Cys Leu His Gly Thr Cys Gln Gln Pro Trp
    690                 695                 700

Gln Cys Asn Cys Gln Glu Gly Trp Gly Gly Leu Phe Cys Asn Gln Gly
705                 710                 715                 720

Ser Ser Gly Ser Ser Gly Phe Val Cys Asp Glu His Tyr Tyr Gly Glu
                725                 730                 735

Gly Cys Ser Val Phe Cys Arg Pro Arg Asp Asp Ala Phe Gly His Phe
            740                 745                 750

Thr Cys Gly Asp Arg Gly Glu Lys Met Cys Asp Pro Gly Trp Lys Gly
        755                 760                 765

Gln Tyr Cys Thr Asp Pro Ile Cys Leu Pro Gly Cys Asp Asp Gln His
    770                 775                 780

Gly Tyr Cys Asp Lys Pro Gly Glu Cys Lys Cys Arg Val Gly Trp Gln
785                 790                 795                 800

Gly Arg Tyr Cys Asp Glu Cys Ile Arg Tyr Pro Gly Cys Leu His Gly
                805                 810                 815

Thr Cys Gln Gln Pro Trp Gln Cys Asn Cys Gln Glu Gly Trp Gly Gly
            820                 825                 830

Leu Phe Cys Asn Gln
        835
```

<210> SEQ ID NO 49
<211> LENGTH: 955
<212> TYPE: PRT
<213> ORGANISM: Artificial Sequence
<220> FEATURE:
<223> OTHER INFORMATION: synthetic construct

<400> SEQUENCE: 49

```
Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45
```

-continued

```
Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
            260                 265                 270

Arg Asp Asp Ala Phe Gly His Phe Thr Cys Gly Asp Arg Gly Glu Lys
        275                 280                 285

Met Cys Asp Pro Gly Trp Lys Gly Gln Tyr Cys Thr Asp Pro Ile Cys
    290                 295                 300

Leu Pro Gly Cys Asp Asp Gln His Gly Tyr Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350

Asn Cys Gln Glu Gly Trp Gly Gly Leu Phe Cys Asn Gln Gly Ser Ser
        355                 360                 365

Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

Gly Asp Arg Gly Glu Lys Met Cys Asp Pro Gly Trp Lys Gly Gln Tyr
                405                 410                 415

Cys Thr Asp Pro Ile Cys Leu Pro Gly Cys Asp Asp Gln His Gly Tyr
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
    450                 455                 460
```

-continued

```
Gln Gln Pro Trp Gln Cys Asn Cys Gln Glu Gly Trp Gly Gly Leu Phe
465                 470                 475                 480

Cys Asn Gln Gly Ser Ser Gly Ser Ser Gly Phe Val Cys Asp Glu His
                485                 490                 495

Tyr Tyr Gly Glu Gly Cys Ser Val Phe Cys Arg Pro Arg Asp Asp Ala
            500                 505                 510

Phe Gly His Phe Thr Cys Gly Asp Arg Gly Glu Lys Met Cys Asp Pro
        515                 520                 525

Gly Trp Lys Gly Gln Tyr Cys Thr Asp Pro Ile Cys Leu Pro Gly Cys
    530                 535                 540

Asp Asp Gln His Gly Tyr Cys Asp Lys Pro Gly Glu Cys Lys Cys Arg
545                 550                 555                 560

Val Gly Trp Gln Gly Arg Tyr Cys Asp Glu Cys Ile Arg Tyr Pro Gly
                565                 570                 575

Cys Leu His Gly Thr Cys Gln Gln Pro Trp Gln Cys Asn Cys Gln Glu
            580                 585                 590

Gly Trp Gly Gly Leu Phe Cys Asn Gln Gly Ser Ser Gly Ser Ser Gly
        595                 600                 605

Phe Val Cys Asp Glu His Tyr Tyr Gly Glu Gly Cys Ser Val Phe Cys
    610                 615                 620

Arg Pro Arg Asp Asp Ala Phe Gly His Phe Thr Cys Gly Asp Arg Gly
625                 630                 635                 640

Glu Lys Met Cys Asp Pro Gly Trp Lys Gly Gln Tyr Cys Thr Asp Pro
                645                 650                 655

Ile Cys Leu Pro Gly Cys Asp Asp Gln His Gly Tyr Cys Asp Lys Pro
            660                 665                 670

Gly Glu Cys Lys Cys Arg Val Gly Trp Gln Gly Arg Tyr Cys Asp Glu
        675                 680                 685

Cys Ile Arg Tyr Pro Gly Cys Leu His Gly Thr Cys Gln Gln Pro Trp
    690                 695                 700

Gln Cys Asn Cys Gln Glu Gly Trp Gly Gly Leu Phe Cys Asn Gln Gly
705                 710                 715                 720

Ser Ser Gly Ser Ser Gly Phe Val Cys Asp Glu His Tyr Tyr Gly Glu
                725                 730                 735

Gly Cys Ser Val Phe Cys Arg Pro Arg Asp Asp Ala Phe Gly His Phe
            740                 745                 750

Thr Cys Gly Asp Arg Gly Glu Lys Met Cys Asp Pro Gly Trp Lys Gly
        755                 760                 765

Gln Tyr Cys Thr Asp Pro Ile Cys Leu Pro Gly Cys Asp Asp Gln His
    770                 775                 780

Gly Tyr Cys Asp Lys Pro Gly Glu Cys Lys Cys Arg Val Gly Trp Gln
785                 790                 795                 800

Gly Arg Tyr Cys Asp Glu Cys Ile Arg Tyr Pro Gly Cys Leu His Gly
                805                 810                 815

Thr Cys Gln Gln Pro Trp Gln Cys Asn Cys Gln Glu Gly Trp Gly Gly
            820                 825                 830

Leu Phe Cys Asn Gln Gly Ser Ser Gly Ser Ser Gly Phe Val Cys Asp
        835                 840                 845

Glu His Tyr Tyr Gly Glu Gly Cys Ser Val Phe Cys Arg Pro Arg Asp
    850                 855                 860

Asp Ala Phe Gly His Phe Thr Cys Gly Asp Arg Gly Glu Lys Met Cys
865                 870                 875                 880

Asp Pro Gly Trp Lys Gly Gln Tyr Cys Thr Asp Pro Ile Cys Leu Pro
```

-continued

```
                885                 890                 895

Gly Cys Asp Asp Gln His Gly Tyr Cys Asp Lys Pro Gly Glu Cys Lys
            900                 905                 910

Cys Arg Val Gly Trp Gln Gly Arg Tyr Cys Asp Glu Cys Ile Arg Tyr
        915                 920                 925

Pro Gly Cys Leu His Gly Thr Cys Gln Gln Pro Trp Gln Cys Asn Cys
    930                 935                 940

Gln Glu Gly Trp Gly Gly Leu Phe Cys Asn Gln
945                 950                 955


<210> SEQ ID NO 50
<211> LENGTH: 250
<212> TYPE: PRT
<213> ORGANISM: Artificial Sequence
<220> FEATURE:
<223> OTHER INFORMATION: synthetic construct

<400> SEQUENCE: 50

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Gly Gly Gly Ser Gly Gly Gly Gly Ser Phe Val Cys Asp Glu
    130                 135                 140

His Tyr Tyr Gly Glu Gly Cys Ser Val Phe Cys Arg Pro Arg Asp Asp
145                 150                 155                 160

Ala Phe Gly His Phe Thr Cys Gly Asp Arg Gly Glu Lys Met Cys Asp
                165                 170                 175

Pro Gly Trp Lys Gly Gln Tyr Cys Thr Asp Pro Ile Cys Leu Pro Gly
            180                 185                 190

Cys Asp Asp Gln His Gly Tyr Cys Asp Lys Pro Gly Glu Cys Lys Cys
        195                 200                 205

Arg Val Gly Trp Gln Gly Arg Tyr Cys Asp Glu Cys Ile Arg Tyr Pro
    210                 215                 220

Gly Cys Leu His Gly Thr Cys Gln Gln Pro Trp Gln Cys Asn Cys Gln
225                 230                 235                 240

Glu Gly Trp Gly Gly Leu Phe Cys Asn Gln
                245                 250


<210> SEQ ID NO 51
<211> LENGTH: 255
<212> TYPE: PRT
<213> ORGANISM: Artificial Sequence
<220> FEATURE:
<223> OTHER INFORMATION: synthetic construct
```

<400> SEQUENCE: 51

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Gly Gly Gly Ser Gly Gly Gly Gly Ser Gly Gly Gly Gly Ser
    130                 135                 140

Phe Val Cys Asp Glu His Tyr Tyr Gly Glu Gly Cys Ser Val Phe Cys
145                 150                 155                 160

Arg Pro Arg Asp Asp Ala Phe Gly His Phe Thr Cys Gly Asp Arg Gly
                165                 170                 175

Glu Lys Met Cys Asp Pro Gly Trp Lys Gly Gln Tyr Cys Thr Asp Pro
            180                 185                 190

Ile Cys Leu Pro Gly Cys Asp Asp Gln His Gly Tyr Cys Asp Lys Pro
        195                 200                 205

Gly Glu Cys Lys Cys Arg Val Gly Trp Gln Gly Arg Tyr Cys Asp Glu
    210                 215                 220

Cys Ile Arg Tyr Pro Gly Cys Leu His Gly Thr Cys Gln Gln Pro Trp
225                 230                 235                 240

Gln Cys Asn Cys Gln Glu Gly Trp Gly Gly Leu Phe Cys Asn Gln
                245                 250                 255

<210> SEQ ID NO 52
<211> LENGTH: 260
<212> TYPE: PRT
<213> ORGANISM: Artificial Sequence
<220> FEATURE:
<223> OTHER INFORMATION: synthetic construct

<400> SEQUENCE: 52

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

```
Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Gly Gly Gly Ser Gly Gly Gly Gly Ser Gly Gly Gly Gly Ser
    130                 135                 140

Gly Gly Gly Gly Ser Phe Val Cys Asp Glu His Tyr Tyr Gly Glu Gly
145                 150                 155                 160

Cys Ser Val Phe Cys Arg Pro Arg Asp Asp Ala Phe Gly His Phe Thr
                165                 170                 175

Cys Gly Asp Arg Gly Glu Lys Met Cys Asp Pro Gly Trp Lys Gly Gln
            180                 185                 190

Tyr Cys Thr Asp Pro Ile Cys Leu Pro Gly Cys Asp Asp Gln His Gly
        195                 200                 205

Tyr Cys Asp Lys Pro Gly Glu Cys Lys Cys Arg Val Gly Trp Gln Gly
    210                 215                 220

Arg Tyr Cys Asp Glu Cys Ile Arg Tyr Pro Gly Cys Leu His Gly Thr
225                 230                 235                 240

Cys Gln Gln Pro Trp Gln Cys Asn Cys Gln Glu Gly Trp Gly Gly Leu
                245                 250                 255

Phe Cys Asn Gln
            260


<210> SEQ ID NO 53
<211> LENGTH: 486
<212> TYPE: PRT
<213> ORGANISM: Artificial Sequence
<220> FEATURE:
<223> OTHER INFORMATION: synthetic construct

<400> SEQUENCE: 53

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190
```

Gln His Gly Tyr Cys Asp Lys Pro Gly Glu Cys Lys Cys Arg Val Gly
195 200 205

Trp Gln Gly Arg Tyr Cys Asp Glu Cys Ile Arg Tyr Pro Gly Cys Leu
210 215 220

His Gly Thr Cys Gln Gln Pro Trp Gln Cys Asn Cys Gln Glu Gly Trp
225 230 235 240

Gly Gly Leu Phe Cys Asn Gln Gly Gly Gly Gly Ser Gly Gly Gly Gly
245 250 255

Ser Phe Val Cys Asp Glu His Tyr Tyr Gly Glu Gly Cys Ser Val Phe
260 265 270

Cys Arg Pro Arg Asp Asp Ala Phe Gly His Phe Thr Cys Gly Asp Arg
275 280 285

Gly Glu Lys Met Cys Asp Pro Gly Trp Lys Gly Gln Tyr Cys Thr Asp
290 295 300

Pro Ile Cys Leu Pro Gly Cys Asp Asp Gln His Gly Tyr Cys Asp Lys
305 310 315 320

Pro Gly Glu Cys Lys Cys Arg Val Gly Trp Gln Gly Arg Tyr Cys Asp
325 330 335

Glu Cys Ile Arg Tyr Pro Gly Cys Leu His Gly Thr Cys Gln Gln Pro
340 345 350

Trp Gln Cys Asn Cys Gln Glu Gly Trp Gly Gly Leu Phe Cys Asn Gln
355 360 365

Gly Ser Ser Gly Ser Ser Gly Phe Val Cys Asp Glu His Tyr Tyr Gly
370 375 380

Glu Gly Cys Ser Val Phe Cys Arg Pro Arg Asp Asp Ala Phe Gly His
385 390 395 400

Phe Thr Cys Gly Asp Arg Gly Glu Lys Met Cys Asp Pro Gly Trp Lys
405 410 415

Gly Gln Tyr Cys Thr Asp Pro Ile Cys Leu Pro Gly Cys Asp Asp Gln
420 425 430

His Gly Tyr Cys Asp Lys Pro Gly Glu Cys Lys Cys Arg Val Gly Trp
435 440 445

Gln Gly Arg Tyr Cys Asp Glu Cys Ile Arg Tyr Pro Gly Cys Leu His
450 455 460

Gly Thr Cys Gln Gln Pro Trp Gln Cys Asn Cys Gln Glu Gly Trp Gly
465 470 475 480

Gly Leu Phe Cys Asn Gln
485

<210> SEQ ID NO 54
<211> LENGTH: 491
<212> TYPE: PRT
<213> ORGANISM: Artificial Sequence
<220> FEATURE:
<223> OTHER INFORMATION: synthetic construct

<400> SEQUENCE: 54

Met Ala Ala His His His His His His Gly Gly Glu Asn Leu Tyr Phe
1 5 10 15

Gln Gly Phe Val Cys Asp Glu His Tyr Tyr Gly Glu Gly Cys Ser Val
20 25 30

Phe Cys Arg Pro Arg Asp Asp Ala Phe Gly His Phe Thr Cys Gly Asp
35 40 45

Arg Gly Glu Lys Met Cys Asp Pro Gly Trp Lys Gly Gln Tyr Cys Thr
50 55 60

-continued

```
Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Gly Gly Gly Ser Gly Gly Gly Gly
                245                 250                 255

Ser Gly Gly Gly Gly Ser Phe Val Cys Asp Glu His Tyr Tyr Gly Glu
            260                 265                 270

Gly Cys Ser Val Phe Cys Arg Pro Arg Asp Asp Ala Phe Gly His Phe
        275                 280                 285

Thr Cys Gly Asp Arg Gly Glu Lys Met Cys Asp Pro Gly Trp Lys Gly
    290                 295                 300

Gln Tyr Cys Thr Asp Pro Ile Cys Leu Pro Gly Cys Asp Asp Gln His
305                 310                 315                 320

Gly Tyr Cys Asp Lys Pro Gly Glu Cys Lys Cys Arg Val Gly Trp Gln
                325                 330                 335

Gly Arg Tyr Cys Asp Glu Cys Ile Arg Tyr Pro Gly Cys Leu His Gly
            340                 345                 350

Thr Cys Gln Gln Pro Trp Gln Cys Asn Cys Gln Glu Gly Trp Gly Gly
        355                 360                 365

Leu Phe Cys Asn Gln Gly Ser Ser Gly Ser Ser Gly Phe Val Cys Asp
    370                 375                 380

Glu His Tyr Tyr Gly Glu Gly Cys Ser Val Phe Cys Arg Pro Arg Asp
385                 390                 395                 400

Asp Ala Phe Gly His Phe Thr Cys Gly Asp Arg Gly Glu Lys Met Cys
                405                 410                 415

Asp Pro Gly Trp Lys Gly Gln Tyr Cys Thr Asp Pro Ile Cys Leu Pro
            420                 425                 430

Gly Cys Asp Asp Gln His Gly Tyr Cys Asp Lys Pro Gly Glu Cys Lys
        435                 440                 445

Cys Arg Val Gly Trp Gln Gly Arg Tyr Cys Asp Glu Cys Ile Arg Tyr
    450                 455                 460

Pro Gly Cys Leu His Gly Thr Cys Gln Gln Pro Trp Gln Cys Asn Cys
465                 470                 475                 480

Gln Glu Gly Trp Gly Gly Leu Phe Cys Asn Gln
```

485 490

<210> SEQ ID NO 55
<211> LENGTH: 496
<212> TYPE: PRT
<213> ORGANISM: Artificial Sequence
<220> FEATURE:
<223> OTHER INFORMATION: synthetic construct

<400> SEQUENCE: 55

Met Ala Ala His His His His His His Gly Gly Glu Asn Leu Tyr Phe
1 5 10 15

Gln Gly Phe Val Cys Asp Glu His Tyr Tyr Gly Glu Gly Cys Ser Val
20 25 30

Phe Cys Arg Pro Arg Asp Asp Ala Phe Gly His Phe Thr Cys Gly Asp
35 40 45

Arg Gly Glu Lys Met Cys Asp Pro Gly Trp Lys Gly Gln Tyr Cys Thr
50 55 60

Asp Pro Ile Cys Leu Pro Gly Cys Asp Asp Gln His Gly Tyr Cys Asp
65 70 75 80

Lys Pro Gly Glu Cys Lys Cys Arg Val Gly Trp Gln Gly Arg Tyr Cys
85 90 95

Asp Glu Cys Ile Arg Tyr Pro Gly Cys Leu His Gly Thr Cys Gln Gln
100 105 110

Pro Trp Gln Cys Asn Cys Gln Glu Gly Trp Gly Gly Leu Phe Cys Asn
115 120 125

Gln Gly Ser Ser Gly Ser Ser Gly Phe Val Cys Asp Glu His Tyr Tyr
130 135 140

Gly Glu Gly Cys Ser Val Phe Cys Arg Pro Arg Asp Asp Ala Phe Gly
145 150 155 160

His Phe Thr Cys Gly Asp Arg Gly Glu Lys Met Cys Asp Pro Gly Trp
165 170 175

Lys Gly Gln Tyr Cys Thr Asp Pro Ile Cys Leu Pro Gly Cys Asp Asp
180 185 190

Gln His Gly Tyr Cys Asp Lys Pro Gly Glu Cys Lys Cys Arg Val Gly
195 200 205

Trp Gln Gly Arg Tyr Cys Asp Glu Cys Ile Arg Tyr Pro Gly Cys Leu
210 215 220

His Gly Thr Cys Gln Gln Pro Trp Gln Cys Asn Cys Gln Glu Gly Trp
225 230 235 240

Gly Gly Leu Phe Cys Asn Gln Gly Gly Gly Gly Ser Gly Gly Gly Gly
245 250 255

Ser Gly Gly Gly Gly Ser Gly Gly Gly Gly Ser Phe Val Cys Asp Glu
260 265 270

His Tyr Tyr Gly Glu Gly Cys Ser Val Phe Cys Arg Pro Arg Asp Asp
275 280 285

Ala Phe Gly His Phe Thr Cys Gly Asp Arg Gly Glu Lys Met Cys Asp
290 295 300

Pro Gly Trp Lys Gly Gln Tyr Cys Thr Asp Pro Ile Cys Leu Pro Gly
305 310 315 320

Cys Asp Asp Gln His Gly Tyr Cys Asp Lys Pro Gly Glu Cys Lys Cys
325 330 335

Arg Val Gly Trp Gln Gly Arg Tyr Cys Asp Glu Cys Ile Arg Tyr Pro
340 345 350

Gly Cys Leu His Gly Thr Cys Gln Gln Pro Trp Gln Cys Asn Cys Gln

```
        355                 360                 365

Glu Gly Trp Gly Gly Leu Phe Cys Asn Gln Gly Ser Ser Gly Ser Ser
    370                 375                 380

Gly Phe Val Cys Asp Glu His Tyr Tyr Gly Glu Gly Cys Ser Val Phe
385                 390                 395                 400

Cys Arg Pro Arg Asp Asp Ala Phe Gly His Phe Thr Cys Gly Asp Arg
                405                 410                 415

Gly Glu Lys Met Cys Asp Pro Gly Trp Lys Gly Gln Tyr Cys Thr Asp
            420                 425                 430

Pro Ile Cys Leu Pro Gly Cys Asp Asp Gln His Gly Tyr Cys Asp Lys
        435                 440                 445

Pro Gly Glu Cys Lys Cys Arg Val Gly Trp Gln Gly Arg Tyr Cys Asp
    450                 455                 460

Glu Cys Ile Arg Tyr Pro Gly Cys Leu His Gly Thr Cys Gln Gln Pro
465                 470                 475                 480

Trp Gln Cys Asn Cys Gln Glu Gly Trp Gly Gly Leu Phe Cys Asn Gln
                485                 490                 495


<210> SEQ ID NO 56
<211> LENGTH: 243
<212> TYPE: PRT
<213> ORGANISM: Artificial Sequence
<220> FEATURE:
<223> OTHER INFORMATION: synthetic construct

<400> SEQUENCE: 56

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Gln Val Trp Ser Ser Gly Val Phe Glu Leu
        35                  40                  45

Lys Leu Gln Glu Phe Val Asn Lys Lys Gly Leu Leu Gly Asn Arg Asn
    50                  55                  60

Cys Cys Arg Gly Gly Ala Gly Pro Pro Pro Cys Ala Cys Arg Thr Phe
65                  70                  75                  80

Phe Arg Val Cys Leu Lys His Tyr Gln Ala Ser Val Ser Pro Glu Pro
                85                  90                  95

Pro Cys Thr Tyr Gly Ser Ala Val Thr Pro Val Leu Gly Val Asp Ser
            100                 105                 110

Phe Ser Leu Pro Asp Gly Gly Gly Ala Asp Ser Ala Phe Ser Asn Pro
        115                 120                 125

Ile Arg Phe Pro Phe Gly Phe Thr Trp Pro Gly Thr Phe Ser Leu Ile
    130                 135                 140

Ile Glu Ala Leu His Thr Asp Ser Pro Asp Asp Leu Ala Thr Glu Asn
145                 150                 155                 160

Pro Glu Arg Leu Ile Ser Arg Leu Ala Thr Gln Arg His Leu Thr Val
                165                 170                 175

Gly Glu Glu Trp Ser Gln Asp Leu His Ser Ser Gly Arg Thr Asp Leu
            180                 185                 190

Lys Tyr Ser Tyr Arg Phe Val Cys Asp Glu His Tyr Tyr Gly Glu Gly
        195                 200                 205

Cys Ser Val Phe Cys Arg Pro Arg Asp Asp Ala Phe Gly His Phe Thr
    210                 215                 220

Cys Gly Glu Arg Gly Glu Lys Val Cys Asn Pro Gly Trp Lys Gly Pro
```

```
225                 230                 235                 240

Tyr Cys Thr


<210> SEQ ID NO 57
<211> LENGTH: 197
<212> TYPE: PRT
<213> ORGANISM: Artificial Sequence
<220> FEATURE:
<223> OTHER INFORMATION: synthetic construct

<400> SEQUENCE: 57

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Gln Val Trp Ser Ser Gly Val Phe Glu Leu
        35                  40                  45

Lys Leu Gln Glu Phe Val Asn Lys Lys Gly Leu Leu Gly Asn Arg Asn
    50                  55                  60

Cys Cys Arg Gly Gly Ala Gly Pro Pro Pro Cys Ala Cys Arg Thr Phe
65                  70                  75                  80

Phe Arg Val Cys Leu Lys His Tyr Gln Ala Ser Val Ser Pro Glu Pro
                85                  90                  95

Pro Cys Thr Tyr Gly Ser Ala Val Thr Pro Val Leu Gly Val Asp Ser
            100                 105                 110

Phe Ser Leu Pro Asp Gly Gly Gly Ala Asp Ser Ala Phe Ser Asn Pro
        115                 120                 125

Ile Arg Phe Pro Phe Gly Phe Thr Trp Pro Gly Thr Phe Ser Leu Ile
    130                 135                 140

Ile Glu Ala Leu His Thr Asp Ser Pro Asp Asp Leu Ala Thr Glu Asn
145                 150                 155                 160

Pro Glu Arg Leu Ile Ser Arg Leu Ala Thr Gln Arg His Leu Thr Val
                165                 170                 175

Gly Glu Glu Trp Ser Gln Asp Leu His Ser Ser Gly Arg Thr Asp Leu
            180                 185                 190

Lys Tyr Ser Tyr Arg
        195


<210> SEQ ID NO 58
<211> LENGTH: 61
<212> TYPE: PRT
<213> ORGANISM: Artificial Sequence
<220> FEATURE:
<223> OTHER INFORMATION: synthetic construct

<400> SEQUENCE: 58

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Glu Arg Gly Glu
        35                  40                  45

Lys Val Cys Asn Pro Gly Trp Lys Gly Pro Tyr Cys Thr
    50                  55                  60


<210> SEQ ID NO 59
<211> LENGTH: 241
<212> TYPE: PRT
```

<213> ORGANISM: Artificial Sequence
<220> FEATURE:
<223> OTHER INFORMATION: synthetic construct

<400> SEQUENCE: 59

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Gln Val Trp Ser Ser Gly Val Phe Glu Leu
        35                  40                  45

Lys Leu Gln Glu Phe Val Asn Lys Lys Gly Leu Leu Gly Asn Arg Asn
    50                  55                  60

Cys Cys Arg Gly Gly Ser Gly Pro Pro Cys Ala Cys Arg Thr Phe Phe
65                  70                  75                  80

Arg Val Cys Leu Lys His Tyr Gln Ala Ser Val Ser Pro Glu Pro Pro
                85                  90                  95

Cys Thr Tyr Gly Ser Ala Val Thr Pro Val Leu Gly Val Asp Ser Phe
            100                 105                 110

Ser Leu Pro Asp Gly Ala Gly Ile Asp Pro Ala Phe Ser Asn Pro Ile
        115                 120                 125

Arg Phe Pro Phe Gly Phe Thr Trp Pro Gly Thr Phe Ser Leu Ile Ile
    130                 135                 140

Glu Ala Leu His Thr Asp Ser Pro Asp Asp Leu Ala Thr Glu Asn Pro
145                 150                 155                 160

Glu Arg Leu Ile Ser Arg Leu Thr Thr Gln Arg His Leu Thr Val Gly
                165                 170                 175

Glu Glu Trp Ser Gln Asp Leu His Ser Ser Gly Arg Thr Asp Leu Arg
            180                 185                 190

Tyr Ser Tyr Arg Phe Val Cys Asp Glu His Tyr Tyr Gly Glu Gly Cys
        195                 200                 205

Ser Val Phe Cys Arg Pro Arg Asp Asp Ala Phe Gly His Phe Thr Cys
    210                 215                 220

Gly Asp Arg Gly Glu Lys Met Cys Asp Pro Gly Trp Lys Gly Gln Tyr
225                 230                 235                 240

Cys
```

<210> SEQ ID NO 60
<211> LENGTH: 196
<212> TYPE: PRT
<213> ORGANISM: Artificial Sequence
<220> FEATURE:
<223> OTHER INFORMATION: synthetic construct

<400> SEQUENCE: 60

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Gly Glu
            20                  25                  30

Asn Leu Tyr Phe Gln Gly Gln Val Trp Ser Ser Gly Val Phe Glu Leu
        35                  40                  45

Lys Leu Gln Glu Phe Val Asn Lys Lys Gly Leu Leu Gly Asn Arg Asn
    50                  55                  60

Cys Cys Arg Gly Gly Ser Gly Pro Pro Cys Ala Cys Arg Thr Phe Phe
65                  70                  75                  80

Arg Val Cys Leu Lys His Tyr Gln Ala Ser Val Ser Pro Glu Pro Pro
```

```
                85                  90                  95

Cys Thr Tyr Gly Ser Ala Val Thr Pro Val Leu Gly Val Asp Ser Phe
            100                 105                 110

Ser Leu Pro Asp Gly Ala Gly Ile Asp Pro Ala Phe Ser Asn Pro Ile
        115                 120                 125

Arg Phe Pro Phe Gly Phe Thr Trp Pro Gly Thr Phe Ser Leu Ile Ile
    130                 135                 140

Glu Ala Leu His Thr Asp Ser Pro Asp Asp Leu Ala Thr Glu Asn Pro
145                 150                 155                 160

Glu Arg Leu Ile Ser Arg Leu Thr Thr Gln Arg His Leu Thr Val Gly
                165                 170                 175

Glu Glu Trp Ser Gln Asp Leu His Ser Ser Gly Arg Thr Asp Leu Arg
            180                 185                 190

Tyr Ser Tyr Arg
        195


<210> SEQ ID NO 61
<211> LENGTH: 60
<212> TYPE: PRT
<213> ORGANISM: Artificial Sequence
<220> FEATURE:
<223> OTHER INFORMATION: synthetic construct

<400> SEQUENCE: 61

His His His His His His Gly Gly Glu Asn Leu Tyr Phe Gln Gly Phe
1               5                   10                  15

Val Cys Asp Glu His Tyr Tyr Gly Glu Gly Cys Ser Val Phe Cys Arg
            20                  25                  30

Pro Arg Asp Asp Ala Phe Gly His Phe Thr Cys Gly Asp Arg Gly Glu
        35                  40                  45

Lys Met Cys Asp Pro Gly Trp Lys Gly Gln Tyr Cys
    50                  55                  60


<210> SEQ ID NO 62
<211> LENGTH: 141
<212> TYPE: PRT
<213> ORGANISM: Artificial Sequence
<220> FEATURE:
<223> OTHER INFORMATION: synthetic construct

<400> SEQUENCE: 62

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125
```

```
Gln Gly Ser Ser Gly Asp Tyr Lys Asp Asp Asp Asp Lys
    130                 135                 140


<210> SEQ ID NO 63
<211> LENGTH: 495
<212> TYPE: PRT
<213> ORGANISM: Artificial Sequence
<220> FEATURE:
<223> OTHER INFORMATION: synthetic construct

<400> SEQUENCE: 63

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
            260                 265                 270

Arg Asp Asp Ala Phe Gly His Phe Thr Cys Gly Asp Arg Gly Glu Lys
        275                 280                 285

Met Cys Asp Pro Gly Trp Lys Gly Gln Tyr Cys Thr Asp Pro Ile Cys
    290                 295                 300

Leu Pro Gly Cys Asp Asp Gln His Gly Tyr Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350
```

-continued

```
Asn Cys Gln Glu Gly Trp Gly Gly Leu Phe Cys Asn Gln Gly Ser Ser
        355                 360                 365

Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

Gly Asp Arg Gly Glu Lys Met Cys Asp Pro Gly Trp Lys Gly Gln Tyr
                405                 410                 415

Cys Thr Asp Pro Ile Cys Leu Pro Gly Cys Asp Asp Gln His Gly Tyr
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
    450                 455                 460

Gln Gln Pro Trp Gln Cys Asn Cys Gln Glu Gly Trp Gly Gly Leu Phe
465                 470                 475                 480

Cys Asn Gln Gly Ser Ser Gly Asp Tyr Lys Asp Asp Asp Asp Lys
                485                 490                 495
```

<210> SEQ ID NO 64
<211> LENGTH: 1068
<212> TYPE: DNA
<213> ORGANISM: Artificial Sequence
<220> FEATURE:
<223> OTHER INFORMATION: synthetic construct

<400> SEQUENCE: 64

```
catatgaagt atctcttgcc tactgccgcg gcagggcttt tacttctcgc agctcagcct     60

gcaatggcag ctcatcacca tcaccatcac ggtggcgaga atctatactt ccagggcttt    120

gtctgtgacg agcattacta tggtgaaggg tgctctgtgt tttgtaggcc aagggacgat    180

gcgttcggac attttacctg cggggaacga ggtgagaagg tttgcaaccc ggggtggaag    240

ggaccctact gcactgaacc aatttgctta ccagggtgtg atgagcaaca cggattctgc    300

gataagccgg gcgaatgtaa gtgtcgggta ggctggcaag gccgctactg cgatgagtgt    360

atacgttacc caggatgttt acacggaaca tgtcagcaac cgtggcagtg taattgccaa    420

gaagggtggg gagggttgtt ttgcaatcaa gacctgaact attgtactca tcacaagccg    480

tgtaaaaacg gagccacgtg tacgaacaca ggtcaaggat catatacgtg ctcgtgtcgc    540

cccggttaca ccggtgctac ttgcgaattg gggtcctcag gatctagtgg attcgtatgc    600

gatgaacatt attacggaga aggctgtagt gttttctgta ggcctagaga cgatgctttc    660

gggcatttta cgtgcggcga gagaggcgag aaagtgtgta atcctgggtg gaaagggccc    720

tattgtacag aaccaatatg ccttccaggt tgcgacgagc aacacggttt ttgtgacaaa    780

cccggcgaat gtaaatgccg ggtcgggtgg cagggccgat attgcgacga atgcatccgt    840

tatcccggat gtctgcatgg tacttgccag caaccttggc agtgtaactg ccaagaagga    900

tggggggggtc tattttgcaa tcaagatctg aattattgca cacaccacaa accgtgcaaa    960

aacggtgcta catgtacgaa taccggtcag ggtagctata cctgcagttg cagacctgga   1020

tacacaggcg cgacctgtga gctaggtagc agcggctgtt aaggatcc                1068
```

<210> SEQ ID NO 65
<211> LENGTH: 1002
<212> TYPE: DNA
<213> ORGANISM: Artificial Sequence
<220> FEATURE:

<223> OTHER INFORMATION: synthetic construct

<400> SEQUENCE: 65
catatgcatc accatcacca tcacggtggc gagaatctat acttccaggg ctttgtctgt 60
gacgagcatt actatggtga agggtgctct gtgttttgta ggccaaggga cgatgcgttc 120
ggacatttta cctgcgggga acgaggtgag aaggtttgca acccggggtg gaagggaccc 180
tactgcactg aaccaatttg cttaccaggg tgtgatgagc aacacggatt ctgcgataag 240
ccgggcgaat gtaagtgtcg ggtaggctgg caaggccgct actgcgatga gtgtatacgt 300
tacccaggat gtttacacgg aacatgtcag caaccgtggc agtgtaattg ccaagaaggg 360
tggggagggt tgttttgcaa tcaagacctg aactattgta ctcatcacaa gccgtgtaaa 420
aacggagcca cgtgtacgaa cacaggtcaa ggatcatata cgtgctcgtg tcgccccggt 480
tacaccggtg ctacttgcga attggggtcc tcaggatcta gtggattcgt atgcgatgaa 540
cattattacg gagaaggctg tagtgttttc tgtaggccta gagacgatgc tttcgggcat 600
tttacgtgcg gcgagagagg cgagaaagtg tgtaatcctg ggtggaaagg gccctattgt 660
acagaaccaa tatgccttcc aggttgcgac gagcaacacg gtttttgtga caaacccggc 720
gaatgtaaat gccgggtcgg gtggcagggc cgatattgcg acgaatgcat ccgttatccc 780
ggatgtctgc atggtacttg ccagcaacct tggcagtgta actgccaaga aggatggggg 840
ggtctatttt gcaatcaaga tctgaattat tgcacacacc acaaaccgtg caaaaacggt 900
gctacatgta cgaataccgg tcagggtagc tatacctgca gttgcagacc tggatacaca 960
ggcgcgacct gtgagctagg tagcagcggc tgttaaggat cc 1002

<210> SEQ ID NO 66
<211> LENGTH: 828
<212> TYPE: DNA
<213> ORGANISM: Artificial Sequence
<220> FEATURE:
<223> OTHER INFORMATION: synthetic construct

<400> SEQUENCE: 66
catatgaagt atctcttgcc tactgccgcg gcagggcttt tacttctcgc agctcagcct 60
gcaatggcag ctcatcacca tcaccatcac ggtggcgaga atctatactt ccagggcttt 120
gtctgtgacg agcattacta tggtgaaggg tgctctgtgt tttgtaggcc aagggacgat 180
gcgttcggac attttacctg cggggaacga ggtgagaagg tttgcaaccc ggggtggaag 240
ggaccctact gcactgaacc aatttgctta ccagggtgtg atgagcaaca cggattctgc 300
gataagccgg gcgaatgtaa gtgtcgggta ggctggcaag gccgctactg cgatgagtgt 360
atacgttacc caggatgttt acacggaaca tgtcagcaac cgtggcagtg taattgccaa 420
gaagggtggg gagggttgtt ctgtaaccag gggtcctcag gatctagtgg attcgtatgc 480
gatgaacatt attacggaga aggctgtagt gttttctgta ggcctagaga cgatgctttc 540
gggcatttta cgtgcggcga gagaggcgag aaagtgtgta atcctgggtg gaaagggccc 600
tattgtacag aaccaatatg ccttccaggt tgcgacgagc aacacggttt ttgtgacaaa 660
cccggcgaat gtaaatgccg ggtcgggtgg cagggccgat attgcgacga atgcatccgt 720
tatcccggat gtctgcatgg tacttgccag caaccttggc agtgtaactg ccaagaagga 780 tggggggggtc tattttgcaa tcaaggtagc agcggctgtt aaggatcc 828

<210> SEQ ID NO 67
<211> LENGTH: 762

<212> TYPE: DNA
<213> ORGANISM: Artificial Sequence
<220> FEATURE:
<223> OTHER INFORMATION: synthetic construct

<400> SEQUENCE: 67
catatgcatc accatcacca tcacggtggc gagaatctat acttccaggg ctttgtctgt 60
gacgagcatt actatggtga agggtgctct gtgttttgta ggccaaggga cgatgcgttc 120
ggacatttta cctgcgggga acgaggtgag aaggtttgca acccggggtg gaagggaccc 180
tactgcactg aaccaatttg cttaccaggg tgtgatgagc aacacggatt ctgcgataag 240
ccgggcgaat gtaagtgtcg ggtaggctgg caaggccgct actgcgatga gtgtatacgt 300
tacccaggat gtttacacgg aacatgtcag caaccgtggc agtgtaattg ccaagaaggg 360
tggggagggt tgttctgtaa ccaggggtcc tcaggatcta gtggattcgt atgcgatgaa 420
cattattacg gagaaggctg tagtgttttc tgtaggccta gagacgatgc tttcgggcat 480
tttacgtgcg gcgagagagg cgagaaagtg tgtaatcctg ggtggaaagg gccctattgt 540
acagaaccaa tatgccttcc aggttgcgac gagcaacacg gtttttgtga caaacccggc 600
gaatgtaaat gccgggtcgg gtggcagggc cgatattgcg acgaatgcat ccgttatccc 660
ggatgtctgc atggtacttg ccagcaacct tggcagtgta actgccaaga aggatggggg 720
ggtctatttt gcaatcaagg tagcagcggc tgttaaggat cc 762

<210> SEQ ID NO 68
<211> LENGTH: 1053
<212> TYPE: DNA
<213> ORGANISM: Artificial Sequence
<220> FEATURE:
<223> OTHER INFORMATION: synthetic construct

<400> SEQUENCE: 68
catatgaagt atctcttgcc tactgccgcg gcagggcttt tacttctcgc agctcagcct 60
gcaatggcag ctcatcacca tcaccatcac ggtggcgaga atctatactt ccagggcttt 120
gtctgtgacg agcattacta tggtgaaggg tgctctgtgt tttgtaggcc aagggacgat 180
gcgttcggac attttacctg cggggaacga ggtgagaagg tttgcaaccc ggggtggaag 240
ggaccctact gcactgaacc aatttgctta ccagggtgtg atgagcaaca cggattctgc 300
gataagccgg gcgaatgtaa gtgtcgggta ggctggcaag gccgctactg cgatgagtgt 360
atacgttacc caggatgttt acacggaaca tgtcagcaac cgtggcagtg taattgccaa 420
gaagggtggg gagggttgtt ttgcaatcaa gacctgaact attgtactca tcacaagccg 480
tgtaaaaacg gagccacgtg tacgaacaca ggtcaaggat catatacgtg ctcgtgtcgc 540
cccggttaca ccggtgctac ttgcgaattg ggtcctcag gatctagtgg attcgtatgc 600
gatgaacatt attacggaga aggctgtagt gttttctgta ggcctagaga cgatgctttc 660
gggcatttta cgtgcggcga gagaggcgag aaagtgtgta atcctgggtg gaaagggccc 720
tattgtacag aaccaatatg ccttccaggt tgcgacgagc aacacggttt ttgtgacaaa 780
cccggcgaat gtaaatgccg ggtcgggtgg cagggccgat attgcgacga atgcatccgt 840
tatcccggat gtctgcatgg tacttgccag caaccttggc agtgtaactg ccaagaagga 900 tggggggggtc tattttgcaa tcaagatctg aattattgca cacaccacaa accgtgcaaa 960
aacggtgcta catgtacgaa taccggtcag ggtagctata cctgcagttg cagacctgga 1020
tacacaggcg cgacctgtga gctataagga tcc 1053

<210> SEQ ID NO 69
<211> LENGTH: 987
<212> TYPE: DNA
<213> ORGANISM: Artificial Sequence
<220> FEATURE:
<223> OTHER INFORMATION: synthetic construct

<400> SEQUENCE: 69
catatgcatc accatcacca tcacggtggc gagaatctat acttccaggg ctttgtctgt 60
gacgagcatt actatggtga agggtgctct gtgttttgta ggccaaggga cgatgcgttc 120
ggacatttta cctgcgggga acgaggtgag aaggtttgca acccggggtg gaagggaccc 180
tactgcactg aaccaatttg cttaccaggg tgtgatgagc aacacggatt ctgcgataag 240
ccgggcgaat gtaagtgtcg ggtaggctgg caaggccgct actgcgatga gtgtatacgt 300
tacccaggat gtttacacgg aacatgtcag caaccgtggc agtgtaattg ccaagaaggg 360
tggggagggt tgttttgcaa tcaagacctg aactattgta ctcatcacaa gccgtgtaaa 420
aacggagcca cgtgtacgaa cacaggtcaa ggatcatata cgtgctcgtg tcgccccggt 480
tacaccggtg ctacttgcga attggggtcc tcaggatcta gtggattcgt atgcgatgaa 540
cattattacg gagaaggctg tagtgttttc tgtaggccta gagacgatgc tttcgggcat 600
tttacgtgcg gcgagagagg cgagaaagtg tgtaatcctg ggtggaaagg gccctattgt 660
acagaaccaa tatgccttcc aggttgcgac gagcaacacg gtttttgtga caaacccggc 720
gaatgtaaat gccgggtcgg gtggcagggc cgatattgcg acgaatgcat ccgttatccc 780
ggatgtctgc atggtacttg ccagcaacct tggcagtgta actgccaaga aggatggggg 840
ggtctatttt gcaatcaaga tctgaattat tgcacacacc acaaaccgtg caaaaacggt 900
gctacatgta cgaataccgg tcagggtagc tatacctgca gttgcagacc tggatacaca 960
ggcgcgacct gtgagctata aggatcc 987

<210> SEQ ID NO 70
<211> LENGTH: 813
<212> TYPE: DNA
<213> ORGANISM: Artificial Sequence
<220> FEATURE:
<223> OTHER INFORMATION: synthetic construct

<400> SEQUENCE: 70
catatgaagt atctcttgcc tactgccgcg gcagggcttt tacttctcgc agctcagcct 60
gcaatggcag ctcatcacca tcaccatcac ggtggcgaga atctatactt ccagggcttt 120
gtctgtgacg agcattacta tggtgaaggg tgctctgtgt tttgtaggcc aagggacgat 180
gcgttcggac attttacctg cggggaacga ggtgagaagg tttgcaaccc ggggtggaag 240
ggaccctact gcactgaacc aatttgctta ccagggtgtg atgagcaaca cggattctgc 300
gataagccgg gcgaatgtaa gtgtcgggta ggctggcaag gccgctactg cgatgagtgt 360
atacgttacc caggatgttt acacggaaca tgtcagcaac cgtggcagtg taattgccaa 420
gaagggtggg gagggttgtt ctgtaaccag gggtcctcag gatctagtgg attcgtatgc 480
gatgaacatt attacggaga aggctgtagt gttttctgta ggcctagaga cgatgctttc 540
gggcatttta cgtgcggcga gagaggcgag aaagtgtgta atcctgggtg gaaagggccc 600
tattgtacag aaccaatatg ccttccaggt tgcgacgagc aacacggttt ttgtgacaaa 660
cccggcgaat gtaaatgccg ggtcgggtgg cagggccgat attgcgacga atgcatccgt 720
tatcccggat gtctgcatgg tacttgccag caaccttggc agtgtaactg ccaagaagga 780 tggggggtc tattttgcaa tcaataagga tcc 813

<210> SEQ ID NO 71
<211> LENGTH: 747
<212> TYPE: DNA
<213> ORGANISM: Artificial Sequence
<220> FEATURE:
<223> OTHER INFORMATION: synthetic construct

<400> SEQUENCE: 71
catatgcatc accatcacca tcacggtggc gagaatctat acttccaggg ctttgtctgt 60
gacgagcatt actatggtga agggtgctct gtgttttgta ggccaaggga cgatgcgttc 120
ggacatttta cctgcgggga acgaggtgag aaggtttgca acccggggtg gaagggaccc 180
tactgcactg aaccaatttg cttaccaggg tgtgatgagc aacacggatt ctgcgataag 240
ccgggcgaat gtaagtgtcg ggtaggctgg caaggccgct actgcgatga gtgtatacgt 300
tacccaggat gtttacacgg aacatgtcag caaccgtggc agtgtaattg ccaagaaggg 360
tggggagggt tgttctgtaa ccaggggtcc tcaggatcta gtggattcgt atgcgatgaa 420
cattattacg gagaaggctg tagtgttttc tgtaggccta gagacgatgc tttcgggcat 480
tttacgtgcg gcgagagagg cgagaaagtg tgtaatcctg ggtggaaagg gccctattgt 540
acagaaccaa tatgccttcc aggttgcgac gagcaacacg gtttttgtga caaacccggc 600
gaatgtaaat gccgggtcgg gtggcagggc cgatattgcg acgaatgcat ccgttatccc 660
ggatgtctgc atggtacttg ccagcaacct tggcagtgta actgccaaga aggatggggg 720
ggtctatttt gcaatcaata aggatcc 747

<210> SEQ ID NO 72
<211> LENGTH: 594
<212> TYPE: DNA
<213> ORGANISM: Artificial Sequence
<220> FEATURE:
<223> OTHER INFORMATION: synthetic construct

<400> SEQUENCE: 72
catatgaagt atctcttgcc tactgccgcg gcagggcttt tacttctcgc agctcagcct 60
gcaatggcag ctcatcacca tcaccatcac ggtggcgaga atctatactt ccagggcttt 120
gtctgtgacg agcattacta tggtgaaggg tgctctgtgt tttgtaggcc aagggacgat 180
gcgttcggac attttacctg cggggaacga ggtgagaagg tttgcaaccc ggggtggaag 240
ggaccctact gcactgaacc aatttgctta ccagggtgtg atgagcaaca cggattctgc 300
gataagccgg gcgaatgtaa gtgtcgggta ggctggcaag gccgctactg cgatgagtgt 360
atacgttacc caggatgttt acacggaaca tgtcagcaac cgtggcagtg taattgccaa 420
gaagggtggg gagggttgtt ttgcaatcaa gacctgaact attgtactca tcacaagccg 480
tgtaaaaacg gagccacgtg tacgaacaca ggtcaaggat catatacgtg ctcgtgtcgc 540
cccggttaca ccggtgctac ttgcgaattg ggtagcagcg gctgttaagg atcc 594

<210> SEQ ID NO 73
<211> LENGTH: 528
<212> TYPE: DNA
<213> ORGANISM: Artificial Sequence
<220> FEATURE:
<223> OTHER INFORMATION: synthetic construct

<400> SEQUENCE: 73

-continued

```
catatgcatc accatcacca tcacggtggc gagaatctat acttccaggg ctttgtctgt     60

gacgagcatt actatggtga agggtgctct gtgttttgta ggccaaggga cgatgcgttc    120

ggacatttta cctgcgggga acgaggtgag aaggtttgca acccggggtg gaagggaccc    180

tactgcactg aaccaatttg cttaccaggg tgtgatgagc aacacggatt ctgcgataag    240

ccgggcgaat gtaagtgtcg ggtaggctgg caaggccgct actgcgatga gtgtatacgt    300

tacccaggat gtttacacgg aacatgtcag caaccgtggc agtgtaattg ccaagaaggg    360

tggggagggt tgttttgcaa tcaagacctg aactattgta ctcatcacaa gccgtgtaaa    420

aacggagcca cgtgtacgaa cacaggtcaa ggatcatata cgtgctcgtg tcgccccggt    480

tacaccggtg ctacttgcga attgggtagc agcggctgtt aaggatcc                  528
```

```
<210> SEQ ID NO 74
<211> LENGTH: 474
<212> TYPE: DNA
<213> ORGANISM: Artificial Sequence
<220> FEATURE:
<223> OTHER INFORMATION: synthetic construct

<400> SEQUENCE: 74

catatgaagt atctcttgcc tactgccgcg gcagggcttt tacttctcgc agctcagcct     60

gcaatggcag ctcatcacca tcaccatcac ggtggcgaga atctatactt ccagggcttt    120

gtctgtgacg agcattacta tggtgaaggg tgctctgtgt tttgtaggcc aagggacgat    180

gcgttcggac attttacctg cggggaacga ggtgagaagg tttgcaaccc ggggtggaag    240

ggaccctact gcactgaacc aatttgctta ccagggtgtg atgagcaaca cggattctgc    300

gataagccgg gcgaatgtaa gtgtcgggta ggctggcaag gccgctactg cgatgagtgt    360

atacgttacc caggatgttt acacggaaca tgtcagcaac cgtggcagtg taattgccaa    420

gaagggtggg gagggttgtt ctgtaaccag ggtagcagcg gctgttaagg atcc           474
```

```
<210> SEQ ID NO 75
<211> LENGTH: 408
<212> TYPE: DNA
<213> ORGANISM: Artificial Sequence
<220> FEATURE:
<223> OTHER INFORMATION: synthetic construct

<400> SEQUENCE: 75

catatgcatc accatcacca tcacggtggc gagaatctat acttccaggg ctttgtctgt     60

gacgagcatt actatggtga agggtgctct gtgttttgta ggccaaggga cgatgcgttc    120

ggacatttta cctgcgggga acgaggtgag aaggtttgca acccggggtg gaagggaccc    180

tactgcactg aaccaatttg cttaccaggg tgtgatgagc aacacggatt ctgcgataag    240

ccgggcgaat gtaagtgtcg ggtaggctgg caaggccgct actgcgatga gtgtatacgt    300

tacccaggat gtttacacgg aacatgtcag caaccgtggc agtgtaattg ccaagaaggg    360

tggggagggt tgttctgtaa ccagggtagc agcggctgtt aaggatcc                  408
```

```
<210> SEQ ID NO 76
<211> LENGTH: 579
<212> TYPE: DNA
<213> ORGANISM: Artificial Sequence
<220> FEATURE:
<223> OTHER INFORMATION: synthetic construct

<400> SEQUENCE: 76

catatgaagt atctcttgcc tactgccgcg gcagggcttt tacttctcgc agctcagcct     60
```

gcaatggcag ctcatcacca tcaccatcac ggtggcgaga atctatactt ccagggcttt 120
gtctgtgacg agcattacta tggtgaaggg tgctctgtgt tttgtaggcc aagggacgat 180
gcgttcggac attttacctg cggggaacga ggtgagaagg tttgcaaccc ggggtggaag 240
ggaccctact gcactgaacc aatttgctta ccagggtgtg atgagcaaca cggattctgc 300
gataagccgg gcgaatgtaa gtgtcgggta ggctggcaag gccgctactg cgatgagtgt 360
atacgttacc caggatgttt acacggaaca tgtcagcaac cgtggcagtg taattgccaa 420
gaagggtggg gagggttgtt ttgcaatcaa gacctgaact attgtactca tcacaagccg 480
tgtaaaaacg gagccacgtg tacgaacaca ggtcaaggat catatacgtg ctcgtgtcgc 540
cccggttaca ccggtgctac ttgcgaattg taaggatcc 579

<210> SEQ ID NO 77
<211> LENGTH: 513
<212> TYPE: DNA
<213> ORGANISM: Artificial Sequence
<220> FEATURE:
<223> OTHER INFORMATION: synthetic construct

<400> SEQUENCE: 77
catatgcatc accatcacca tcacggtggc gagaatctat acttccaggg ctttgtctgt 60
gacgagcatt actatggtga agggtgctct gtgttttgta ggccaaggga cgatgcgttc 120
ggacatttta cctgcgggga acgaggtgag aaggtttgca acccggggtg gaagggaccc 180
tactgcactg aaccaatttg cttaccaggg tgtgatgagc aacacggatt ctgcgataag 240
ccgggcgaat gtaagtgtcg ggtaggctgg caaggccgct actgcgatga gtgtatacgt 300
tacccaggat gtttacacgg aacatgtcag caaccgtggc agtgtaattg ccaagaaggg 360
tggggagggt tgttttgcaa tcaagacctg aactattgta ctcatcacaa gccgtgtaaa 420
aacggagcca cgtgtacgaa cacaggtcaa ggatcatata cgtgctcgtg tcgccccggt 480
tacaccggtg ctacttgcga attgtaagga tcc 513

<210> SEQ ID NO 78
<211> LENGTH: 459
<212> TYPE: DNA
<213> ORGANISM: Artificial Sequence
<220> FEATURE:
<223> OTHER INFORMATION: synthetic construct

<400> SEQUENCE: 78
catatgaagt atctcttgcc tactgccgcg gcagggcttt tacttctcgc agctcagcct 60
gcaatggcag ctcatcacca tcaccatcac ggtggcgaga atctatactt ccagggcttt 120
gtctgtgacg agcattacta tggtgaaggg tgctctgtgt tttgtaggcc aagggacgat 180
gcgttcggac attttacctg cggggaacga ggtgagaagg tttgcaaccc ggggtggaag 240
ggaccctact gcactgaacc aatttgctta ccagggtgtg atgagcaaca cggattctgc 300
gataagccgg gcgaatgtaa gtgtcgggta ggctggcaag gccgctactg cgatgagtgt 360
atacgttacc caggatgttt acacggaaca tgtcagcaac cgtggcagtg taattgccaa 420
gaagggtggg gagggttgtt ctgtaaccag taaggatcc 459

<210> SEQ ID NO 79
<211> LENGTH: 393
<212> TYPE: DNA
<213> ORGANISM: Artificial Sequence
<220> FEATURE:

<223> OTHER INFORMATION: synthetic construct

<400> SEQUENCE: 79
catatgcatc accatcacca tcacggtggc gagaatctat acttccaggg ctttgtctgt 60
gacgagcatt actatggtga agggtgctct gtgttttgta ggccaaggga cgatgcgttc 120
ggacatttta cctgcgggga acgaggtgag aaggtttgca acccggggtg gaagggaccc 180
tactgcactg aaccaatttg cttaccaggg tgtgatgagc aacacggatt ctgcgataag 240
ccgggcgaat gtaagtgtcg ggtaggctgg caaggccgct actgcgatga gtgtatacgt 300
tacccaggat gtttacacgg aacatgtcag caaccgtggc agtgtaattg ccaagaaggg 360
tggggagggt tgttctgtaa ccagtaagga tcc 393

<210> SEQ ID NO 80
<211> LENGTH: 1056
<212> TYPE: DNA
<213> ORGANISM: Artificial Sequence
<220> FEATURE:
<223> OTHER INFORMATION: synthetic construct

<400> SEQUENCE: 80
catatgaaat atcttctccc cacagccgct gcaggacttc tgttattggc cgcacaaccc 60
gcgatggctg cacatcacca tcaccatcac gggggagaga atctttactt ccagggccaa 120
gtgtggagct ctggagtatt cgagttgaaa ctacaagaat tcgttaacaa gaaaggcttg 180
ctgggaaatc gtaattgctg tcggggtgga gcgggaccgc ccccttgcgc ttgtcgcact 240
ttctttcgtg tgtgtttaaa gcactatcag gctagtgtat ctcctgagcc gccttgcacc 300
tatggaagtg ccgtaacccc ggttctgggg gtagactcgt ttagtctccc cgatggtggc 360
ggggcggatt ctgctttttc caatccaatc agatttccgt tcgggtttac atggccaggg 420
acttttagct taataatcga ggccttgcac actgatagcc cagacgatct agcaacggaa 480
aatcccgaaa gattaatttc acgactcgca acccagaggc atttaacggt cggagaggaa 540
tggtcccagg accttcactc gagtgggagg accgacttga agtactcata taggtttgtt 600
tgcgacgaac attattacgg cgaaggttgt tcggtctttt gccggccgcg agatgacgcc 660
ttcggtcatt ttacctgtgg cgaacgcggc gagaaggtgt gtaaccctgg gtggaaaggt 720
ccctattgta cagaaccgat atgcctacca ggttgtgatg aacaacacgg gttctgcgac 780
aagccaggag agtgcaagtg ccgtgtcggc tggcaggggc gatattgtga tgagtgcatt 840
agatacccag gttgtctcca tggaacttgc caacagcctt ggcagtgtaa ctgccaagag 900
ggttggggcg gactattctg caaccaagat ctaaactact gtacacatca caaaccttgt 960
aaaaatggtg cgacgtgtac aaacacaggc caaggctcat acacgtgctc ctgtcggcca 1020
ggttacacgg gggcgacttg cgaactgtaa ggatcc 1056

<210> SEQ ID NO 81
<211> LENGTH: 991
<212> TYPE: DNA
<213> ORGANISM: Artificial Sequence
<220> FEATURE:
<223> OTHER INFORMATION: synthetic construct

<400> SEQUENCE: 81
catatgacat caccatcacc atcacggggg agagaatctt tacttccagg gccaagtgtg 60
gagctctgga gtattcgagt tgaaactaca agaattcgtt aacaagaaag gcttgctggg 120
aaatcgtaat tgctgtcggg gtggagcggg accgccccct tgcgcttgtc gcactttctt 180
tcgtgtgtgt ttaaagcact atcaggctag tgtatctcct gagccgcctt gcacctatgg 240
aagtgccgta accccggttc tgggggtaga ctcgtttagt ctccccgatg gtggcggggc 300
ggattctgct ttttccaatc caatcagatt tccgttcggg tttacatggc cagggacttt 360
tagcttaata atcgaggcct tgcacactga tagcccagac gatctagcaa cggaaaatcc 420
cgaaagatta atttcacgac tcgcaaccca gaggcattta acggtcggag aggaatggtc 480
ccaggacctt cactcgagtg ggaggaccga cttgaagtac tcatataggt ttgtttgcga 540
cgaacattat tacggcgaag gttgttcggt cttttgccgg ccgcgagatg acgccttcgg 600
tcattttacc tgtggcgaac gcggcgagaa ggtgtgtaac cctgggtgga aaggtcccta 660
ttgtacagaa ccgatatgcc taccaggttg tgatgaacaa cacgggttct gcgacaagcc 720
aggagagtgc aagtgccgtg tcggctggca ggggcgatat tgtgatgagt gcattagata 780
cccaggttgt ctccatggaa cttgccaaca gccttggcag tgtaactgcc aagagggttg 840
gggcggacta ttctgcaacc aagatctaaa ctactgtaca catcacaaac cttgtaaaaa 900
tggtgcgacg tgtacaaaca caggccaagg ctcatacacg tgctcctgtc ggccaggtta 960
cacgggggcg acttgcgaac tgtaaggatc c 991

<210> SEQ ID NO 82
<211> LENGTH: 933
<212> TYPE: DNA
<213> ORGANISM: Artificial Sequence
<220> FEATURE:
<223> OTHER INFORMATION: synthetic construct

<400> SEQUENCE: 82
catatgaaat atcttctccc cacagccgct gcaggacttc tgttattggc cgcacaaccc 60
gcgatggctg cacatcacca tcaccatcac gggggagaga atctttactt ccagggccaa 120
gtgtggagct ctggagtatt cgagttgaaa ctacaagaat tcgttaacaa gaaaggcttg 180
ctgggaaatc gtaattgctg tcggggtgga gcgggaccgc cccccttgcgc ttgtcgcact 240 ttctttcgtg tgtgtttaaa gcactatcag gctagtgtat ctcctgagcc gccttgcacc 300
tatggaagtg ccgtaacccc ggttctgggg gtagactcgt ttagtctccc cgatggtggc 360
ggggcggatt ctgctttttc caatccaatc agatttccgt tcgggtttac atggccaggg 420
acttttagct taataatcga ggccttgcac actgatagcc cagacgatct agcaacggaa 480
aatcccgaaa gattaatttc acgactcgca acccagaggc atttaacggt cggagaggaa 540
tggtcccagg accttcactc gagtgggagg accgacttga agtactcata taggtttgtt 600
tgcgacgaac attattacgg cgaaggttgt tcggtctttt gccggccgcg agatgacgcc 660
ttcggtcatt ttacctgtgg cgaacgcggc gagaaggtgt gtaaccctgg gtggaaaggt 720
ccctattgta cagaaccgat atgcctacca ggttgtgatg aacaacacgg gttctgcgac 780
aagccaggag agtgcaagtg ccgtgtcggc tggcaggggc gatattgtga tgagtgcatt 840
agatacccag gttgtctcca tggaacttgc caacagcctt ggcagtgtaa ctgccaagag 900
ggttggggcg gactattctg caactaagga tcc 933

<210> SEQ ID NO 83
<211> LENGTH: 868
<212> TYPE: DNA
<213> ORGANISM: Artificial Sequence
<220> FEATURE:
<223> OTHER INFORMATION: synthetic construct

<400> SEQUENCE: 83
catatgacat caccatcacc atcacggggg agagaatctt tacttccagg gccaagtgtg 60
gagctctgga gtattcgagt tgaaactaca agaattcgtt aacaagaaag gcttgctggg 120
aaatcgtaat tgctgtcggg gtggagcggg accgccccct tgcgcttgtc gcactttctt 180
tcgtgtgtgt ttaaagcact atcaggctag tgtatctcct gagccgcctt gcacctatgg 240
aagtgccgta accccggttc tgggggtaga ctcgtttagt ctccccgatg gtggcggggc 300
ggattctgct ttttccaatc caatcagatt tccgttcggg tttacatggc cagggacttt 360
tagcttaata atcgaggcct tgcacactga tagcccagac gatctagcaa cggaaaatcc 420
cgaaagatta atttcacgac tcgcaaccca gaggcattta acggtcggag aggaatggtc 480
ccaggacctt cactcgagtg ggaggaccga cttgaagtac tcatataggt ttgtttgcga 540
cgaacattat tacggcgaag gttgttcggt cttttgccgg ccgcgagatg acgccttcgg 600
tcattttacc tgtggcgaac gcggcgagaa ggtgtgtaac cctgggtgga aaggtcccta 660
ttgtacagaa ccgatatgcc taccaggttg tgatgaacaa cacgggttct gcgacaagcc 720
aggagagtgc aagtgccgtg tcggctggca ggggcgatat tgtgatgagt gcattagata 780
cccaggttgt ctccatggaa cttgccaaca gccttggcag tgtaactgcc aagagggttg 840
gggcggacta ttctgcaact aaggatcc 868

<210> SEQ ID NO 84
<211> LENGTH: 1068
<212> TYPE: DNA
<213> ORGANISM: Artificial Sequence
<220> FEATURE:
<223> OTHER INFORMATION: synthetic construct

<400> SEQUENCE: 84
catatgaagt atctcttgcc cacggccgct gcagggttgc tgttgcttgc ggcacagccg 60
gctatggcag ctcatcacca tcaccatcac ggtggggaga atctctattt ccaggggttc 120
gtatgtgacg aacactatta cggagagggg tgcagtgtct tctgccgtcc gagagacgat 180
gcctttggtc actttacgtg tggagacaga ggcgaaaaaa tgtgtgatcc aggatggaaa 240
ggacagtatt gtacggaccc catttgcctt cctggctgcg atgaccaaca cgggtattgt 300
gacaaacccg gcgagtgcaa gtgtcgtgtt gggtggcaag ggcgatactg cgacgagtgc 360
ataagatacc ctggttgcct gcacgggacc tgccagcaac cttggcaatg taactgtcaa 420
gaaggatggg gaggcctatt ctgcaatcag gacttgaatt actgtactca ccataaacct 480
tgtaggaacg gagcaacttg tacaaacaca ggtcaaggtt catacacatg cagctgtcgt 540
cccggttaca ctggcgcaaa ttgcgagctg ggctcgtctg gctcctcggg gtttgtatgc 600
gacgaacatt attacggcga ggggtgctca gttttttgtc ggccacgcga tgacgcgttc 660
ggtcatttta cctgcggcga tcgaggcgag aaaatgtgtg atccaggatg gaaggggcag 720
tactgcacag atccgatatg cttaccgggt tgcgatgacc aacatggtta ctgtgataag 780
ccgggggaat gcaagtgcag ggtggggtgg caaggaaggt attgcgatga atgcatccga 840
tatccaggct gtctacacgg aacttgtcag caaccctggc agtgcaattg tcaggaagga 900
tggggtggac ttttttgtaa tcaggatctc aactattgca cgcatcataa accatgtcgc 960
aacggtgcaa cctgtactaa tacgggccaa ggtagttata cctgttcctg tcggcctgga 1020
tacacaggag ctaactgtga attaggtagc agcggctgtt aaggatcc 1068

<210> SEQ ID NO 85
<211> LENGTH: 1002
<212> TYPE: DNA
<213> ORGANISM: Artificial Sequence
<220> FEATURE:
<223> OTHER INFORMATION: synthetic construct

<400> SEQUENCE: 85
catatgcatc accatcacca tcacggtggg gagaatctct atttccaggg gttcgtatgt 60
gacgaacact attacggaga ggggtgcagt gtcttctgcc gtccgagaga cgatgccttt 120
ggtcacttta cgtgtggaga cagaggcgaa aaaatgtgtg atccaggatg gaaaggacag 180
tattgtacgg accccatttg ccttcctggc tgcgatgacc aacacgggta ttgtgacaaa 240
cccggcgagt gcaagtgtcg tgttgggtgg caagggcgat actgcgacga gtgcataaga 300
taccctggtt gcctgcacgg gacctgccag caaccttggc aatgtaactg tcaagaagga 360
tggggaggcc tattctgcaa tcaggacttg aattactgta ctcaccataa accttgtagg 420
aacggagcaa cttgtacaaa cacaggtcaa ggttcataca catgcagctg tcgtcccggt 480
tacactggcg caaattgcga gctgggctcg tctggctcct cggggtttgt atgcgacgaa 540
cattattacg gcgaggggtg ctcagttttt tgtcggccac gcgatgacgc gttcggtcat 600
tttacctgcg gcgatcgagg cgagaaaatg tgtgatccag gatggaaggg gcagtactgc 660
acagatccga tatgcttacc gggttgcgat gaccaacatg gttactgtga taagccgggg 720
gaatgcaagt gcagggtggg gtggcaagga aggtattgcg atgaatgcat ccgatatcca 780
ggctgtctac acggaacttg tcagcaaccc tggcagtgca attgtcagga aggatggggt 840
ggactttttt gtaatcagga tctcaactat tgcacgcatc ataaaccatg tcgcaacggt 900
gcaacctgta ctaatacggg ccaaggtagt tatacctgtt cctgtcggcc tggatacaca 960
ggagctaact gtgaattagg tagcagcggc tgttaaggat cc 1002

<210> SEQ ID NO 86
<211> LENGTH: 828
<212> TYPE: DNA
<213> ORGANISM: Artificial Sequence
<220> FEATURE:
<223> OTHER INFORMATION: synthetic construct

<400> SEQUENCE: 86
catatgaagt atctcttgcc cacggccgct gcagggttgc tgttgcttgc ggcacagccg 60
gctatggcag ctcatcacca tcaccatcac ggtggggaga atctctattt ccaggggttc 120
gtatgtgacg aacactatta cggagagggg tgcagtgtct tctgccgtcc gagagacgat 180
gcctttggtc actttacgtg tggagacaga ggcgaaaaaa tgtgtgatcc aggatggaaa 240
ggacagtatt gtacggaccc catttgcctt cctggctgcg atgaccaaca cgggtattgt 300
gacaaacccg gcgagtgcaa gtgtcgtgtt gggtggcaag ggcgatactg cgacgagtgc 360
ataagatacc ctggttgcct gcacgggacc tgccagcaac cttggcaatg taactgtcaa 420
gaaggatggg gaggcttatt ctgcaaccaa ggctcgtctg gctcctcggg gtttgtatgc 480
gacgaacatt attacggcga ggggtgctca gttttttgtc ggccacgcga tgacgcgttc 540
ggtcatttta cctgcggcga tcgaggcgag aaaatgtgtg atccaggatg gaaggggcag 600
tactgcacag atccgatatg cttaccgggt tgcgatgacc aacatggtta ctgtgataag 660
ccgggggaat gcaagtgcag ggtggggtgg caaggaaggt attgcgatga atgcatccga 720
tatccaggct gtctacacgg aacttgtcag caaccctggc agtgcaattg tcaggaagga 780
tggggtggac ttttttgtaa tcagggtagc agcggctgtt aaggatcc 828

<210> SEQ ID NO 87
<211> LENGTH: 762
<212> TYPE: DNA
<213> ORGANISM: Artificial Sequence
<220> FEATURE:
<223> OTHER INFORMATION: synthetic construct

<400> SEQUENCE: 87
catatgcatc accatcacca tcacggtggg gagaatctct atttccaggg gttcgtatgt 60
gacgaacact attacggaga ggggtgcagt gtcttctgcc gtccgagaga cgatgccttt 120
ggtcacttta cgtgtggaga cagaggcgaa aaaatgtgtg atccaggatg gaaaggacag 180
tattgtacgg accccatttg ccttcctggc tgcgatgacc aacacgggta ttgtgacaaa 240
cccggcgagt gcaagtgtcg tgttgggtgg caagggcgat actgcgacga gtgcataaga 300
taccctggtt gcctgcacgg gacctgccag caaccttggc aatgtaactg tcaagaagga 360
tggggaggct tattctgcaa ccaaggctcg tctggctcct cggggtttgt atgcgacgaa 420
cattattacg gcgaggggtg ctcagttttt tgtcggccac gcgatgacgc gttcggtcat 480
tttacctgcg gcgatcgagg cgagaaaatg tgtgatccag gatggaaggg gcagtactgc 540
acagatccga tatgcttacc gggttgcgat gaccaacatg gttactgtga taagccgggg 600
gaatgcaagt gcagggtggg gtggcaagga aggtattgcg atgaatgcat ccgatatcca 660
ggctgtctac acggaacttg tcagcaaccc tggcagtgca attgtcagga aggatggggt 720
ggactttttt gtaatcaggg tagcagcggc tgttaaggat cc 762

<210> SEQ ID NO 88
<211> LENGTH: 1053
<212> TYPE: DNA
<213> ORGANISM: Artificial Sequence
<220> FEATURE:
<223> OTHER INFORMATION: synthetic construct

<400> SEQUENCE: 88
catatgaagt atctcttgcc cacggccgct gcagggttgc tgttgcttgc ggcacagccg 60
gctatggcag ctcatcacca tcaccatcac ggtggggaga atctctattt ccaggggttc 120
gtatgtgacg aacactatta cggagagggg tgcagtgtct tctgccgtcc gagagacgat 180
gcctttggtc actttacgtg tggagacaga ggcgaaaaaa tgtgtgatcc aggatggaaa 240
ggacagtatt gtacggaccc catttgcctt cctggctgcg atgaccaaca cgggtattgt 300
gacaaacccg gcgagtgcaa gtgtcgtgtt gggtggcaag ggcgatactg cgacgagtgc 360
ataagatacc ctggttgcct gcacgggacc tgccagcaac cttggcaatg taactgtcaa 420
gaaggatggg gaggcctatt ctgcaatcag gacttgaatt actgtactca ccataaacct 480
tgtaggaacg gagcaacttg tacaaacaca ggtcaaggtt catacacatg cagctgtcgt 540
cccggttaca ctggcgcaaa ttgcgagctg ggctcgtctg gctcctcggg gtttgtatgc 600
gacgaacatt attacggcga ggggtgctca gtttttttgtc ggccacgcga tgacgcgttc 660
ggtcatttta cctgcggcga tcgaggcgag aaaatgtgtg atccaggatg gaaggggcag 720
tactgcacag atccgatatg cttaccgggt tgcgatgacc aacatggtta ctgtgataag 780
ccgggggaat gcaagtgcag ggtggggtgg caaggaaggt attgcgatga atgcatccga 840
tatccaggct gtctacacgg aacttgtcag caaccctggc agtgcaattg tcaggaagga 900
tggggtggac ttttttgtaa tcaggatctc aactattgca cgcatcataa accatgtcgc 960

```
aacggtgcaa cctgtactaa tacgggccaa ggtagttata cctgttcctg tcggcctgga   1020

tacacaggag ctaactgtga attataagga tcc                                1053


<210> SEQ ID NO 89
<211> LENGTH: 987
<212> TYPE: DNA
<213> ORGANISM: Artificial Sequence
<220> FEATURE:
<223> OTHER INFORMATION: synthetic construct

<400> SEQUENCE: 89

catatgcatc accatcacca tcacggtggg gagaatctct atttccaggg gttcgtatgt     60

gacgaacact attacggaga ggggtgcagt gtcttctgcc gtccgagaga cgatgccttt    120

ggtcacttta cgtgtggaga cagaggcgaa aaaatgtgtg atccaggatg gaaaggacag    180

tattgtacgg accccatttg ccttcctggc tgcgatgacc aacacgggta ttgtgacaaa    240

cccggcgagt gcaagtgtcg tgttgggtgg caagggcgat actgcgacga gtgcataaga    300

taccctggtt gcctgcacgg gacctgccag caaccttggc aatgtaactg tcaagaagga    360

tggggaggcc tattctgcaa tcaggacttg aattactgta ctcaccataa accttgtagg    420

aacggagcaa cttgtacaaa cacaggtcaa ggttcataca catgcagctg tcgtcccggt    480

tacactggcg caaattgcga gctgggctcg tctggctcct cggggtttgt atgcgacgaa    540

cattattacg gcgaggggtg ctcagttttt tgtcggccac gcgatgacgc gttcggtcat    600

tttacctgcg gcgatcgagg cgagaaaatg tgtgatccag gatggaaggg gcagtactgc    660

acagatccga tatgcttacc gggttgcgat gaccaacatg gttactgtga taagccgggg    720

gaatgcaagt gcagggtggg gtggcaagga aggtattgcg atgaatgcat ccgatatcca    780

ggctgtctac acggaacttg tcagcaaccc tggcagtgca attgtcagga aggatggggt    840

ggactttttt gtaatcagga tctcaactat tgcacgcatc ataaaccatg tcgcaacggt    900

gcaacctgta ctaatacggg ccaaggtagt tatacctgtt cctgtcggcc tggatacaca    960

ggagctaact gtgaattata aggatcc                                        987


<210> SEQ ID NO 90
<211> LENGTH: 813
<212> TYPE: DNA
<213> ORGANISM: Artificial Sequence
<220> FEATURE:
<223> OTHER INFORMATION: synthetic construct

<400> SEQUENCE: 90

catatgaagt atctcttgcc cacggccgct gcagggttgc tgttgcttgc ggcacagccg     60

gctatggcag ctcatcacca tcaccatcac ggtggggaga atctctattt ccaggggttc    120

gtatgtgacg aacactatta cggagagggg tgcagtgtct tctgccgtcc gagagacgat    180

gcctttggtc actttacgtg tggagacaga ggcgaaaaaa tgtgtgatcc aggatggaaa    240

ggacagtatt gtacggaccc catttgcctt cctggctgcg atgaccaaca cgggtattgt    300

gacaaacccg gcgagtgcaa gtgtcgtgtt gggtggcaag ggcgatactg cgacgagtgc    360

ataagatacc ctggttgcct gcacgggacc tgccagcaac cttggcaatg taactgtcaa    420

gaaggatggg gaggcttatt ctgcaaccaa ggctcgtctg gctcctcggg gtttgtatgc    480

gacgaacatt attacggcga ggggtgctca gtttttttgtc ggccacgcga tgacgcgttc    540

ggtcatttta cctgcggcga tcgaggcgag aaaatgtgtg atccaggatg gaaggggcag    600
```

-continued

```
tactgcacag atccgatatg cttaccgggt tgcgatgacc aacatggtta ctgtgataag    660

ccgggggaat gcaagtgcag ggtggggtgg caaggaaggt attgcgatga atgcatccga    720

tatccaggct gtctacacgg aacttgtcag caaccctggc agtgcaattg tcaggaagga    780

tggggtggac ttttttgtaa tcagtaagga tcc                                 813
```

<210> SEQ ID NO 91
<211> LENGTH: 747
<212> TYPE: DNA
<213> ORGANISM: Artificial Sequence
<220> FEATURE:
<223> OTHER INFORMATION: synthetic construct

<400> SEQUENCE: 91

```
catatgcatc accatcacca tcacggtggg gagaatctct atttccaggg gttcgtatgt     60

gacgaacact attacggaga ggggtgcagt gtcttctgcc gtccgagaga cgatgccttt    120

ggtcacttta cgtgtggaga cagaggcgaa aaaatgtgtg atccaggatg gaaaggacag    180

tattgtacgg accccatttg ccttcctggc tgcgatgacc aacacgggta ttgtgacaaa    240

cccggcgagt gcaagtgtcg tgttgggtgg caagggcgat actgcgacga gtgcataaga    300

taccctggtt gcctgcacgg gacctgccag caaccttggc aatgtaactg tcaagaagga    360

tggggaggct tattctgcaa ccaaggctcg tctggctcct cggggtttgt atgcgacgaa    420

cattattacg gcgaggggtg ctcagttttt tgtcggccac gcgatgacgc gttcggtcat    480

tttacctgcg gcgatcgagg cgagaaaatg tgtgatccag gatggaaggg gcagtactgc    540

acagatccga tatgcttacc gggttgcgat gaccaacatg gttactgtga taagccgggg    600

gaatgcaagt gcagggtggg gtggcaagga aggtattgcg atgaatgcat ccgatatcca    660

ggctgtctac acggaacttg tcagcaaccc tggcagtgca attgtcagga aggatggggt    720

ggactttttt gtaatcagta aggatcc                                        747
```

<210> SEQ ID NO 92
<211> LENGTH: 594
<212> TYPE: DNA
<213> ORGANISM: Artificial Sequence
<220> FEATURE:
<223> OTHER INFORMATION: synthetic construct

<400> SEQUENCE: 92

```
catatgaagt atctcttgcc cacggccgct gcagggttgc tgttgcttgc ggcacagccg     60

gctatggcag ctcatcacca tcaccatcac ggtggggaga atctctattt ccaggggttc    120

gtatgtgacg aacactatta cggagagggg tgcagtgtct tctgccgtcc gagagacgat    180

gcctttggtc actttacgtg tggagacaga ggcgaaaaaa tgtgtgatcc aggatggaaa    240

ggacagtatt gtacggaccc catttgcctt cctggctgcg atgaccaaca cgggtattgt    300

gacaaacccg gcgagtgcaa gtgtcgtgtt gggtggcaag ggcgatactg cgacgagtgc    360

ataagatacc ctggttgcct gcacgggacc tgccagcaac cttggcaatg taactgtcaa    420

gaaggatggg gaggcctatt ctgcaatcag gacttgaatt actgtactca ccataaacct    480

tgtaggaacg gagcaacttg tacaaacaca ggtcaaggtt catacacatg cagctgtcgt    540

cccggttaca ctggcgcaaa ttgcgagctg ggtagcagcg gctgttaagg atcc          594
```

<210> SEQ ID NO 93
<211> LENGTH: 528
<212> TYPE: DNA
<213> ORGANISM: Artificial Sequence
<220> FEATURE:
<223> OTHER INFORMATION: synthetic construct

<400> SEQUENCE: 93
catatgcatc accatcacca tcacggtggg gagaatctct atttccaggg gttcgtatgt 60
gacgaacact attacggaga ggggtgcagt gtcttctgcc gtccgagaga cgatgccttt 120
ggtcacttta cgtgtggaga cagaggcgaa aaaatgtgtg atccaggatg gaaaggacag 180
tattgtacgg accccatttg ccttcctggc tgcgatgacc aacacgggta ttgtgacaaa 240
cccggcgagt gcaagtgtcg tgttgggtgg caagggcgat actgcgacga gtgcataaga 300
taccctggtt gcctgcacgg gacctgccag caaccttggc aatgtaactg tcaagaagga 360
tggggaggcc tattctgcaa tcaggacttg aattactgta ctcaccataa accttgtagg 420
aacggagcaa cttgtacaaa cacaggtcaa ggttcataca catgcagctg tcgtcccggt 480
tacactggcg caaattgcga gctgggtagc agcggctgtt aaggatcc 528

<210> SEQ ID NO 94
<211> LENGTH: 474
<212> TYPE: DNA
<213> ORGANISM: Artificial Sequence
<220> FEATURE:
<223> OTHER INFORMATION: synthetic construct

<400> SEQUENCE: 94
catatgaagt atctcttgcc cacggccgct gcagggttgc tgttgcttgc ggcacagccg 60
gctatggcag ctcatcacca tcaccatcac ggtggggaga atctctattt ccaggggttc 120
gtatgtgacg aacactatta cggagagggg tgcagtgtct tctgccgtcc gagagacgat 180
gcctttggtc actttacgtg tggagacaga ggcgaaaaaa tgtgtgatcc aggatggaaa 240
ggacagtatt gtacggaccc catttgcctt cctggctgcg atgaccaaca cgggtattgt 300
gacaaacccg gcgagtgcaa gtgtcgtgtt gggtggcaag ggcgatactg cgacgagtgc 360
ataagatacc ctggttgcct gcacgggacc tgccagcaac cttggcaatg taactgtcaa 420
gaaggatggg gaggcttatt ctgcaaccaa ggtagcagcg gctgttaagg atcc 474

<210> SEQ ID NO 95
<211> LENGTH: 408
<212> TYPE: DNA
<213> ORGANISM: Artificial Sequence
<220> FEATURE:
<223> OTHER INFORMATION: synthetic construct

<400> SEQUENCE: 95
catatgcatc accatcacca tcacggtggg gagaatctct atttccaggg gttcgtatgt 60
gacgaacact attacggaga ggggtgcagt gtcttctgcc gtccgagaga cgatgccttt 120
ggtcacttta cgtgtggaga cagaggcgaa aaaatgtgtg atccaggatg gaaaggacag 180
tattgtacgg accccatttg ccttcctggc tgcgatgacc aacacgggta ttgtgacaaa 240
cccggcgagt gcaagtgtcg tgttgggtgg caagggcgat actgcgacga gtgcataaga 300
taccctggtt gcctgcacgg gacctgccag caaccttggc aatgtaactg tcaagaagga 360
tggggaggct tattctgcaa ccaaggtagc agcggctgtt aaggatcc 408

<210> SEQ ID NO 96
<211> LENGTH: 579
<212> TYPE: DNA
<213> ORGANISM: Artificial Sequence
<220> FEATURE:

<223> OTHER INFORMATION: synthetic construct

<400> SEQUENCE: 96
catatgaagt atctcttgcc cacggccgct gcagggttgc tgttgcttgc ggcacagccg 60
gctatggcag ctcatcacca tcaccatcac ggtggggaga atctctattt ccaggggttc 120
gtatgtgacg aacactatta cggagagggg tgcagtgtct tctgccgtcc gagagacgat 180
gcctttggtc actttacgtg tggagacaga ggcgaaaaaa tgtgtgatcc aggatggaaa 240
ggacagtatt gtacggaccc catttgcctt cctggctgcg atgaccaaca cgggtattgt 300
gacaaacccg gcgagtgcaa gtgtcgtgtt gggtggcaag ggcgatactg cgacgagtgc 360
ataagatacc ctggttgcct gcacgggacc tgccagcaac cttggcaatg taactgtcaa 420
gaaggatggg gaggcctatt ctgcaatcag gacttgaatt actgtactca ccataaacct 480
tgtaggaacg gagcaacttg tacaaacaca ggtcaaggtt catacacatg cagctgtcgt 540
cccggttaca ctggcgcaaa ttgcgagctg taaggatcc 579

<210> SEQ ID NO 97
<211> LENGTH: 513
<212> TYPE: DNA
<213> ORGANISM: Artificial Sequence
<220> FEATURE:
<223> OTHER INFORMATION: synthetic construct

<400> SEQUENCE: 97
catatgcatc accatcacca tcacggtggg gagaatctct atttccaggg gttcgtatgt 60
gacgaacact attacggaga ggggtgcagt gtcttctgcc gtccgagaga cgatgccttt 120
ggtcacttta cgtgtggaga cagaggcgaa aaaatgtgtg atccaggatg gaaaggacag 180
tattgtacgg accccatttg ccttcctggc tgcgatgacc aacacgggta ttgtgacaaa 240
cccggcgagt gcaagtgtcg tgttgggtgg caagggcgat actgcgacga gtgcataaga 300
taccctggtt gcctgcacgg gacctgccag caaccttggc aatgtaactg tcaagaagga 360
tggggaggcc tattctgcaa tcaggacttg aattactgta ctcaccataa accttgtagg 420
aacggagcaa cttgtacaaa cacaggtcaa ggttcataca catgcagctg tcgtcccggt 480
tacactggcg caaattgcga gctgtaagga tcc 513

<210> SEQ ID NO 98
<211> LENGTH: 459
<212> TYPE: DNA
<213> ORGANISM: Artificial Sequence
<220> FEATURE:
<223> OTHER INFORMATION: synthetic construct

<400> SEQUENCE: 98
catatgaagt atctcttgcc cacggccgct gcagggttgc tgttgcttgc ggcacagccg 60
gctatggcag ctcatcacca tcaccatcac ggtggggaga atctctattt ccaggggttc 120
gtatgtgacg aacactatta cggagagggg tgcagtgtct tctgccgtcc gagagacgat 180
gcctttggtc actttacgtg tggagacaga ggcgaaaaaa tgtgtgatcc aggatggaaa 240
ggacagtatt gtacggaccc catttgcctt cctggctgcg atgaccaaca cgggtattgt 300
gacaaacccg gcgagtgcaa gtgtcgtgtt gggtggcaag ggcgatactg cgacgagtgc 360
ataagatacc ctggttgcct gcacgggacc tgccagcaac cttggcaatg taactgtcaa 420
gaaggatggg gaggcttatt ctgcaaccaa taaggatcc 459

<210> SEQ ID NO 99
<211> LENGTH: 393
<212> TYPE: DNA
<213> ORGANISM: Artificial Sequence
<220> FEATURE:
<223> OTHER INFORMATION: synthetic construct

<400> SEQUENCE: 99
catatgcatc accatcacca tcacggtggg gagaatctct atttccaggg gttcgtatgt 60
gacgaacact attacggaga ggggtgcagt gtcttctgcc gtccgagaga cgatgccttt 120
ggtcacttta cgtgtggaga cagaggcgaa aaaatgtgtg atccaggatg gaaaggacag 180
tattgtacgg accccatttg ccttcctggc tgcgatgacc aacacgggta ttgtgacaaa 240
cccggcgagt gcaagtgtcg tgttgggtgg caagggcgat actgcgacga gtgcataaga 300
taccctggtt gcctgcacgg gacctgccag caaccttggc aatgtaactg tcaagaagga 360
tggggaggct tattctgcaa ccaataagga tcc 393

<210> SEQ ID NO 100
<211> LENGTH: 1053
<212> TYPE: DNA
<213> ORGANISM: Artificial Sequence
<220> FEATURE:
<223> OTHER INFORMATION: synthetic construct

<400> SEQUENCE: 100
catatgaaat acttgctacc aaccgcagcg gcaggcttac ttttgttagc agcgcaacct 60
gcgatggcgg cccatcacca tcaccatcac ggtggcgaga atctgtattt ccagggacaa 120
gtgtggagct caggtgtctt cgaacttaag ttgcaagaat tcgtaaataa gaaaggacta 180
ttgggaaacc ggaactgctg tcgtggcggt tcgggcccac cgtgcgcttg caggacattc 240
tttcgggttt gtctgaagca ctatcaggcc tccgtcagcc cggaaccgcc ctgtacttat 300
ggtagtgccg tgacacccgt tctgggtgtc gatagtttct cgctccccga tggtgccggt 360
attgatcctg ctttcagcaa ccccatccgt tttcctttcg ggtttacatg gcctggcacc 420
ttttctctta taattgaggc actccacacg gacagtccag acgatttggc tactgagaac 480
ccggaaaggc tcatatcacg attaacgact caacgtcatc tcacagtggg ggaagagtgg 540
agtcaggacc tgcattcctc tggaagaacg gacttaagat attcgtatcg cttcgtatgc 600
gacgagcatt actatgggga gggctgttcc gttttttgca gaccgagaga tgacgctttt 660
ggtcacttta cttgtggaga caggggggaa aaaatgtgcg accccgggtg gaagggccag 720
tactgtactg accctatatg tttaccagga tgtgatgatc aacatggata ctgcgataag 780
ccaggcgagt gcaaatgtcg ggtagggtgg caaggccgct actgtgatga atgcatccga 840
tatccaggat gcctacatgg gacctgtcaa cagccctggc aatgtaattg ccaggaggga 900 tggggggggcc ttttttgcaa tcaggatcta aactattgta cgcaccacaa accgtgcagg 960
aacggtgcaa catgtaccaa tacagggcaa gggtcataca cgtgttcttg ccgacctgga 1020
tacaccggtg ctaattgcga actataagga tcc 1053

<210> SEQ ID NO 101
<211> LENGTH: 987
<212> TYPE: DNA
<213> ORGANISM: Artificial Sequence
<220> FEATURE:
<223> OTHER INFORMATION: synthetic construct

<400> SEQUENCE: 101

```
catatgcatc accatcacca tcacggtggc gagaatctgt atttccaggg acaagtgtgg     60
agctcaggtg tcttcgaact taagttgcaa gaattcgtaa ataagaaagg actattggga    120
aaccggaact gctgtcgtgg cggttcgggc ccaccgtgcg cttgcaggac attctttcgg    180
gtttgtctga agcactatca ggcctccgtc agcccggaac cgccctgtac ttatggtagt    240
gccgtgacac ccgttctggg tgtcgatagt ttctcgctcc ccgatggtgc cggtattgat    300
cctgctttca gcaaccccat ccgttttcct ttcgggttta catggcctgg caccttttct    360
cttataattg aggcactcca cacggacagt ccagacgatt tggctactga gaacccggaa    420
aggctcatat cacgattaac gactcaacgt catctcacag tgggggaaga gtggagtcag    480
gacctgcatt cctctggaag aacggactta agatattcgt atcgcttcgt atgcgacgag    540
cattactatg gggagggctg ttccgttttt tgcagaccga gagatgacgc ttttggtcac    600
tttacttgtg gagacagggg ggaaaaaatg tgcgaccccg ggtggaaggg ccagtactgt    660
actgacccta tatgtttacc aggatgtgat gatcaacatg gatactgcga taagccaggc    720
gagtgcaaat gtcgggtagg gtggcaaggc cgctactgtg atgaatgcat ccgatatcca    780
ggatgcctac atgggacctg tcaacagccc tggcaatgta attgccagga gggatggggg    840
ggcctttttt gcaatcagga tctaaactat tgtacgcacc acaaaccgtg caggaacggt    900
gcaacatgta ccaatacagg gcaagggtca tacacgtgtt cttgccgacc tggatacacc    960
ggtgctaatt gcgaactata aggatcc                                        987
```

<210> SEQ ID NO 102
<211> LENGTH: 930
<212> TYPE: DNA
<213> ORGANISM: Artificial Sequence
<220> FEATURE:
<223> OTHER INFORMATION: synthetic construct

<400> SEQUENCE: 102

```
catatgaaat acttgctacc aaccgcagcg gcaggcttac ttttgttagc agcgcaacct     60
gcgatggcgg cccatcacca tcaccatcac ggtggcgaga atctgtattt ccagggacaa    120
gtgtggagct caggtgtctt cgaacttaag ttgcaagaat tcgtaaataa gaaaggacta    180
ttgggaaacc ggaactgctg tcgtggcggt tcgggcccac cgtgcgcttg caggacattc    240
tttcgggttt gtctgaagca ctatcaggcc tccgtcagcc cggaaccgcc ctgtacttat    300
ggtagtgccg tgacacccgt tctgggtgtc gatagtttct cgctccccga tggtgccggt    360
attgatcctg ctttcagcaa ccccatccgt tttcctttcg ggtttacatg gcctggcacc    420
ttttctctta taattgaggc actccacacg gacagtccag acgatttggc tactgagaac    480
ccggaaaggc tcatatcacg attaacgact caacgtcatc tcacagtggg ggaagagtgg    540
agtcaggacc tgcattcctc tggaagaacg gacttaagat attcgtatcg cttcgtatgc    600
gacgagcatt actatgggga gggctgttcc gtttttttgca gaccgagaga tgacgctttt    660
ggtcacttta cttgtggaga caggggggaa aaaatgtgcg accccgggtg gaagggccag    720
tactgtactg accctatatg tttaccagga tgtgatgatc aacatggata ctgcgataag    780
ccaggcgagt gcaaatgtcg ggtagggtgg caaggccgct actgtgatga atgcatccga    840
tatccaggat gcctacatgg gacctgtcaa cagccctggc aatgtaattg ccaggaggga    900
tgggggggcc tttttttgcaa ttaaggatcc                                    930
```

<210> SEQ ID NO 103
<211> LENGTH: 864

<212> TYPE: DNA
<213> ORGANISM: Artificial Sequence
<220> FEATURE:
<223> OTHER INFORMATION: synthetic construct

<400> SEQUENCE: 103
catatgcatc accatcacca tcacggtggc gagaatctgt atttccaggg acaagtgtgg 60
agctcaggtg tcttcgaact taagttgcaa gaattcgtaa ataagaaagg actattggga 120
aaccggaact gctgtcgtgg cggttcgggc ccaccgtgcg cttgcaggac attctttcgg 180
gtttgtctga agcactatca ggcctccgtc agcccggaac cgccctgtac ttatggtagt 240
gccgtgacac ccgttctggg tgtcgatagt ttctcgctcc ccgatggtgc cggtattgat 300
cctgctttca gcaaccccat ccgttttcct ttcgggttta catggcctgg cacctttttct 360 cttataattg aggcactcca cacggacagt ccagacgatt tggctactga gaacccggaa 420
aggctcatat cacgattaac gactcaacgt catctcacag tgggggaaga gtggagtcag 480
gacctgcatt cctctggaag aacggactta agatattcgt atcgcttcgt atgcgacgag 540
cattactatg ggagggctg ttccgttttt tgcagaccga gagatgacgc ttttggtcac 600
tttacttgtg gagacagggg ggaaaaaatg tgcgaccccg ggtggaaggg ccagtactgt 660
actgacccta tatgtttacc aggatgtgat gatcaacatg gatactgcga taagccaggc 720
gagtgcaaat gtcgggtagg gtggcaaggc cgctactgtg atgaatgcat ccgatatcca 780
ggatgcctac atgggacctg tcaacagccc tggcaatgta attgccagga gggatggggg 840
ggcctttttt gcaattaagg atcc 864

<210> SEQ ID NO 104
<211> LENGTH: 1101
<212> TYPE: DNA
<213> ORGANISM: Artificial Sequence
<220> FEATURE:
<223> OTHER INFORMATION: synthetic construct

<400> SEQUENCE: 104
catatgcatc accatcacca tcacggtggc gagaatctat acttccaggg ctttgtctgt 60
gacgagcatt actatggtga agggtgctct gtgttttgta ggccaaggga cgatgcgttc 120
ggacatttta cctgcgggga acgaggtgag aaggtttgca acccggggtg gaagggaccc 180
tactgcactg aaccaatttg cttaccaggg tgtgatgagc aacacggatt ctgcgataag 240
ccgggcgaat gtaagtgtcg ggtaggctgg caaggccgct actgcgatga gtgtatacgt 300
tacccaggat gtttacacgg aacatgtcag caaccgtggc agtgtaattg ccaagaaggg 360
tggggagggt tgttctgtaa ccaggggtcc tcaggatcta gtggatttgt ctgtgacgag 420
cattactatg gtgaagggtg ctctgtgttt tgtaggccaa gggacgatgc gttcggacat 480
tttacctgcg gggaacgagg tgagaaggtt tgcaacccgg ggtggaaggg accctactgc 540
actgaaccaa tttgcttacc agggtgtgat gagcaacacg gattctgcga taagccgggc 600
gaatgtaagt gtcgggtagg ctggcaaggc cgctactgcg atgagtgtat acgttaccca 660
ggatgtttac acggaacatg tcagcaaccg tggcagtgta attgccaaga agggtgggga 720
gggttgttct gtaaccaggg gtcctcagga tctagtggat tcgtatgcga tgaacattat 780
tacggagaag gctgtagtgt tttctgtagg cctagagacg atgctttcgg gcattttacg 840
tgcggcgaga gaggcgagaa agtgtgtaat cctgggtgga aagggcccta ttgtacagaa 900
ccaatatgcc ttccaggttg cgacgagcaa cacggttttt gtgacaaacc cggcgaatgt 960
aaatgccggg tcgggtggca gggccgatat tgcgacgaat gcatccgtta tcccggatgt 1020
ctgcatggta cttgccagca accttggcag tgtaactgcc aagaaggatg ggggggtcta 1080
ttttgcaatc aataaggatc c 1101

<210> SEQ ID NO 105
<211> LENGTH: 1455
<212> TYPE: DNA
<213> ORGANISM: Artificial Sequence
<220> FEATURE:
<223> OTHER INFORMATION: synthetic construct

<400> SEQUENCE: 105
catatgcatc accatcacca tcacggtggc gagaatctat acttccaggg ctttgtctgt 60
gacgagcatt actatggtga agggtgctct gtgttttgta ggccaaggga cgatgcgttc 120
ggacatttta cctgcgggga acgaggtgag aaggtttgca acccggggtg gaagggaccc 180
tactgcactg aaccaatttg cttaccaggg tgtgatgagc aacacggatt ctgcgataag 240
ccgggcgaat gtaagtgtcg ggtaggctgg caaggccgct actgcgatga gtgtatacgt 300
tacccaggat gtttacacgg aacatgtcag caaccgtggc agtgtaattg ccaagaaggg 360
tggggagggt tgttctgtaa ccaggggtcc tcaggatcta gtggatttgt ctgtgacgag 420
cattactatg gtgaagggtg ctctgtgttt tgtaggccaa gggacgatgc gttcggacat 480
tttacctgcg gggaacgagg tgagaaggtt tgcaacccgg ggtggaaggg accctactgc 540
actgaaccaa tttgcttacc agggtgtgat gagcaacacg gattctgcga taagccgggc 600
gaatgtaagt gtcgggtagg ctggcaaggc cgctactgcg atgagtgtat acgttaccca 660
ggatgtttac acggaacatg tcagcaaccg tggcagtgta attgccaaga agggtgggga 720
gggttgttct gtaaccaggg gtcctcagga tctagtggat ttgtctgtga cgagcattac 780
tatggtgaag ggtgctctgt gttttgtagg ccaagggacg atgcgttcgg acattttacc 840
tgcggggaac gaggtgagaa ggtttgcaac ccggggtgga agggacccta ctgcactgaa 900
ccaatttgct taccagggtg tgatgagcaa cacggattct gcgataagcc gggcgaatgt 960
aagtgtcggg taggctggca aggccgctac tgcgatgagt gtatacgtta cccaggatgt 1020
ttacacggaa catgtcagca accgtggcag tgtaattgcc aagaagggtg gggagggttg 1080
ttctgtaacc aggggtcctc aggatctagt ggattcgtat gcgatgaaca ttattacgga 1140
gaaggctgta gtgttttctg taggcctaga gacgatgctt tcgggcattt tacgtgcggc 1200
gagagaggcg agaaagtgtg taatcctggg tggaaagggc cctattgtac agaaccaata 1260
tgccttccag gttgcgacga gcaacacggt ttttgtgaca aacccggcga atgtaaatgc 1320
cgggtcgggt ggcagggccg atattgcgac gaatgcatcc gttatcccgg atgtctgcat 1380
ggtacttgcc agcaaccttg gcagtgtaac tgccaagaag gatggggggg tctattttgc 1440
aatcaataag gatcc 1455

<210> SEQ ID NO 106
<211> LENGTH: 1809
<212> TYPE: DNA
<213> ORGANISM: Artificial Sequence
<220> FEATURE:
<223> OTHER INFORMATION: synthetic construct

<400> SEQUENCE: 106
catatgcatc accatcacca tcacggtggc gagaatctat acttccaggg ctttgtctgt 60
gacgagcatt actatggtga agggtgctct gtgttttgta ggccaaggga cgatgcgttc 120
ggacatttta cctgcgggga acgaggtgag aaggtttgca acccggggtg gaagggaccc 180
tactgcactg aaccaatttg cttaccaggg tgtgatgagc aacacggatt ctgcgataag 240
ccgggcgaat gtaagtgtcg ggtaggctgg caaggccgct actgcgatga gtgtatacgt 300
tacccaggat gtttacacgg aacatgtcag caaccgtggc agtgtaattg ccaagaaggg 360
tggggagggt tgttctgtaa ccaggggtcc tcaggatcta gtggatttgt ctgtgacgag 420
cattactatg gtgaagggtg ctctgtgttt tgtaggccaa gggacgatgc gttcggacat 480
tttacctgcg gggaacgagg tgagaaggtt tgcaacccgg ggtggaaggg accctactgc 540
actgaaccaa tttgcttacc agggtgtgat gagcaacacg gattctgcga taagccgggc 600
gaatgtaagt gtcgggtagg ctggcaaggc cgctactgcg atgagtgtat acgttaccca 660
ggatgtttac acggaacatg tcagcaaccg tggcagtgta attgccaaga agggtgggga 720
gggttgttct gtaaccaggg gtcctcagga tctagtggat ttgtctgtga cgagcattac 780
tatggtgaag ggtgctctgt gttttgtagg ccaagggacg atgcgttcgg acattttacc 840
tgcggggaac gaggtgagaa ggtttgcaac ccggggtgga agggacccta ctgcactgaa 900
ccaatttgct taccagggtg tgatgagcaa cacggattct gcgataagcc gggcgaatgt 960
aagtgtcggg taggctggca aggccgctac tgcgatgagt gtatacgtta cccaggatgt 1020
ttacacggaa catgtcagca accgtggcag tgtaattgcc aagaagggtg gggagggttg 1080
ttctgtaacc aggggtcctc aggatctagt ggatttgtct gtgacgagca ttactatggt 1140
gaagggtgct ctgtgttttg taggccaagg gacgatgcgt tcggacattt tacctgcggg 1200
gaacgaggtg agaaggtttg caacccgggg tggaagggac cctactgcac tgaaccaatt 1260
tgcttaccag ggtgtgatga gcaacacgga ttctgcgata agccgggcga atgtaagtgt 1320
cgggtaggct ggcaaggccg ctactgcgat gagtgtatac gttacccagg atgtttacac 1380
ggaacatgtc agcaaccgtg gcagtgtaat tgccaagaag ggtggggagg gttgttctgt 1440
aaccaggggt cctcaggatc tagtggattc gtatgcgatg aacattatta cggagaaggc 1500
tgtagtgttt tctgtaggcc tagagacgat gctttcgggc attttacgtg cggcgagaga 1560
ggcgagaaag tgtgtaatcc tgggtggaaa gggccctatt gtacagaacc aatatgcctt 1620
ccaggttgcg acgagcaaca cggtttttgt gacaaacccg gcgaatgtaa atgccgggtc 1680
gggtggcagg gccgatattg cgacgaatgc atccgttatc ccggatgtct gcatggtact 1740
tgccagcaac cttggcagtg taactgccaa gaaggatggg gggtctatt ttgcaatcaa 1800 taaggatcc 1809

<210> SEQ ID NO 107
<211> LENGTH: 1101
<212> TYPE: DNA
<213> ORGANISM: Artificial Sequence
<220> FEATURE:
<223> OTHER INFORMATION: synthetic construct

<400> SEQUENCE: 107
catatgcatc accatcacca tcacggtggg gagaatctct atttccaggg gttcgtatgt 60
gacgaacact attacggaga ggggtgcagt gtcttctgcc gtccgagaga cgatgccttt 120
ggtcacttta cgtgtggaga cagaggcgaa aaaatgtgtg atccaggatg gaaaggacag 180
tattgtacgg accccatttg ccttcctggc tgcgatgacc aacacgggta ttgtgacaaa 240
cccggcgagt gcaagtgtcg tgttgggtgg caagggcgat actgcgacga gtgcataaga 300

-continued

```
taccctggtt gcctgcacgg gacctgccag caaccttggc aatgtaactg tcaagaagga    360

tggggaggct tattctgcaa ccaaggctcg tctggctcct cggggttcgt atgtgacgaa    420

cactattacg gagaggggtg cagtgtcttc tgccgtccga gagacgatgc ctttggtcac    480

tttacgtgtg gagacagagg cgaaaaaatg tgtgatccag gatggaaagg acagtattgt    540

acggacccca tttgccttcc tggctgcgat gaccaacacg ggtattgtga caaacccggc    600

gagtgcaagt gtcgtgttgg gtggcaaggg cgatactgcg acgagtgcat aagataccct    660

ggttgcctgc acgggacctg ccagcaacct tggcaatgta actgtcaaga aggatgggga    720

ggcttattct gcaaccaagg ctcgtctggc tcctcggggt ttgtatgcga cgaacattat    780

tacggcgagg ggtgctcagt tttttgtcgg ccacgcgatg acgcgttcgg tcattttacc    840

tgcggcgatc gaggcgagaa aatgtgtgat ccaggatgga aggggcagta ctgcacagat    900

ccgatatgct taccgggttg cgatgaccaa catggttact gtgataagcc gggggaatgc    960

aagtgcaggg tggggtggca aggaaggtat tgcgatgaat gcatccgata tccaggctgt   1020

ctacacggaa cttgtcagca accctggcag tgcaattgtc aggaaggatg ggtggactt   1080

ttttgtaatc agtaaggatc c                                             1101
```

<210> SEQ ID NO 108
<211> LENGTH: 1455
<212> TYPE: DNA
<213> ORGANISM: Artificial Sequence
<220> FEATURE:
<223> OTHER INFORMATION: synthetic construct

<400> SEQUENCE: 108

```
catatgcatc accatcacca tcacggtggg gagaatctct atttccaggg gttcgtatgt     60

gacgaacact attacggaga ggggtgcagt gtcttctgcc gtccgagaga cgatgccttt    120

ggtcacttta cgtgtggaga cagaggcgaa aaaatgtgtg atccaggatg gaaaggacag    180

tattgtacgg accccatttg ccttcctggc tgcgatgacc aacacgggta ttgtgacaaa    240

cccggcgagt gcaagtgtcg tgttgggtgg caagggcgat actgcgacga gtgcataaga    300

taccctggtt gcctgcacgg gacctgccag caaccttggc aatgtaactg tcaagaagga    360

tggggaggct tattctgcaa ccaaggctcg tctggctcct cggggttcgt atgtgacgaa    420

cactattacg gagaggggtg cagtgtcttc tgccgtccga gagacgatgc ctttggtcac    480

tttacgtgtg gagacagagg cgaaaaaatg tgtgatccag gatggaaagg acagtattgt    540

acggacccca tttgccttcc tggctgcgat gaccaacacg ggtattgtga caaacccggc    600

gagtgcaagt gtcgtgttgg gtggcaaggg cgatactgcg acgagtgcat aagataccct    660

ggttgcctgc acgggacctg ccagcaacct tggcaatgta actgtcaaga aggatgggga    720

ggcttattct gcaaccaagg ctcgtctggc tcctcggggt ttgtatgcga cgaacattat    780

tacggcgagg ggtgctcagt tttttgtcgg ccacgcgatg acgcgttcgg tcattttacc    840

tgcggcgatc gaggcgagaa aatgtgtgat ccaggatgga aggggcagta ctgcacagat    900

ccgatatgct taccgggttg cgatgaccaa catggttact gtgataagcc gggggaatgc    960

aagtgcaggg tggggtggca aggaaggtat tgcgatgaat gcatccgata tccaggctgt   1020

ctacacggaa cttgtcagca accctggcag tgcaattgtc aggaaggatg ggtggactt   1080

ttttgtaatc agggctcgtc tggctcctcg ggtttgtat gcgacgaaca ttattacggc   1140

gaggggtgct cagttttttg tcggccacgc gatgacgcgt tcggtcattt tacctgcggc   1200

gatcgaggcg agaaaatgtg tgatccagga tggaaggggc agtactgcac agatccgata   1260
```

tgcttaccgg gttgcgatga ccaacatggt tactgtgata agccggggga atgcaagtgc 1320
agggtggggt ggcaaggaag gtattgcgat gaatgcatcc gatatccagg ctgtctacac 1380
ggaacttgtc agcaaccctg gcagtgcaat tgtcaggaag gatggggtgg actttttttgt 1440 aatcagtaag gatcc 1455

<210> SEQ ID NO 109
<211> LENGTH: 1815
<212> TYPE: DNA
<213> ORGANISM: Artificial Sequence
<220> FEATURE:
<223> OTHER INFORMATION: synthetic construct

<400> SEQUENCE: 109
catatggccg cacatcatca tcaccaccat ggtggtgaaa acctgtattt tcagggcttt 60
gtgtgcgatg agcattatta cggtgaaggc tgtagcgtgt tttgtcgacc gcgtgatgac 120
gcatttggcc attttacctg cggtgaccgc ggcgagaaaa tgtgcgatcc gggctggaaa 180
ggtcagtatt gtacagaccc tatttgtctg ccgggctgtg acgatcagca cggctactgt 240
gacaagccgg gcgaatgtaa atgtcgcgtt ggctggcagg gtcgctattg tgatgaatgc 300
atccgctacc cgggttgctt acatggcaca tgccaacagc cttggcaatg taattgtcag 360
gaaggctggg gaggtttatt ttgtaatcaa ggcagttcag ggtctagtgg ttttgtgtgc 420
gacgaacatt actacggcga gggctgcagc gtgttctgtc gacctcgtga cgacgctttt 480
ggccacttca cctgcggcga tcgcggcgag aagatgtgcg atcctggctg gaaaggccag 540
tactgcacag atccgatttg cctgccgggc tgtgatgacc aacatggcta ttgtgataag 600
ccgggcgagt gtaagtgccg tgttggttgg caaggccgct attgcgatga gtgcatccgt 660
tatcctggct gtctgcatgg cacttgtcag caaccgtggc aatgcaactg ccaagagggt 720
tggggtgggt tgttctgcaa tcagggatct tcggggtcct ctggttttgt gtgtgacgaa 780
cactattacg gcgagggctg cagtgtgttc tgccgccctc gtgacgacgc cttcggtcat 840
ttcacctgtg gcgatcgtgg cgaaaagatg tgtgatcctg gttggaaggg tcaatactgt 900
accgacccga tctgtctgcc tggctgcgac gaccagcatg gttactgtga caaaccgggc 960
gagtgtaaat gccgtgttgg ttggcaaggc cgctactgtg atgagtgcat tcgctatcct 1020
ggttgcctgc acggtacctg ccagcaacct tggcaatgca actgccagga aggttggggg 1080
ggcctgttct gcaaccaggg tagctctggc tcatccgggt tcgtttgcga cgagcattat 1140
tacggcgaag gctgtagtgt ttctgccgt cctcgtgacg acgcatttgg ccatttcacc 1200
tgtggtgacc gcggcgaaaa aatgtgtgac cctggctgga agggccaata ttgcactgat 1260
ccgatttgtc tgccgggttg tgacgatcaa cacggctact gcgataagcc gggcgaatgt 1320
aagtgccgtg tgggttggca aggccgctat tgtgatgaat gcattcgcta tccgggctgt 1380
ctgcacggca cttgccagca gccgtggcaa tgtaattgcc aagaaggttg gggcggactc 1440
ttttgtaacc aaggatcatc aggtagtagc ggctttgttt gtgacgagca ctactatggt 1500
gaaggctgca gcgtttttttg tcgtccgcgc gatgatgcct ttggtcattt cacctgtggc 1560
gaccgcggcg agaaaatgtg cgatcctggt tggaaaggcc agtattgcac cgatccgatc 1620
tgcctgccgg gctgcgacga tcaacacggc tattgtgaca aaccgggtga atgcaaatgt 1680
cgtgtgggtt ggcagggccg ctactgcgat gagtgtattc gttatcctgg ttgcctgcat 1740
ggcacatgtc aacagccgtg gcagtgcaat tgtcaggaag gttggggcgg cctgttctgc 1800

-continued aaccagtaag gatcc 1815

<210> SEQ ID NO 110
<211> LENGTH: 2169
<212> TYPE: DNA
<213> ORGANISM: Artificial Sequence
<220> FEATURE:
<223> OTHER INFORMATION: synthetic construct

<400> SEQUENCE: 110
catatggccg cacatcatca tcaccaccat ggtggtgaaa acctgtattt tcagggcttt 60
gtgtgcgatg agcattatta cggtgaaggc tgtagcgtgt tttgtcgacc gcgtgatgac 120
gcatttggcc attttacctg cggtgaccgc ggcgagaaaa tgtgcgatcc gggctggaaa 180
ggtcagtatt gtacagatcc tatctgcctg ccgggttgtg acgatcaaca cggttattgc 240
gacaagccgg gtgaatgcaa gtgtcgtgtg ggctggcagg gccgttattg tgacgaatgt 300
attcgctatc cgggttgctt acacggcaca tgtcaacagc cgtggcagtg taattgccag 360
gaaggttggg gaggtttatt ttgtaatcaa ggttcttccg gatcgagtgg cttcgtgtgt 420
gacgagcact actatggcga gggttgtagc gttttctgtc gcccgcgcga cgacgctttt 480
ggccacttta cctgtggcga tcgcggtgag aaaatgtgtg atcctggttg gaagggccag 540
tactgcacag acccgatttg tctgccgggt tgcgatgatc agcatggcta ctgcgacaaa 600
ccgggtgaat gcaaatgtcg tgtgggctgg cagggccgct attgcgacga gtgtattcgc 660
tacccgggtt gcttacatgg cacatgccaa cagccttggc aatgtaattg tcaggaaggc 720
tggggaggtt tattttgtaa tcaaggcagt tcagggtcta gtggttttgt gtgcgacgaa 780
cattactacg gcgagggctg cagcgtgttc tgtcgacctc gtgacgacgc ttttggccac 840
ttcacctgcg gcgatcgcgg cgagaagatg tgcgatcctg gctggaaagg ccagtactgc 900
acagatccga tttgcctgcc gggctgtgat gaccaacatg gctattgtga taagccgggc 960
gagtgtaagt gccgtgttgg ttggcaaggc cgctattgcg atgagtgcat ccgttatcct 1020
ggctgtctgc atggcacttg tcagcaaccg tggcaatgca actgccaaga gggttggggt 1080
gggttgttct gcaatcaggg atcttcgggg tcctctggtt ttgtgtgtga cgaacactat 1140
tacggcgagg gctgcagtgt gttctgccgc cctcgtgacg acgccttcgg tcatttcacc 1200
tgtggcgatc gtggcgaaaa gatgtgtgat cctggttgga agggtcaata ctgtaccgac 1260
ccgatctgtc tgcctggctg cgacgaccag catggttact gtgacaaacc gggcgagtgt 1320
aaatgccgtg ttggttggca aggccgctac tgtgatgagt gcattcgcta tcctggttgc 1380
ctgcacggta cctgccagca accttggcaa tgcaactgcc aggaaggttg ggggggcctg 1440
ttctgcaacc agggtagctc tggctcatcc gggttcgttt gcgacgagca ttattacggc 1500
gaaggctgta gtgttttctg ccgtcctcgt gacgacgcat ttggccattt cacctgtggt 1560
gaccgcggcg aaaaaatgtg tgaccctggc tggaagggcc aatattgcac tgatccgatt 1620
tgtctgccgg gttgtgacga tcaacacggc tactgcgata agccgggcga atgtaagtgc 1680
cgtgtgggtt ggcaaggccg ctattgtgat gaatgcattc gctatccggg ctgtctgcac 1740
ggcacttgcc agcagccgtg gcaatgtaat tgccaagaag gttggggcgg actcttttgt 1800
aaccaaggat catcaggtag tagcggcttt gtttgtgacg agcactacta tggtgaaggc 1860
tgcagcgttt tttgtcgtcc gcgcgatgat gcctttggtc atttcacctg tggcgaccgc 1920
ggcgagaaaa tgtgcgatcc tggttggaaa ggccagtatt gcaccgatcc gatctgcctg 1980
ccgggctgcg acgatcaaca cggctattgt gacaaaccgg gtgaatgcaa atgtcgtgtg 2040
ggttggcagg gccgctactg cgatgagtgt attcgttatc ctggttgcct gcatggcaca 2100
tgtcaacagc cgtggcagtg caattgtcag gaaggttggg gcggcctgtt ctgcaaccag 2160
taaggatcc 2169

<210> SEQ ID NO 111
<211> LENGTH: 2523
<212> TYPE: DNA
<213> ORGANISM: Artificial Sequence
<220> FEATURE:
<223> OTHER INFORMATION: synthetic construct

<400> SEQUENCE: 111
catatggccg cacatcatca tcaccaccat ggtggtgaaa acctgtattt tcagggcttt 60
gtgtgcgatg agcattatta cggtgaaggc tgtagcgtgt tttgtcgacc gcgtgatgac 120
gcatttggcc attttacctg cggtgaccgc ggcgagaaaa tgtgcgatcc gggctggaaa 180
ggtcagtatt gtacagaccc tatttgtctg ccgggctgtg acgatcagca cggctactgt 240
gacaagccgg gcgaatgtaa atgtcgcgtt ggctggcagg gtcgctattg tgatgaatgc 300
atccgctacc cgggctgcct gcacggtacc tgtcagcagc cgtggcaatg caattgtcaa 360
gagggctggg gaggtttatt ttgtaatcaa ggctcgagtg gaagctcagg ctttgtgtgt 420
gatgagcatt attacggcga aggctgcagc gttttctgtc gcccgcgcga tgacgcattt 480
ggccacttca catgtggcga tcgcggcgaa aagatgtgcg accctggctg gaaaggccaa 540
tattgtacag atcctatctg cctgccgggt tgtgacgatc aacacggtta ttgcgacaag 600
ccgggtgaat gcaagtgtcg tgtgggctgg cagggccgtt attgtgacga atgtattcgc 660
tatccgggtt gcttacacgg cacatgtcaa cagccgtggc agtgtaattg ccaggaaggt 720
tggggaggtt tattttgtaa tcaaggttct tccggatcga gtggcttcgt gtgtgacgag 780
cactactatg gcgagggttg tagcgttttc tgtcgcccgc gcgacgacgc ttttggccac 840
tttacctgtg gcgatcgcgg tgagaaaatg tgtgatcctg gttggaaggg ccagtactgc 900
acagacccga tttgtctgcc gggttgcgat gatcagcatg gctactgcga caaaccgggt 960
gaatgcaaat gtcgtgtggg ctggcagggc cgctattgcg acgagtgtat tcgctacccg 1020
ggttgcttac atggcacatg ccaacagcct tggcaatgta attgtcagga aggctgggga 1080
ggtttatttt gtaatcaagg cagttcaggg tctagtggtt ttgtgtgcga cgaacattac 1140
tacggcgagg gctgcagcgt gttctgtcga cctcgtgacg acgcttttgg ccacttcacc 1200
tgcggcgatc gcggcgagaa gatgtgcgat cctggctgga aaggccagta ctgcacagat 1260
ccgatttgcc tgccgggctg tgatgaccaa catggctatt gtgataagcc gggcgagtgt 1320
aagtgccgtg ttggttggca aggccgctat tgcgatgagt gcatccgtta tcctggctgt 1380
ctgcatggca cttgtcagca accgtggcaa tgcaactgcc aagagggttg gggtgggttg 1440
ttctgcaatc agggatcttc ggggtcctct ggttttgtgt gtgacgaaca ctattacggc 1500
gagggctgca gtgtgttctg ccgccctcgt gacgacgcct tcggtcattt cacctgtggc 1560
gatcgtggcg aaaagatgtg tgatcctggt tggaagggtc aatactgtac cgacccgatc 1620
tgtctgcctg gctgcgacga ccagcatggt tactgtgaca aaccgggcga gtgtaaatgc 1680
cgtgttggtt ggcaaggccg ctactgtgat gagtgcattc gctatcctgg ttgcctgcac 1740
ggtacctgcc agcaaccttg gcaatgcaac tgccaggaag gttggggggg cctgttctgc 1800
aaccagggta gctctggctc atccgggttc gtttgcgacg agcattatta cggcgaaggc 1860

```
tgtagtgttt tctgccgtcc tcgtgacgac gcatttggcc atttcacctg tggtgaccgc   1920

ggcgaaaaaa tgtgtgaccc tggctggaag ggccaatatt gcactgatcc gatttgtctg   1980

ccgggttgtg acgatcaaca cggctactgc gataagccgg gcgaatgtaa gtgccgtgtg   2040

ggttggcaag gccgctattg tgatgaatgc attcgctatc cgggctgtct gcacggcact   2100

tgccagcagc cgtggcaatg taattgccaa gaaggttggg gcggactctt ttgtaaccaa   2160

ggatcatcag gtagtagcgg ctttgtttgt gacgagcact actatggtga aggctgcagc   2220

gttttttgtc gtccgcgcga tgatgccttt ggtcatttca cctgtggcga ccgcggcgag   2280

aaaatgtgcg atcctggttg gaaaggccag tattgcaccg atccgatctg cctgccgggc   2340

tgcgacgatc aacacggcta ttgtgacaaa ccgggtgaat gcaaatgtcg tgtgggttgg   2400

cagggccgct actgcgatga gtgtattcgt tatcctggtt gcctgcatgg cacatgtcaa   2460

cagccgtggc agtgcaattg tcaggaaggt tggggcggcc tgttctgcaa ccagtaagga   2520

tcc                                                                 2523
```

<210> SEQ ID NO 112
<211> LENGTH: 2877
<212> TYPE: DNA
<213> ORGANISM: Artificial Sequence
<220> FEATURE:
<223> OTHER INFORMATION: synthetic construct

<400> SEQUENCE: 112

```
catatggccg cacatcatca tcaccaccat ggtggtgaaa acctgtattt tcagggcttt     60

gtgtgcgatg agcattatta cggtgaaggc tgtagcgtgt tttgtcgacc gcgtgatgac    120

gcatttggcc attttacctg cggtgaccgc ggcgagaaaa tgtgcgatcc gggctggaaa    180

ggtcagtatt gtacagaccc tatttgtctg ccgggctgtg acgatcagca cggctactgt    240

gacaagccgg gcgaatgtaa atgtcgcgtt ggctggcagg gtcgctattg tgatgaatgc    300

atccgctacc cgggctgcct gcacggtacc tgtcagcagc cgtggcaatg caattgtcaa    360

gagggctggg gaggtttatt ttgtaatcaa ggctcgagcg gttcatcggg atttgtttgc    420

gatgaacact attatggtga aggttgtagt gtgttttgcc gcccgcgcga cgacgctttt    480

ggtcatttta catgcggcga tcgcggtgaa aaaatgtgcg atccgggttg gaagggccag    540

tactgtaccg atccgatttg tctgccgggt tgcgatgatc agcatggcta ttgtgacaag    600

ccgggtgagt gcaagtgtcg tgtgggttgg cagggccgct actgtgacga gtgcattcgc    660

tatccgggct gtttacacgg cacctgtcag cagccgtggc aatgtaattg tcaagaaggc    720

tggggaggtt tattttgtaa tcaaggctcg agtggaagct caggctttgt gtgtgatgag    780

cattattacg gcgaaggctg cagcgttttc tgtcgcccgc gcgatgacgc atttggccac    840

ttcacatgtg gcgatcgcgg cgaaaagatg tgcgaccctg gctggaaagg ccaatattgt    900

acagatccta tctgcctgcc gggttgtgac gatcaacacg gttattgcga caagccgggt    960

gaatgcaagt gtcgtgtggg ctggcagggc cgttattgtg acgaatgtat tcgctatccg   1020

ggttgcttac acggcacatg tcaacagccg tggcagtgta attgccagga aggttgggga   1080

ggtttatttt gtaatcaagg ttcttccgga tcgagtggct tcgtgtgtga cgagcactac   1140

tatggcgagg gttgtagcgt ttctgtcgc ccgcgcgacg acgcttttgg ccactttacc    1200

tgtggcgatc gcggtgagaa aatgtgtgat cctggttgga agggccagta ctgcacagac   1260

ccgatttgtc tgccgggttg cgatgatcag catggctact gcgacaaacc gggtgaatgc   1320

aaatgtcgtg tgggctggca gggccgctat tgcgacgagt gtattcgcta cccgggttgc   1380
```

```
ttacatggca catgccaaca gccttggcaa tgtaattgtc aggaaggctg gggaggttta   1440
ttttgtaatc aaggcagttc agggtctagt ggttttgtgt gcgacgaaca ttactacggc   1500
gagggctgca gcgtgttctg tcgacctcgt gacgacgctt ttggccactt cacctgcggc   1560
gatcgcggcg agaagatgtg cgatcctggc tggaaaggcc agtactgcac agatccgatt   1620
tgcctgccgg gctgtgatga ccaacatggc tattgtgata agccgggcga gtgtaagtgc   1680
cgtgttggtt ggcaaggccg ctattgcgat gagtgcatcc gttatcctgg ctgtctgcat   1740
ggcacttgtc agcaaccgtg gcaatgcaac tgccaagagg gttggggtgg gttgttctgc   1800
aatcagggat cttcggggtc ctctggtttt gtgtgtgacg aacactatta cggcgagggc   1860
tgcagtgtgt tctgccgccc tcgtgacgac gccttcggtc atttcacctg tggcgatcgt   1920
ggcgaaaaga tgtgtgatcc tggttggaag ggtcaatact gtaccgaccc gatctgtctg   1980
cctggctgcg acgaccagca tggttactgt gacaaaccgg gcgagtgtaa atgccgtgtt   2040
ggttggcaag gccgctactg tgatgagtgc attcgctatc ctggttgcct gcacggtacc   2100
tgccagcaac cttggcaatg caactgccag gaaggttggg ggggcctgtt ctgcaaccag   2160
ggtagctctg gctcatccgg gttcgtttgc gacgagcatt attacggcga aggctgtagt   2220
gttttctgcc gtcctcgtga cgacgcattt ggccatttca cctgtggtga ccgcggcgaa   2280
aaaatgtgtg accctggctg gaagggccaa tattgcactg atccgatttg tctgccgggt   2340
tgtgacgatc aacacggcta ctgcgataag ccgggcgaat gtaagtgccg tgtgggttgg   2400
caaggccgct attgtgatga atgcattcgc tatccgggct gtctgcacgg cacttgccag   2460
cagccgtggc aatgtaattg ccaagaaggt tggggcggac tcttttgtaa ccaaggatca   2520
tcaggtagta gcggctttgt ttgtgacgag cactactatg gtgaaggctg cagcgttttt   2580
tgtcgtccgc gcgatgatgc ctttggtcat ttcacctgtg gcgaccgcgg cgagaaaatg   2640
tgcgatcctg gttggaaagg ccagtattgc accgatccga tctgcctgcc gggctgcgac   2700
gatcaacacg gctattgtga caaaccgggt gaatgcaaat gtcgtgtggg ttggcagggc   2760
cgctactgcg atgagtgtat tcgttatcct ggttgcctgc atggcacatg tcaacagccg   2820
tggcagtgca attgtcagga aggttggggc ggcctgttct gcaaccagta aggatcc      2877
```

<210> SEQ ID NO 113
<211> LENGTH: 756
<212> TYPE: DNA
<213> ORGANISM: Artificial Sequence
<220> FEATURE:
<223> OTHER INFORMATION: synthetic construct

<400> SEQUENCE: 113

```
catatgcatc accatcacca tcacggtggg gagaatctct atttccaggg gttcgtatgt     60
gacgaacact attacggaga ggggtgcagt gtcttctgcc gtccgagaga cgatgccttt    120
ggtcacttta cgtgtggaga cagaggcgaa aaaatgtgtg atccaggatg gaaaggacag    180
tattgtacgg accccatttg ccttcctggc tgcgatgacc aacacgggta ttgtgacaaa    240
cccggcgagt gcaagtgtcg tgttgggtgg caagggcgat actgcgacga gtgcataaga    300
taccctggtt gcctgcacgg gacctgccag caaccttggc aatgtaactg tcaagaagga    360
tggggaggct tattctgcaa ccaaggcgga ggaggctctg gcggaggtgg ctcttttgta    420
tgcgacgaac attattacgg cgaggggtgc tcagtttttt gtcggccacg cgatgacgcg    480
ttcggtcatt ttacctgcgg cgatcgaggc gagaaaatgt gtgatccagg atggaagggg    540
```

```
cagtactgca cagatccgat atgcttaccg ggttgcgatg accaacatgg ttactgtgat    600

aagccggggg aatgcaagtg cagggtgggg tggcaaggaa ggtattgcga tgaatgcatc    660

cgatatccag gctgtctaca cggaacttgt cagcaaccct ggcagtgcaa ttgtcaggaa    720

ggatggggtg gactttttg taatcagtaa ggatcc                              756
```

<210> SEQ ID NO 114
<211> LENGTH: 771
<212> TYPE: DNA
<213> ORGANISM: Artificial Sequence
<220> FEATURE:
<223> OTHER INFORMATION: synthetic construct

<400> SEQUENCE: 114

```
catatgcatc accatcacca tcacggtggg gagaatctct atttccaggg gttcgtatgt     60

gacgaacact attacggaga ggggtgcagt gtcttctgcc gtccgagaga cgatgccttt    120

ggtcacttta cgtgtggaga cagaggcgaa aaaatgtgtg atccaggatg gaaaggacag    180

tattgtacgg accccatttg ccttcctggc tgcgatgacc aacacgggta ttgtgacaaa    240

cccggcgagt gcaagtgtcg tgttgggtgg caagggcgat actgcgacga gtgcataaga    300

taccctggtt gcctgcacgg gacctgccag caaccttggc aatgtaactg tcaagaagga    360

tggggaggct tattctgcaa ccaaggcgga ggaggctctg gcggaggtgg ctctggcgga    420

ggtggctcat ttgtatgcga cgaacattat tacggcgagg ggtgctcagt tttttgtcgg    480

ccacgcgatg acgcgttcgg tcattttacc tgcggcgatc gaggcgagaa aatgtgtgat    540

ccaggatgga aggggcagta ctgcacagat ccgatatgct taccgggttg cgatgaccaa    600

catggttact gtgataagcc gggggaatgc aagtgcaggg tggggtggca aggaaggtat    660

tgcgatgaat gcatccgata tccaggctgt ctacacggaa cttgtcagca accctggcag    720

tgcaattgtc aggaaggatg gggtggactt ttttgtaatc agtaaggatc c             771
```

<210> SEQ ID NO 115
<211> LENGTH: 786
<212> TYPE: DNA
<213> ORGANISM: Artificial Sequence
<220> FEATURE:
<223> OTHER INFORMATION: synthetic construct

<400> SEQUENCE: 115

```
catatgcatc accatcacca tcacggtggg gagaatctct atttccaggg gttcgtatgt     60

gacgaacact attacggaga ggggtgcagt gtcttctgcc gtccgagaga cgatgccttt    120

ggtcacttta cgtgtggaga cagaggcgaa aaaatgtgtg atccaggatg gaaaggacag    180

tattgtacgg accccatttg ccttcctggc tgcgatgacc aacacgggta ttgtgacaaa    240

cccggcgagt gcaagtgtcg tgttgggtgg caagggcgat actgcgacga gtgcataaga    300

taccctggtt gcctgcacgg gacctgccag caaccttggc aatgtaactg tcaagaagga    360

tggggaggct tattctgcaa ccaaggcgga ggaggctctg gcggaggtgg ctctggcgga    420

ggtggcagcg gcggaggtgg atcatttgta tgcgacgaac attattacgg cgaggggtgc    480

tcagtttttt gtcggccacg cgatgacgcg ttcggtcatt ttacctgcgg cgatcgaggc    540

gagaaaatgt gtgatccagg atggaagggg cagtactgca cagatccgat atgcttaccg    600

ggttgcgatg accaacatgg ttactgtgat aagccggggg aatgcaagtg cagggtgggg    660

tggcaaggaa ggtattgcga tgaatgcatc cgatatccag gctgtctaca cggaacttgt    720

cagcaaccct ggcagtgcaa ttgtcaggaa ggatggggtg gactttttg taatcagtaa    780
```

-continued

| | |
|---|---|
| ggatcc | 786 |

<210> SEQ ID NO 116
<211> LENGTH: 1464
<212> TYPE: DNA
<213> ORGANISM: Artificial Sequence
<220> FEATURE:
<223> OTHER INFORMATION: synthetic construct

<400> SEQUENCE: 116

| | |
|---|---|
| catatgcatc accatcacca tcacggtggg gagaatctct atttccaggg gttcgtatgt | 60 |
| gacgaacact attacggaga ggggtgcagt gtcttctgcc gtccgagaga cgatgccttt | 120 |
| ggtcacttta cgtgtggaga cagaggcgaa aaaatgtgtg atccaggatg gaaaggacag | 180 |
| tattgtacgg accccatttg ccttcctggc tgcgatgacc aacacgggta ttgtgacaaa | 240 |
| cccggcgagt gcaagtgtcg tgttgggtgg caagggcgat actgcgacga gtgcataaga | 300 |
| taccctggtt gcctgcacgg gacctgccag caaccttggc aatgtaactg tcaagaagga | 360 |
| tggggaggct tattctgcaa ccaaggctcg tctggctcct cggggttcgt atgtgacgaa | 420 |
| cactattacg gagaggggtg cagtgtcttc tgccgtccga gagacgatgc ctttggtcac | 480 |
| tttacgtgtg gagacagagg cgaaaaaatg tgtgatccag gatggaaagg acagtattgt | 540 |
| acggacccca tttgccttcc tggctgcgat gaccaacacg ggtattgtga caaacccggc | 600 |
| gagtgcaagt gtcgtgttgg gtggcaaggg cgatactgcg acgagtgcat aagataccct | 660 |
| ggttgcctgc acgggacctg ccagcaacct tggcaatgta actgtcaaga aggatgggga | 720 |
| ggcttattct gcaaccaagg cggaggaggc tctggcggag gtggctcttt tgtatgcgac | 780 |
| gaacattatt acggcgaggg tgtgctcagt ttttgtcggc cacgcgatga cgcgttcggt | 840 |
| cattttacct gcggcgatcg aggcgagaaa atgtgtgatc caggatggaa ggggcagtac | 900 |
| tgcacagatc cgatatgctt accgggttgc gatgaccaac atggttactg tgataagccg | 960 |
| ggggaatgca agtgcagggt ggggtggcaa ggaaggtatt gcgatgaatg catccgatat | 1020 |
| ccaggctgtc tacacggaac ttgtcagcaa ccctggcagt gcaattgtca ggaaggatgg | 1080 |
| ggtggacttt tttgtaatca gggctcgtct ggctcctcgg ggtttgtatg cgacgaacat | 1140 |
| tattacggcg aggggtgctc agttttttgt cggccacgcg atgacgcgtt cggtcatttt | 1200 |
| acctgcggcg atcgaggcga gaaaatgtgt gatccaggat ggaaggggca gtactgcaca | 1260 |
| gatccgatat gcttaccggg ttgcgatgac caacatggtt actgtgataa gccgggggaa | 1320 |
| tgcaagtgca gggtggggtg gcaaggaagg tattgcgatg aatgcatccg atatccaggc | 1380 |
| tgtctacacg gaacttgtca gcaaccctgg cagtgcaatt gtcaggaagg atggggtgga | 1440 |
| cttttttgta atcagtaagg atcc | 1464 |

<210> SEQ ID NO 117
<211> LENGTH: 1479
<212> TYPE: DNA
<213> ORGANISM: Artificial Sequence
<220> FEATURE:
<223> OTHER INFORMATION: synthetic construct

<400> SEQUENCE: 117

| | |
|---|---|
| catatgcatc accatcacca tcacggtggg gagaatctct atttccaggg gttcgtatgt | 60 |
| gacgaacact attacggaga ggggtgcagt gtcttctgcc gtccgagaga cgatgccttt | 120 |
| ggtcacttta cgtgtggaga cagaggcgaa aaaatgtgtg atccaggatg gaaaggacag | 180 |

```
tattgtacgg accccatttg ccttcctggc tgcgatgacc aacacgggta ttgtgacaaa    240
cccggcgagt gcaagtgtcg tgttgggtgg caagggcgat actgcgacga gtgcataaga    300
taccctggtt gcctgcacgg gacctgccag caaccttggc aatgtaactg tcaagaagga    360
tggggaggct tattctgcaa ccaaggctcg tctggctcct cggggttcgt atgtgacgaa    420
cactattacg gagaggggtg cagtgtcttc tgccgtccga gagacgatgc ctttggtcac    480
tttacgtgtg gagacagagg cgaaaaaatg tgtgatccag gatggaaagg acagtattgt    540
acggacccca tttgccttcc tggctgcgat gaccaacacg ggtattgtga caaacccggc    600
gagtgcaagt gtcgtgttgg gtggcaaggg cgatactgcg acgagtgcat aagataccct    660
ggttgcctgc acgggacctg ccagcaacct tggcaatgta actgtcaaga aggatgggga    720
ggcttattct gcaaccaagg cggaggaggc tctggcggag gtggctctgg cggaggtggc    780
tcatttgtat gcgacgaaca ttattacggc gaggggtgct cagttttttg tcggccacgc    840
gatgacgcgt tcggtcattt tacctgcggc gatcgaggcg agaaaatgtg tgatccagga    900
tggaaggggc agtactgcac agatccgata tgcttaccgg gttgcgatga ccaacatggt    960
tactgtgata agccggggga atgcaagtgc agggtggggt ggcaaggaag gtattgcgat   1020
gaatgcatcc gatatccagg ctgtctacac ggaacttgtc agcaaccctg gcagtgcaat   1080
tgtcaggaag gatggggtgg actttttgt aatcagggct cgtctggctc ctcggggttt   1140
gtatgcgacg aacattatta cggcgagggg tgctcagttt tttgtcggcc acgcgatgac   1200
gcgttcggtc attttacctg cggcgatcga ggcgagaaaa tgtgtgatcc aggatggaag   1260
gggcagtact gcacagatcc gatatgctta ccgggttgcg atgaccaaca tggttactgt   1320
gataagccgg gggaatgcaa gtgcagggtg gggtggcaag gaaggtattg cgatgaatgc   1380
atccgatatc caggctgtct acacggaact tgtcagcaac cctggcagtg caattgtcag   1440
gaaggatggg gtggactttt ttgtaatcag taaggatcc                          1479

<210> SEQ ID NO 118
<211> LENGTH: 1493
<212> TYPE: DNA
<213> ORGANISM: Artificial Sequence
<220> FEATURE:
<223> OTHER INFORMATION: synthetic construct

<400> SEQUENCE: 118

catatgcatc accatcacca tcacggtggg gagaatctct atttccaggg gttcgtatgt     60
gacgaacact attacggaga ggggtgcagt gtcttctgcc gtccgagaga cgatgccttt    120
ggtcacttta cgtgtggaga cagaggcgaa aaaatgtgtg atccaggatg gaaaggacag    180
tattgtacgg accccatttg ccttcctggc tgcgatgacc aacacgggta ttgtgacaaa    240
cccggcgagt gcaagtgtcg tgttgggtgg caagggcgat actgcgacga gtgcataaga    300
taccctggtt gcctgcacgg gacctgccag caaccttggc aatgtaactg tcaagaagga    360
tggggaggct tattctgcaa ccaggctcgt ctggctcctc ggggttcgta tgtgacgaac    420
actattacgg agaggggtgc agtgtcttct gccgtccgag agacgatgcc tttggtcact    480
ttacgtgtgg agacagaggc gaaaaaatgt gtgatccagg atggaaagga cagtattgta    540
cggaccccat ttgccttcct ggctgcgatg accaacacgg gtattgtgac aaacccggcg    600
agtgcaagtg tcgtgttggg tggcaagggc gatactgcga cgagtgcata agataccctg    660
gttgcctgca cgggacctgc cagcaacctt ggcaatgtaa ctgtcaagaa ggatggggag    720
gcttattctg caaccaaggc ggaggaggct ctggcggagg tggctctggc ggaggtggca    780
```

```
gcggcggagg tggatcattt gtatgcgacg aacattatta cggcgagggg tgctcagttt    840

tttgtcggcc acgcgatgac gcgttcggtc attttacctg cggcgatcga ggcgagaaaa    900

tgtgtgatcc aggatggaag gggcagtact gcacagatcc gatatgctta ccgggttgcg    960

atgaccaaca tggttactgt gataagccgg gggaatgcaa gtgcagggtg gggtggcaag   1020

gaaggtattg cgatgaatgc atccgatatc caggctgtct acacggaact tgtcagcaac   1080

cctggcagtg caattgtcag gaaggatggg gtggactttt ttgtaatcag ggctcgtctg   1140

gctcctcggg gtttgtatgc gacgaacatt attacggcga ggggtgctca gtttttttgtc  1200

ggccacgcga tgacgcgttc ggtcatttta cctgcggcga tcgaggcgag aaaatgtgtg   1260

atccaggatg gaaggggcag tactgcacag atccgatatg cttaccgggt tgcgatgacc   1320

aacatggtta ctgtgataag ccgggggaat gcaagtgcag ggtggggtgg caaggaaggt   1380

attgcgatga atgcatccga tatccaggct gtctacacgg aacttgtcag caaccctggc   1440

agtgcaattg tcaggaagga tggggtggac tttttttgtaa tcagtaagga tcc          1493
```

<210> SEQ ID NO 119
<211> LENGTH: 435
<212> TYPE: DNA
<213> ORGANISM: Artificial Sequence
<220> FEATURE:
<223> OTHER INFORMATION: synthetic construct

<400> SEQUENCE: 119

```
catatggcas ctcatcacca tcaccatcac ggtggggaga atctctattt ccaggggttc     60

gtatgtgacg aacactatta cggagagggg tgcagtgtct tctgccgtcc gagagacgat    120

gcctttggtc actttacstg tggagacaga ggcgaaaaaa tgtgtgatcc aggatggaag    180

gggcagtact gcacagatcc gatatgctta ccgggttgcg atgaccaaca tggttactgt    240

gataagccgg gggaatgcaa gtgcagggtg gggtggcaag gaaggtattg cgatgaatgc    300

atccgatatc caggctgtct acacggaact tgtcagcaac cctggcagtg caattgtcag    360

gaaggatggg gtggactttt ttgtaatcag ggtagcagcg gcgactacaa ggatgacgac    420

gataagtaag gatcc                                                     435
```

<210> SEQ ID NO 120
<211> LENGTH: 1491
<212> TYPE: DNA
<213> ORGANISM: Artificial Sequence
<220> FEATURE:
<223> OTHER INFORMATION: synthetic construct

<400> SEQUENCE: 120

```
catatgcatc accatcacca tcacggtggg gagaatctct atttccaggg gttcgtatgt     60

gacgaacact attacggaga ggggtgcagt gtcttctgcc gtccgagaga cgatgccttt    120

ggtcacttta cgtgtggaga cagaggcgaa aaaatgtgtg atccaggatg gaaaggacag    180

tattgtacgg accccatttg ccttcctggc tgcgatgacc aacacgggta ttgtgacaaa    240

cccggcgagt gcaagtgtcg tgttgggtgg caagggcgat actgcgacga gtgcataaga    300

taccctggtt gcctgcacgg gacctgccag caaccttggc aatgtaactg tcaagaagga    360

tggggaggct tattctgcaa ccaaggctcg tctggctcct cggggttcgt atgtgacgaa    420

cactattacg gagaggggtg cagtgtcttc tgccgtccga gagacgatgc ctttggtcac    480

tttacgtgtg gagacagagg cgaaaaaatg tgtgatccag gatggaaagg acagtattgt    540
```

```
acggacccca tttgccttcc tggctgcgat gaccaacacg ggtattgtga caaacccggc    600
gagtgcaagt gtcgtgttgg gtggcaaggg cgatactgcg acgagtgcat aagataccct    660
ggttgcctgc acgggacctg ccagcaacct tggcaatgta actgtcaaga aggatgggga    720
ggcttattct gcaaccaagg ctcgtctggc tcctcggggt ttgtatgcga cgaacattat    780
tacggcgagg ggtgctcagt tttttgtcgg ccacgcgatg acgcgttcgg tcattttacc    840
tgcggcgatc gaggcgagaa aatgtgtgat ccaggatgga aggggcagta ctgcacagat    900
ccgatatgct taccgggttg cgatgaccaa catggttact gtgataagcc gggggaatgc    960
aagtgcaggg tggggtggca aggaaggtat tgcgatgaat gcatccgata tccaggctgt   1020
ctacacggaa cttgtcagca accctggcag tgcaattgtc aggaaggatg gggtggactt   1080
ttttgtaatc agggctcgtc tggctcctcg gggtttgtat gcgacgaaca ttattacggc   1140
gaggggtgct cagtttttttg tcggccacgc gatgacgcgt tcggtcattt tacctgcggc   1200
gatcgaggcg agaaaatgtg tgatccagga tggaaggggc agtactgcac agatccgata   1260
tgcttaccgg gttgcgatga ccaacatggt tactgtgata agccggggga atgcaagtgc   1320
agggtggggt ggcaaggaag gtattgcgat gaatgcatcc gatatccagg ctgtctacac   1380
ggaacttgtc agcaaccctg gcagtgcaat tgtcaggaag gatggggtgg actttttttgt   1440
aatcagggta gcagcggcga ctacaaggat gacgacgata agtaaggatc c             1491
```

<210> SEQ ID NO 121
<211> LENGTH: 2877
<212> TYPE: DNA
<213> ORGANISM: Artificial Sequence
<220> FEATURE:
<223> OTHER INFORMATION: synthetic construct

<400> SEQUENCE: 121

```
catatggccg cacatcatca tcaccaccat ggtggtgaaa acctgtattt tcagggcttt     60
gtgtgcgatg agcattatta cggtgaaggc tgtagcgtgt tttgtcgacc gcgtgatgac    120
gcatttggcc attttacctg cggtgaccgc ggcgagaaaa tgtgcgatcc gggctggaaa    180
ggtcagtatt gtacagaccc tatttgtctg ccgggctgtg acgatcagca cggctactgt    240
gacaagccgg gcgaatgtaa atgtcgcgtt ggctggcagg gtcgctattg tgatgaatgc    300
atccgctacc cgggctgcct gcacggtacc tgtcagcagc cgtggcaatg caattgtcaa    360
gagggctggg gaggtttatt ttgtaatcaa ggctcgagcg gttcatcggg atttgtttgc    420
gatgaacact attatggtga aggttgtagt gtgttttgcc gcccgcgcga cgacgctttt    480
ggtcatttta catgcggcga tcgcggtgaa aaaatgtgcg atccgggttg gaagggccag    540
tactgtaccg atccgatttg tctgccgggt tgcgatgatc agcatggcta ttgtgacaag    600
ccgggtgagt gcaagtgtcg tgtgggttgg cagggccgct actgtgacga gtgcattcgc    660
tatccgggct gtttacacgg cacctgtcag cagccgtggc aatgtaattg tcaagaaggc    720
tggggaggtt tattttgtaa tcaaggctcg agtggaagct caggctttgt gtgtgatgag    780
cattattacg gcgaaggctg cagcgttttc tgtcgcccgc gcgatgacgc atttggccac    840
ttcacatgtg gcgatcgcgg cgaaaaagatg tgcgaccctg gctggaaagg ccaatattgt    900
acagatccta tctgcctgcc gggttgtgac gatcaacacg gttattgcga caagccgggt    960
gaatgcaagt gtcgtgtggg ctggcagggc cgttattgtg acgaatgtat tcgctatccg   1020
ggttgcttac acggcacatg tcaacagccg tggcagtgta attgccagga aggttgggga   1080
ggtttatttt gtaatcaagg ttcttccgga tcgagtggct tcgtgtgtga cgagcactac   1140
```

```
tatggcgagg gttgtagcgt tttctgtcgc ccgcgcgacg acgcttttgg ccactttacc   1200
tgtggcgatc gcggtgagaa aatgtgtgat cctggttgga agggccagta ctgcacagac   1260
ccgatttgtc tgccgggttg cgatgatcag catggctact gcgacaaacc gggtgaatgc   1320
aaatgtcgtg tgggctggca gggccgctat tgcgacgagt gtattcgcta cccgggttgc   1380
ttacatggca catgccaaca gccttggcaa tgtaattgtc aggaaggctg ggaggtttta   1440
ttttgtaatc aaggcagttc agggtctagt ggttttgtgt gcgacgaaca ttactacggc   1500
gagggctgca gcgtgttctg tcgacctcgt gacgacgctt ttggccactt cacctgcggc   1560
gatcgcggcg agaagatgtg cgatcctggc tggaaaggcc agtactgcac agatccgatt   1620
tgcctgccgg gctgtgatga ccaacatggc tattgtgata agccgggcga gtgtaagtgc   1680
cgtgttggtt ggcaaggccg ctattgcgat gagtgcatcc gttatcctgg ctgtctgcat   1740
ggcacttgtc agcaaccgtg gcaatgcaac tgccaagagg gttggggtgg gttgttctgc   1800
aatcagggat cttcggggtc ctctggtttt gtgtgtgacg aacactatta cggcgagggc   1860
tgcagtgtgt tctgccgccc tcgtgacgac gccttcggtc atttcacctg tggcgatcgt   1920
ggcgaaaaga tgtgtgatcc tggttggaag ggtcaatact gtaccgaccc gatctgtctg   1980
cctggctgcg acgaccagca tggttactgt gacaaaccgg gcgagtgtaa atgccgtgtt   2040
ggttggcaag gccgctactg tgatgagtgc attcgctatc ctggttgcct gcacggtacc   2100
tgccagcaac cttggcaatg caactgccag gaaggttggg ggggcctgtt ctgcaaccag   2160
ggtagctctg gctcatccgg gttcgtttgc gacgagcatt attacggcga aggctgtagt   2220
gttttctgcc gtcctcgtga cgacgcattt ggccatttca cctgtggtga ccgcggcgaa   2280
aaaatgtgtg accctggctg gaagggccaa tattgcactg atccgatttg tctgccgggt   2340
tgtgacgatc aacacggcta ctgcgataag ccgggcgaat gtaagtgccg tgtgggttgg   2400
caaggccgct attgtgatga atgcattcgc tatccgggct gtctgcacgg cacttgccag   2460
cagccgtggc aatgtaattg ccaagaaggt tggggcggac tcttttgtaa ccaaggatca   2520
tcaggtagta gcggctttgt ttgtgacgag cactactatg gtgaaggctg cagcgttttt   2580
tgtcgtccgc gcgatgatgc ctttggtcat ttcacctgtg gcgaccgcgg cgagaaaatg   2640
tgcgatcctg gttggaaagg ccagtattgc accgatccga tctgcctgcc gggctgcgac   2700
gatcaacacg gctattgtga caaaccgggt gaatgcaaat gtcgtgtggg ttggcagggc   2760
cgctactgcg atgagtgtat tcgttatcct ggttgcctgc atggcacatg tcaacagccg   2820
tggcagtgca attgtcagga aggttggggc ggcctgttct gcaaccagta aggatcc      2877
```

```
<210> SEQ ID NO 122
<211> LENGTH: 955
<212> TYPE: PRT
<213> ORGANISM: Artificial Sequence
<220> FEATURE:
<223> OTHER INFORMATION: synthetic construct

<400> SEQUENCE: 122

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
```

-continued

```
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
            260                 265                 270

Arg Asp Asp Ala Phe Gly His Phe Thr Cys Gly Asp Arg Gly Glu Lys
        275                 280                 285

Met Cys Asp Pro Gly Trp Lys Gly Gln Tyr Cys Thr Asp Pro Ile Cys
    290                 295                 300

Leu Pro Gly Cys Asp Asp Gln His Gly Tyr Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350

Asn Cys Gln Glu Gly Trp Gly Gly Leu Phe Cys Asn Gln Gly Ser Ser
        355                 360                 365

Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

Gly Asp Arg Gly Glu Lys Met Cys Asp Pro Gly Trp Lys Gly Gln Tyr
                405                 410                 415

Cys Thr Asp Pro Ile Cys Leu Pro Gly Cys Asp Asp Gln His Gly Tyr
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
    450                 455                 460

Gln Gln Pro Trp Gln Cys Asn Cys Gln Glu Gly Trp Gly Gly Leu Phe
465                 470                 475                 480
```

-continued

```
Cys Asn Gln Gly Ser Ser Gly Ser Ser Gly Phe Val Cys Asp Glu His
                485                 490                 495

Tyr Tyr Gly Glu Gly Cys Ser Val Phe Cys Arg Pro Arg Asp Asp Ala
            500                 505                 510

Phe Gly His Phe Thr Cys Gly Asp Arg Gly Glu Lys Met Cys Asp Pro
        515                 520                 525

Gly Trp Lys Gly Gln Tyr Cys Thr Asp Pro Ile Cys Leu Pro Gly Cys
    530                 535                 540

Asp Asp Gln His Gly Tyr Cys Asp Lys Pro Gly Glu Cys Lys Cys Arg
545                 550                 555                 560

Val Gly Trp Gln Gly Arg Tyr Cys Asp Glu Cys Ile Arg Tyr Pro Gly
                565                 570                 575

Cys Leu His Gly Thr Cys Gln Gln Pro Trp Gln Cys Asn Cys Gln Glu
            580                 585                 590

Gly Trp Gly Gly Leu Phe Cys Asn Gln Gly Ser Ser Gly Ser Ser Gly
        595                 600                 605

Phe Val Cys Asp Glu His Tyr Tyr Gly Glu Gly Cys Ser Val Phe Cys
    610                 615                 620

Arg Pro Arg Asp Asp Ala Phe Gly His Phe Thr Cys Gly Asp Arg Gly
625                 630                 635                 640

Glu Lys Met Cys Asp Pro Gly Trp Lys Gly Gln Tyr Cys Thr Asp Pro
                645                 650                 655

Ile Cys Leu Pro Gly Cys Asp Asp Gln His Gly Tyr Cys Asp Lys Pro
            660                 665                 670

Gly Glu Cys Lys Cys Arg Val Gly Trp Gln Gly Arg Tyr Cys Asp Glu
        675                 680                 685

Cys Ile Arg Tyr Pro Gly Cys Leu His Gly Thr Cys Gln Gln Pro Trp
    690                 695                 700

Gln Cys Asn Cys Gln Glu Gly Trp Gly Gly Leu Phe Cys Asn Gln Gly
705                 710                 715                 720

Ser Ser Gly Ser Ser Gly Phe Val Cys Asp Glu His Tyr Tyr Gly Glu
                725                 730                 735

Gly Cys Ser Val Phe Cys Arg Pro Arg Asp Asp Ala Phe Gly His Phe
            740                 745                 750

Thr Cys Gly Asp Arg Gly Glu Lys Met Cys Asp Pro Gly Trp Lys Gly
        755                 760                 765

Gln Tyr Cys Thr Asp Pro Ile Cys Leu Pro Gly Cys Asp Asp Gln His
    770                 775                 780

Gly Tyr Cys Asp Lys Pro Gly Glu Cys Lys Cys Arg Val Gly Trp Gln
785                 790                 795                 800

Gly Arg Tyr Cys Asp Glu Cys Ile Arg Tyr Pro Gly Cys Leu His Gly
                805                 810                 815

Thr Cys Gln Gln Pro Trp Gln Cys Asn Cys Gln Glu Gly Trp Gly Gly
            820                 825                 830

Leu Phe Cys Asn Gln Gly Ser Ser Gly Ser Ser Gly Phe Val Cys Asp
        835                 840                 845

Glu His Tyr Tyr Gly Glu Gly Cys Ser Val Phe Cys Arg Pro Arg Asp
    850                 855                 860

Asp Ala Phe Gly His Phe Thr Cys Gly Asp Arg Gly Glu Lys Met Cys
865                 870                 875                 880

Asp Pro Gly Trp Lys Gly Gln Tyr Cys Thr Asp Pro Ile Cys Leu Pro
                885                 890                 895
```

-continued

```
Gly Cys Asp Asp Gln His Gly Tyr Cys Asp Lys Pro Gly Glu Cys Lys
            900                 905                 910

Cys Arg Val Gly Trp Gln Gly Arg Tyr Cys Asp Glu Cys Ile Arg Tyr
        915                 920                 925

Pro Gly Cys Leu His Gly Thr Cys Gln Gln Pro Trp Gln Cys Asn Cys
    930                 935                 940

Gln Glu Gly Trp Gly Gly Leu Phe Cys Asn Gln
945                 950                 955
```

<210> SEQ ID NO 123
<211> LENGTH: 2523
<212> TYPE: DNA
<213> ORGANISM: Artificial Sequence
<220> FEATURE:
<223> OTHER INFORMATION: synthetic construct

<400> SEQUENCE: 123

```
catatggccg cacatcatca tcaccaccat ggtggtgaaa acctgtattt tcagggcttt      60

gtgtgcgatg agcattatta cggtgaaggc tgtagcgtgt tttgtcgacc gcgtgatgac     120

gcatttggcc attttacctg cggtgaccgc ggcgagaaaa tgtgcgatcc gggctggaaa     180

ggtcagtatt gtacagaccc tatttgtctg ccgggctgtg acgatcagca cggctactgt     240

gacaagccgg gcgaatgtaa atgtcgcgtt ggctggcagg gtcgctattg tgatgaatgc     300

atccgctacc cgggctgcct gcacggtacc tgtcagcagc cgtggcaatg caattgtcaa     360

gagggctggg gaggtttatt ttgtaatcaa ggctcgagtg gaagctcagg ctttgtgtgt     420

gatgagcatt attacggcga aggctgcagc gttttctgtc gcccgcgcga tgacgcattt     480

ggccacttca catgtggcga tcgcggcgaa aagatgtgcg accctggctg gaaaggccaa     540

tattgtacag atcctatctg cctgccgggt tgtgacgatc aacacggtta ttgcgacaag     600

ccgggtgaat gcaagtgtcg tgtgggctgg cagggccgtt attgtgacga atgtattcgc     660

tatccgggtt gcttacacgg cacatgtcaa cagccgtggc agtgtaattg ccaggaaggt     720

tggggaggtt tattttgtaa tcaaggttct tccggatcga gtggcttcgt gtgtgacgag     780

cactactatg gcgagggttg tagcgttttc tgtcgcccgc gcgacgacgc ttttggccac     840

tttacctgtg gcgatcgcgg tgagaaaatg tgtgatcctg gttggaaggg ccagtactgc     900

acagacccga tttgtctgcc gggttgcgat gatcagcatg gctactgcga caaaccgggt     960

gaatgcaaat gtcgtgtggg ctggcagggc cgctattgcg acgagtgtat tcgctacccg    1020

ggttgcttac atggcacatg ccaacagcct tggcaatgta attgtcagga aggctgggga    1080

ggtttatttt gtaatcaagg cagttcaggg tctagtggtt ttgtgtgcga cgaacattac    1140

tacggcgagg gctgcagcgt gttctgtcga cctcgtgacg acgcttttgg ccacttcacc    1200

tgcggcgatc gcggcgagaa gatgtgcgat cctggctgga aaggccagta ctgcacagat    1260

ccgatttgcc tgccgggctg tgatgaccaa catggctatt gtgataagcc gggcgagtgt    1320

aagtgccgtg ttggttggca aggccgctat tgcgatgagt gcatccgtta tcctggctgt    1380

ctgcatggca cttgtcagca accgtggcaa tgcaactgcc aagagggttg ggtgggttg    1440

ttctgcaatc agggatcttc ggggtcctct ggttttgtgt gtgacgaaca ctattacggc    1500

gagggctgca gtgtgttctg ccgccctcgt gacgacgcct tcggtcattt cacctgtggc    1560

gatcgtggcg aaaagatgtg tgatcctggt tggaagggtc aatactgtac cgacccgatc    1620

tgtctgcctg gctgcgacga ccagcatggt tactgtgaca aaccgggcga gtgtaaatgc    1680

cgtgttggtt ggcaaggccg ctactgtgat gagtgcattc gctatcctgg ttgcctgcac    1740
```

```
ggtacctgcc agcaaccttg gcaatgcaac tgccaggaag gttggggggg cctgttctgc   1800

aaccagggta gctctggctc atccgggttc gtttgcgacg agcattatta cggcgaaggc   1860

tgtagtgttt tctgccgtcc tcgtgacgac gcatttggcc atttcacctg tggtgaccgc   1920

ggcgaaaaaa tgtgtgaccc tggctggaag ggccaatatt gcactgatcc gatttgtctg   1980

ccgggttgtg acgatcaaca cggctactgc gataagccgg gcgaatgtaa gtgccgtgtg   2040

ggttggcaag gccgctattg tgatgaatgc attcgctatc cgggctgtct gcacggcact   2100

tgccagcagc cgtggcaatg taattgccaa gaaggttggg gcggactctt ttgtaaccaa   2160

ggatcatcag gtagtagcgg ctttgtttgt gacgagcact actatggtga aggctgcagc   2220

gtttttgtc gtccgcgcga tgatgccttt ggtcatttca cctgtggcga ccgcggcgag   2280

aaaatgtgcg atcctggttg gaaaggccag tattgcaccg atccgatctg cctgccgggc   2340

tgcgacgatc aacacggcta ttgtgacaaa ccgggtgaat gcaaatgtcg tgtgggttgg   2400

cagggccgct actgcgatga gtgtattcgt tatcctggtt gcctgcatgg cacatgtcaa   2460

cagccgtggc agtgcaattg tcaggaaggt tggggcggcc tgttctgcaa ccagtaagga   2520

tcc                                                                 2523
```

<210> SEQ ID NO 124
<211> LENGTH: 837
<212> TYPE: PRT
<213> ORGANISM: Artificial Sequence
<220> FEATURE:
<223> OTHER INFORMATION: synthetic construct

<400> SEQUENCE: 124

```
Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
```

```
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
            260                 265                 270

Arg Asp Asp Ala Phe Gly His Phe Thr Cys Gly Asp Arg Gly Glu Lys
        275                 280                 285

Met Cys Asp Pro Gly Trp Lys Gly Gln Tyr Cys Thr Asp Pro Ile Cys
    290                 295                 300

Leu Pro Gly Cys Asp Asp Gln His Gly Tyr Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350

Asn Cys Gln Glu Gly Trp Gly Gly Leu Phe Cys Asn Gln Gly Ser Ser
        355                 360                 365

Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

Gly Asp Arg Gly Glu Lys Met Cys Asp Pro Gly Trp Lys Gly Gln Tyr
                405                 410                 415

Cys Thr Asp Pro Ile Cys Leu Pro Gly Cys Asp Asp Gln His Gly Tyr
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
    450                 455                 460

Gln Gln Pro Trp Gln Cys Asn Cys Gln Glu Gly Trp Gly Gly Leu Phe
465                 470                 475                 480

Cys Asn Gln Gly Ser Ser Gly Ser Ser Gly Phe Val Cys Asp Glu His
                485                 490                 495

Tyr Tyr Gly Glu Gly Cys Ser Val Phe Cys Arg Pro Arg Asp Asp Ala
            500                 505                 510

Phe Gly His Phe Thr Cys Gly Asp Arg Gly Glu Lys Met Cys Asp Pro
        515                 520                 525

Gly Trp Lys Gly Gln Tyr Cys Thr Asp Pro Ile Cys Leu Pro Gly Cys
    530                 535                 540

Asp Asp Gln His Gly Tyr Cys Asp Lys Pro Gly Glu Cys Lys Cys Arg
545                 550                 555                 560

Val Gly Trp Gln Gly Arg Tyr Cys Asp Glu Cys Ile Arg Tyr Pro Gly
                565                 570                 575

Cys Leu His Gly Thr Cys Gln Gln Pro Trp Gln Cys Asn Cys Gln Glu
            580                 585                 590

Gly Trp Gly Gly Leu Phe Cys Asn Gln Gly Ser Ser Gly Ser Ser Gly
        595                 600                 605

Phe Val Cys Asp Glu His Tyr Tyr Gly Glu Gly Cys Ser Val Phe Cys
    610                 615                 620

Arg Pro Arg Asp Asp Ala Phe Gly His Phe Thr Cys Gly Asp Arg Gly
625                 630                 635                 640
```

```
Glu Lys Met Cys Asp Pro Gly Trp Lys Gly Gln Tyr Cys Thr Asp Pro
                645                 650                 655

Ile Cys Leu Pro Gly Cys Asp Asp Gln His Gly Tyr Cys Asp Lys Pro
            660                 665                 670

Gly Glu Cys Lys Cys Arg Val Gly Trp Gln Gly Arg Tyr Cys Asp Glu
        675                 680                 685

Cys Ile Arg Tyr Pro Gly Cys Leu His Gly Thr Cys Gln Gln Pro Trp
    690                 695                 700

Gln Cys Asn Cys Gln Glu Gly Trp Gly Gly Leu Phe Cys Asn Gln Gly
705                 710                 715                 720

Ser Ser Gly Ser Ser Gly Phe Val Cys Asp Glu His Tyr Tyr Gly Glu
                725                 730                 735

Gly Cys Ser Val Phe Cys Arg Pro Arg Asp Asp Ala Phe Gly His Phe
            740                 745                 750

Thr Cys Gly Asp Arg Gly Glu Lys Met Cys Asp Pro Gly Trp Lys Gly
        755                 760                 765

Gln Tyr Cys Thr Asp Pro Ile Cys Leu Pro Gly Cys Asp Asp Gln His
    770                 775                 780

Gly Tyr Cys Asp Lys Pro Gly Glu Cys Lys Cys Arg Val Gly Trp Gln
785                 790                 795                 800

Gly Arg Tyr Cys Asp Glu Cys Ile Arg Tyr Pro Gly Cys Leu His Gly
                805                 810                 815

Thr Cys Gln Gln Pro Trp Gln Cys Asn Cys Gln Glu Gly Trp Gly Gly
            820                 825                 830

Leu Phe Cys Asn Gln
        835
```

<210> SEQ ID NO 125
<211> LENGTH: 2169
<212> TYPE: DNA
<213> ORGANISM: Artificial Sequence
<220> FEATURE:
<223> OTHER INFORMATION: synthetic construct

<400> SEQUENCE: 125

```
catatggccg cacatcatca tcaccaccat ggtggtgaaa acctgtattt tcagggcttt     60

gtgtgcgatg agcattatta cggtgaaggc tgtagcgtgt tttgtcgacc gcgtgatgac    120

gcatttggcc attttacctg cggtgaccgc ggcgagaaaa tgtgcgatcc gggctggaaa    180

ggtcagtatt gtacagatcc tatctgcctg ccgggttgtg acgatcaaca cggttattgc    240

gacaagccgg gtgaatgcaa gtgtcgtgtg ggctggcagg gccgttattg tgacgaatgt    300

attcgctatc cgggttgctt acacggcaca tgtcaacagc cgtggcagtg taattgccag    360

gaaggttggg gaggtttatt ttgtaatcaa ggttcttccg gatcgagtgg cttcgtgtgt    420

gacgagcact actatggcga gggttgtagc gttttctgtc gcccgcgcga cgacgctttt    480

ggccacttta cctgtggcga tcgcggtgag aaaatgtgtg atcctggttg gaagggccag    540

tactgcacag acccgatttg tctgccgggt tgcgatgatc agcatggcta ctgcgacaaa    600

ccgggtgaat gcaaatgtcg tgtgggctgg cagggccgct attgcgacga gtgtattcgc    660

tacccgggtt gcttacatgg cacatgccaa cagccttggc aatgtaattg tcaggaaggc    720

tggggaggtt tattttgtaa tcaaggcagt tcagggtcta gtggttttgt gtgcgacgaa    780

cattactacg gcgagggctg cagcgtgttc tgtcgacctc gtgacgacgc ttttggccac    840

ttcacctgcg gcgatcgcgg cgagaagatg tgcgatcctg gctggaaagg ccagtactgc    900
```

```
acagatccga tttgcctgcc gggctgtgat gaccaacatg gctattgtga taagccgggc    960

gagtgtaagt gccgtgttgg ttggcaaggc cgctattgcg atgagtgcat ccgttatcct   1020

ggctgtctgc atggcacttg tcagcaaccg tggcaatgca actgccaaga gggttggggt   1080

gggttgttct gcaatcaggg atcttcgggg tcctctggtt ttgtgtgtga cgaacactat   1140

tacggcgagg gctgcagtgt gttctgccgc cctcgtgacg acgccttcgg tcatttcacc   1200

tgtggcgatc gtggcgaaaa gatgtgtgat cctggttgga agggtcaata ctgtaccgac   1260

ccgatctgtc tgcctggctg cgacgaccag catggttact gtgacaaacc gggcgagtgt   1320

aaatgccgtg ttggttggca aggccgctac tgtgatgagt gcattcgcta tcctggttgc   1380

ctgcacggta cctgccagca accttggcaa tgcaactgcc aggaaggttg ggggggcctg   1440

ttctgcaacc agggtagctc tggctcatcc gggttcgttt gcgacgagca ttattacggc   1500

gaaggctgta gtgttttctg ccgtcctcgt gacgacgcat ttggccattt cacctgtggt   1560

gaccgcggcg aaaaaatgtg tgaccctggc tggaagggcc aatattgcac tgatccgatt   1620

tgtctgccgg gttgtgacga tcaacacggc tactgcgata agccgggcga atgtaagtgc   1680

cgtgtgggtt ggcaaggccg ctattgtgat gaatgcattc gctatccggg ctgtctgcac   1740

ggcacttgcc agcagccgtg gcaatgtaat tgccaagaag gttggggcgg actcttttgt   1800

aaccaaggat catcaggtag tagcggcttt gtttgtgacg agcactacta tggtgaaggc   1860

tgcagcgttt tttgtcgtcc gcgcgatgat gcctttggtc atttcacctg tggcgaccgc   1920

ggcgagaaaa tgtgcgatcc tggttggaaa ggccagtatt gcaccgatcc gatctgcctg   1980

ccgggctgcg acgatcaaca cggctattgt gacaaaccgg gtgaatgcaa atgtcgtgtg   2040

ggttggcagg gccgctactg cgatgagtgt attcgttatc ctggttgcct gcatggcaca   2100

tgtcaacagc cgtggcagtg caattgtcag gaaggttggg gcggcctgtt ctgcaaccag   2160

taaggatcc                                                           2169
```

```
<210> SEQ ID NO 126
<211> LENGTH: 719
<212> TYPE: PRT
<213> ORGANISM: Artificial Sequence
<220> FEATURE:
<223> OTHER INFORMATION: synthetic construct

<400> SEQUENCE: 126

Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125
```

-continued

```
Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
            260                 265                 270

Arg Asp Asp Ala Phe Gly His Phe Thr Cys Gly Asp Arg Gly Glu Lys
        275                 280                 285

Met Cys Asp Pro Gly Trp Lys Gly Gln Tyr Cys Thr Asp Pro Ile Cys
    290                 295                 300

Leu Pro Gly Cys Asp Asp Gln His Gly Tyr Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350

Asn Cys Gln Glu Gly Trp Gly Gly Leu Phe Cys Asn Gln Gly Ser Ser
        355                 360                 365

Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

Gly Asp Arg Gly Glu Lys Met Cys Asp Pro Gly Trp Lys Gly Gln Tyr
                405                 410                 415

Cys Thr Asp Pro Ile Cys Leu Pro Gly Cys Asp Asp Gln His Gly Tyr
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
    450                 455                 460

Gln Gln Pro Trp Gln Cys Asn Cys Gln Glu Gly Trp Gly Gly Leu Phe
465                 470                 475                 480

Cys Asn Gln Gly Ser Ser Gly Ser Ser Gly Phe Val Cys Asp Glu His
                485                 490                 495

Tyr Tyr Gly Glu Gly Cys Ser Val Phe Cys Arg Pro Arg Asp Asp Ala
            500                 505                 510

Phe Gly His Phe Thr Cys Gly Asp Arg Gly Glu Lys Met Cys Asp Pro
        515                 520                 525

Gly Trp Lys Gly Gln Tyr Cys Thr Asp Pro Ile Cys Leu Pro Gly Cys
    530                 535                 540

Asp Asp Gln His Gly Tyr Cys Asp Lys Pro Gly Glu Cys Lys Cys Arg
```

-continued 545 550 555 560

Val Gly Trp Gln Gly Arg Tyr Cys Asp Glu Cys Ile Arg Tyr Pro Gly
565 570 575

Cys Leu His Gly Thr Cys Gln Gln Pro Trp Gln Cys Asn Cys Gln Glu
580 585 590

Gly Trp Gly Gly Leu Phe Cys Asn Gln Gly Ser Ser Gly Ser Ser Gly
595 600 605

Phe Val Cys Asp Glu His Tyr Tyr Gly Glu Gly Cys Ser Val Phe Cys
610 615 620

Arg Pro Arg Asp Asp Ala Phe Gly His Phe Thr Cys Gly Asp Arg Gly
625 630 635 640

Glu Lys Met Cys Asp Pro Gly Trp Lys Gly Gln Tyr Cys Thr Asp Pro
645 650 655

Ile Cys Leu Pro Gly Cys Asp Asp Gln His Gly Tyr Cys Asp Lys Pro
660 665 670

Gly Glu Cys Lys Cys Arg Val Gly Trp Gln Gly Arg Tyr Cys Asp Glu
675 680 685

Cys Ile Arg Tyr Pro Gly Cys Leu His Gly Thr Cys Gln Gln Pro Trp
690 695 700

Gln Cys Asn Cys Gln Glu Gly Trp Gly Gly Leu Phe Cys Asn Gln
705 710 715

<210> SEQ ID NO 127
<211> LENGTH: 1815
<212> TYPE: DNA
<213> ORGANISM: Artificial Sequence
<220> FEATURE:
<223> OTHER INFORMATION: synthetic construct

<400> SEQUENCE: 127
catatggccg cacatcatca tcaccaccat ggtggtgaaa acctgtattt tcagggcttt 60
gtgtgcgatg agcattatta cggtgaaggc tgtagcgtgt tttgtcgacc gcgtgatgac 120
gcatttggcc attttacctg cggtgaccgc ggcgagaaaa tgtgcgatcc gggctggaaa 180
ggtcagtatt gtacagaccc tatttgtctg ccgggctgtg acgatcagca cggctactgt 240
gacaagccgg gcgaatgtaa atgtcgcgtt ggctggcagg gtcgctattg tgatgaatgc 300
atccgctacc cgggttgctt acatggcaca tgccaacagc cttggcaatg taattgtcag 360
gaaggctggg gaggtttatt ttgtaatcaa ggcagttcag ggtctagtgg ttttgtgtgc 420
gacgaacatt actacggcga gggctgcagc gtgttctgtc gacctcgtga cgacgctttt 480
ggccacttca cctgcggcga tcgcggcgag aagatgtgcg atcctggctg gaaaggccag 540
tactgcacag atccgatttg cctgccgggc tgtgatgacc aacatggcta ttgtgataag 600
ccgggcgagt gtaagtgccg tgttggttgg caaggccgct attgcgatga gtgcatccgt 660
tatcctggct gtctgcatgg cacttgtcag caaccgtggc aatgcaactg ccaagagggt 720
tggggtgggt tgttctgcaa tcagggatct tcggggtcct ctggttttgt gtgtgacgaa 780
cactattacg gcgagggctg cagtgtgttc tgccgccctc gtgacgacgc cttcggtcat 840
ttcacctgtg gcgatcgtgg cgaaaagatg tgtgatcctg gttggaaggg tcaatactgt 900
accgacccga tctgtctgcc tggctgcgac gaccagcatg gttactgtga caaaccgggc 960
gagtgtaaat gccgtgttgg ttggcaaggc cgctactgtg atgagtgcat tcgctatcct 1020
ggttgcctgc acggtacctg ccagcaacct tggcaatgca actgccagga aggttggggg 1080
ggcctgttct gcaaccaggg tagctctggc tcatccgggt tcgtttgcga cgagcattat 1140

```
tacggcgaag gctgtagtgt tttctgccgt cctcgtgacg acgcatttgg ccatttcacc    1200

tgtggtgacc gcggcgaaaa aatgtgtgac cctggctgga agggccaata ttgcactgat    1260

ccgatttgtc tgccgggttg tgacgatcaa cacggctact gcgataagcc gggcgaatgt    1320

aagtgccgtg tgggttggca aggccgctat tgtgatgaat gcattcgcta tccgggctgt    1380

ctgcacggca cttgccagca gccgtggcaa tgtaattgcc aagaaggttg gggcggactc    1440

ttttgtaacc aaggatcatc aggtagtagc ggctttgttt gtgacgagca ctactatggt    1500

gaaggctgca gcgttttttg tcgtccgcgc gatgatgcct ttggtcattt cacctgtggc    1560

gaccgcggcg agaaaatgtg cgatcctggt tggaaaggcc agtattgcac cgatccgatc    1620

tgcctgccgg gctgcgacga tcaacacggc tattgtgaca aaccgggtga atgcaaatgt    1680

cgtgtgggtt ggcagggccg ctactgcgat gagtgtattc gttatcctgg ttgcctgcat    1740

ggcacatgtc aacagccgtg gcagtgcaat tgtcaggaag gttggggcgg cctgttctgc    1800

aaccagtaag gatcc                                                     1815
```

<210> SEQ ID NO 128
<211> LENGTH: 601
<212> TYPE: PRT
<213> ORGANISM: Artificial Sequence
<220> FEATURE:
<223> OTHER INFORMATION: synthetic construct

<400> SEQUENCE: 128

```
Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Asp
        35                  40                  45

Arg Gly Glu Lys Met Cys Asp Pro Gly Trp Lys Gly Gln Tyr Cys Thr
    50                  55                  60

Asp Pro Ile Cys Leu Pro Gly Cys Asp Asp Gln His Gly Tyr Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Asp Arg Gly Glu Lys Met Cys Asp Pro Gly Trp
                165                 170                 175

Lys Gly Gln Tyr Cys Thr Asp Pro Ile Cys Leu Pro Gly Cys Asp Asp
            180                 185                 190

Gln His Gly Tyr Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240
```

```
Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
            260                 265                 270

Arg Asp Asp Ala Phe Gly His Phe Thr Cys Gly Asp Arg Gly Glu Lys
        275                 280                 285

Met Cys Asp Pro Gly Trp Lys Gly Gln Tyr Cys Thr Asp Pro Ile Cys
    290                 295                 300

Leu Pro Gly Cys Asp Asp Gln His Gly Tyr Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350

Asn Cys Gln Glu Gly Trp Gly Gly Leu Phe Cys Asn Gln Gly Ser Ser
        355                 360                 365

Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

Gly Asp Arg Gly Glu Lys Met Cys Asp Pro Gly Trp Lys Gly Gln Tyr
                405                 410                 415

Cys Thr Asp Pro Ile Cys Leu Pro Gly Cys Asp Asp Gln His Gly Tyr
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
    450                 455                 460

Gln Gln Pro Trp Gln Cys Asn Cys Gln Glu Gly Trp Gly Gly Leu Phe
465                 470                 475                 480

Cys Asn Gln Gly Ser Ser Gly Ser Ser Gly Phe Val Cys Asp Glu His
                485                 490                 495

Tyr Tyr Gly Glu Gly Cys Ser Val Phe Cys Arg Pro Arg Asp Asp Ala
            500                 505                 510

Phe Gly His Phe Thr Cys Gly Asp Arg Gly Glu Lys Met Cys Asp Pro
        515                 520                 525

Gly Trp Lys Gly Gln Tyr Cys Thr Asp Pro Ile Cys Leu Pro Gly Cys
    530                 535                 540

Asp Asp Gln His Gly Tyr Cys Asp Lys Pro Gly Glu Cys Lys Cys Arg
545                 550                 555                 560

Val Gly Trp Gln Gly Arg Tyr Cys Asp Glu Cys Ile Arg Tyr Pro Gly
                565                 570                 575

Cys Leu His Gly Thr Cys Gln Gln Pro Trp Gln Cys Asn Cys Gln Glu
            580                 585                 590

Gly Trp Gly Gly Leu Phe Cys Asn Gln
        595                 600
```

<210> SEQ ID NO 129
<211> LENGTH: 8
<212> TYPE: PRT
<213> ORGANISM: Artificial Sequence
<220> FEATURE:
<223> OTHER INFORMATION: synthetic construct

<400> SEQUENCE: 129

Phe Glu Gln Asn Thr Ala Gln Pro
1 5

<210> SEQ ID NO 130
<211> LENGTH: 151
<212> TYPE: PRT
<213> ORGANISM: Artificial Sequence
<220> FEATURE:
<223> OTHER INFORMATION: synthetic construct

<400> SEQUENCE: 130

Met Ala Ala His His His His His His Gly Gly Glu Asn Leu Tyr Phe
1 5 10 15

Gln Gly Phe Val Cys Asp Glu His Tyr Tyr Gly Glu Gly Cys Ser Val
20 25 30

Phe Cys Arg Pro Arg Asp Asp Ala Phe Gly His Phe Thr Cys Gly Asp
35 40 45

Arg Gly Glu Lys Met Cys Asp Pro Gly Trp Lys Gly Gln Tyr Cys Thr
50 55 60

Asp Pro Ile Cys Leu Pro Gly Cys Asp Asp Gln His Gly Tyr Cys Asp
65 70 75 80

Lys Pro Gly Glu Cys Lys Cys Arg Val Gly Trp Gln Gly Arg Tyr Cys
85 90 95

Asp Glu Cys Ile Arg Tyr Pro Gly Cys Leu His Gly Thr Cys Gln Gln
100 105 110

Pro Trp Gln Cys Asn Cys Gln Glu Gly Trp Gly Gly Leu Phe Cys Asn
115 120 125

Gln Gly Ser Ser Gly Ser Ser Gly Gly Leu Asn Asp Ile Phe Glu Ala
130 135 140

Gln Lys Ile Glu Trp His Glu
145 150

<210> SEQ ID NO 131
<211> LENGTH: 465
<212> TYPE: DNA
<213> ORGANISM: Artificial Sequence
<220> FEATURE:
<223> OTHER INFORMATION: synthetic construct

<400> SEQUENCE: 131
catatggcag ctcatcacca tcaccatcac ggtggggaga atctctattt ccaggggttc 60
gtatgtgacg aacactatta cggagagggg tgcagtgtct tctgccgtcc gagagacgat 120
gcctttggtc actttacgtg tggagacaga ggcgaaaaaa tgtgtgatcc aggatggaaa 180
ggacagtatt gtacggaccc catttgcctt cctggctgcg atgaccaaca cgggtattgt 240
gacaaacccg gcgagtgcaa gtgtcgtgtt gggtggcaag ggcgatactg cgacgagtgc 300
ataagatacc ctggttgcct gcacgggacc tgccagcaac cttggcaatg taactgtcaa 360
gaaggatggg gaggcttatt ctgcaaccaa ggctcgtctg gctcctcggg gggtctgaat 420
gatatcttcg aagcgcagaa aattgaatgg cacgaataag gatcc 465

<210> SEQ ID NO 132
<211> LENGTH: 5
<212> TYPE: PRT
<213> ORGANISM: Artificial Sequence
<220> FEATURE:
<223> OTHER INFORMATION: synthetic construct

<400> SEQUENCE: 132

Gly Gly Gly Gly Ser
1 5

<210> SEQ ID NO 133
<211> LENGTH: 7
<212> TYPE: PRT
<213> ORGANISM: Artificial Sequence
<220> FEATURE:
<223> OTHER INFORMATION: synthetic construct

<400> SEQUENCE: 133

Gly Ser Ser Gly Ser Ser Gly
1 5

<210> SEQ ID NO 134
<211> LENGTH: 8
<212> TYPE: PRT
<213> ORGANISM: Artificial Sequence
<220> FEATURE:
<223> OTHER INFORMATION: synthetic construct

<400> SEQUENCE: 134

Phe Glu Gln Asn Thr Ala Gln Pro
1 5

<210> SEQ ID NO 135
<211> LENGTH: 20
<212> TYPE: DNA
<213> ORGANISM: Artificial Sequence
<220> FEATURE:
<223> OTHER INFORMATION: synthetic construct

<400> SEQUENCE: 135
gccaatttgc ctttctcatc 20

<210> SEQ ID NO 136
<211> LENGTH: 20
<212> TYPE: DNA
<213> ORGANISM: Artificial Sequence
<220> FEATURE:
<223> OTHER INFORMATION: synthetic construct

<400> SEQUENCE: 136
agccactgga aggtgacact 20

<210> SEQ ID NO 137
<211> LENGTH: 20
<212> TYPE: DNA
<213> ORGANISM: Artificial Sequence
<220> FEATURE:
<223> OTHER INFORMATION: synthetic construct

<400> SEQUENCE: 137
ctctcagcct tccccttttc 20

<210> SEQ ID NO 138
<211> LENGTH: 20
<212> TYPE: DNA
<213> ORGANISM: Artificial Sequence
<220> FEATURE:
<223> OTHER INFORMATION: synthetic construct

<400> SEQUENCE: 138
atctctgtcc cccaaggtct 20

<210> SEQ ID NO 139
<211> LENGTH: 45
<212> TYPE: PRT
<213> ORGANISM: Artificial Sequence
<220> FEATURE:
<223> OTHER INFORMATION: synthetic construct

<400> SEQUENCE: 139

Phe Val Cys Asp Glu His Tyr Tyr Gly Glu Gly Cys Ser Val Phe Cys
1 5 10 15

Arg Pro Arg Asp Asp Ala Phe Gly His Phe Thr Cys Gly Asp Arg Gly
20 25 30

Glu Lys Met Cys Asp Pro Gly Trp Lys Gly Gln Tyr Cys
35 40 45

<210> SEQ ID NO 140
<211> LENGTH: 29
<212> TYPE: PRT
<213> ORGANISM: Artificial Sequence
<220> FEATURE:
<223> OTHER INFORMATION: synthetic construct

<400> SEQUENCE: 140

Cys Leu Pro Gly Cys Asp Asp Gln His Gly Tyr Cys Asp Lys Pro Gly
1 5 10 15

Glu Cys Lys Cys Arg Val Gly Trp Gln Gly Arg Tyr Cys
20 25

<210> SEQ ID NO 141
<211> LENGTH: 29
<212> TYPE: PRT
<213> ORGANISM: Artificial Sequence
<220> FEATURE:
<223> OTHER INFORMATION: synthetic construct

<400> SEQUENCE: 141

Cys Ile Arg Tyr Pro Gly Cys Leu His Gly Thr Cys Gln Gln Pro Trp
1 5 10 15

Gln Cys Asn Cys Gln Glu Gly Trp Gly Gly Leu Phe Cys
20 25

<210> SEQ ID NO 142
<211> LENGTH: 34
<212> TYPE: PRT
<213> ORGANISM: Artificial Sequence
<220> FEATURE:
<223> OTHER INFORMATION: synthetic construct

<400> SEQUENCE: 142

Cys Thr His His Lys Pro Cys Arg Asn Gly Ala Thr Cys Thr Asn Thr
1 5 10 15

Gly Gln Gly Ser Tyr Thr Cys Ser Cys Arg Pro Gly Tyr Thr Gly Ala
20 25 30

Asn Cys

<210> SEQ ID NO 143
<211> LENGTH: 159
<212> TYPE: PRT
<213> ORGANISM: Artificial Sequence
<220> FEATURE:
<223> OTHER INFORMATION: synthetic construct

<400> SEQUENCE: 143

Gln Val Trp Ser Ser Gly Val Phe Glu Leu Lys Leu Gln Glu Phe Val

-continued

```
1               5                   10                  15

Asn Lys Lys Gly Leu Leu Gly Asn Arg Asn Cys Cys Arg Gly Gly Ala
            20                  25                  30

Gly Pro Pro Pro Cys Ala Cys Arg Thr Phe Phe Arg Val Cys Leu Lys
        35                  40                  45

His Tyr Gln Ala Ser Val Ser Pro Glu Pro Pro Cys Thr Tyr Gly Ser
    50                  55                  60

Ala Val Thr Pro Val Leu Gly Val Asp Ser Phe Ser Leu Pro Asp Gly
65                  70                  75                  80

Gly Gly Ala Asp Ser Ala Phe Ser Asn Pro Ile Arg Phe Pro Phe Gly
                85                  90                  95

Phe Thr Trp Pro Gly Thr Phe Ser Leu Ile Ile Glu Ala Leu His Thr
            100                 105                 110

Asp Ser Pro Asp Asp Leu Ala Thr Glu Asn Pro Glu Arg Leu Ile Ser
        115                 120                 125

Arg Leu Ala Thr Gln Arg His Leu Thr Val Gly Glu Glu Trp Ser Gln
    130                 135                 140

Asp Leu His Ser Ser Gly Arg Thr Asp Leu Lys Tyr Ser Tyr Arg
145                 150                 155
```

<210> SEQ ID NO 144
<211> LENGTH: 411
<212> TYPE: DNA
<213> ORGANISM: Artificial Sequence
<220> FEATURE:
<223> OTHER INFORMATION: synthetic construct

<400> SEQUENCE: 144

```
catatggcag ctcatcacca tcaccatcac ggtggcgaga atctatactt ccagggcttt     60

gtctgtgacg agcattacta tggtgaaggg tgctctgtgt tttgtaggcc aagggacgat    120

gcgttcggac attttacctg cggggaacga ggtgagaagg tttgcaaccc tgggtggaag    180

ggaccctact gcactgaacc aatttgctta ccagggtgtg atgagcaaca cggattctgc    240

gataagccgg gcgaatgtaa gtgtcgggta ggctggcaag gccgctactg cgatgagtgt    300

atacgttacc caggatgttt acacggaaca tgtcagcaac cgtggcagtg taattgccaa    360

gaagggtggg gagggttgtt ctgtaaccag ggtcctcag gatctagtgg a              411
```

<210> SEQ ID NO 145
<211> LENGTH: 2877
<212> TYPE: DNA
<213> ORGANISM: Artificial Sequence
<220> FEATURE:
<223> OTHER INFORMATION: synthetic construct

<400> SEQUENCE: 145

```
catatggcag ctcatcacca tcaccatcac ggtggcgaga atctatactt ccagggcttt     60

gtctgtgacg agcattacta tggtgaaggg tgctctgtgt tttgtcgacc aagggacgat    120

gcgttcggac attttacctg cggggaacga ggtgagaagg tttgcaaccc tgggtggaag    180

ggaccctact gtacagaacc aatttgctta ccagggtgtg atgagcaaca cggattctgc    240

gataagccgg gcgaatgtaa gtgtcgggta ggctggcaag gccgctactg cgatgaatgc    300

atccgttacc cgggatgttt acacggtacc tgtcagcaac cgtggcagtg caattgccaa    360

gaagggtggg gagggttgtt ctgtaaccag ggctcgagcg gttcatcggg atttgtctgt    420

gacgagcatt actatggtga agggtgctct gtgttttgta ggccaaggga cgatgcgttc    480
```

-continued

```
ggacatttta cctgcgggga acgaggtgag aaggtttgca accctgggtg gaagggaccc    540
tactgcactg aaccaatttg cttaccaggg tgtgatgagc aacacggatt ctgcgataag    600
ccgggcgaat gtaagtgtcg ggtaggctgg caaggccgct actgcgatga gtgtatacgt    660
tacccaggat gtttacacgg aacatgtcag caaccgtggc agtgtaattg ccaagaaggg    720
tggggagggt tgttctgtaa ccagggctcg agcggaagct caggctttgt ctgtgacgag    780
cattactatg gtgaagggtg ctctgtgttt tgtaggccaa gggacgatgc gttcggacat    840
tttacctgcg gggaacgagg tgagaaggtt tgcaaccctg ggtggaaggg accctactgt    900
acagaaccaa tttgcttacc agggtgtgat gagcaacacg gattctgcga taagccgggc    960
gaatgtaagt gtcgggtagg ctggcaaggc cgctactgcg atgagtgtat acgttaccca   1020
ggatgtttac acggaacatg tcagcaaccg tggcagtgta attgccaaga agggtgggga   1080
gggttgttct gtaaccaggg ttcttccgga tcgagtggct ttgtctgtga cgagcattac   1140
tatggtgaag ggtgctctgt gttttgtagg ccaagggacg atgcgttcgg acattttacc   1200
tgcggggaac gaggtgagaa ggtttgcaac cctgggtgga agggacccta ctgcactgaa   1260
ccaatttgct taccagggtg tgatgagcaa cacggattct gcgataagcc gggcgaatgt   1320
aagtgtcggg taggctggca aggccgctac tgcgatgagt gtatacgtta cccgggatgt   1380
ttacacggaa catgtcagca accgtggcag tgtaattgcc aagaagggtg gggagggttg   1440
ttctgtaacc agggcagttc agggtctagt ggttttgtct gtgacgagca ttactatggt   1500
gaagggtgct ctgtgttttg tcgaccaagg gacgatgcgt tcggacattt tacctgcggg   1560
gaacgaggtg agaaggtttg caaccctggg tggaagggac cctactgcac tgaaccaatt   1620
tgcttaccag ggtgtgatga gcaacacgga ttctgcgata agccgggcga atgtaagtgt   1680
cgggtaggct ggcaaggccg ctactgcgat gagtgtatac gttacccagg atgtttacac   1740
ggaacatgtc agcaaccgtg gcagtgtaat tgccaagaag ggtggggagg gttgttctgt   1800
aaccagggat cttcggggtc ctctggtttt gtctgtgacg agcattacta tggtgaaggg   1860
tgctctgtgt tttgtaggcc aagggacgat gcgttcggac attttacctg cggggaacga   1920
ggtgagaagg tttgcaaccc tgggtggaag ggaccctact gcactgaacc aatttgctta   1980
ccagggtgtg atgagcaaca cggattctgc gataagccgg gcgaatgtaa gtgtcgggta   2040
ggctggcaag gccgctactg cgatgagtgt atacgttacc caggatgttt acacggtacc   2100
tgtcagcaac cgtggcagtg taattgccaa gaagggtggg gagggttgtt ctgtaaccag   2160
ggtagctctg gctcatccgg gtttgtctgt gacgagcatt actatggtga agggtgctct   2220
gtgttttgta ggccaaggga cgatgcgttc ggacatttta cctgcgggga acgaggtgag   2280
aaggtttgca accctgggtg gaagggaccc tactgcactg aaccaatttg cttaccaggg   2340
tgtgatgagc aacacggatt ctgcgataag ccgggcgaat gtaagtgtcg ggtaggctgg   2400
caaggccgct actgcgatga atgcatccgt tacccaggat gtttacacgg aacatgtcag   2460
caaccgtggc agtgtaattg ccaagaaggg tggggagggt tgttctgtaa ccagggatca   2520
tcaggtagta gcggctttgt ctgtgacgag cattactatg gtgaagggtg ctctgtgttt   2580
tgtaggccaa gggacgatgc gttcggacat tttacctgcg gggaacgagg tgagaaggtt   2640
tgcaaccctg ggtggaaggg accctactgc actgaaccaa tttgcttacc agggtgtgat   2700
gagcaacacg gattctgcga taagccgggc gaatgtaagt gtcgggtagg ctggcaaggc   2760
cgctactgcg atgagtgtat acgttaccca ggatgtttac acggaacatg tcagcaaccg   2820
tggcagtgca attgccaaga agggtgggga gggttgttct gtaaccagta aggatcc      2877
```

<210> SEQ ID NO 146
<211> LENGTH: 955
<212> TYPE: PRT
<213> ORGANISM: Artificial Sequence
<220> FEATURE:
<223> OTHER INFORMATION: synthetic construct

<400> SEQUENCE: 146

Met Ala Ala His His His His His His Gly Gly Glu Asn Leu Tyr Phe
1 5 10 15

Gln Gly Phe Val Cys Asp Glu His Tyr Tyr Gly Glu Gly Cys Ser Val
20 25 30

Phe Cys Arg Pro Arg Asp Asp Ala Phe Gly His Phe Thr Cys Gly Glu
35 40 45

Arg Gly Glu Lys Val Cys Asn Pro Gly Trp Lys Gly Pro Tyr Cys Thr
50 55 60

Glu Pro Ile Cys Leu Pro Gly Cys Asp Glu Gln His Gly Phe Cys Asp
65 70 75 80

Lys Pro Gly Glu Cys Lys Cys Arg Val Gly Trp Gln Gly Arg Tyr Cys
85 90 95

Asp Glu Cys Ile Arg Tyr Pro Gly Cys Leu His Gly Thr Cys Gln Gln
100 105 110

Pro Trp Gln Cys Asn Cys Gln Glu Gly Trp Gly Gly Leu Phe Cys Asn
115 120 125

Gln Gly Ser Ser Gly Ser Ser Gly Phe Val Cys Asp Glu His Tyr Tyr
130 135 140

Gly Glu Gly Cys Ser Val Phe Cys Arg Pro Arg Asp Asp Ala Phe Gly
145 150 155 160

His Phe Thr Cys Gly Glu Arg Gly Glu Lys Val Cys Asn Pro Gly Trp
165 170 175

Lys Gly Pro Tyr Cys Thr Glu Pro Ile Cys Leu Pro Gly Cys Asp Glu
180 185 190

Gln His Gly Phe Cys Asp Lys Pro Gly Glu Cys Lys Cys Arg Val Gly
195 200 205

Trp Gln Gly Arg Tyr Cys Asp Glu Cys Ile Arg Tyr Pro Gly Cys Leu
210 215 220

His Gly Thr Cys Gln Gln Pro Trp Gln Cys Asn Cys Gln Glu Gly Trp
225 230 235 240

Gly Gly Leu Phe Cys Asn Gln Gly Ser Ser Gly Ser Ser Gly Phe Val
245 250 255

Cys Asp Glu His Tyr Tyr Gly Glu Gly Cys Ser Val Phe Cys Arg Pro
260 265 270

Arg Asp Asp Ala Phe Gly His Phe Thr Cys Gly Glu Arg Gly Glu Lys
275 280 285

Val Cys Asn Pro Gly Trp Lys Gly Pro Tyr Cys Thr Glu Pro Ile Cys
290 295 300

Leu Pro Gly Cys Asp Glu Gln His Gly Phe Cys Asp Lys Pro Gly Glu
305 310 315 320

Cys Lys Cys Arg Val Gly Trp Gln Gly Arg Tyr Cys Asp Glu Cys Ile
325 330 335

Arg Tyr Pro Gly Cys Leu His Gly Thr Cys Gln Gln Pro Trp Gln Cys
340 345 350

Asn Cys Gln Glu Gly Trp Gly Gly Leu Phe Cys Asn Gln Gly Ser Ser
355 360 365

-continued

```
Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

Gly Glu Arg Gly Glu Lys Val Cys Asn Pro Gly Trp Lys Gly Pro Tyr
                405                 410                 415

Cys Thr Glu Pro Ile Cys Leu Pro Gly Cys Asp Glu Gln His Gly Phe
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
    450                 455                 460

Gln Gln Pro Trp Gln Cys Asn Cys Gln Glu Gly Trp Gly Gly Leu Phe
465                 470                 475                 480

Cys Asn Gln Gly Ser Ser Gly Ser Ser Gly Phe Val Cys Asp Glu His
                485                 490                 495

Tyr Tyr Gly Glu Gly Cys Ser Val Phe Cys Arg Pro Arg Asp Asp Ala
            500                 505                 510

Phe Gly His Phe Thr Cys Gly Glu Arg Gly Glu Lys Val Cys Asn Pro
        515                 520                 525

Gly Trp Lys Gly Pro Tyr Cys Thr Glu Pro Ile Cys Leu Pro Gly Cys
    530                 535                 540

Asp Glu Gln His Gly Phe Cys Asp Lys Pro Gly Glu Cys Lys Cys Arg
545                 550                 555                 560

Val Gly Trp Gln Gly Arg Tyr Cys Asp Glu Cys Ile Arg Tyr Pro Gly
                565                 570                 575

Cys Leu His Gly Thr Cys Gln Gln Pro Trp Gln Cys Asn Cys Gln Glu
            580                 585                 590

Gly Trp Gly Gly Leu Phe Cys Asn Gln Gly Ser Ser Gly Ser Ser Gly
        595                 600                 605

Phe Val Cys Asp Glu His Tyr Tyr Gly Glu Gly Cys Ser Val Phe Cys
    610                 615                 620

Arg Pro Arg Asp Asp Ala Phe Gly His Phe Thr Cys Gly Glu Arg Gly
625                 630                 635                 640

Glu Lys Val Cys Asn Pro Gly Trp Lys Gly Pro Tyr Cys Thr Glu Pro
                645                 650                 655

Ile Cys Leu Pro Gly Cys Asp Glu Gln His Gly Phe Cys Asp Lys Pro
            660                 665                 670

Gly Glu Cys Lys Cys Arg Val Gly Trp Gln Gly Arg Tyr Cys Asp Glu
        675                 680                 685

Cys Ile Arg Tyr Pro Gly Cys Leu His Gly Thr Cys Gln Gln Pro Trp
    690                 695                 700

Gln Cys Asn Cys Gln Glu Gly Trp Gly Gly Leu Phe Cys Asn Gln Gly
705                 710                 715                 720

Ser Ser Gly Ser Ser Gly Phe Val Cys Asp Glu His Tyr Tyr Gly Glu
                725                 730                 735

Gly Cys Ser Val Phe Cys Arg Pro Arg Asp Asp Ala Phe Gly His Phe
            740                 745                 750

Thr Cys Gly Glu Arg Gly Glu Lys Val Cys Asn Pro Gly Trp Lys Gly
        755                 760                 765

Pro Tyr Cys Thr Glu Pro Ile Cys Leu Pro Gly Cys Asp Glu Gln His
    770                 775                 780
```

```
Gly Phe Cys Asp Lys Pro Gly Glu Cys Lys Cys Arg Val Gly Trp Gln
785                 790                 795                 800

Gly Arg Tyr Cys Asp Glu Cys Ile Arg Tyr Pro Gly Cys Leu His Gly
                805                 810                 815

Thr Cys Gln Gln Pro Trp Gln Cys Asn Cys Gln Glu Gly Trp Gly Gly
            820                 825                 830

Leu Phe Cys Asn Gln Gly Ser Ser Gly Ser Ser Gly Phe Val Cys Asp
        835                 840                 845

Glu His Tyr Tyr Gly Glu Gly Cys Ser Val Phe Cys Arg Pro Arg Asp
    850                 855                 860

Asp Ala Phe Gly His Phe Thr Cys Gly Glu Arg Gly Glu Lys Val Cys
865                 870                 875                 880

Asn Pro Gly Trp Lys Gly Pro Tyr Cys Thr Glu Pro Ile Cys Leu Pro
                885                 890                 895

Gly Cys Asp Glu Gln His Gly Phe Cys Asp Lys Pro Gly Glu Cys Lys
            900                 905                 910

Cys Arg Val Gly Trp Gln Gly Arg Tyr Cys Asp Glu Cys Ile Arg Tyr
        915                 920                 925

Pro Gly Cys Leu His Gly Thr Cys Gln Gln Pro Trp Gln Cys Asn Cys
    930                 935                 940

Gln Glu Gly Trp Gly Gly Leu Phe Cys Asn Gln
945                 950                 955
```

<210> SEQ ID NO 147
<211> LENGTH: 1632
<212> TYPE: DNA
<213> ORGANISM: Artificial Sequence
<220> FEATURE:
<223> OTHER INFORMATION: synthetic construct

<400> SEQUENCE: 147

```
catatggcag ctcatcacca tcaccatcac ggtggcgaga atctatactt ccagggcttt     60

gtctgtgacg agcattacta tggtgaaggg tgctctgtgt tttgtaggcc aagggacgat    120

gcgttcggac attttacctg cggggaacga ggtgagaagg tttgcaaccc tgggtggaag    180

ggaccctact gcactgaacc aatttgctta ccagggtgtg atgagcaaca cggattctgc    240

gataagccgg gcgaatgtaa gtgtcgggta ggctggcaag gccgctactg cgatgagtgt    300

atacgttacc caggatgttt acacggaaca tgtcagcaac cgtggcagtg taattgccaa    360

gaagggtggg gagggttgtt ctgtaaccag gggtcctcag gatctagtgg acatatggca    420

gctcatcacc atcaccatca cggtggcgag aatctatact tccagggctt tgtctgtgac    480

gagcattact atggtgaagg gtgctctgtg ttttgtaggc caagggacga tgcgttcgga    540

cattttacct gcggggaacg aggtgagaag gtttgcaacc ctgggtggaa gggaccctac    600

tgcactgaac caatttgctt accagggtgt gatgagcaac acggattctg cgataagccg    660

ggcgaatgta agtgtcgggt aggctggcaa ggccgctact gcgatgagtg tatacgttac    720

ccaggatgtt tacacggaac atgtcagcaa ccgtggcagt gtaattgcca agaagggtgg    780

ggagggttgt tctgtaacca ggggtcctca ggatctagtg gacatatggc agctcatcac    840

catcaccatc acggtggcga gaatctatac ttccagggct ttgtctgtga cgagcattac    900

tatggtgaag ggtgctctgt gttttgtagg ccaagggacg atgcgttcgg acattttacc    960

tgcggggaac gaggtgagaa ggtttgcaac cctgggtgga agggacccta ctgcactgaa   1020

ccaatttgct taccagggtg tgatgagcaa cacggattct gcgataagcc gggcgaatgt   1080
```

```
aagtgtcggg taggctggca aggccgctac tgcgatgagt gtatacgtta cccaggatgt   1140

ttacacggaa catgtcagca accgtggcag tgtaattgcc aagaagggtg gggagggttg   1200

ttctgtaacc aggggtcctc aggatctagt ggacatatgg cagctcatca ccatcaccat   1260

cacggtggcg agaatctata cttccagggc tttgtctgtg acgagcatta ctatggtgaa   1320

gggtgctctg tgttttgtag gccaagggac gatgcgttcg gacattttac ctgcggggaa   1380

cgaggtgaga aggtttgcaa ccctgggtgg aagggaccct actgcactga accaatttgc   1440

ttaccagggt gtgatgagca acacggattc tgcgataagc cgggcgaatg taagtgtcgg   1500

gtaggctggc aaggccgcta ctgcgatgag tgtatacgtt acccaggatg tttacacgga   1560

acatgtcagc aaccgtggca gtgtaattgc caagaagggt ggggagggtt gttctgtaac   1620

cagtaaggat cc                                                       1632
```

<210> SEQ ID NO 148
<211> LENGTH: 483
<212> TYPE: PRT
<213> ORGANISM: Artificial Sequence
<220> FEATURE:
<223> OTHER INFORMATION: synthetic construct

<400> SEQUENCE: 148

```
Met Ala Ala His His His His His His Gly Gly Glu Asn Leu Tyr Phe
1               5                   10                  15

Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Glu
        35                  40                  45

Arg Gly Glu Lys Val Cys Asn Pro Gly Trp Lys Gly Pro Tyr Cys Thr
    50                  55                  60

Glu Pro Ile Cys Leu Pro Gly Cys Asp Glu Gln His Gly Phe Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln Gly Ser Ser Gly Ser Ser Gly Phe Val Cys Asp Glu His Tyr Tyr
    130                 135                 140

Gly Glu Gly Cys Ser Val Phe Cys Arg Pro Arg Asp Asp Ala Phe Gly
145                 150                 155                 160

His Phe Thr Cys Gly Glu Arg Gly Glu Lys Val Cys Asn Pro Gly Trp
                165                 170                 175

Lys Gly Pro Tyr Cys Thr Glu Pro Ile Cys Leu Pro Gly Cys Asp Glu
            180                 185                 190

Gln His Gly Phe Cys Asp Lys Pro Gly Glu Cys Lys Cys Arg Val Gly
        195                 200                 205

Trp Gln Gly Arg Tyr Cys Asp Glu Cys Ile Arg Tyr Pro Gly Cys Leu
    210                 215                 220

His Gly Thr Cys Gln Gln Pro Trp Gln Cys Asn Cys Gln Glu Gly Trp
225                 230                 235                 240

Gly Gly Leu Phe Cys Asn Gln Gly Ser Ser Gly Ser Ser Gly Phe Val
                245                 250                 255

Cys Asp Glu His Tyr Tyr Gly Glu Gly Cys Ser Val Phe Cys Arg Pro
```

```
            260                 265                 270

Arg Asp Asp Ala Phe Gly His Phe Thr Cys Gly Glu Arg Gly Glu Lys
        275                 280                 285

Val Cys Asn Pro Gly Trp Lys Gly Pro Tyr Cys Thr Glu Pro Ile Cys
    290                 295                 300

Leu Pro Gly Cys Asp Glu Gln His Gly Phe Cys Asp Lys Pro Gly Glu
305                 310                 315                 320

Cys Lys Cys Arg Val Gly Trp Gln Gly Arg Tyr Cys Asp Glu Cys Ile
                325                 330                 335

Arg Tyr Pro Gly Cys Leu His Gly Thr Cys Gln Gln Pro Trp Gln Cys
            340                 345                 350

Asn Cys Gln Glu Gly Trp Gly Gly Leu Phe Cys Asn Gln Gly Ser Ser
        355                 360                 365

Gly Ser Ser Gly Phe Val Cys Asp Glu His Tyr Tyr Gly Glu Gly Cys
    370                 375                 380

Ser Val Phe Cys Arg Pro Arg Asp Asp Ala Phe Gly His Phe Thr Cys
385                 390                 395                 400

Gly Glu Arg Gly Glu Lys Val Cys Asn Pro Gly Trp Lys Gly Pro Tyr
                405                 410                 415

Cys Thr Glu Pro Ile Cys Leu Pro Gly Cys Asp Glu Gln His Gly Phe
            420                 425                 430

Cys Asp Lys Pro Gly Glu Cys Lys Cys Arg Val Gly Trp Gln Gly Arg
        435                 440                 445

Tyr Cys Asp Glu Cys Ile Arg Tyr Pro Gly Cys Leu His Gly Thr Cys
    450                 455                 460

Gln Gln Pro Trp Gln Cys Asn Cys Gln Glu Gly Trp Gly Gly Leu Phe
465                 470                 475                 480

Cys Asn Gln


<210> SEQ ID NO 149
<211> LENGTH: 411
<212> TYPE: DNA
<213> ORGANISM: Artificial Sequence
<220> FEATURE:
<223> OTHER INFORMATION: synthetic construct

<400> SEQUENCE: 149

catatggcag ctcatcacca tcaccatcac ggtggcgaga atctatactt ccagggcttt      60

gtctgtgacg agcattacta tggtgaaggg tgctctgtgt tttgtaggcc aagggacgat     120

gcgttcggac attttacctg cggggaacga ggtgagaagg tttgcaaccc tgggtggaag     180

ggaccctact gcactgaacc aatttgctta ccagggtgtg atgagcaaca cggattctgc     240

gataagccgg gcgaatgtaa gtgtcgggta ggctggcaag gccgctactg cgatgagtgt     300

atacgttacc caggatgttt acacggaaca tgtcagcaac cgtggcagtg taattgccaa     360

gaagggtggg gagggttgtt ctgtaaccag gggtcctcag gatctagtgg a              411


<210> SEQ ID NO 150
<211> LENGTH: 129
<212> TYPE: PRT
<213> ORGANISM: Artificial Sequence
<220> FEATURE:
<223> OTHER INFORMATION: synthetic construct

<400> SEQUENCE: 150

Met Ala Ala His His His His His His Gly Gly Glu Asn Leu Tyr Phe
1               5                   10                  15
```

```
Gln Gly Phe Val Cys Asp Glu His Tyr Tyr Gly Glu Gly Cys Ser Val
            20                  25                  30

Phe Cys Arg Pro Arg Asp Asp Ala Phe Gly His Phe Thr Cys Gly Glu
        35                  40                  45

Arg Gly Glu Lys Val Cys Asn Pro Gly Trp Lys Gly Pro Tyr Cys Thr
    50                  55                  60

Glu Pro Ile Cys Leu Pro Gly Cys Asp Glu Gln His Gly Phe Cys Asp
65                  70                  75                  80

Lys Pro Gly Glu Cys Lys Cys Arg Val Gly Trp Gln Gly Arg Tyr Cys
                85                  90                  95

Asp Glu Cys Ile Arg Tyr Pro Gly Cys Leu His Gly Thr Cys Gln Gln
            100                 105                 110

Pro Trp Gln Cys Asn Cys Gln Glu Gly Trp Gly Gly Leu Phe Cys Asn
        115                 120                 125

Gln


<210> SEQ ID NO 151
<211> LENGTH: 722
<212> TYPE: PRT
<213> ORGANISM: Artificial Sequence
<220> FEATURE:
<223> OTHER INFORMATION: synthetic construct

<400> SEQUENCE: 151

Met Gly Arg Arg Ser Ala Leu Ala Leu Ala Val Val Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ser Gly Pro Pro Cys Ala Cys Arg Thr Phe Phe Arg Val Cys Leu Lys
    50                  55                  60

His Tyr Gln Ala Ser Val Ser Pro Glu Pro Pro Cys Thr Tyr Gly Ser
65                  70                  75                  80

Ala Val Thr Pro Val Leu Gly Val Asp Ser Phe Ser Leu Pro Asp Gly
                85                  90                  95

Ala Gly Ile Asp Pro Ala Phe Ser Asn Pro Ile Arg Phe Pro Phe Gly
            100                 105                 110

Phe Thr Trp Pro Gly Thr Phe Ser Leu Ile Ile Glu Ala Leu His Thr
        115                 120                 125

Asp Ser Pro Asp Asp Leu Ala Thr Glu Asn Pro Glu Arg Leu Ile Ser
    130                 135                 140

Arg Leu Thr Thr Gln Arg His Leu Thr Val Gly Glu Glu Trp Ser Gln
145                 150                 155                 160

Asp Leu His Ser Ser Gly Arg Thr Asp Leu Arg Tyr Ser Tyr Arg Phe
                165                 170                 175

Val Cys Asp Glu His Tyr Tyr Gly Glu Gly Cys Ser Val Phe Cys Arg
            180                 185                 190

Pro Arg Asp Asp Ala Phe Gly His Phe Thr Cys Gly Asp Arg Gly Glu
        195                 200                 205

Lys Met Cys Asp Pro Gly Trp Lys Gly Gln Tyr Cys Thr Asp Pro Ile
    210                 215                 220

Cys Leu Pro Gly Cys Asp Asp Gln His Gly Tyr Cys Asp Lys Pro Gly
225                 230                 235                 240
```

-continued

```
Glu Cys Lys Cys Arg Val Gly Trp Gln Gly Arg Tyr Cys Asp Glu Cys
                245                 250                 255

Ile Arg Tyr Pro Gly Cys Leu His Gly Thr Cys Gln Gln Pro Trp Gln
            260                 265                 270

Cys Asn Cys Gln Glu Gly Trp Gly Gly Leu Phe Cys Asn Gln Asp Leu
        275                 280                 285

Asn Tyr Cys Thr His His Lys Pro Cys Arg Asn Gly Ala Thr Cys Thr
    290                 295                 300

Asn Thr Gly Gln Gly Ser Tyr Thr Cys Ser Cys Arg Pro Gly Tyr Thr
305                 310                 315                 320

Gly Ala Asn Cys Glu Leu Glu Val Asp Glu Cys Ala Pro Ser Pro Cys
                325                 330                 335

Lys Asn Gly Ala Ser Cys Thr Asp Leu Glu Asp Ser Phe Ser Cys Thr
            340                 345                 350

Cys Pro Pro Gly Phe Tyr Gly Lys Val Cys Glu Leu Ser Ala Met Thr
        355                 360                 365

Cys Ala Asp Gly Pro Cys Phe Asn Gly Gly Arg Cys Ser Asp Asn Pro
    370                 375                 380

Asp Gly Gly Tyr Thr Cys His Cys Pro Leu Gly Phe Ser Gly Phe Asn
385                 390                 395                 400

Cys Glu Lys Lys Met Asp Leu Cys Gly Ser Ser Pro Cys Ser Asn Gly
                405                 410                 415

Ala Lys Cys Val Asp Leu Gly Asn Ser Tyr Leu Cys Arg Cys Gln Ala
            420                 425                 430

Gly Phe Ser Gly Arg Tyr Cys Glu Asp Asn Val Asp Asp Cys Ala Ser
        435                 440                 445

Ser Pro Cys Ala Asn Gly Gly Thr Cys Arg Asp Ser Val Asn Asp Phe
    450                 455                 460

Ser Cys Thr Cys Pro Pro Gly Tyr Thr Gly Lys Asn Cys Ser Ala Pro
465                 470                 475                 480

Val Ser Arg Cys Glu His Ala Pro Cys His Asn Gly Ala Thr Cys His
                485                 490                 495

Gln Arg Gly Gln Arg Tyr Met Cys Glu Cys Ala Gln Gly Tyr Gly Gly
            500                 505                 510

Pro Asn Cys Gln Phe Leu Leu Pro Glu Pro Pro Pro Gly Pro Met Val
        515                 520                 525

Val Asp Leu Ser Glu Arg His Met Glu Ser Gln Gly Gly Pro Phe Pro
    530                 535                 540

Trp Val Ala Val Cys Ala Gly Val Val Leu Val Leu Leu Leu Leu Leu
545                 550                 555                 560

Gly Cys Ala Ala Val Val Val Cys Val Arg Leu Lys Leu Gln Lys His
                565                 570                 575

Gln Pro Pro Pro Glu Pro Cys Gly Gly Glu Thr Glu Thr Met Asn Asn
            580                 585                 590

Leu Ala Asn Cys Gln Arg Glu Lys Asp Val Ser Val Ser Ile Ile Gly
        595                 600                 605

Ala Thr Gln Ile Lys Asn Thr Asn Lys Lys Ala Asp Phe His Gly Asp
    610                 615                 620

His Gly Ala Glu Lys Ser Ser Phe Lys Val Arg Tyr Pro Thr Val Asp
625                 630                 635                 640

Tyr Asn Leu Val Arg Asp Leu Lys Gly Asp Glu Ala Thr Val Arg Asp
                645                 650                 655

Thr His Ser Lys Arg Asp Thr Lys Cys Gln Ser Gln Ser Ser Ala Gly
```

```
            660                 665                 670

Glu Glu Lys Ile Ala Pro Thr Leu Arg Gly Gly Glu Ile Pro Asp Arg
        675                 680                 685

Lys Arg Pro Glu Ser Val Tyr Ser Thr Ser Lys Asp Thr Lys Tyr Gln
    690                 695                 700

Ser Val Tyr Val Leu Ser Ala Glu Lys Asp Glu Cys Val Ile Ala Thr
705                 710                 715                 720

Glu Val


<210> SEQ ID NO 152
<211> LENGTH: 723
<212> TYPE: PRT
<213> ORGANISM: Artificial Sequence
<220> FEATURE:
<223> OTHER INFORMATION: synthetic construct

<400> SEQUENCE: 152

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300
```

```
Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
        355                 360                 365

Thr Cys Ala Asp Gly Pro Cys Phe Asn Gly Gly Arg Cys Ser Asp Ser
    370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
                405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
        435                 440                 445

Ser Ser Pro Cys Ala Asn Gly Gly Thr Cys Arg Asp Gly Val Asn Asp
    450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
                485                 490                 495

His Glu Arg Gly His Arg Tyr Val Cys Glu Cys Ala Arg Gly Tyr Gly
            500                 505                 510

Gly Pro Asn Cys Gln Phe Leu Leu Pro Glu Leu Pro Pro Gly Pro Ala
        515                 520                 525

Val Val Asp Leu Thr Glu Lys Leu Glu Gly Gln Gly Gly Pro Phe Pro
    530                 535                 540

Trp Val Ala Val Cys Ala Gly Val Ile Leu Val Leu Met Leu Leu Leu
545                 550                 555                 560

Gly Cys Ala Ala Val Val Val Cys Val Arg Leu Arg Leu Gln Lys His
                565                 570                 575

Arg Pro Pro Ala Asp Pro Cys Arg Gly Glu Thr Glu Thr Met Asn Asn
            580                 585                 590

Leu Ala Asn Cys Gln Arg Glu Lys Asp Ile Ser Val Ser Ile Ile Gly
        595                 600                 605

Ala Thr Gln Ile Lys Asn Thr Asn Lys Lys Ala Asp Phe His Gly Asp
    610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655

Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
        675                 680                 685

Arg Lys Arg Pro Asp Ser Gly Cys Ser Thr Ser Lys Asp Thr Lys Tyr
    690                 695                 700

Gln Ser Val Tyr Val Ile Ser Glu Glu Lys Asp Glu Cys Val Ile Ala
705                 710                 715                 720
```

Thr Glu Val

<210> SEQ ID NO 153
<211> LENGTH: 45
<212> TYPE: PRT
<213> ORGANISM: Artificial Sequence
<220> FEATURE:
<223> OTHER INFORMATION: synthetic construct

<400> SEQUENCE: 153

Phe Val Cys Asp Glu His Tyr Tyr Gly Glu Gly Cys Ser Val Phe Cys
1 5 10 15

Arg Pro Arg Asp Asp Ala Phe Gly His Phe Thr Cys Gly Glu Arg Gly
20 25 30

Glu Lys Val Cys Asn Pro Gly Trp Lys Gly Pro Tyr Cys
35 40 45

<210> SEQ ID NO 154
<211> LENGTH: 29
<212> TYPE: PRT
<213> ORGANISM: Artificial Sequence
<220> FEATURE:
<223> OTHER INFORMATION: synthetic construct

<400> SEQUENCE: 154

Cys Leu Pro Gly Cys Asp Glu Gln His Gly Phe Cys Asp Lys Pro Gly
1 5 10 15

Glu Cys Lys Cys Arg Val Gly Trp Gln Gly Arg Tyr Cys
20 25

<210> SEQ ID NO 155
<211> LENGTH: 29
<212> TYPE: PRT
<213> ORGANISM: Artificial Sequence
<220> FEATURE:
<223> OTHER INFORMATION: synthetic construct

<400> SEQUENCE: 155

Cys Ile Arg Tyr Pro Gly Cys Leu His Gly Thr Cys Gln Gln Pro Trp
1 5 10 15

Gln Cys Asn Cys Gln Glu Gly Trp Gly Gly Leu Phe Cys
20 25

<210> SEQ ID NO 156
<211> LENGTH: 34
<212> TYPE: PRT
<213> ORGANISM: Artificial Sequence
<220> FEATURE:
<223> OTHER INFORMATION: synthetic construct -continued

```
<400> SEQUENCE: 156

Cys Thr His His Lys Pro Cys Lys Asn Gly Ala Thr Cys Thr Asn Thr
1               5                   10                  15

Gly Gln Gly Ser Tyr Thr Cys Ser Cys Arg Pro Gly Tyr Thr Gly Ala
            20                  25                  30

Thr Cys


<210> SEQ ID NO 157
<211> LENGTH: 12
<212> TYPE: PRT
<213> ORGANISM: Artificial Sequence
<220> FEATURE:
<223> OTHER INFORMATION: synthetic construct

<400> SEQUENCE: 157

Phe Tyr Gln Leu Ala Lys Thr Cys Pro Val Gln Leu
1               5                   10
```

MODULATORS OF NOTCH SIGNALING AND METHODS OF USE THEREOF

CROSS-REFERENCE TO RELATED APPLICATIONS

This application is a national stage application filed under 35 U.S.C. § 371 of PCT/US2018/024343 filed Mar. 26, 2018, which claims the benefit of U.S. Provisional Patent Application Ser. No. 62/476,616 filed Mar. 24, 2017, which are expressly incorporated herein by reference.

FIELD

The present disclosure relates generally to the field of peptide therapeutics and methods of treatment using the same. Described are monomeric and multimeric peptide compositions derived from Delta-like (DLL) proteins and Jagged (Jag) proteins, compositions comprising the peptides, and methods of use thereof.

BACKGROUND

The Notch gene was identified over 100 years ago in *Drosophila* and has been revealed to be part of a pervasive pathway of intracellular communication. Notch, a transmembrane receptor, regulates a wide array of processes in the development and differentiation of most tissues. The mammalian Notch family includes four cell-bound receptors (Notch1-Notch4) and five cell-bound Notch ligands, which fall into two families: Delta-like ligands (DLL1, DLL3, DLL4) and Serrate-like Jagged ligands (Jag1, Jag2). Notch signaling, typically between two different cells, is affected when, upon binding, complex endocytosis by the ligand-bearing cell creates a pulling force that results in a conformational change leading to two proteolytic events (ADAM and γ-secretase) in the receptor. This releases the Notch intracellular domain to de-repress transcriptional regulators in the nucleus. There are multiple Notch target genes including Hes, Hey, and Deltex, which negatively regulate the expression of genes like tissue-specific transcriptional activators. The Notch pathway is highly pleotropic with multiple context-dependent outputs; it is important for embryonic development and immune cell differentiation, and it is a key player in carcinogenesis and tumor progression, among other conditions.

An important role for Notch signaling in T cell differentiation into all known effector subsets has been revealed in recent studies. Notch has been implicated in governing effector cell differentiation, regulation of cytokine expression by CD8+ T cells, and maintenance of memory T cells.

Evidence is mounting that Notch signaling induces expression of lineage-defining transcription factors and enables Th cell differentiation into all Th lineages in a ligand-specific manner. Most gain-of-function studies indicate that DLL1 and DLL4 promote Th1 commitment of CD4+ T cells and up-regulate T-bet and IFNγ expression. Regulation of IL17 and RORγt promoters and activation of Th17 differentiation associated with DLL4 have also been reported. Notch has a prominent role in Th2 cell differentiation, with Jagged ligands being implicated in direct trans-activation of Th2-promoting target genes IL4 and Gata3. Stimulation of Notch by Jagged ligands, and specifically by Jag1, elicited and maintained Treg cells with suppressive capacity, likely via up-regulation of IL9. Interference with Notch signaling enhanced regulatory function of Treg in vivo. Unlike other ligands, DLL3 is unable to activate Notch in cultured cells and seems to be a dedicated inhibitor of Notch signaling. Antigen-presenting cells (APCs) and dendritic cells (DCs) in particular are integral to the differentiation of T cells. Along with other stimuli, they express and provide Notch ligands for T cells, as shown in FIG. 1. The biophysical basis for the functional differentiation of the Notch receptor-ligand interactions is poorly understood. A subdomain of the ligands, called DSL, appears to be critical for interaction with three EGF repeats in the Notch receptor, but the basis of ligand-specific responses it unknown.

Aberrant presentation of Notch ligands under pathological conditions has a profound effect on immune function. Indeed, pharmacological activation of DLL1/Notch signaling, could result in tumor inhibition and induction of somatic mutant oncogene-specific T-cells. Similarly, in animal models of autoimmune diseases or allograft transplantation associated with immune over reactivity, targeting DLL-mediated Notch activation by antibodies has resulted in decreased T cell mediated pathology. Thus, pharmacological Notch ligand-specific activation or inhibition could be exploited for the induction of the desired type of immune response.

Thus, there remains a need in the art for agents, compositions and methods for modulating the immune response in a subject through modulation of the Notch signaling pathway. The compounds, compositions, and methods disclosed herein address these and other needs.

SUMMARY

Described herein are peptides and peptide compositions that modulate Notch signaling and can thereby increase or decrease the activity of the immune system, and methods using the disclosed peptides to treat various diseases or conditions.

In one aspect, the present disclosure provides Notch-modulating peptides comprising at least four monomeric units connected by peptide linkers, the monomeric units comprising: a mammalian DSL domain; and two or three mammalian EGF domains.

In some embodiments, the mammalian DSL and EGF domains are human DSL and EGF domains, while in some embodiments, they may be murine DSL and EGF domains.

In some embodiments, the monomeric unit comprises no more than two EGF domains (i.e., only two EGF domains), while in some embodiments the monomeric unit comprises three EGF domains.

In some embodiments, the DSL domain and EGF domains are derived from Delta-like (DLL) family protein or Jagged family proteins. For examples the DSL domain and EGF domains may be derived from DLL1, DLL3, or DLL4. Alternatively, the DSL domain and EGF domains may be derived from Jagged 1 or Jagged 2.

In some embodiments, the peptide linkers comprise 10 or fewer amino acids. For example, the peptide linker may be 9 or fewer, 8 or fewer, 7 or fewer, 6 or fewer, or 5 or fewer amino acids. In some embodiments, the peptide linkers comprise the amino acid sequence GGGGS (SEQ ID NO:132) or GSSGSSG (SEQ ID NO:133). For example, the peptide linkers may consist of two repeats of the amino acid sequence GGGGS, or the peptide linkers may consist of the amino acid sequence GSSGSSG. In some embodiments, the peptide linkers comprise a BirA tag sequence, such as an *E. coli* BirA tag sequence.

In some embodiments, the monomeric units may further comprise a MNNL domain.

In some embodiments, the disclosed Notch-modulating peptides are oligomers of the disclosed monomeric units.

For instance, in some embodiments, the Notch-modulating peptides may be tetramers, pentamers, hexamers, septamers, octamers, or larger.

In some embodiments, the Notch-modulating peptides are encoded by a single gene sequence or the peptide is expressed as a single, uninterrupted amino acid chain (i.e., polypeptide).

In some embodiments, the disclosed Notch-modulating peptides activate Notch signaling, while in some embodiments, the disclosed Notch-modulating peptides inhibit Notch signaling.

In another aspect, the present disclosure provides methods of treating cancer in a subject, comprising administering a therapeutically effective amount of a multimeric Notch-modulating peptide to a subject in need thereof, the multimeric Notch-modulating peptide comprising at least four monomeric units connected by peptide linkers, wherein the monomeric units comprise: a mammalian Delta-like (DLL) protein DSL domain; and two or three mammalian DLL EGF domains. For the purposes of these treatment methods, the DLL-based multimeric Notch-modulating peptides may possess applicable features and elements described in the first aspect above.

In some embodiments, the disclosed methods of treating cancer may further comprise administering to the subject in need thereof a therapeutically effective amount of a second Notch-modulating peptide comprising a monovalent fragment of Jagged comprising: a mammalian Jagged (Jag) protein DSL domain; and two or three mammalian Jag EGF domains. In some embodiments, the Jag DSL domain and Jag EGF domains are derived from Jag1 or Jag2. In some embodiments, the Jag DSL domain and Jag EGF domains are human, while in some embodiments that are murine. In some embodiments, the monovalent fragment of Jagged has two EGF domain repeats, while in some embodiments, the monovalent fragment of Jagged has three EGF domain repeats. Thus, for the purposes of these treatment methods, the Jag-based monovalent fragment may possess these or any other applicable features and elements described in the first aspect above.

In another aspect, the present disclosure provides methods of treating cancer in a subject, comprising administering a therapeutically effective amount of a Notch-modulating peptide to a subject in need thereof, the Notch-modulating peptide comprising a monovalent fragment of a Jagged family protein comprising: a mammalian Jagged (Jag) protein DSL domain; and two or three mammalian Jag EGF domains. For the purposes of these treatment methods, the Jag-based monovalent fragment may possess applicable features and elements described in the first aspect above.

In some embodiments, the disclosed methods of treating cancer may further comprise administering to the subject in need thereof a therapeutically effective amount of a multimeric Notch-modulating peptide, the multimeric Notch-modulating peptide comprising at least four monomeric units connected by peptide linkers, wherein the monomeric units comprise: a mammalian Delta-like (DLL) protein DSL domain; and two or three mammalian DLL EGF domains. For the purposes of these treatment methods, the DLL-based multimeric Notch-modulating peptides may possess applicable features and elements described in the first aspect above.

In some embodiments, the disclosed methods of treating cancer may further comprise administering to the subject in need thereof a therapeutically effective amount of an additional therapeutic agent. For example, the additional therapeutic agent may be an oncogene-targeted therapy, a checkpoint inhibitor, or an EGFR inhibitor.

In some embodiments, the disclosed methods of treating cancer, the subject's immune system is stimulated. In some embodiments, the cancer is selected from breast cancer, brain cancer, colon cancer, cervical cancer, ovarian cancer, testicular cancer, stomach cancer, skin cancer, head & neck cancer, lung cancer, pancreatic cancer, liver cancer, uterine cancer, bladder cancer, a hematological cancer (e.g., lymphoma, Non-Hodgkin's lymphoma, chronic lymphocytic leukemia, or multiple myeloma), prostate cancer, melanoma, sarcoma, fibrosarcoma or HIV/AIDS-related cancer. The cancer may be metastatic cancer, recurrent cancer or multidrug resistant cancer. The method may further comprise administering to said subject a second cancer therapy, such as radiotherapy, chemotherapy, immunotherapy, hormonal therapy, toxin therapy, cryotherapy, gene therapy or surgery.

In another aspect, the present disclosure provides methods of suppressing the immune system of a subject, comprising administering a therapeutically effective amount of a multimeric Notch-modulating peptide to a subject in need thereof, the multimeric Notch-modulating peptide comprising at least four monomeric units connected by peptide linkers, wherein the monomeric units comprise: a mammalian Jagged (Jag) protein DSL domain; and two or three mammalian Jag EGF domains. For the purposes of these methods, the Jag-based multimeric Notch-modulating peptides may possess applicable features and elements described in the first aspect above. For the purposes of these treatment methods, the Jag-based multimeric Notch-modulating peptides may possess applicable features and elements described in the first aspect above.

In some embodiments, the disclosed methods of suppressing a subject's immune system may further comprise administering to the subject in need thereof a therapeutically effective amount of a second Notch-modulating peptide comprising a monovalent fragment of a Delta-like protein comprising: a mammalian Delta-like (DLL) protein DSL domain; and two or three mammalian DLL EGF domains. In some embodiments, the DLL DSL domain and DLL EGF domains are derived from DLL1, DLL3, or DLL4. In some embodiments, the DLL DSL domain and DLL EGF domains are human, while in some embodiments that are murine. In some embodiments, the monovalent fragment of DLL has two EGF domain repeats, while in some embodiments, the monovalent fragment of DLL has three EGF domain repeats. Thus, for the purposes of these treatment methods, the DLL-based monovalent fragment may possess these or any other applicable features and elements described in the first aspect above.

In another aspect, the present disclosure provides methods of suppressing the immune system in a subject, comprising administering a therapeutically effective amount of a Notch-modulating peptide to a subject in need thereof, the Notch-modulating peptide comprising a monovalent fragment of a Delta-like family protein comprising: a mammalian Delta-like (DLL) protein DSL domain; and two or three mammalian DLL EGF domains. For the purposes of these treatment methods, the DLL-based monovalent fragment may possess applicable features and elements described in the first aspect above.

In some embodiments, the disclosed methods of suppressing a subject's immune system may further comprise administering to the subject in need thereof a therapeutically effective amount of a multimeric Notch-modulating peptide, the multimeric Notch-modulating peptide comprising at least four monomeric units connected by peptide linkers, wherein the monomeric units comprise: a mammalian Jagged (Jag) protein DSL domain; and two or three mammalian Jag EGF domains. For the purposes of these treatment methods, the Jag-based multimeric Notch-modulating peptides may possess applicable features and elements described in the first aspect above.

In some embodiments of the disclosed methods of suppressing a subject's immune system, the subject has received an organ transplant, is suffering from graft-versus-host disease (GVHD), is suffering from an allergy, or is suffering from an autoimmune disease. In some embodiments, the subject has T-cell leukemia and lymphoma.

The foregoing general description and following detailed description are exemplary and explanatory and are intended to provide further explanation of the invention.

BRIEF DESCRIPTION OF THE DRAWINGS

The accompanying figures, which are incorporated in and constitute a part of this specification, illustrate several aspects described below.

(FIG. 3A) Mouse construct #42 consisting of DSL and EGF repeats 1,2 immobilized on plastic activates Notch in mouse EL4 T cells in dose-dependent manner; (FIG. 3B) Monovalent human DLL1 construct #36 comprising DSL and EGF repeats 1-3 inhibits clustered DLL1-mediated Notch activation in human H460 epithelial cells; Ratios of Hes1 or Hey1 mRNA to β-actin were determined by qRT-PCR. Mean±SEM, n=4. (FIG. 3C) Monovalent construct #42 inhibits IFNγ secretion by mouse splenocytes activated by CD3/CD28 antibodies as assessed by ELISPOT assay using $200\times10^3$ cells. Representative wells with average numbers of spots are also shown. Mean±SEM, n=3. (FIG. 3D) Pharmacological activation of DLL1 or Jag1 in mice results in attenuation or acceleration of tumor growth and enhancement or inhibition of immune responses, respectively. Activation of DLL1-mediated Notch signaling in LLC tumor-bearing mice by administering clustered DLL1 decreased tumor growth and increased numbers of IFNγ-producing TIL; activation of Jag1 had the opposite effect. Representative IFNγ ELISPOT data for TIL with average number of spots for three groups are shown. Mean±SEM, n=5-7.

(FIG. 4A) Heart allograft survival. (FIG. 4B) IFNγ ELISPOT assay on recipient CD8 T cells isolated at the time of rejection and restimulated with mitomycin C treated donor BALB/c spleen cells in the presence of self antigen presenting cells. (FIG. 4C) Percentage of FoxP3+ cells among CD4+ spleen cells at the time of rejection. (FIG. 4D) Serum titers of donor-reactive IgG alloantibody determined by flow cytometry.

(FIG. 26C) MT5 tumor growth in $CD11c^+$ cell specific $Dll1^{-/-}$ knockout and wild type mice. (FIG. 26D) LLC tumor growth in $CD11c^+$ cell specific Jag2' knockout and wild type littermates. Mean±SEM, 8-10 mice per group; mouse numbers, *$p<0.05$; **$p<0.01$.

(FIG. 27E) IFN-γ-producing cells were enumerated by ELISPOT assay in tumor-draining lymph node cells of the same group of $Dll1^{-/-}$ knockout or wild type littermates following re-stimulation with anti-CD3/CD28 beads. Mean±SEM, 5 mice per group, *$p<0.05$, **$p<0.01$.

(FIG. 30A) Expression of Notch downstream target Hes1 protein was assessed by Western blotting in murine EL4 T cells treated with clustered DLL1 or with clustered DLL1 and soluble DLL1 construct for 24 h. (FIG. 30B) Tumor volume was measured in LLC tumor bearing mice treated with monovalent soluble DLL1 construct 1 mg/kg body weight, i.p. every 2 days. (FIG. 30C) IFN-γ producing tumor-infiltrating lymphocytes from these mice were enumerated by ELISPOT assay on day 18 after LLC tumor initiation. Mean±SEM, n=8, *$p<0.05$; **$p<0.01$. (FIG. 30D, 30E) T cell proliferation was measured after co-incubating allogeneic T cells labeled with Cell Tracer Violet fluorescent dye with bone marrow derived $Dll1^{-/-}$ or wild type DC in the presence of soluble anti-CD3 for 5 days. In some T cell cultures with wild type DC soluble DLL1 construct was added at the indicated concentrations. A representative Cell Tracer Violet dye dilution profile is shown (FIG. 30E). (FIG. 30F, 30G) C57BL/6 mice were transplanted with BALB/c heart allografts and treated with soluble DLL1 fragment 1 mg/kg i.p. every 2 days. (FIG. 30F) Heart allograft survival and (FIG. 30G) IFN-γ ELISPOT assay on recipient CD8 T cells isolated at the time of rejection and re-stimulated with mitomycin C treated donor spleen cells in the presence of donor BALB/c splenocytes alone or mixed with recipient C57BL/6 splenocytes. Mean±SEM, n=4-8, *$p<0.05$; **$p<0.01$.

(FIG. 31D, 31E) Inhibition of Jag1-mediated Notch signaling with soluble extracellular domain of Jag1 significantly attenuates tumor growth and reduces regulatory (Treg) generation. (FIG. 31D) Tumor growth in LLC tumor bearing mice treated with monovalent soluble Jag1 construct 1 mg/kg body weight, i.p. every 2 days. (FIG. 31E) Percentage of $FoxP3^+$ cells among $CD4^+$ cells in combined splenocytes and LN cells in these mice on day 18 after LLC tumor initiation. Mean±SEM, 8-10 mice per group, *p<0.05; **p<0.01.

DETAILED DESCRIPTION

Figure 1:
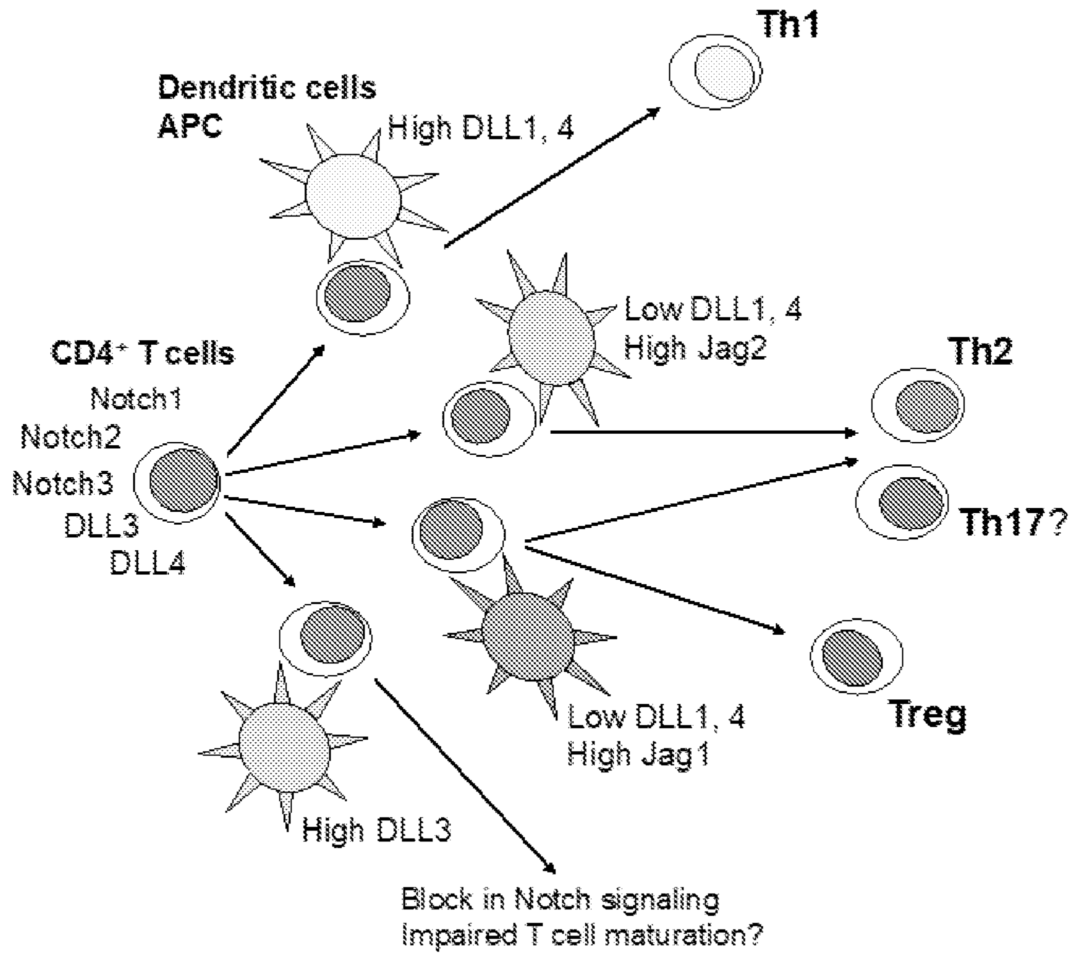
FIG. 1 shows how Notch ligands function in the regulation and differentiation of Th cells.

Disclosed herein are a series of fragments of Notch ligand extracellular domains, in particular, of mouse and human Delta-like ligands (e.g., DLL1) and Jagged ligands (e.g., Jag1), and linked discrete oligomers thereof, that suppress or stimulate the immune system by inhibition or activation of the Notch signaling pathway in a ligand-specific manner. Inhibitory molecules constitute a novel class of immunosuppressants with potential use in allograft transplantation, autoimmune disease, and allergic disease, as well as the treatment of certain cancers like T cell leukemia and lymphoma. Activating molecules represent a novel class of immune stimulatory agents that can be used as, for example, anticancer agents operating by direct stimulation of the Notch signaling pathway (e.g., the Notch1 and Notch2 receptors in the case of DLL1). These molecules can complement the use of oncogene-targeted therapies and other immunotherapies such as checkpoint blockade antibodies since they work by different mechanisms.

Described herein are Notch-modulating peptide monomers and multimers, compositions comprising the peptides, and methods of use thereof, including methods for treating cancer, inhibiting organ transplant rejection, or treating graft-versus-host diseases in a subject in need thereof.

The invention of these novel Notch-modulating peptide compounds and compositions stemmed from the initial observation of one of the inventors that a clustered (polymeric) DLL1 extracellular domain could activate Notch and reduce tumor growth in LLC mouse models. However, these earlier molecules were unsuitable as drugs due to their polymeric, heterogeneous nature. Therefore, the inventors, as described herein, developed a novel and discrete product that can modulate Notch1. This required a number of non-obvious steps:

1. The minimal Notch1-binding fragment that could be expressed and is stable had to be determined. It was found that the DSL-EGF1-EFG2 fragment (construct NL 42) (SEQ ID NO:36) could be refolded from inclusion bodies from expression in *E. coli*, and was sufficient for inhibition of Notch1 signaling, including increasing tumor growth and reducing allograft rejection. A procedure was developed for efficient refolding of these molecules to enable their preparation. These Notch1 inhibiting DLL1 fragment monomers represent a new immunosuppressing modality with use against allograft rejection and other immune disease processes.

2. Several strategies for conjugation of this monomer unit into oligomers were attempted, including with a C-terminal cysteine for conjugation to maleimide PEG linkers and using the N-terminal amine for reductive amination PEG aldehyde linkers. None of these attempts were successful. Genetic fusions of the monomer units with short linkers were also generated, with 2× to 8× chains of the monomers. It was not clear that these molecules would fold, but it was found they could be produced in significant amounts.

3. Although it was clear that the DLL1 monomer (and the fragment monomer) is a Notch inhibitor and that a clustered DLL1 polymer is an activator, it was not clear what degree of oligomerization would switch the fragment monomer to activation. It was found that dimers and trimers did not activate, but tetramers did. This murine tandem tetramer is construct NL 83 (SEQ ID NO:45). Larger (5×-8×) fragments are also disclosed herein (See FIG. 23). The long repetitive sequences made the molecules difficult to sequence completely, and thoughtful, non-obvious, non-redundant DNA sequences had to be employed for these molecules.

4. Because the topology of the DLL1 molecules on the cell surface is usually parallel and the monomers are sequential in the oligomers, the correct length for the peptide linkers between the monomers is non-obvious. Unexpectedly, shorter linkers gave rise to stronger activation. Two different murine short linker 4× constructs (NL 83 (SEQ ID NO:45) and NL 87 (SEQ ID NO:53)) activated most strongly.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

The following definitions are provided for the full understanding of terms used in this specification.

Definitions

As used herein, the singular forms "a", "an" and "the" are used interchangeably and intended to include the plural forms as well and fall within each meaning, unless the context clearly indicates otherwise. Also, as used herein, "and/or" refers to and encompasses any and all possible permutations and combinations of one or more of the listed items.

As used herein, the term "about" is understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.,* 22:1859-1862 (1981), or by the triester method according to Matteucci, et al., *J. Am. Chem. Soc.,* 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" or "nucleotide sequence" or "nucleic acid sequence" refers to a single or double stranded polymer composed of nucleotide monomers.

The term "polypeptide" refers to a compound made up of a single chain of D- or L-amino acids or a mixture of D- and L-amino acids joined by peptide bonds.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 6'7%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "variant" or "derivative" as used herein refers to an amino acid sequence derived from the amino acid sequence of the parent protein having one or more amino acid substitutions, insertions, and/or deletions.

As used herein, the phrases "therapeutically effective amount" and "therapeutic level" mean a Notch-modulating peptide dosage or plasma concentration in a subject that provides the specific pharmacological effect for which the Notch-modulating peptide is administered to a subject in need of such treatment, e.g., to activate the immune response of a cancer patient or to inhibit the immune response of an organ transplant recipient. It is emphasized that a therapeutically effective amount or therapeutic level of a Notch-modulating peptide will not always be effective in treating the given condition of every subject, even though such dosage is deemed to be a therapeutically effective amount by those of skill in the art. For convenience only, exemplary amounts are provided herein.

Those skilled in the art can adjust such amounts in accordance with standard practices as needed to treat a specific subject. The therapeutically effective amount may vary based on the route of administration and dosage form, the age and weight of the subject, and/or the subject's condition, including the severity, stage, and/or extent of the disease or condition at the time of treatment.

The terms "treatment" or "treating" as used herein with reference to use of the disclosed Notch-modulating peptides refer to one or more of: reducing, ameliorating or eliminating one or more symptoms or effects of a disease or condition such as cancer or graft-versus-host disease; activating or inhibiting Notch signaling in the subject; and/or activating or inhibiting the immune response of the subject. As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

The terms "individual," "subject," "host," and "patient" are used interchangeably herein, and refer to any individual mammal subject, e.g., bovine, canine, feline, equine, or human.

As used herein, the term "DSL domain" refers to an extracellular protein domain (DSL: Delta/Serrate/Lag-2) which modulates members of the Lin-12/Notch receptor family. Like EGF motifs, the DSL domain can contain six conserved cysteines spanning different sequence lengths. Some proteins known to contain a DSL domain are, for example, DLL proteins, JAG proteins, and the mammalian Serrate proteins.

The term "EGF domain" as used herein refers to a protein domain found in the sequence of epidermal growth factor (EGF) and has also been shown to be present, in a more or less conserved form, in a large number of other, mostly animal proteins. EGF domains are generally found in the extracellular domain of membrane-bound proteins or in proteins known to be secreted. The EGF domain can include six cysteine residues which have been shown to be involved in disulfide bonds. Some proteins known to contain an EGF domain include, for example, DLL proteins, JAG proteins, the mammalian Serrate proteins, and the human Tan-1 protein. The EGF domain is known in the art to occur in a number of other proteins as well.

Notch Signaling

The Notch system has emerged as a broad regulator of effector cell differentiation and function, both in CD4 and in CD8 T lymphocytes, with important implications for immune function in carcinogenesis and tumor progression. The Notch receptor-ligand interaction is an important regulatory point governing the induction or inhibition of specific types of immune responses through variable expression of Notch ligands in hematopoietic cells. Four Notch transmembrane receptors (Notch1-4) interact with five cell surface ligands (DLL1, DLL3, DLL4, Jag1, Jag2). The ligands can influence T cell differentiation and function. It is thought that DLL1 and DLL4 direct T cell polarization toward T helper type 1 (Th1), whereas Jag1 and Jag2 promote Th2; Jag1 is also implicated in regulatory T cell (Treg) responses.

An important characteristic of Notch signaling is that the activation of Notch requires a polyvalent interaction between multiple receptor and ligand molecules to induce sufficient cell membrane tension to expose Notch proteolytic cleavage sites required for activation. In contrast, soluble monovalent forms of ligands act as competitive inhibitors. This observation opens opportunities for pharmacological modulators of ligand-specific Notch signaling.

Figure 2:
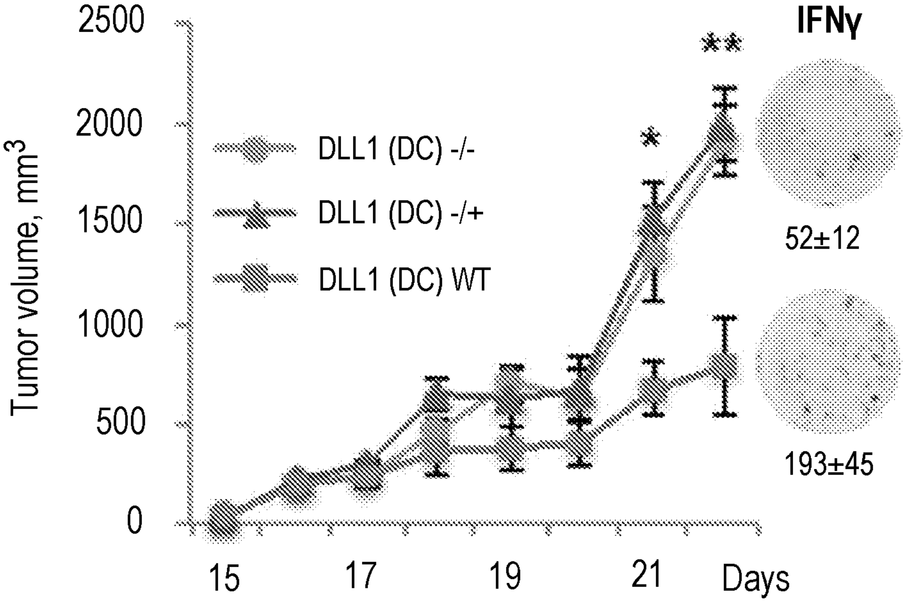
FIG. 2 shows hetero- and homozygous genetic deletion of DLL1 in CD11c+DC results in impaired immune responses and accelerated tumor growth. One or two alleles of DLL1 were deleted in Dll1flox/flox mice by breeding with mice carrying Cre recombinase under control of CD11c promoter. Growth of LLC subcutaneous (s.q.) tumor and representative IFNγ ELISPOT data for TIL with average number of spots for Dll1−/+(Dll1(DC)−/+), Dll1−/−(Dll1(DC)−/−) and control mice with wild type alleles (Dll1(DC)WT) are shown. Mean±SEM; n=7-8.

For example, aberrant DLL1 presentation by dendritic cells (DC) leads to the impairment of Th1 immune responses and accelerated tumor growth. These experiments in mice with the ligand lineage-specific deletion in antigen-presenting DC confirm the critical importance of adequate Notch ligand presentation for eliciting respective immune responses. Deletion of even one allele of DLL1 in CD11c+ DC resulted in attenuated Th1 type anti-tumor responses, as revealed by the remarkably decreased numbers of tumor-infiltrating lymphocytes (TIL) producing IFNγ and accelerated Lewis Lung Carcinoma (LLC) tumor growth (FIG. 2). Mice with deletion of one or two Jag2 alleles in CD11c+DC did not show any significant difference in tumor growth compared with wild type animals.

Disclosed herein are data that demonstrate the efficacy of clustered DLL1-mediated Notch activation in the reversion of tumor-induced immunosuppression, and induction of Th1 anti-tumor responses in animal models, as well as data that DLL1 Notch-binding fragments in monovalent form can decrease T cell cytotoxicity and prolong cardiac allograft survival in animals. DLL1 Notch interacting fragments showed efficacy in regulation of Th1 and regulatory T cell (Treg) responses in vivo.

Thus, mono- and multivalent forms of Notch ligand receptor-binding domains were developed and utilized for the induction of the desired type of immune response via pharmacological activation or inhibition of ligand-specific signaling. Herein, mono- and polyvalent forms of DLL1 and Jag1 protein fragments are used for modulation of Th1 and Treg immune responses, and their immunological efficacy and therapeutic potential in the pre-clinical setting in cancer and cardiac allograft animal models was tested.

Notch-Modulating Peptides

Described herein are Delta-like (DLL) and Jagged (Jag) based mono- and polyvalent fragments that can be used as monomers or multimers to elicit desired immunological effects in a subject. The present disclosure provides a novel approach of direct modulation of the complex Notch pathway with authentic signaling molecules engineered for favorable physical properties.

Figure 3A:
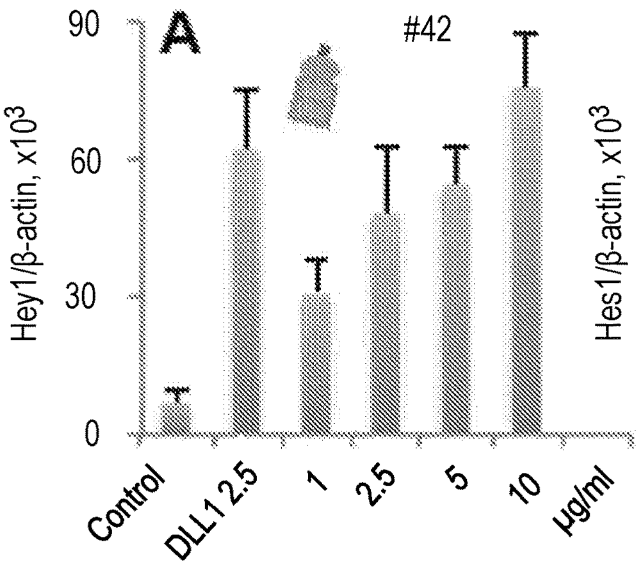
FIGS. 3A-3D show DLL1 protein constructs comprising Notch binding domains activate Notch signaling in multimeric form while inhibit signaling and cytokine production by T cells in monomeric form.
Figure 3B:
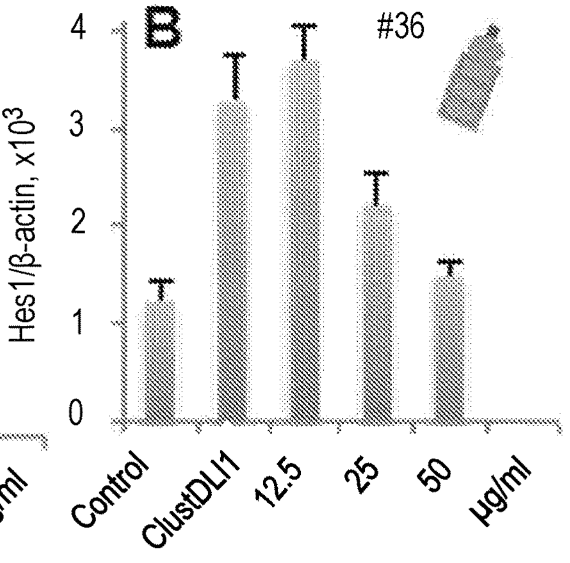
Figure 3C:
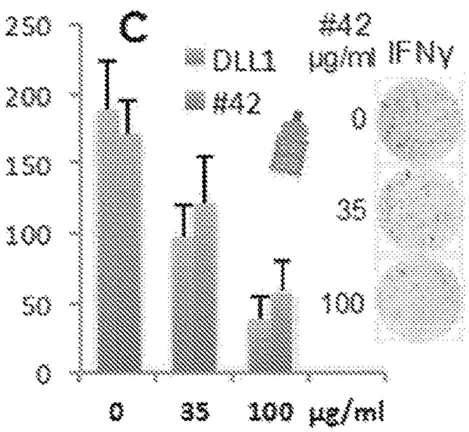

DLL1 fragments comprising a Notch receptor binding domain can be employed for manipulating Notch signaling and T cell function. A number of human and mouse DLL1 constructs comprising the DSL domain and two or three adjacent EGF repeats were generated and tested in vitro for their ability to modulate Notch signaling in Notch expressing cells, and to regulate IFNγ expression by T cells. Human or mouse constructs or the control full-length extracellular domain of DLL1 were adsorbed on the cell culture plastic to mimic polyvalency. In this format, human H460 cells or mouse EL4 T cells expressing Notch exhibited significant activation of Notch signaling in a dose-dependent manner as revealed by the expression of Notch downstream target genes Hes1 and Hey1 mRNA (FIG. 3A). In the other format, Notch was activated by the clustered full-length DLL1 complex and soluble DLL1 fragments were added at varying doses as competitive inhibitors. They efficiently blocked Notch activation (FIG. 3B). To evaluate the ability of the DLL1 fragments to modulate cytokine secretion, a key functional property of T cells, the fragments were added to mouse splenocyte cultures activated by CD3/CD28 antibodies to induce cytokine production, and secretion of IFNγ was measured by the ELISPOT assay. Interference with DLL1 signaling by adding the soluble DSL-EGF12 fragment significantly decreased numbers of IFNγ-producing cells (FIG. 3C). This provides the rationale for the application of ligand-based reagents for regulation of T cell functionality.

Figure 3D:
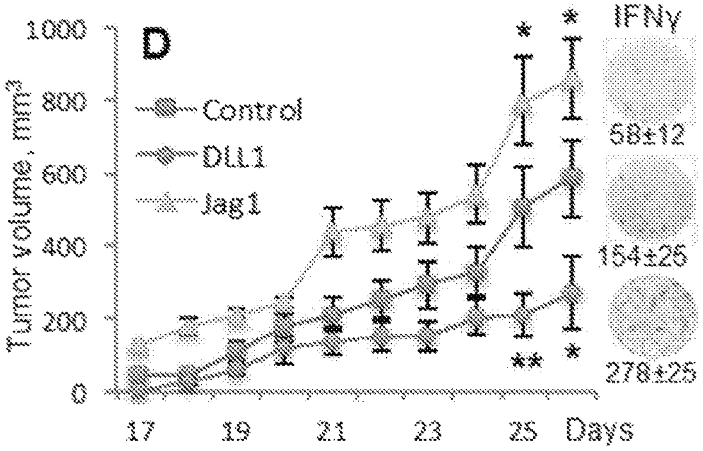

Activation of DLL1 and Jag1-mediated Notch signaling produces dramatically different effects in tumor models. Very different outcomes of pharmacological Notch activation by different ligands in cancer are illustrated by experiments with an LLC tumor model. When DLL1-mediated signaling was activated using clustered DLL1, tumor growth was significantly attenuated and associated with remarkably improved anti-tumor cytotoxic T lymphocyte (CTL) responses. In contrast, activation of Jag1 had the opposite effect, accelerating tumor growth and inhibiting immune responses compared to control animal group (FIG. 3D).

Figure 4A:
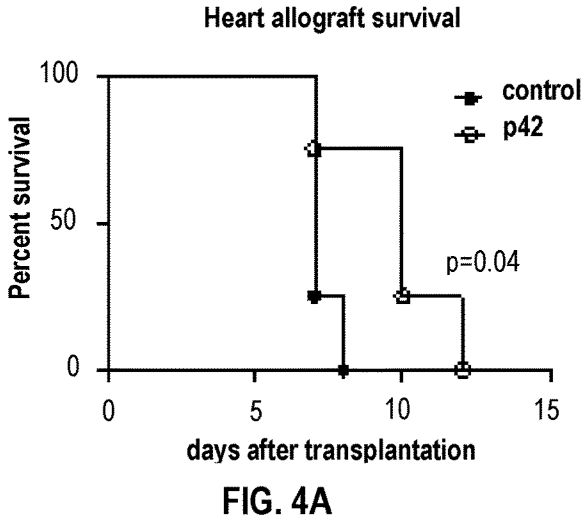
FIGS. 4A-4D shows cardiac allograft survival and T cell response. C57BL/6 (B6) mice were transplanted with BALB/c heart allografts and treated with DLL1(DSL-EGF12) (20 μg i.p.) or vehicle control (glycerol+PBS) on d. −3, −1, 1, 3, 5, 7 related to transplantation.
Figure 4B:
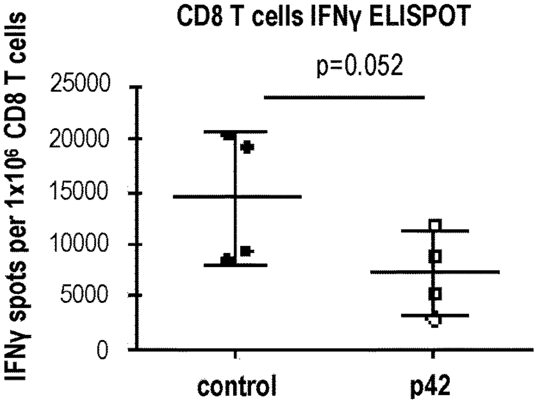
Figure 4C:
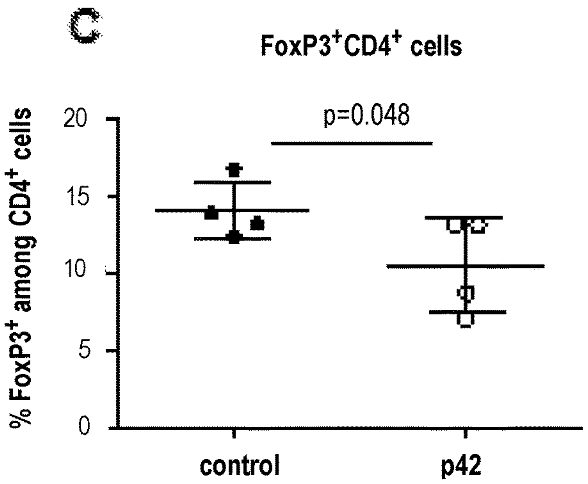
Figure 4D:
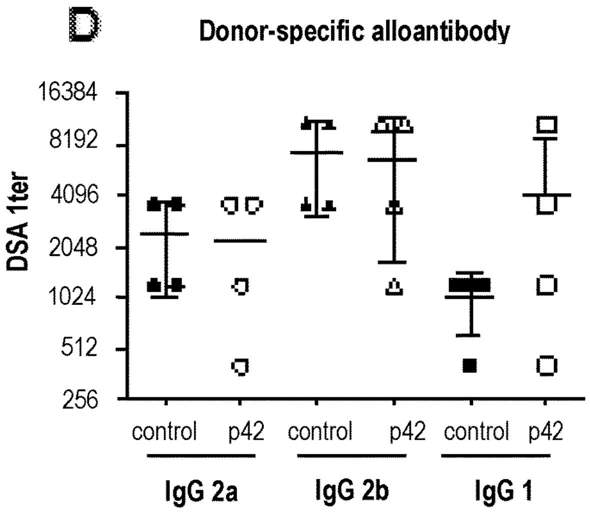

On the other hand, the monomeric form of a DLL1 fragment (DSL-EGF12) reduces alloreactive T cell responses and prolongs mouse heart allograft survival. C57BL/6 (B6) recipients of fully MHC-mismatched heterotopic BALB/c heart allografts were treated with the fragment or vehicle control around the time of transplantation. The fragment modestly but significantly prolonged allograft survival compared to control treatment (FIG. 4A). The prolonged survival was associated with the decreased production of IFNγ by donor-reactive CD8 T cells (FIG. 4B) without shift to IL-4 or IL-17 (82±7 vs 84±8 IL-4 spots and 16±5 vs 18±2 IL-17 spots/1×106 spleen cells for control and fragment treated groups, respectively), and with reduced numbers of FoxP3+ regulatory T cells in recipient spleen (FIG. 4C). Both fragment-treated and control heart allograft recipients had comparable serum titers of donor specific alloantibodies (DSA) at the time of rejection (FIG. 4D).

This data indicates that activation of the DLL1/Notch axis and/or inhibition of the Jag1 signal in cancer are valuable therapeutic approaches to improved anti-tumor immunity and can provide clinical benefit. Conversely, DLL1 inhibition or Jag1 activation could reduce organ transplant rejection. Thus, the data suggest clinical applicability of mono- and multivalent DLL1 and Jag1 constructs.

Figure 5:
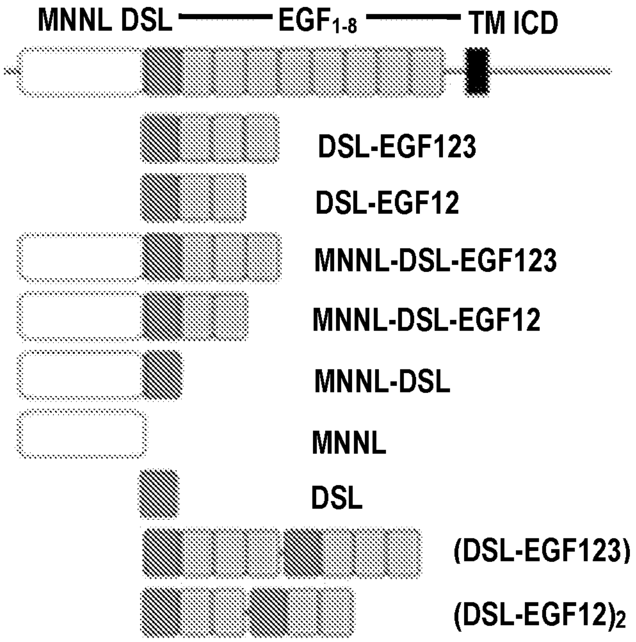
FIG. 5 shows DLL1 and constructed fragments. Both human and mouse sequences have been constructed. The bottom two constructs are tandem fusions.

Based on domain deletion studies of DLL1, DLL4, and Jag1, a series of DLL1 fragments were designed to evaluate the structures in terms of ease of production and efficacy in Notch signaling. The DSL domain and first several EGF repeat domains C-terminal to the DSL domain have been implicated in Notch1 binding, and recent studies suggest that the MNNL domain N-terminal to the DSL domain may also be important for signaling. Thus, the disclosed fragments or monomers may comprise one or more of the MNNL, DSL and first three EGF repeat domains, as shown in FIG. 5.

Genes for the longest corresponding constructs from human and mouse DLL1 were ordered from Genewiz, and subfragments were amplified by PCR and subcloned into a T7 expression vector built in the lab called pHLIC. Constructs for all DLL1 fragments shown in FIG. 5 have been subcloned and sequence confirmed. A similar set of human and mouse Jag1 fragments are produced analogously.

Figure 6:
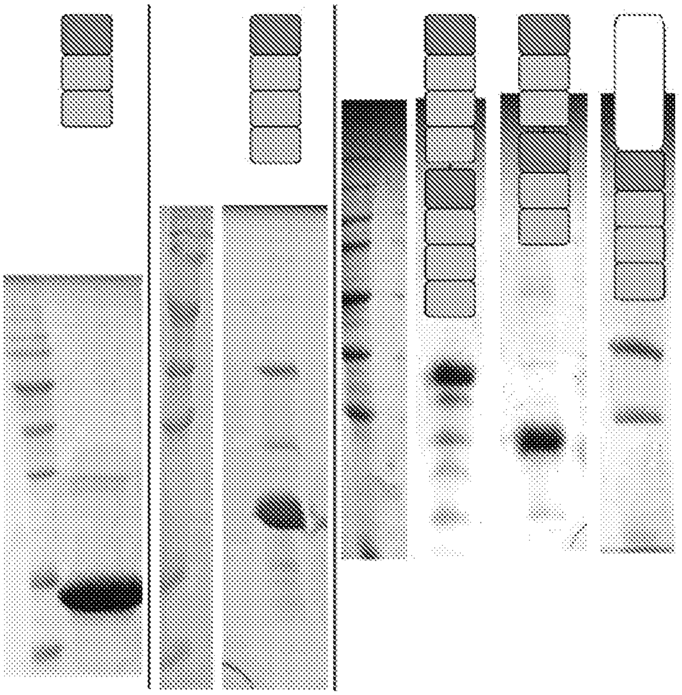
FIG. 6 shows NiNTA purification of selected DLL1 fragments from *E. coli* cytoplasmic expression and refolding. Ion exchange was used to remove contaminants and degradation products.

Maltose binding protein (MBP) fusion and periplasmic expression of several of the fragments were examined, but it was surprisingly found that all the DLL1 fragments could be isolated with refolding of GdnHC1-extract from the insoluble fraction from *E. coli* cytoplasmic expression. (No critical posttranslational modifications of DLL1 are known in the MNNL to EGF3 region). Additionally, it was discovered that moving to on-column refolding of NiNTA-bound 6×His-tagged fragments, with subsequent proteolysis of the tag with TEV protease, provided significantly higher yields than dialysis refolding (FIG. 6). The proteins are quite pure on re-passage over NiNTA after proteolysis, with some degradation observed for MNNL-containing constructs. Analogous Jag1 constructs are amenable to purification by similar methods, and NMR studies of various bacterially-produced Jag1 fragments support that notion.

The fact that soluble, refolded constructs can be obtained with little sign of degradation by gel shows the fragments are well folded. Cell-based and mouse model assays of the DSL-EFG12 and DSL-EGF123 constructs show that these molecules bind to the Notch receptor and activate the Notch pathway when artificially multimerized on a plate surface (FIG. 3), further arguing that fragments are folded correctly.

Methods known in the art can be used to multimerize the disclosed monomeric fragments of DLL and Jag proteins. For example, two methods of generation of homogeneous multimeric forms of the disclosed DLL1 and Jag1 fragments include genetic fusion and polyethylene glycol (PEG) conjugation.

Tandem repeats of DSL-EGF12 and DSL-EGF123 were generated with a short peptide linker, and these multimers can be refolded and purified (FIG. 6). A similar approach is used to produce a series of these molecules with longer linkers and 3 and 4 monomers in tandem. Additionally or alternatively, the fragments can be conjugated to dimers or higher order multimers using commercially available PEGs with aldehyde termini for N-terminal amine crosslinking, followed by sodium cyanoborohydride reduction of the imine to an amine linker. Higher oligomers can be created by derivatization of multiarm aldehyde PEGs, such as by Swern or Dess-Martin periodinane oxidation of commercially available 4-arm and 8-arm PEG alcohols.

a. Monomeric Units

The Notch-modulating peptides disclosed herein include monomeric units derived from wild-type DLL or Jagged peptides (e.g., DLL1 or Jag1), as well as multimeric peptides comprising oligomerized monomers. The monomeric units comprise a DSL domain, one or more EGF repeat domains (preferably two or three), and, optionally, a MNNL domain preceding the DSL domain.

The disclosed monomeric units may possess different activities depending on what peptide they are derived from. For example, a DLL1 monomer comprising a DSL domain and two or three ECF repeats inhibits Notch signaling and results in suppression of the immune system. Conversely, a Jag1 monomer comprising a DSL domain and two or three ECF repeats activates Notch signaling and results in stimulation of the immune system.

The monomeric units may be derived from any known DLL or Jagged proteins, including DLL1, DLL3, DLL4, Jag1, and Jag2. In some embodiments, the monomers comprise 1, 2, 3, 4, or 5 EGF repeat domains. In some embodiments, the monomer comprises or consists, from N-terminus to C-terminus of:

DSL-EGF-EGF
DSL-EGF-EGF-EGF
DSL-EGF-EGF-EGF-EGF
DSL-EGF-EGF-EGF-EGF-EGF
MNNL-DSL-EGF-EGF
MNNL-DSL-EGF-EGF-EGF
MNNL-DSL-EGF-EGF-EGF-EGF
MNNL-DSL-EGF-EGF-EGF-EGF-EGF wherein the DSL and EGF domains are derived from DLL1, DLL3, DLL4, Jag1, or Jag2. Additionally, the monomers may comprise a PelB leader sequence and/or an N-terminal His tag for ease of purification/processing.

In some embodiments, the monomeric unit of a Notch-modulating peptide as described herein comprises a DSL domain comprising the sequence (SEQ ID NO: 139)
FVCDEHYYGEGCSVFCRPRDDAFGHFTCGDRGEKMCDPGWKGQYC.

In some embodiments, the monomeric unit of a Notch-modulating peptide as described herein comprises an EGF domain (EGF1) comprising the sequence (SEQ ID NO: 140)
CLPGCDDQHGYCDKPGECKCRVGWQGRYC.

In some embodiments, the monomeric unit of a Notch-modulating peptide as described herein comprises an EGF domain (EGF2) comprising the sequence (SEQ ID NO: 141)
CIRYPGCLHGTCQQPWQCNCQEGWGGLFC.

In some embodiments, the monomeric unit of a Notch-modulating peptide as described herein comprises an EGF domain (EGF3) comprising the sequence (SEQ ID NO: 142)
CTHHKPCRNGATCTNTGQGSYTCSCRPGYTGANC.

In some embodiments, the monomeric unit of a Notch-modulating peptide as described herein comprises a MNNL domain comprising the sequence (SEQ ID NO: 143)
QVWSSGVFELKLQEFVNKKGLLGNRNCCRGGSGPPCACRTFFRVCLKHYQ

ASVSPEPPCTYGSAVTPVLGVDSFSLPDGAGIDPAFSNPIRFPFGFTWPG

TFSLIIEALHTDSPDDLATENPERLISRLTTQRHLTVGEEWSQDLHSSGR

TDLRYSYR.

The Universal Protein Resource (UniProt) is a comprehensive resource for protein sequence and annotation data (http://www.uniprot.org/). The following Accession Numbers for the DLL and Jagged sequences from UniProt are as follows:

DLL1
UniProtKB—000548 (DLL1_HUMAN)
UniProtKB—Q61483 (DLL1_MOUSE)
DLL3
UniProtKB—Q9NYJ7 (DLL3_HUMAN)
UniProtKB—088516 (DLL3_MOUSE)
DLL4
UniProtKB—Q9NR61 (DLL4_HUMAN)
UniProtKB—Q9JI71 (DLL4_MOUSE)
Jag1
UniProtKB—P78504 (JAG1_HUMAN)
UniProtKB—Q9QXX0 (JAG1_MOUSE)
Jag2
UniProtKB—Q9Y219 (JAG2_HUMAN)
UniProtKB—Q9QYE5 (JAG2_MOUSE)

The sequences of the DSL and EGF domains are noted in the UNIPROT entries (see Family and Domains). For example, based on the full-length sequence for mouse DLL1 (Q61483; SEQ ID NO:151), the DSL domain ranged from about amino acids 176-220 of the DLL1 protein (SEQ ID NO:139); the EGF1 domain ranged from about amino acids 225-253 of the DLL1 protein (SEQ ID NO:140); the EGF2 domain ranged from about amino acids 256-284 of the DLL1 protein (SEQ ID NO:141); and the EGF3 domain ranged from about amino acids 291-324 of the DLL1 protein (SEQ ID NO:142). In some embodiments, the peptide also comprises an MNNL domain of the DLL1 protein (SEQ ID NO:143). In some embodiments, the peptide also comprises additional EGF repeats, for example, EGF4, EGF5, EGF6, EGF7, and/or EGF8 domains.

In some embodiments, the monomeric unit of a Notch-modulating peptide as described herein comprises SEQ ID NO:139, SEQ ID NO:140, SEQ ID NO:141, SEQ ID NO:142, SEQ ID NO:143, or combinations thereof. In some embodiments, the monomeric unit of a Notch-modulating peptide as described herein comprises SEQ ID NO:139, SEQ ID NO:140, and SEQ ID NO:141. In some embodiments, the monomeric unit of a Notch-modulating peptide as described herein comprises SEQ ID NO:139, SEQ ID NO:140, SEQ ID NO:141, and SEQ ID NO:142.

In some embodiments, the monomeric unit of the Notch-modulating peptide comprises an amino acid sequence that is at least 70% identical to one of SEQ ID NO:139, SEQ ID NO:140, SEQ ID NO:141, SEQ ID NO:142, or SEQ ID NO:143. In some embodiments, the monomeric unit of the Notch-modulating peptide comprises an amino acid sequence that is at least 75% identical, at least 80% identical, at least 85% identical, at least 90% identical, at least 95% identical, or at least 99% identical to one of SEQ ID NO:139, SEQ ID NO:140, SEQ ID NO:141, SEQ ID NO:142, or SEQ ID NO:143.

For constructs based from the human sequences, the sequences of the DSL and EGF domains are noted in the UNIPROT entries (see Family and Domains). For example, based on the full-length sequence for human DLL1 (000548; SEQ ID NO:152), the DSL domain ranged from about amino acids 177-221 of the DLL1 protein (SEQ ID NO:153); the EGF1 domain ranged from about amino acids 226-254 of the DLL1 protein (SEQ ID NO:154); the EGF2 domain ranged from about amino acids 257-285 of the DLL1 protein (SEQ ID NO:155); and the EGF3 domain ranged from about amino acids 292-325 of the DLL1 protein (SEQ ID NO:156). In some embodiments, the peptide also comprises an MNNL domain of the human DLL1 protein. In some embodiments, the peptide also comprises additional EGF repeats, for example, EGF4, EGF5, EGF6, EGF7, and/or EGF8 domains.

In some embodiments, the monomeric unit of a Notch-modulating peptide as described herein comprises a DSL domain comprising the sequence SEQ ID NO:153. In some embodiments, the monomeric unit of a Notch-modulating peptide as described herein comprises an EGF domain (EGF1) comprising the sequence SEQ ID NO:154. In some embodiments, the monomeric unit of a Notch-modulating peptide as described herein comprises an EGF domain (EGF2) comprising the sequence SEQ ID NO:155. In some embodiments, the monomeric unit of a Notch-modulating peptide as described herein comprises an EGF domain (EGF3) comprising the sequence SEQ ID NO:156.

In some embodiments, the monomeric unit of the Notch-modulating peptide comprises an amino acid sequence that is at least 70% identical to one of SEQ ID NO:153, SEQ ID NO:154, SEQ ID NO:155, or SEQ ID NO:156. In some embodiments, the monomeric unit of the Notch-modulating peptide comprises an amino acid sequence that is at least 75% identical, at least 80% identical, at least 85% identical, at least 90% identical, at least 95% identical, or at least 99% identical to one of SEQ ID NO:153, SEQ ID NO:154, SEQ ID NO:155, or SEQ ID NO:156.

In some embodiments, the monomeric unit of a Notch-modulating peptide as described herein comprises SEQ ID NO:153, SEQ ID NO:154, and SEQ ID NO:155. In some embodiments, the monomeric unit of a Notch-modulating peptide as described herein comprises SEQ ID NO:153, SEQ ID NO:154, SEQ ID NO:155, and SEQ ID NO:156.

For example, the exemplary DLL1 monomers and multimers disclosed below in Tables 1 and 2 can be broken down into three categories which are separated in the name by a period. The first describes if the sequence is human (HuDLL1) or mouse (MuDLL1). The second indicates the presence of a PelB leader sequence in the construct (by the presence of PelB-) and if the construct has two or three EGF domains (EFG12 vs EGF123). The third category indicates whether or not the DSL-EGF domains are repeated in tandem connected by a GSSGSSG linker (Tan), the construct contains a C-terminal cysteine for potential chemical conjugation (Cys), both (Tan/Cys) or neither. In some embodiments, the constructs contain an N-terminal 6× histidine affinity tag followed directly by a TEV cleavage site.

TABLE 1

| Exemplary Human and Mouse DLL1 Monomer and Multimer Peptide Sequences | |
|---|---|
| HuDLL1.PelB-DSL-EGF123.Tan/Cys (SEQ ID NO: 1) | MKYLLPTAAAGLLLLAAQPAMAAHHHHHHGGENLYFQGFVCDEHYYGEGC<br>SVFCRPRDDAFGHFTCGERGEKVCNPGWKGPYCTEPICLPGCDEQHGFCD<br>KPGECKCRVGWQGRYCDECIRYPGCLHGTCQQPWQCNCQEGWGGLFCNQD<br>LNYCTHHKPCKNGATCTNTGQGSYTCSCRPGYTGATCELGSSGSSGFVCD<br>EHYYGEGCSVFCRPRDDAFGHFTCGERGEKVCNPGWKGPYCTEPICLPGC<br>DEQHGFCDKPGECKCRVGWQGRYCDECIRYPGCLHGTCQQPWQCNCQEGW<br>GGLFCNQDLNYCTHHKPCKNGATCTNTGQGSYTCSCRPGYTGATCELGSS<br>GC |
| HuDLL1.DSL-EGF123.Tan/Cys (SEQ ID NO: 2) | HHHHHHGGENLYFQGFVCDEHYYGEGCSVFCRPRDDAFGHFTCGERGEKV<br>CNPGWKGPYCTEPICLPGCDEQHGFCDKPGECKCRVGWQGRYCDECIRYP<br>GCLHGTCQQPWQCNCQEGWGGLFCNQDLNYCTHHKPCKNGATCTNTGQGS<br>YTCSCRPGYTGATCELGSSGSSGFVCDEHYYGEGCSVFCRPRDDAFGHFT<br>CGERGEKVCNPGWKGPYCTEPICLPGCDEQHGFCDKPGECKCRVGWQGRY<br>CDECIRYPGCLHGTCQQPWQCNCQEGWGGLFCNQDLNYCTHHKPCKNGAT<br>CTNTGQGSYTCSCRPGYTGATCELGSSGC |
| HuDLL1.DSL-EGF12.Tan/Cys (SEQ ID NO: 4) | HHHHHHGGENLYFQGFVCDEHYYGEGCSVFCRPRDDAFGHFTCGERGEKV<br>CNPGWKGPYCTEPICLPGCDEQHGFCDKPGECKCRVGWQGRYCDECIRYP<br>GCLHGTCQQPWQCNCQEGWGGLFCNQGSSGSSGFVCDEHYYGEGCSVFCR<br>PRDDAFGHFTCGERGEKVCNPGWKGPYCTEPICLPGCDEQHGFCDKPGEC<br>KCRVGWQGRYCDECIRYPGCLHGTCQQPWQCNCQEGWGGLFCNQGSSGC |
| HuDLL1.DSL-EGF12.Tan (SEQ ID NO: 8) | HHHHHHGGENLYFQGFVCDEHYYGEGCSVFCRPRDDAFGHFTCGERGEKV<br>CNPGWKGPYCTEPICLPGCDEQHGFCDKPGECKCRVGWQGRYCDECIRYP<br>GCLHGTCQQPWQCNCQEGWGGLFCNQGSSGSSGFVCDEHYYGEGCSVFCR<br>PRDDAFGHFTCGERGEKVCNPGWKGPYCTEPICLPGCDEQHGFCDKPGEC<br>KCRVGWQGRYCDECIRYPGCLHGTCQQPWQCNCQEGWGGLFCNQ |
| HuDLL1.DSL-EGF123.Cys (SEQ ID NO: 10) | HHHHHHGGENLYFQGFVCDEHYYGEGCSVFCRPRDDAFGHFTCGERGEKV<br>CNPGWKGPYCTEPICLPGCDEQHGFCDKPGECKCRVGWQGRYCDECIRYP<br>GCLHGTCQQPWQCNCQEGWGGLFCNQDLNYCTHHKPCKNGATCTNTGQGS<br>YTCSCRPGYTGATCELGSSGC |
| HuDLL1.DSL-EGF12.Cys (SEQ ID NO: 12) | HHHHHHGGENLYFQGFVCDEHYYGEGCSVFCRPRDDAFGHFTCGERGEKV<br>CNPGWKGPYCTEPICLPGCDEQHGFCDKPGECKCRVGWQGRYCDECIRYP<br>GCLHGTCQQPWQCNCQEGWGGLFCNQGSSGC |
| HuDLL1.MNNL-DSL-EGF12 (SEQ ID NO: 20) | HHHHHHGGENLYFQGQVWSSGVFELKLQEFVNKKGLLGNRNCCRGGAGPP<br>PCACRTFFRVCLKHYQASVSPEPPCTYGSAVTPVLGVDSFSLPDGGGADS<br>AFSNPIRFPFGFTWPGTFSLIIEALHTDSPDDLATENPERLISRLATQRH<br>LTVGEEWSQDLHSSGRTDLKYSYRFVCDEHYYGEGCSVFCRPRDDAFGHF<br>TCGERGEKVCNPGWKGPYCTEPICLPGCDEQHGFCDKPGECKCRVGWQGR<br>YCDECIRYPGCLHGTCQQPWQCNCQEGWGGLFCN |
| MuDLL1.MNNL-DSL-EGF123 (SEQ ID NO: 38) | HHHHHHGGENLYFQGQVWSSGVFELKLQEFVNKKGLLGNRNCCRGGSGPP<br>CACRTFFRVCLKHYQASVSPEPPCTYGSAVTPVLGVDSFSLPDGAGIDPA<br>FSNPIRFPFGFTWPGTFSLIIEALHTDSPDDLATENPERLISRLTTQRHL<br>TVGEEWSQDLHSSGRTDLRYSYRFVCDEHYYGEGCSVFCRPRDDAFGHFT<br>CGDRGEKMCDPGWKGQYCTDPICLPGCDDQHGYCDKPGECKCRVGWQGRY<br>CDECIRYPGCLHGTCQQPWQCNCQEGWGGLFCNQDLNYCTHHKPCRNGAT<br>CTNTGQGSYTCSCRPGYTGANCEL |
| HuDLL1.DSL-EGF12.Tan4 (SEQ ID NO: 42) | MAAHRHHHHGGENLYFQGFVCDEHYYGEGCSVFCRPRDDAFGHFTCGERG<br>EKVCNPGWKGPYCTEPICLPGCDEQHGFCDKPGECKCRVGWQGRYCDECI<br>RYPGCLHGTCQQPWQCNCQEGWGGLFCNQDLNYCTHHKPCKNGATCTNTG<br>QGSYTCSCRPGYTGATCELGSSGSSGFVCDEHYYGEGCSVFCRPRDDAFG<br>HFTCGERGEKVCNPGWKGPYCTEPICLPGCDEQHGFCDKPGECKCRVGWQ<br>GRYCDECIRYPGCLHGTCQQPWQCNCQEGWGGLFCNQDLNYCTHHKPCKN<br>GATCTNTGQGSYTCSCRPGYTGATCELGSSGSSGFVCDEHYYGEGCSVFC<br>RPRDDAFGHFTCGERGEKVCNPGWKGPYCTEPICLPGCDEQHGFCDKPGE |

TABLE 1-continued

| Exemplary Human and Mouse DLL1 Monomer and Multimer Peptide Sequences | |
|---|---|
| | CKCRVGWQGRYCDECIRYPGCLHGTCQQPWQCNCQEGWGGLFCNQDLNYC THHKPCKNGATCTNTGQGSYTCSCRPGYTGATCELGSSGSSGFVCDEHYY GEGCSVFCRPRDDAFGHFTCGERGEKVCNPGWKGPYCTEPICLPGCDEQH GFCDKPGECKCRVGWQGRYCDECIRYPGCLHGTCQQPWQCNCQEGWGGLF CNQDLNYCTHHKPCKNGATCTNTGQGSYTCSCRPGYTGATCEL |
| MuDLL1.DSL-EGF12.G4S3.Tan4 (SEQ ID NO: 54) | MAAHHHHHHGGENLYFQGFVCDEHYYGEGCSVFCRPRDDAFGHFTCGDRG EKMCDPGWKGQYCTDPICLPGCDDQHGYCDKPGECKCRVGWQGRYCDECI RYPGCLHGTCQQPWQCNCQEGWGGLFCNQGSSGSSGFVCDEHYYGEGCSV FCRPRDDAFGHFTCGDRGEKMCDPGWKGQYCTDPICLPGCDDQHGYCDKP GECKCRVGWQGRYCDECIRYPGCLHGTCQQPWQCNCQEGWGGLFCNQGGG GSGGGGSGGGGSFVCDEHYYGEGCSVFCRPRDDAFGHFTCGDRGEKMCDP GWKGQYCTDPICLPGCDDQHGYCDKPGECKCRVGWQGRYCDECIRYPGCL HGTCQQPWQCNCQEGWGGLFCNQGSSGSSGFVCDEHYYGEGCSVFCRPRD DAFGHFTCGDRGEKMCDPGWKGQYCTDPICLPGCDDQHGYCDKPGECKCR VGWQGRYCDECIRYPGCLHGTCQQPWQCNCQEGWGGLFCNQ |
| MuDLL1.DSL-EGF12.G4S4.Tan4 (SEQ ID NO: 55) | MAAHHHHHHGGENLYFQGFVCDEHYYGEGCSVFCRPRDDAFGHFTCGDRG EKMCDPGWKGQYCTDPICLPGCDDQHGYCDKPGECKCRVGWQGRYCDECI RYPGCLHGTCQQPWQCNCQEGWGGLFCNQGSSGSSGFVCDEHYYGEGCSV FCRPRDDAFGHFTCGDRGEKMCDPGWKGQYCTDPICLPGCDDQHGYCDKP GECKCRVGWQGRYCDECIRYPGCLHGTCQQPWQCNCQEGWGGLFCNQGGG GSGGGGSGGGGSGGGGSFVCDEHYYGEGCSVFCRPRDDAFGHFTCGDRGE KMCDPGWKGQYCTDPICLPGCDDQHGYCDKPGECKCRVGWQGRYCDECIR YPGCLHGTCQQPWQCNCQEGWGGLFCNQGSSGSSGFVCDEHYYGEGCSVF CRPRDDAFGHFTCGDRGEKMCDPGWKGQYCTDPICLPGCDDQHGYCDKPG ECKCRVGWQGRYCDECIRYPGCLHGTCQQPWQCNCQEGWGGLFCNQ |
| Avitagged.MuDLL1 (SEQ ID NO: 130) | MAAHHHHHHGGENLYFQGFVCDEHYYGEGCSVFCRPRDDAFGHFTCGDRG EKMCDPGWKGQYCTDPICLPGCDDQHGYCDKPGECKCRVGWQGRYCDECI RYPGCLHGTCQQPWQCNCQEGWGGLFCNQGSSGSSGGLNDIFEAQKIEWH E |

TABLE 2

| Exemplary Human and Mouse DLL1 Monomer and Multimer DNA Sequences | |
|---|---|
| HuDLL1.PelB-DSL-EGF123.Tan/Cys (SEQ ID NO: 64) | CATATGAAGTATCTCTTGCCTACTGCCGCGGCAGGGCTTTTACTTCTCGC AGCTCAGCCTGCAATGGCAGCTCATCACCATCACCATCACGGTGGCGAGA ATCTATACTTCCAGGGCTTTGTCTGTGACGAGCATTACTATGGTGAAGGG TGCTCTGTGTTTTGTAGGCCAAGGGACGATGCGTTCGGACATTTTACCTG CGGGGAACGAGGTGAGAAGGTTTGCAACCCGGGGTGGAAGGGACCTACTG CACTGAACCAATTTGCTTACCAGGGTGTGATGAGCAACACGGATTCTGCG ATAAGCCGGGCGAATGTAAGTGTCGGGTAGGCTGGCAAGGCCGCTACTGC GATGAGTGTATACGTTACCCAGGATGTTTACACGGAACATGTCAGCAACC GTGGCAGTGTAATTGCCAAGAAGGGTGGGGAGGGTTGTTTTGCAATCAAG ACCTGAACTATTGTACTCATCACAAGCCGTGTAAAAACGGAGCCACGTGT ACGAACACAGGTCAAGGATCATATACGTGCTCGTGTCGCCCCGGTTACAC CGGTGCTACTTGCGAATTGGGGTCCTCAGGATCTAGTGGATTCGTATGCG ATGAACATTATTACGGAGAAGGCTGTAGTGTTTTCTGTAGGCCTAGAGAC GATGCTTTCGGGCATTTTACGTGCGGCGAGAGAGGCGAGAAAGTGTGTAA TCCTGGGTGGAAAGGGCCCTATTGTACAGAACCAATATGCCTTCCAGGTT GCGACGAGCAACACGGTTTTTGTGACAAACCCGGCGAATGTAAATGCCGG GTCGGGTGGCAGGGCCGATATTGCGACGAATGCATCCGTTATCCCGGATG TCTGCATGGTACTTGCCAGCAACCTTGGCAGTGTAACTGCCAAGAAGGAT GGGGGGGTCTATTTTGCAATCAAGATCTGAATTATTGCACACACCACAAA CCGTGCAAAAACGGTGCTACATGTACGAATACCGGTCAGGGTAGCTATAC CTGCAGTTGCAGACCTGGATACACAGGCGCGACCTGTGAGCTAGGT AGC AGC GGC TGT TAAGGATCC |
| HuDLL1.DSL-EGF123.Tan/Cys (SEQ ID NO: 65) | CATATGCATCACCATCACCATCACGGTGGCGAGAATCTATACTTCCAGGG CTTTGTCTGTGACGAGCATTACTATGGTGAAGGGTGCTCTGTGTTTTGTA GGCCAAGGGACGATGCGTTCGGACATTTTACCTGCGGGGAACGAGGTGAG AAGGTTTGCAACCCGGGGTGGAAGGGACCCTACTGCACTGAACCAATTTG CTTACCAGGGTGTGATGAGCAACACGGATTCTGCGATAAGCCGGGCGAAT GTAAGTGTCGGGTAGGCTGGCAAGGCCGCTACTGCGATGAGTGTATACGT TACCCAGGATGTTTACACGGAACATGTCAGCAACCGTGGCAGTGTAATTG CCAAGAAGGGTGGGGAGGGTTGTTTTGCAATCAAGACCTGAACTATTGTA CTCATCACAAGCCGTGTAAAAACGGAGCCACGTGTACGAACACAGGTCAA GGATCATATACGTGCTCGTGTCGCCCCGGTTACACCGGTGCTACTTGCGA ATTGGGGTCCTCAGGATCTAGTGGATTCGTATGCGATGAACATTATTACG GAGAAGGCTGTAGTGTTTTCTGTAGGCCTAGAGACGATGCTTTCGGGCAT TTTACGTGCGGCGAGAGAGGCGAGAAAGTGTGTAATCCTGGGTGGAAAGG GCCCTATTGTACAGAACCAATATGCCTTCCAGGTTGCGACGAGCAACACG GTTTTTGTGACAAACCCGGCGAATGTAAATGCCGGGTCGGGTGGCAGGGC |

TABLE 2-continued

| Exemplary Human and Mouse DLL1 Monomer and Multimer DNA Sequences | |
|---|---|
| | CGATATTGCGACGAATGCATCCGTTATCCCGGATGTCTGCATGGTACTTG CCAGCAACCTTGGCAGTGTAACTGCCAAGAAGGATGGGGGGGTCTATTTT GCAATCAAGATCTGAATTATTGCACACACCACAAACCGTGCAAAAACGGT GCTACATGTACGAATACCGGTCAGGGTAGCTATACCTGCAGTTGCAGACC TGGATACACAGGCGCGACCTGTGAGCTAGGT AGC AGC GGC TGT TAAGGATCC |
| HuDLL1.DSL-EGF12.Tan/Cys (SEQ ID NO: 66) | CATATGCATCACCATCACCATCACGGTGGCGAGAATCTATACTTCCAGGG CTTTGTCTGTGACGAGCATTACTATGGTGAAGGGTGCTCTGTGTTTTGTA GGCCAAGGGACGATGCGTTCGGACATTTTACCTGCGGGGAACGAGGTGAG AAGGTTTGCAACCCGGGGTGGAAGGGACCCTACTGCACTGAACCAATTTG CTTACCAGGGTGTGATGAGCAACACGGATTCTGCGATAAGCCGGGCGAAT GTAAGTGTCGGGTAGGCTGGCAAGGCCGCTACTGCGATGAGTGTATACGT TACCCAGGATGTTTACACGGAACATGTCAGCAACCGTGGCAGTGTAATTG CCAAGAAGGGTGGGGAGGGTTGTTCTGTAACCAGGGGTCCTCAGGATCTA GTGGATTCGTATGCGATGAACATTATTACGGAGAAGGCTGTAGTGTTTTC TGTAGGCCTAGAGACGATGCTTTCGGGCATTTTACGTGCGGCGAGAGAGG CGAGAAAGTGTGTAATCCTGGGTGGAAAGGGCCCTATTGTACAGAACCAA TATGCCTTCCAGGTTGCGACGAGCAACACGGTTTTTGTGACAAACCCGGC GAATGTAAATGCCGGGTCGGGTGGCAGGGCCGATATTGCGACGAATGCAT CCGTTATCCCGGATGTCTGCATGGTACTTGCCAGCAACCTTGGCAGTGTA ACTGCCAAGAAGGATGGGGGGGTCTATTTTGCAATCAAGGT AGC AGC GGC TGT TAAGGATCC |
| HuDLL1.DSL-EGF12.Tan (SEQ ID NO: 71) | CATATGCATCACCATCACCATCACGGTGGCGAGAATCTATACTTCCAGGG CTTTGTCTGTGACGAGCATTACTATGGTGAAGGGTGCTCTGTGTTTTGTA GGCCAAGGGACGATGCGTTCGGACATTTTACCTGCGGGGAACGAGGTGAG AAGGTTTGCAACCCGGGGTGGAAGGGACCCTACTGCACTGAACCAATTTG CTTACCAGGGTGTGATGAGCAACACGGATTCTGCGATAAGCCGGGCGAAT GTAAGTGTCGGGTAGGCTGGCAAGGCCGCTACTGCGATGAGTGTATACGT TACCCAGGATGTTTACACGGAACATGTCAGCAACCGTGGCAGTGTAATTG CCAAGAAGGGTGGGGAGGGTTGTTCTGTAACCAGGGGTCCTCAGGATCTA GTGGATTCGTATGCGATGAACATTATTACGGAGAAGGCTGTAGTGTTTTC TGTAGGCCTAGAGACGATGCTTTCGGGCATTTTACGTGCGGCGAGAGAGG CGAGAAAGTGTGTAATCCTGGGTGGAAAGGGCCCTATTGTACAGAACCAA TATGCCTTCCAGGTTGCGACGAGCAACACGGTTTTTGTGACAAACCCGGC GAATGTAAATGCCGGGTCGGGTGGCAGGGCCGATATTGCGACGAATGCAT CCGTTATCCCGGATGTCTGCATGGTACTTGCCAGCAACCTTGGCAGTGTA ACTGCCAAGAAGGATGGGGGGGTCTATTTTGCAATCAA TAAGGATCC |
| HuDLL1.DSL-EGF123.Cys (SEQ ID NO: 72) | CATATGCATCACCATCACCATCACGGTGGCGAGAATCTATACTTCCAGGG CTTTGTCTGTGACGAGCATTACTATGGTGAAGGGTGCTCTGTGTTTTGTA GGCCAAGGGACGATGCGTTCGGACATTTTACCTGCGGGGAACGAGGTGAG AAGGTTTGCAACCCGGGGTGGAAGGGACCCTACTGCACTGAACCAATTTG CTTACCAGGGTGTGATGAGCAACACGGATTCTGCGATAAGCCGGGCGAAT GTAAGTGTCGGGTAGGCTGGCAAGGCCGCTACTGCGATGAGTGTATACGT TACCCAGGATGTTTACACGGAACATGTCAGCAACCGTGGCAGTGTAATTG CCAAGAAGGGTGGGGAGGGTTGTTTTGCAATCAAGACCTGAACTATTGTA CTCATCACAAGCCGTGTAAAAACGGAGCCACGTGTACGAACACAGGTCAA GGATCATATACGTGCTCGTGTCGCCCCGGTTACACCGGTGCTACTTGCGA ATTGGGTAGCAGCGGCTGTTAAGGATCC |
| HuDLL1.DSL-EGF12.Cys (SEQ ID NO: 75) | CATATGCATCACCATCACCATCACGGTGGCGAGAATCTATACTTCCAGGG CTTTGTCTGTGACGAGCATTACTATGGTGAAGGGTGCTCTGTGTTTTGTA GGCCAAGGGACGATGCGTTCGGACATTTTACCTGCGGGGAACGAGGTGAG AAGGTTTGCAACCCGGGGTGGAAGGGACCCTACTGCACTGAACCAATTTG CTTACCAGGGTGTGATGAGCAACACGGATTCTGCGATAAGCCGGGCGAAT GTAAGTGTCGGGTAGGCTGGCAAGGCCGCTACTGCGATGAGTGTATACGT TACCCAGGATGTTTACACGGAACATGTCAGCAACCGTGGCAGTGTAATTG CCAAGAAGGGTGGGGAGGGTTGTTCTGTAACCAGGGT AGC AGC GGC TGT TAAGGATCC |
| HuDLL1.MNNL-DSL-EGF12 (SEQ ID NO: 83) | CATATGACATCACCATCACCATCACGGGGGAGAGAATCTTTACTTCCAGG GCCAAGTGTGGAGCTCTGGAGTATTCGAGTTGAAACTACAAGAATTCGTT AACAAGAAAGGCTTGCTGGGAAATCGTAATTGCTGTCGGGGTGGAGCGGG ACCGCCCCCTTGCGCTTGTCGCACTTTCTTTCGTGTGTGTTTAAAGCACT ATCAGGCTAGTGTATCTCCTGAGCCGCCTTGCACCTATGGAAGTGCCGTA ACCCCGGTTCTGGGGGTAGACTCGTTTAGTCTCCCCGATGGTGGCGGGGC GGATTCTGCTTTTTCCAATCCAATCAGATTTCCGTTCGGGTTTACATGGC CAGGGACTTTTAGCTTAATAATCGAGGCCTTGCACACTGATAGCCCAGAC GATCTAGCAACGGAAAATCCCGAAAGATTAATTTCACGACTCGCAACCCA GAGGCATTTAACGGTCGGAGAGGAATGGTCCCAGGACCTTCACTCGAGTG GGAGGACCGACTTGAAGTACTCATATAGGTTTGTTTGCGACGAACATTAT TACGGCGAAGGTTGTTCGGTCTTTTGCCGGCCGCGAGATGACGCCTTCGG TCATTTTACCTGTGGCGAACGCGGCGAGAAGGTGTGTAACCCTGGGTGGA AAGGTCCCTATTGTACAGAACCGATATGCCTACCAGGTTGTGATGAACAA CACGGGTTCTGCGACAAGCCAGGAGAGTGCAAGTGCCGTGTCGGCTGGCA GGGGCGATATTGTGATGAGTGCATTAGATACCCAGGTTGTCTCCATGGAA |

TABLE 2-continued

| Exemplary Human and Mouse DLL1 Monomer and Multimer DNA Sequences | |
|---|---|
| | CTTGCCAACAGCCTTGGCAGTGTAACTGCCAAGAGGGTTGGGGCGGACTA<br>TTCTGCAAC TAAGGATCC |
| MuDLL1.MNNL-<br>DSL-EGF123<br>(SEQ ID NO: 101) | CATATGCATCACCATCACCATCACGGTGGCGAGAATCTGTATTTCCAGGG<br>ACAAGTGTGGAGCTCAGGTGTCTTCGAACTTAAGTTGCAAGAATTCGTAA<br>ATAAGAAAGGACTATTGGGAAACCGGAACTGCTGTCGTGGCGGTTCGGGC<br>CCACCGTGCGCTTGCAGGACATTCTTTCGGGTTTGTCTGAAGCACTATCA<br>GGCCTCCGTCAGCCCGGAACCGCCCTGTACTTATGGTAGTGCCGTGACAC<br>CCGTTCTGGGTGTCGATAGTTTCTCGCTCCCCGATGGTGCCGGTATTGAT<br>CCTGCTTTCAGCAACCCCATCCGTTTTCCTTTCGGGTTTACATGGCCTGG<br>CACCTTTTCTCTTATAATTGAGGCACTCCACACGGACAGTCCAGACGATT<br>TGGCTACTGAGAACCCGGAAAGGCTCATATCACGATTAACGACTCAACGT<br>CATCTCACAGTGGGGGAAGAGTGGAGTCAGGACCTGCATTCCTCTGGAAG<br>AACGGACTTAAGATATTCGTATCGCTTCGTATGCGACGAGCATTACTATG<br>GGGAGGGCTGTTCCGTTTTTTGCAGACCGAGAGATGACGCTTTTGGTCAC<br>TTTACTTGTGGAGACAGGGGGGAAAAAATGTGCGACCCCGGGTGGAAGGG<br>CCAGTACTGTACTGACCCTATATGTTTACCAGGATGTGATGATCAACATG<br>GATACTGCGATAAGCCAGGCGAGTGCAAATGTCGGGTAGGGTGGCAAGGC<br>CGCTACTGTGATGAATGCATCCGATATCCAGGATGCCTACATGGGACCTG<br>TCAACAGCCCTGGCAATGTAATTGCCAGGAGGGATGGGGGGGCCTTTTTT<br>GCAATCAGGATCTAAACTATTGTACGCACCACAAACCGTGCAGGAACGGT<br>GCAACATGTACCAATACAGGGCAAGGGTCATACACGTGTTCTTGCCGACC<br>TGGATACACCGGTGCTAATTGCGAACTATAAGGATCC |
| Avitagged.MuDLL1<br>(SEQ ID NO: 131) | CATATGGCAGCTCATCACCATCACCATCACGGTGGGGAGAATCTCTATTT<br>CCAGGGGTTCGTATGTGACGAACACTATTACGGAGAGGGGTGCAGTGTCT<br>TCTGCCGTCCGAGAGACGATGCCTTTGGTCACTTTACGTGTGGAGACAGA<br>GGCGAAAAAATGTGTGATCCAGGATGGAAAGGACAGTATTGTACGGACCC<br>CATTTGCCTTCCTGGCTGCGATGACCAACACGGGTATTGTGACAAACCCG<br>GCGAGTGCAAGTGTCGTGTTGGGTGGCAAGGGCGATACTGCGACGAGTGC<br>ATAAGATACCCTGGTTGCCTGCACGGGACCTGCCAGCAACCTTGGCAATG<br>TAACTGTCAAGAAGGATGGGGAGGCTTATTCTGCAACCAAGGCTCGTCTG<br>GCTCCTCGGGGGGTCTGAATGATATCTTCGAAGCGCAGAAAATTGAATGG<br>CACGAATAAGGATCC |

In some embodiments, the monomeric units may comprise an *E. coli* (BirA) biotinylation sequence at the C-terminus of the monomer (see, e.g., Fairhead and Howarth, *Methods Mol Biol.* 2015; 1266: 171-184), to which an avidin (or streptavidin or NeutrAvidin) can be conjugated. This provides an additional linking mechanism for oligomerizing the monomeric units into multimers. Avidin has four biotin binding sites. Thus, mixing four biotinylated monomers (e.g. DLL1 monomers) with avidin results in a tetramer with different topology than a tetramer that is encoded by a single DNA sequence and thus expressed as a single linear peptide with the monomeric units in tandem. This is an alternative to the C-terminal Cys which can connect monomers via a PEG-maleimide linker.

In some embodiments, the monomeric unit of the Notch-modulating peptide comprises an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40 (also referred to as SEQ ID NO:1-40). In some embodiments, the monomeric unit of the Notch-modulating peptide comprises an amino acid sequence that is at least 70% identical to one of SEQ ID NO:1-40. In some embodiments, the monomeric unit of the Notch-modulating peptide comprises an amino acid sequence that is at least 75% identical, at least 80% identical, at least 85% identical, at least 90% identical, at least 95% identical, or at least 99% identical to one of SEQ ID NO:1-40.

In some embodiments, the monomeric unit of the Notch-modulating peptide comprises a nucleotide sequence selected from SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103 (also referred to as SEQ ID NO: 64-103). In some embodiments, the monomeric unit of the Notch-modulating peptide comprises a nucleotide sequence that is at least 70% identical to one of SEQ ID NO:64-103. In some embodiments, the monomeric unit of the Notch-modulating peptide comprises a nucleotide sequence that is at least 75% identical, at least 80% identical, at least 85% identical, at least 90% identical, at least 95% identical, or at least 99% identical to one of SEQ ID NO: 64-103.

The nucleotide sequence can be that of the wild type nucleic acid sequence encoding an amino acid sequence disclosed herein. In some embodiments, the nucleotide sequence is modified from the wild type sequence, but due to the degeneracy of the genetic code, can still encode for the same amino acid sequence. In some embodiments, the nucleotide sequence is a variant of one of the sequences disclosed herein (or encodes a variant protein sequence). In some embodiments, the nucleotide sequence is a fragment of one of the nucleic acids herein, or encodes a fragment of one of the amino acids disclosed herein. In some embodiments, the nucleotide sequence is codon optimized (for example, to improve expression).

In some embodiments, the monomeric unit of a Notch-modulating peptide may comprise one or more mutations in the DSL domain or EGF repeats relative to the wild-type peptide from which it is derived, such as one or more conservative substitutions, non-conservative substitutions, additions, or deletions. For example, a monomeric unit of a Notch-modulating peptide as described herein may have a DSL domain or EGF domains that are at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the wild-type peptide from which it is derived.

Multimeric Peptides

The multimeric Notch-modulating peptides can be prepared by oligomerizing 2, 3, 4, 5, 6, 7, 8, 9, or 10 or more of the disclosed monomeric units by connecting the monomers with a linker. In preferred embodiments, the linker is a peptide linker.

In some embodiments, the monomers may be dimers, trimers, tetramers, pentamers, hexamers, septamers, octamers, etc. In some embodiments, the multimeric Notch-modulating peptides may comprise one or more mutations in the individual DSL domain or EGF repeats relative to the wild-type peptide from which it is derived, such as one or more conservative substitutions, non-conservative substitutions, additions, or deletions. For example, a monomeric unit of a Notch-modulating peptide as described herein may have a DSL domain or EGF domains that are at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the wild-type peptide from which it is derived.

The peptide linker can comprise 0, 1, 2, 3, 4, 5, 6, 7, 8, 9, 10, 11, 12, 13, 14, or 15 or more amino acids. In some embodiments, the peptide linkers comprise 10 or fewer amino acids, 9 or fewer amino acids, 8 or fewer amino acids, 7 or fewer amino acids, 6 or fewer amino acids, 5 or fewer amino acids, or 4 or fewer amino acids.

Suitable linkers include poly-Gly linkers and Gly/Ser linkers. For example, in some embodiments, the peptide linker may comprise the amino acid sequence GGGGS or GSSGSSG or combinations or repeats thereof. For example, the peptide linker may comprise two repeats of GGGGS or GSSGSSG.

The disclosed multimeric Notch-modulating peptides may be organized in various ways. In some embodiments, the monomer units may be linked head to tail to form a multimeric string of monomers aligned in the same linear direction. In some embodiments, adjacent monomeric units may be linked head-to-head or tail-to-tail, with every other monomer in the sequence facing the opposite direction of the preceding monomer.

The disclosed multimeric peptides may possess different activities depending on what peptide they are derived from and on the number of monomeric units making up the multimer. For example, a DLL1 multimer comprising four or more monomeric units comprising a DSL domain and two or three ECF repeats activates Notch signaling and results in stimulation of the immune system. Conversely, a Jag1 multimer comprising four or more monomeric units comprising a DSL domain and two or three ECF repeats inhibits Notch signaling and results in suppression of the immune system.

The Notch-modulating peptides (both monomers and multimers) may exhibit increased or decreased signaling capacity relative to the wild-type peptides on which they are based (e.g., DLL1 or Jag1). Likewise, the disclosed monomers or multimers may comprise one or more mutations relative to the amino acid sequence of the wild-type peptides on which they are based, including one or more deletions, additions, or substitutions. A substitution mutation may be "conservative" or "non-conservative." "Conservative" refers to a substitution within the same family of amino acids, while "non-conservative" refers to substitutions across families of amino acids. Families of amino acids and "conservative" and "non-conservative" substitutions relative thereto are known in the art. For example, the naturally occurring amino acids may be divided into the following four families and conservative substitutions will take place within those families, while non-conservative substitutions will take place across different families.

1) Amino acids with basic side chains: lysine, arginine, histidine.

2) Amino acids with acidic side chains: aspartic acid, glutamic acid

3) Amino acids with uncharged polar side chains: asparagine, glutamine, serine, threonine, tyrosine.

4) Amino acids with nonpolar side chains: glycine, alanine, valine, leucine, isoleucine, proline, phenylalanine, methionine, tryptophan, cysteine.

In some embodiments, the disclosed Notch-modulating peptides can exhibit increased Notch signaling capacity relative to the wild-type peptide from which it is derived. For example, the disclosed Notch-modulating peptides may increase Notch signaling by at least about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 550%, about 600%, about 650%, about 700%, about 750%, about 800%, about 850%, about 900%, about 950%, about 1000%, about 1100%, about 1200%, about 1300%, about 1400%, about 1500%, about 1600%, about 1700%, about 1800%, about 1900%, about 2000%, about 2250%, about 2500%, about 2750%, about 3000%, about 3250%, about 3500%, about 3750%, about 4000%, about 4250%, about 4500%, about 4750%, or about 5000% relative to the wild-type peptide from which it is derived.

In other embodiments, the disclosed Notch-modulating peptides may decrease Notch signaling by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% relative to the wild-type peptide from which it is derived.

In some embodiments, the Notch-modulating peptide comprises an amino acid sequence encoded by a nucleic acid selected from SEQ ID NO:105, SEQ ID NO:106, SEQ ID NO:108, SEQ ID NO:109, SEQ ID NO:110, SEQ ID NO:111, SEQ ID NO:112, SEQ ID NO:116, SEQ ID NO:117, SEQ ID NO:118, or SEQ ID NO:120. In some embodiments, the Notch-modulating peptide comprises an amino acid sequence encoded by a nucleic acid that is at least 70% identical to SEQ ID NO:105, SEQ ID NO:106, SEQ ID NO:108, SEQ ID NO:109, SEQ ID NO:110, SEQ ID NO:111, SEQ ID NO:112, SEQ ID NO:116, SEQ ID NO:117, SEQ ID NO:118, or SEQ ID NO:120. In some embodiments, the Notch-modulating peptide comprises an amino acid sequence encoded by a nucleic acid that is at least 75% identical, at least 80% identical, at least 85% identical, at least 90% identical, at least 95% identical, or at least 99% identical to SEQ ID NO:105, SEQ ID NO:106, SEQ ID NO:108, SEQ ID NO:109, SEQ ID NO:110, SEQ ID NO:111, SEQ ID NO:116, SEQ ID NO:117, SEQ ID NO:118, or SEQ ID NO:120.

In some embodiments, the Notch-modulating peptide comprises an amino acid sequence selected from SEQ ID NO:42, SEQ ID NO:43, SEQ ID NO:45, SEQ ID NO:46, SEQ ID NO:47, SEQ ID NO:48, SEQ ID NO:49, SEQ ID NO:53, SEQ ID NO:54, SEQ ID NO:55, or SEQ ID NO:63. In some embodiments, the Notch-modulating peptide comprises an amino acid sequence that is at least 70% identical to SEQ ID NO:42, SEQ ID NO:43, SEQ ID NO:45, SEQ ID NO:46, SEQ ID NO:47, SEQ ID NO:48, SEQ ID NO:49, SEQ ID NO:53, SEQ ID NO:54, SEQ ID NO:55, or SEQ ID NO:63. In some embodiments, the Notch-modulating peptide comprises an amino acid sequence that is at least 75% identical, at least 80% identical, at least 85% identical, at least 90% identical, at least 95% identical, or at least 99% identical to SEQ ID NO:42, SEQ ID NO:43, SEQ ID NO:45, SEQ ID NO:46, SEQ ID NO:47, SEQ ID NO:48, SEQ ID NO:49, SEQ ID NO:53, SEQ ID NO:54, SEQ ID NO:55, or SEQ ID NO:63.

In some embodiments, the Notch-modulating peptide comprises an amino acid sequence selected from SEQ ID NO:122, SEQ ID NO:124, SEQ ID NO:126, or SEQ ID NO:128. In some embodiments, the Notch-modulating peptide comprises an amino acid sequence that is at least 70% identical to SEQ ID NO:122, SEQ ID NO:124, SEQ ID NO:126, or SEQ ID NO:128. In some embodiments, the Notch-modulating peptide comprises an amino acid sequence that is at least 75% identical, at least 80% identical, at least 85% identical, at least 90% identical, at least 95% identical, or at least 99% identical to SEQ ID NO:122, SEQ ID NO:124, SEQ ID NO:126, or SEQ ID NO:128.

In some embodiments, the Notch-modulating peptide comprises a nucleotide sequence selected from SEQ ID NO:121, SEQ ID NO:123, SEQ ID NO:125, or SEQ ID NO:127. In some embodiments, the Notch-modulating peptide comprises a nucleotide sequence that is at least 70% identical to SEQ ID NO:121, SEQ ID NO:123, SEQ ID NO:125, or SEQ ID NO:127. In some embodiments, the Notch-modulating peptide comprises a nucleotide sequence that is at least 75% identical, at least 80% identical, at least 85% identical, at least 90% identical, at least 95% identical, or at least 99% identical to SEQ ID NO:121, SEQ ID NO:123, SEQ ID NO:125, or SEQ ID NO:127.

Pharmaceutical Compositions

The Notch-modulating peptides disclosed herein can be formulated into pharmaceutical compositions suitable for administration to the target subject (i.e., a human or other mammal) via a predetermined route of administration, as discussed in more detail below.

Pharmaceutical compositions may include one or more Notch-modulating peptides as described herein and a pharmaceutically acceptable carrier or diluent. For example, in some embodiments, a pharmaceutical composition may comprise a Notch-modulating peptide comprising at least four monomeric units connected by peptide linkers, the monomeric units comprising: a mammalian DSL domain and two or three mammalian EGF domains, along in combination with a monomeric peptide derived from a different parent protein.

The compositions may be formulated for intravenous, subcutaneous, intraperitoneal, intramuscular, oral, nasal, pulmonary, ocular, vaginal, or rectal administration. In some embodiments, the compositions are formulated for intravenous, subcutaneous, intraperitoneal, or intramuscular administration, such as in a solution, suspension, emulsion, liposome formulation, etc. The pharmaceutical compositions can be formulated to be an immediate-release composition, sustained-release composition, delayed-release composition, etc., using techniques known in the art Pharmaceutically acceptable carriers for various dosage forms are known in the art. For example, excipients, lubricants, binders, and disintegrants for solid preparations are known; solvents, solubilizing agents, suspending agents, isotonicity agents, buffers, and soothing agents for liquid preparations are known. In some embodiments, the pharmaceutical compositions include one or more additional components, such as one or more preservatives, antioxidants, colorants, sweetening/flavoring agents, adsorbing agents, wetting agents and the like.

In some embodiments, the composition is formulated for administration by injection or infusion, such as subcutaneous, intramuscular, or intravenous administration.

In some embodiments, the Notch-modulating peptides may be modified in order to extend its half-life in vivo (after administration). Various techniques are known in the art for extending the circulating half-life of peptides. For example, in some embodiments the Notch-modulating peptide is conjugated to polyethylene glycol (PEG) or a similar polymer that prolongs half-life. In some embodiments, the Notch-modulating peptide is fused to an albumin-binding peptide, an albumin-binding protein domain, human serum albumin, or an inert polypeptide. Exemplary inert polypeptides that have been used to increase the circulating half-life of peptides include, but are not limited to, XTEN® (also known as recombinant PEG or "rPEG"), a homo-amino acid polymer (HAP; HAPylation), a proline-alanine serine polymer (PAS; PASylation), or an elastin-like peptide (ELP; ELPylation). As used herein, "fused to" includes genetic fusion, directly or through a linker, resulting in a single polypeptide containing multiple domains, unless otherwise specified.

Methods of Use

The disclosed methods capitalize on the novel findings of Notch-mediated molecular mechanisms of immune regulation, and provides an approach for immune modulation that could lead to novel cancer therapies and improved organ transplantation. The disclosed methods take advantage of this novel approach for efficiently overcoming cancer-induced immunosuppression and eliciting potent anti-tumor immunity via activation of DLL1-mediated Notch signaling and inhibition of Jag1 mediated signaling for down-regulation of suppressive immune responses. The opposite approach may be used to improve transplantation efficacy and efficiency.

In cancer, Treg differentiation prevails, whereas the Th1 immune response needed for tumor rejection is suppressed. Thus, activation of Th1 and induction of the effector and memory T cells by the DLL-enhanced Notch signaling, or inhibition of Treg differentiation by interference with Jag1, are valuable therapeutic strategies.

In contrast, organ transplant rejection is mediated by induction of Th1 alloimmune responses. The strategy to prolong allograft survival includes inhibition of Th1 type responses by inhibiting DLL/Notch interaction and induction of Treg responses via activation of Jag1/Notch signaling.

As noted above, the Notch-modulating peptides described herein are useful in methods of treating cancer or graft-versus-host disease (GVHD) and inhibiting rejection of an organ transplant in a mammalian subject in need thereof. In some embodiments, the subject is a human subject.

The disclosed methods generally involve administering a therapeutically effective amount of at least one Notch-modulating peptide as described herein (or a pharmaceutical composition comprising the same) to the subject. In some embodiments, a therapeutically effective amount of a Notch-modulating peptide is an amount effective to activate or inhibit the subject's immune system, as necessary, in order to reduce, ameliorate, or reverse the disease or condition being treated.

The specific amount of a Notch-modulating peptide that is administered may depend on one or more of the age and/or weight of the subject, the disease or condition being treated, and/or the severity of the disease or condition. In some embodiments, a Notch-modulating peptide is administered at a dose of from about 0.01 to about 20 mg/kg, about 0.1 mg/kg to about 18 mg/kg, about 1 mg/kg to about 16 mg/kg, about 2 mg/kg to about 14 mg/kg, or about 5 mg/kg to about 10 mg/kg. In some embodiments, a Notch-modulating peptide is administered at a dose of about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8/5 mg/kg, about 9 mg/kg, about 9.5 mg/kg, about 10 mg/kg, about 10.5 mg/kg, about 12 mg/kg, about 12.5 mg/kg, about 13 mg/kg, about 13.5 mg/kg, about 14 mg/kg, about 14.5 mg/kg, about 15 mg/kg, about 15.5 mg/kg, about 16 mg/kg, about 16.5 mg/kg, about 17 mg/kg, about 17.5 mg/kg, about 18 mg/kg, about 18.5 mg/kg, about 19 mg/kg, about 19.5 mg/kg, or about 20 mg/kg. In some embodiments, a Notch-modulating peptide is administered at a dose of about 0.01 mg, about 0.05 mg, about 0.01 mg, about 0.5 mg, about 1 mg, about 2.5 mg, about 5 mg, about 10 mg, about 15 mg, about 20 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 550 mg, about 600, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100, about 2150 mg, about 2200 mg, about 2250 mg, about 2300 mg, about 2350 mg, about 2400 mg, about 2450 mg, or about 2500 mg. When more than one Notch-modulating peptide is administered, the total amount of peptides administered may be in accordance with the foregoing guidance.

In some embodiments, the methods comprise administering a single dose of a Notch-modulating peptide (or composition comprising the same). In some embodiments, the method comprises administering repeated doses, such as for a predetermined period of time of until the symptoms or effects of the disease (e.g., cancer or GVHD) are reduced, ameliorated, or eliminated or until the subject has ceased needing treatment. In some embodiments, treatment is repeated with additional doses of the Notch-modulating peptides if signs/symptoms/effects persist or if the subject experiences a disease flare after a period of remission.

In some embodiments, the methods comprise administering a Notch-modulating peptide (or composition comprising the same) three or more times a day, twice a day, or once a day. In some embodiments, the methods comprise administering a Notch-modulating peptide (or composition comprising the same) once every other day, three times a week, twice a week, once a week, once every other week, once every three weeks, once a month, once every other month, once every three months, once every four months, once every five months, once every six months, once every seven months, once every eight months, once every nine months, once every ten months, once every eleven months, or once a year. In such embodiments, the Notch-modulating peptides may be long-acting peptides that have been modified as described above.

In some embodiments, treatment may continue for 1, 2, 3, 4, 5, 6, 7, 8, 9, 10, 11, 12, 13, 14, 15, 16, 17, 18, 19, 20, or 21 or more days; 1, 2, 3, 4, 5, 6, 7, 8, 9, 10, 11, 12, 13, 14, 15, 16, 17, or 18 or weeks months; or 1, 2, 3, 4, 5, 6, 7, 8, 9, 10, 11, or 12 or more months; or 1, 2, or 3 or more years or until the subject has been cured or symptoms of the disease being treated no longer persist.

Methods of Activating Notch Signaling

Tumor-induced immune suppression by multiple mechanisms is a major impediment to the success of cancer therapy. Recent studies have revealed that an intact immune system-specifically Th cells—is required for the induction of sustained tumor regression upon inactivation of the tumor-driving oncogenes. The Notch signaling pathway plays an important role in T cell regulation and differentiation while bring extremely pleotropic with an interrelated network of receptor-ligand interactions. Thus, the disclosed Notch-modulating peptides that activate Notch signaling may be used in methods of stimulating the immune system to treat cancer.

Particularly useful Notch-activating peptides include multimers of DLL peptides comprising 4 or more monomeric units and Jagged monomers. In some embodiments of the disclosed methods, a subject in need of immune stimulation (e.g., a cancer patient) may be administered a therapeutically effective amount of a multimeric Notch-modulating peptide comprising at least four monomeric units connected by peptide linkers, wherein the monomeric units comprise: a mammalian Delta-like (DLL) protein DSL domain; and two or three mammalian DLL EGF domains. In some embodiments, the DLL protein is DLL1, DLL3, or DLL4. In preferred embodiments, the DLL protein is DLL1.

In some embodiments of the disclosed methods, a subject in need of immune stimulation (e.g., a cancer patient) may be administered a therapeutically effective amount of a monovalent fragment of Jagged comprising: a mammalian Jagged (Jag) protein DSL domain; and two or three mammalian Jag EGF domains. In some embodiments, the Jag protein is Jag1 or Jag2. In preferred embodiments, the Jag protein is Jag1.

In some embodiments, both DLL multimers and Jag monomers may be administered to the same subject in order to stimulate the subject's immune response. The multimers and monomers may be administered sequentially or concurrently.

In some embodiments, the Notch-activating peptides (i.e. DLL multimers and Jag monomers) may be administered with an additional therapeutic for treating cancer in the subject, such as an oncogene-targeting therapy, a checkpoint inhibitor, a tumor-targeting antibody, or a chemotherapeutic. Exemplary oncogene-targeting therapies include, but are not limited to, a BTK inhibitor (e.g. ibrutinib), an EGFR inhibitor (e.g. CK-101), a BET inhibitor (e.g. CK-103), a PARP inhibitor (e.g. olaparib or CK-102), a PI3Kdelta inhibitor (e.g. TGR-1202), or a BRAF inhibitor (e.g. Vemurafenib). Exemplary checkpoint inhibitors include, but are not limited to, anti-GITR antibody, an anti-OX40 antibody, an anti-CD137 antibody, a TLR agonist, or anti-CD40 antibody. Exemplary tumor-targeting antibodies include, but are not limited to, an anti-CAIX antibody, an anti-CD19 antibody, an anti-HER2 antibody, an anti-BCMA, an anti-CS-1, an anti-CD20 (e.g. Ublituximab), an anti-Her2, an anti-PCSA, or an anti-FcRL5.

In some embodiments, the disclosed methods provide treatment for a subject with cancer wherein the cancer is breast cancer, brain cancer, colon cancer, cervical cancer, ovarian cancer, testicular cancer, stomach cancer, skin cancer, head & neck cancer, lung cancer, pancreatic cancer, liver cancer, uterine cancer, bladder cancer, a hematological cancer (e.g., lymphoma, Non-Hodgkin's lymphoma, chronic lymphocytic leukemia, or multiple myeloma), prostate cancer, melanoma, sarcoma, fibrosarcoma or HIV/AIDS-related cancer. The cancer may be metastatic cancer, recurrent cancer or multidrug resistant cancer. The method may further comprise administering to said subject a second cancer therapy, such as radiotherapy, chemotherapy, immunotherapy, hormonal therapy, toxin therapy, cryotherapy, gene therapy or surgery.

Dosage regimens are adjusted to provide the desired response (e.g., a therapeutic response like tumor regression or remission). For example, in some embodiments, a single bolus may be administered, while in some embodiments, several divided doses may be administered over time or the dose may be proportionally reduced or increased as indicated by the situation. For example, in some embodiments the disclosed antibodies or functional fragments may be administered once or twice weekly by subcutaneous or intravenous injection. In some embodiments, the disclosed antibodies or functional fragments may be administered once or twice monthly by subcutaneous injection. In some embodiments, the disclosed antibodies or functional fragments may be administered once every week, once every other week, once every three weeks, once every four weeks, once every other month, once every three months, once every four months, once every five months, or once every six months.

Exemplary doses can vary according to the size and health of the individual being treated, as well as the condition being treated.

Particular treatment regimens may be evaluated according to whether it will improve a given patient's outcome, meaning it will reduce the risk of recurrence or increase the likelihood of progression-free survival of the given cancer.

Thus, for the purposes of this disclosure, a subject is treated if one or more beneficial or desired results, including desirable clinical results, are obtained. For example, beneficial or desired clinical results include, but are not limited to, one or more of the following: decreasing one or more symptoms resulting from the disease, increasing the quality of life of those suffering from the disease, decreasing the dose of other medications required to treat the disease, delaying the progression of the disease, and/or prolonging survival of individuals.

Furthermore, while the subject of the methods is generally a cancer patient, the age of the patient is not limited. The disclosed methods are useful for treating cancer, malignant disease, or cancer cell proliferation with various recurrence and prognostic outcomes across all age groups and cohorts. Thus, in some embodiments, the subject may be a pediatric subject, while in other embodiments, the subject may be an adult subject.

Methods of Inhibiting Notch Signaling

Immune suppression is a cornerstone of treatment for many conditions, including the treatment of graft-versus-host disease (GVHD), many autoimmune conditions, and, in some cases, allergies and allergic conditions. Immune suppression is also necessary to ensure allografts are not rejected by their hosts. Thus, the disclosed Notch-modulating peptides that inhibit Notch signaling may be used in methods of suppressing the immune system to treat these conditions.

Particularly useful Notch-inhibiting peptides include multimers of Jag peptides comprising 4 or more monomeric units and DLL monomers. In some embodiments of the disclosed methods, a subject in need of immune inhibition (e.g., a patient that has received a transplant or suffers from an autoimmune disease) may be administered a therapeutically effective amount of a multimeric Notch-modulating peptide comprising at least four monomeric units connected by peptide linkers, wherein the monomeric units comprise: a mammalian Jagged (Jag) protein DSL domain; and two or three mammalian Jag EGF domains. In some embodiments, the Jag protein is Jag1 or Jag2. In preferred embodiments, the Jag protein is Jag1.

In some embodiments of the disclosed methods, a subject in need of immune stimulation (e.g., a patient that has received a transplant or suffers from an autoimmune disease) may be administered a therapeutically effective amount of a monovalent fragment of DLL comprising: a mammalian Delta-like (DLL) protein DSL domain; and two or three mammalian DLL EGF domains. In some embodiments, the DLL protein is DLL1, DLL3, or DLL4. In preferred embodiments, the DLL protein is DLL1.

In some embodiments, both Jag multimers and DLL monomers may be administered to the same subject in order to suppress the subject's immune response. The multimers and monomers may be administered sequentially or concurrently.

In some embodiments, the Notch-inhibiting peptides (i.e. Jag multimers and DLL monomers) may be administered with an additional therapeutic for the subject, depending on the subject's condition. For instance, a subject that has recently received an allograft or transplant may also be administered cyclophosphamide, cyclosporine, tacrolimus, azathioprine, or steroids. A subject with an autoimmune disease may also be administered steroids, methotrexate, anti-TNFα antibodies, celecoxib, naproxen, sulfasalazine, interferons (e.g., IFNβ), azathioprine, natalizumab, mitoxantrone, etc.

In some embodiments, the disclosed methods provide treatment for a subject with an autoimmune disease wherein the autoimmune disease is rheumatoid arthritis, lupus, celiac disease, Sjögren's syndrome, polymyalgia rheumatica, multiple sclerosis, ankylosing spondylitis, Type 1 diabetes, Crohn's disease, or ulcerative colitis. The disease may be active or it may be in remission.

In some embodiments, the Notch-inhibiting peptides may also be administered in methods for treating T-cell leukemia and lymphoma, as well as in overcoming chemoresistance in non-small cell lung cancer (NSCLC) and breast cancer. Notch-inhibiting peptides may also be used in methods of inhibiting angiogenesis related to tumor growth.

Dosage regimens are adjusted to provide the desired response (e.g., a therapeutic response like allograft survival or remission). For example, in some embodiments, a single bolus may be administered, while in some embodiments, several divided doses may be administered over time or the dose may be proportionally reduced or increased as indicated by the situation. For example, in some embodiments the disclosed antibodies or functional fragments may be administered once or twice weekly by subcutaneous or intravenous injection. In some embodiments, the disclosed antibodies or functional fragments may be administered once or twice monthly by subcutaneous injection. In some embodiments, the disclosed antibodies or functional fragments may be administered once every week, once every other week, once every three weeks, once every four weeks, once every other month, once every three months, once every four months, once every five months, or once every six months.

Exemplary doses can vary according to the size and health of the individual being treated, as well as the condition being treated.

Particular treatment regimens may be evaluated according to whether it will improve a given patient's outcome, meaning it will reduce the risk of recurrence of active disease or increase the likelihood of progression-free survival or sustained remission.

Thus, for the purposes of this disclosure, a subject is treated if one or more beneficial or desired results, including desirable clinical results, are obtained. For example, beneficial or desired clinical results include, but are not limited to, one or more of the following: decreasing one or more symptoms resulting from the disease, increasing the quality of life of those suffering from the disease, decreasing the dose of other medications required to treat the disease, delaying the progression of the disease, and/or prolonging survival of individuals.

Furthermore, the age of the patient is not limited. The disclosed methods are useful for treating cancer, malignant disease, or cancer cell proliferation with various recurrence and prognostic outcomes across all age groups and cohorts. Thus, in some embodiments, the subject may be a pediatric subject, while in other embodiments, the subject may be an adult subject.

One skilled in the art will readily appreciate that the present disclosure is well adapted to carry out the objects and obtain the ends and advantages mentioned, as well as those inherent therein. Modifications therein and other uses will occur to those skilled in the art. These modifications are encompassed within the spirit of the disclosure. The following examples are given to illustrate the present invention. It should be understood, however, that the invention is not limited to the specific conditions or details of these examples.

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Evaluation of Functional Efficacy and Safety of DLL1 and Jag1 Ligand-Based Mono- and Polyvalent Constructs To facilitate in vivo testing, both human and mouse fragments undergo a three-step screening for functional efficacy and safety in cell-based assays using sets of normal and malignant human and mouse cells.

The functional efficacy of the disclosed constructs is tested using three approaches:

(1) Each DLL1 or Jag1 protein construct is tested for its ability to interfere with Notch activation in its soluble monovalent form and for the capacity to activate Notch when immobilized on the culture plastic using a set of lymphoid cell lines: human MOLT-4, Jurkat and HDLM2, and mouse EL4 and S49.1, which endogenously express various Notch receptors. In one assay, Notch is activated by soluble three-component clustered DLL1 or Jag1, or by immobilization of full-length ligand on culture plastic, which in known to activate Notch. Soluble monovalent ligand constructs are added at variable concentrations and their ability to inhibit Notch activation is assessed. In the second format, ligand constructs are immobilized at various doses on plastic, cells are cultured, and Notch activation is evaluated. The Notch activation is assessed by the expression of key Notch downstream targets Hes1 and Hey1, and Deltex1 by qRT-PCR5 and/or by Western blotting. Dose escalation and variable treatment time studies are performed to compare relative potency of the constructs. Additionally, 3T3 fibroblasts lacking endogenous Notch are used, but transfected to express either one of four human or mouse Notch receptors, to determine any receptor-specific preferences of the compounds. The signaling properties of these compounds and compositions are characterized and their activation of downstream pathways is compared with physiological cell-cell Notch activation (using 3T3 cells expressing DLL1 or Jag1) by Notch Signaling Pathway Target Genes PCR array to identify any potential differences.

(2) Functionally active compounds are tested for safety by their effects on proliferation and colony formation on the panel of human and mouse tumor cell lines. As a positive control in these assays, clustered DLL1 is utilized.

(3) Compounds are also tested in ELISPOT assays for their ability to regulate one of the key functions of T cells—cytokine secretion, as presented above. Soluble mono- or polyvalent constructs are added at varying doses to mouse splenocytes stimulated by CD3/CD28 antibodies or to T cells from OT-I and OT-II transgenic mice stimulated in antigen-specific manner with the respective ovalbumin peptides. The numbers of IFNγ and IL4 positive cells are evaluated.

The Notch non-activating cross-species molecules are used as precise negative controls, while commercially available ECD is used for comparison. Data in this example demonstrating functional activity of initially generated DLL1 fragments in different systems shows the therapeutic value of the peptides disclosed herein (FIG. 3).

An array of DLL1 fragments in active form have been produced. Jag1 and Notch receptor fragment production is similar to the methods for production of DLL1 fragments as disclosed herein, and standard methods of production are known to those skilled in the art.

Example 2. Evaluation of Antitumor and Immunological Efficacy of Multivalent DLL1 and Monovalent Jag1 Fragments in Tumor Models The data in FIG. 3D shows that the enhancement of Notch signaling by different ligands results in drastically different clinical and immunological outcomes. Thus, clinically relevant drugs comprising multiple receptor-binding domains of DLL1 Notch ligand can mimic DLL1-presenting cells and provide for efficient multivalent interaction with cell-bound Notch receptors. Monovalent Notch-binding fragments of Jag1 can interfere with Jag1-mediated Notch signaling and decrease generation of immunosuppressive Treg cells. Such therapeutics are effective in the pharmacological ligand-specific activation or inhibition of Notch to reverse cancer-induced immunosuppression and induce robust anti-tumor immune responses. Mouse and/or human compounds are evaluated for therapeutic and immunological efficacy by their ability to induce anti-tumor immune responses in mouse tumor models. Efficacy of the therapeutic combinations with oncogene-targeted treatment is also evaluated.

To evaluate the efficacy of Notch ligand drug compounds as a monotherapy, a Lewis Lung Carcinoma (LLC) model is used. This is a vascularized aggressive metastatic tumor in C57BL/6 mice responsive to immune stimulatory treatments. Tumor-associated antigen MUT1 has been characterized and antigen-specific CTL can be elicited, which makes possible the assessment of tumor antigen-specific immune responses. C57BL/6 mice are challenged s.c. with $0.35\times10^6$ LLC tumor cells. Treatments are initiated when tumors reach 4 mm in size. Experimental and control groups include: multivalent DLL1 drug; monovalent Jag1 drug; and two respective controls presenting non-activating cross species homologs. In the initial experiments with escalating doses, treatments continue until tumor size or mouse health reach exclusion criteria (normally, 3.5-4 weeks for untreated mice) to determine the overall survival benefit of the treatment. In additional experiments, tumors are allowed to develop for 12 days (early tumor) or 24 days (late stage tumor) and mice are sacrificed at these time points for immunological analysis.

One of the intended applications of the Notch modulatory treatment is a combination with oncogene-targeted therapy, specifically with EGF receptor (EGFR) inhibition that showed remarkable clinical benefit and enhanced progression-free survival (PFS) in pre-clinical investigations. The efficacy of Notch ligand compounds is evaluated as an adjuvant treatment with erlotinib in a model of spontaneous lung cancer in mice caring a human transgene with oncogenic L858R EGFR mutation in lung epithelial cells. The outline and methodology of the experiments are similar to that described herein; tumors are induced by feeding mice with doxycycline-impregnated food and visualized by MRI. Treatment groups are: erlotinib plus multivalent DLL1; erlotinib plus Jag1; erlotinib with respective controls, as above. When lung tumors become detectable by MRI, normally after two weeks of doxycycline induction, the treatments start with multivalent DLL1 or monovalent Jag1 constructs to reverse cancer immunosuppression; 3 days later, it is continued by combination treatments of Notch ligand constructs with erlotinib for 10 days. Erlotinib treatment is stopped and followed by the DLL1 or Jag1-based drug alone for 3 more days to provide immune stimulation in concert with the massive tumor antigen release to induce immune responses. After that time, treatments are stopped and tumor progression is monitored by MRI. Progression-free survival (PFS) under tumor-inducing conditions (doxycycline-induced expression of mutant EGFR) is measured as the time from the end of erlotinib therapy to the first evidence of tumor recurrence or progression determined by MRI. For the evaluation of immunological parameters, some mice are sacrificed a week after the end of the treatments and at the time of tumor progression to determine the effect of combined therapies on both induction of primary immune responses and T cell memory.

Dose escalation is performed in the LLC model starting with 0.2 mg/kg of Notch ligand construct either in monomeric or polymeric form, which corresponds to the minimally effective concentration previously determined in experiments with clustered DLL1. Thus, three doses of multivalent DLL1 or monovalent Jag1 are tested: 0.2 mg/kg, 0.7 mg/kg and 2.5 mg/kg i.p. every other day. A dose showing the highest efficacy without visible signs of toxicity is used in subsequent experiments. Erlotinib is given i.p. at 25 mg/kg dose daily, which induces complete or partial tumor response.

Although, the combination of Notch modulating compounds with EGFR inhibition is disclosed in this example, other therapeutic combinations where stimulation of Th1 immune responses or inhibition of immune suppressive mechanisms can provide additional clinical benefit. Specifically, DLL1 activation with immune checkpoint blockers and DLL1 activation with Jag1 inhibition is also tested in the LLC model.

Primary endpoints of the therapeutic efficacy studies are tumor growth for the isograft model and the PFS for the mutant EGFR model. Secondary endpoints are immunological parameters.

For the LLC model, the volume of primary tumor and enumerating lung metastatic nodules are measured; gross tumor morphology and necrosis are assessed by H&E staining of sections. For the mutant EGFR model, initial tumor growth, response to treatment and recurrence/progression in live mice are evaluated by MRI with axial and coronal images of lungs taken. Tumor-bearing mice are considered to have a complete response if a scan is negative for lung opacities after treatment; a partial response call is made when lung opacities are decreased but still clearly present; recurrent or progressive disease is determined if the follow-up MRI shows an increase by 30% in lung opacities compared with the post-treatment scan.

Immune infiltration of tumor is assessed by staining primary tumor sections (LLC model) or lungs (EGFR model) with antibodies to T cells (CD3, CD4, CD8), B cells (CD19), macrophages (CD11b), DCs (CD11c), and granulocytes (Gr1). Tumor-infiltrating CD45+ cells are isolated from tumor or lung single cells suspensions by immunomagnetic technique, and immune cell populations are evaluated by flow cytometry and used for immunological assays.

T cell responses are evaluated to determine the effect of treatments on the induction of tumor-specific CTL and Th cell polarization in TIL or lung infiltrating immune cells, draining lymph nodes (LN) cells and splenocytes from experimental and control animals. Anti-tumor MUT1-specific CTL is evaluated for LLC model by enumerating IFNγ-producing T cells within CD8+ T cell population by intracellular staining after cell restimulation with MUT1 peptide for 4 days. For evaluation of LLC tumor cell lysis, CD45+ cells isolated from tumor, spleen and LN (effector cells) is not or is re-stimulated with MUT1 peptide and then incubated with CFSE-labeled target LLC cells; target cell lysis is measured using Cell-Mediated Cytotoxicity Assay (Cayman). For assessment of Th polarization, CD45+ tumor-infiltrating cells, splenocytes and LN cells are stimulated with irradiated LLC cells, as described, 62 for 4 days and Th1, Th2 and Th17 cytokine-producing T cells are enumerated by intracellular staining of IFNγ, IL4, IL17A, IL-21 and Granzyme B within CD4+ T cell by flow cytometry or by ELISPOT. Alternatively, cells are stimulated with anti-CD3/CD28 antibody beads, in the same assay to determine antigen-independent Th responses. For the EGFR model, primary cell cultures derived from nodules of lung tumors are utilized in the same assays. For evaluation of Treg, CD4+CD25+FoxP3+ cells are enumerated by flow cytometry in primary LLC tumor or lungs of mutant EGFR mice, LN and spleen; expression of markers of Treg inhibitory activity (CD39, CTLA4, GITR, and CD73), expansion and activation (CD127, CD122, CD44, GARP, CD103) are assessed within Treg population.

Antigen-presenting cells are characterized by their ability to induce antigen-specific T cell polarization and proliferation of naïve T cells in vitro and by the expression of Notch ligands. CD11c+ dendritic cells (DCs) are isolated from spleen, pulsed with the antigenic ovalbumin peptides and incubated with T cells from the transgenic OT-I and OT-II mice for 5 days; activation markers and Th cell subsets are quantified by flow cytometry, intracellular cytokine staining or ELISPOT. T cell proliferation is assayed by CFSE dilution.

The Notch system is characterized in CD45+ T cells and CD11c+DC, isolated by immunomagnetic techniques from LLC tumor or mutant EGFR mouse lung, spleen and draining LN by the expression of Notch receptors, ligands and downstream targets Hes1, Hes5, and Deltex1 by qRT-PCR and Western blotting.

Together, in vivo and in vitro experiments identify DLL1 and Jag1 constructs that are able to induce or inhibit specific Th differentiation and T cells effector functions. Activation of DLL1 or inhibition of Jag1 ligand-specific signaling causes measurable changes in the immunological and clinical parameters. The correlation between stronger immune responses and better clinical outcome indicates the role for immune mechanisms in tumor rejection.

Based on observations with clustered DLL1, a multivalent DLL1 construct is a potent immune stimulatory agent with ability to enhance cell T cell cytotoxicity and memory and elicit robust tumor-specific responses. In concert with EGFR inhibition, it can produce significantly improved PFS in mutant EGFR mouse model than erlotinib alone. This shows that utilizing ligand-mediated Notch signaling can be used for inducing robust immune responses in combination with tumor targeted therapies.

The experiments shed light on the significance of Jag1 in T cell tolerance. Enhanced inflammatory and decreased regulatory T cell responses in monovalent Jag1 drug treated mice confirm its regulatory role and identify as a valuable target to overcome immunosuppression in cancer. Improved clinical and immunological outcomes show that the treatments activate T cell-mediated tumor rejection. Statistically significant differences in the number of or cytokine production by any given Th cell subset in the treated versus control mice are attributed to the positive role of DLL1 and negative role of Jag1 in driving differentiation of this subset. Combination treatment by multivalent DLL1 plus monovalent Jag1 drug determines whether DLL1 and Jag1 have directly opposing function. Stronger effects in combination treatment point to differing functions and possible combination therapy opportunities.

Analysis of Notch gene expression in DCs can reveal their strong regulation by exogenous multivalent DLL1, as was the case with clustered DLL1. Whether blocking of Jag1-mediated signaling regulates Notch ligand expression in DC is also determined. Additional modifications like PEGylation can also be used.

Example 3. Testing the Efficacy of Notch Modulation by Monovalent DLL1 and Multivalent Jag1 Fragments in Prolonging Mouse Cardiac Allograft Survival The Notch pathway has emerged as an important regulator of T cell alloimmunity and an attractive therapeutic target to inhibit solid organ transplant rejection and graft-versus-host disease (GVHD). The effects of Notch inhibition have been ascribed to a shift from Th1 to Th2 cytokines, induction and increased functions of Tregs, and direct targeting of alloreactive B cells. The accumulating data underscore the complex nature of T cell regulation by Notch and warrant future investigations of this pathway with the ultimate objective of therapeutic manipulation. The goal of in this example is to investigate the immunosuppressive properties of the monomeric forms of DLL1 fragments that inhibit the activation of the canonical Notch signaling pathway and polyvalent forms of Jag1 fragments implicated in the induction of Treg.

Inhibiting Notch signaling with DLL1(DSL-EGF12) inhibits alloreactive T cell responses regardless of differentiation profile (FIG. 4). DLL1 and Jag1 fragments are investigated for an effect on donor-reactive pathogenic and regulatory T cells and alloantibody generation and how these effects translate into cardiac allograft prolongation. Notch inhibition is tested whether it synergizes with costimulatory blockade or lymphoablation to prolong heart allograft survival. Finally, it is investigated whether proposed treatments affect functions of preexisting donor-reactive memory T cells and improve allograft survival in sensitized recipients. The information obtained from these experiments are clinically relevant and novel as memory T cells interfere with successful organ transplantation, and the role of Notch pathway in alloreactive T cell memory is not known.

To determine the mechanisms of cardiac allograft prolongation in the absence of other immunosuppression. Fully MHC mismatched male BALB/c (H-2d) heart transplants are placed into the abdomen of female C57BL/6 (B6, H-2b) mice. Recipients are checked daily, and the rejection is defined as the cessation of a heartbeat and confirmed by laparotomy and histology. Here, the same fragments as in Example 2 are used, but the monovalent form of DLL1 and multivalent Jag1 is used. Recipients are treated with monovalent DLL1 or multivalent Jag1 fragments (dose as described above, i.p. on d. 0, 1, 3, 5, 7 posttransplant) or controls and sacrificed at rejection or on d. 7 (rejection in control group), and cells are isolated from spleen and from the graft by collagenase digestion. Numbers of CD4 and CD8 T lymphocytes and the expression of CD44, CD25, CD69, CD62L markers are measured by flow cytometry. To evaluate proliferation, differentiation and effector functions of donor-reactive T cells, CD4 and CD8 cells are isolated by magnetic beads and tested against donor and third-party antigens in CFSE dilution proliferation assays, IFNγ, IL-4, IL-17, IL-21 and Granzyme B ELISPOT assays, and JAM cytotoxicity assays. The effects of Notch signaling inhibition are investigated using TCR transgenic donor-reactive T cells with known specificities.

Marilyn (Mar) TCR tg CD4 T cells recognize donor HY male antigen presented by recipient I-Ab and 2C TCRC tg CD8 T cells recognize donor MHC class I Ld molecule. $2\times10^6$ naïve congenic CD45 Mar or 2C cells are adoptively transferred into B6.CD45.1 female recipients of BALB/c male heart allografts treated with fragment or vehicle control. The numbers, activation, differentiation, effector functions and trafficking of tracer CD45.2+ T cell subsets are evaluated at rejection and at d. 7 posttransplant as outlined above. To test the effects of fragment treatment on Treg induction and functions, the numbers of CD4+CD25+ FoxP3+ cells in blood, spleen, and in the heart graft is determined by flow cytometry at d. 7 post-transplant and at rejection. Cell surface expression of markers associated with Treg cell expansion (CD25, CD127, CD122), activation (CD44, GARP, CD103) and suppressive functions (CTLA4, GITR, CD39 and CD73) are analyzed. To test suppressor functions of Tregs, GFP-FoxP3 reporter mice are used as heart allograft recipients. Following treatment with fragment or control vehicle, CD4+GFP+ cells are isolated and their ability to inhibit proliferation of naïve or memory T cells in response to donor stimulator cells or to anti-CD3/anti-CD28 stimulation is tested.

B cell populations in recipient spleen and bone marrow is analyzed by flow cytometry focusing on B220+CD21/35+ IgM+ follicular B cells, B220+CD21/35hiIgMhi marginal zone B cells, B220+CD21/35loIgM+ transitional and B220+ CD38-GL7+ germinal center B cells, B220+CD38hiIgDlo memory B cells, and B220loCD138hi plasma cells. Serum samples are analyzed for IgM, IgG1, IgG2c, IgG2b and IgG3 donor specific alloantibody (DSA) by flow cytometry as was previously published.

It is next tested whether Notch inhibition with ligand fragments synergizes with other graft prolonging strategies. Fragment treatment is used in combination with either lymphoablative induction by murine Thymoglobulin analog, mATG, or other regimens inhibiting CD28/CD80/CD86 or CD40/CD154 pathways (Table 3). These strategies are distinct in the mechanisms of graft prolongation, in that immune regulation is important for the effects of CTLA4-Ig or anti-CD154 but dispensable for the effects of mATG. The readouts are heart allograft survival and donor specific T cell and alloantibody responses. The results are compared to heart allograft survival and immune recall responses in B6 recipients of BALB/c heart allografts treated with fragment or control above.

TABLE 3

| Gr # | Heart recipient | Heart donor | Notch inhibition | Other immunosuppression | Anticipated mean survival time (MST) |
|---|---|---|---|---|---|
| 1 | B6 | BALB/c | Control, i.p. on d. 0, 1, 3, 5, 7 | CTLA4-Ig, 0.2 mg i.p. on d. 2 | −21 days |
| 2 | B6 | BALB/c | Monovalent DLL1 or multivalent Jag1 fragment, i.p. on d. 0, 1, 3, 5, 7 | CTLA4-Ig | More than 21 days |
| 3 | B6 | BALB/c | Control | Anti-CD154 mAb, clone MR1 0.2 mg i.v. on d. −1 | −24 days |
| 4 | B6 | BALB/c | DLL1 or multi-Jag1 fragment | Anti-CD154 mAb | More than 24 days |
| 5 | B6 | BALB/c | Control | mATG, 0.5 mg i.p. on d. 0 and 4 | −17 days |
| 6 | B6 | BALB/c | DLL1 or muilt-Jag1 fragment | mATG | More than 17 days |

Next, the effects of ligand fragment treatment are tested on survival, reactivation and functions of preexisting donor-reactive memory T cells, and on heart allograft survival in sensitized recipients. Whereas alloreactive memory T cells present a significant hurdle in clinical transplantation, the potential involvement of Notch in memory T cell alloresponses has not been previously investigated. It is tested whether Notch modulation interferes with reactivation and effector functions of donor-reactive memory T cells. First, CD44hi memory CD4 and CD8 T cells are isolated from B6 recipients of BALB/c heart allografts 4-6 weeks after transplantation and test how fragments affect their in vitro proliferation, cytokine secretion, and cytotoxicity in response to BALB/c antigens. It is also tested whether combining Notch inhibitor with costimulatory blockade prolongs heart allograft survival in T cell sensitized recipients. BALB/c skin allografts are placed onto B6 recipients, CD4+CD44hi and CD8+CD44hi memory T cells are isolated 6 weeks after skin transplantation and adoptively transferred into naïve B6 mice ($5\times10^6$ CD4 or CD8 T cells i.v.). Such recipients are resistant to high doses of costimulatory blockade due to memory T cell effector functions. B6 mice containing either CD4 or CD8 memory T cells are transplanted with BALB/c heart allografts and test whether treatment with fragment plus CTLA4-Ig (i.p. on d. 0, 2, 4, 6) or fragment plus anti-CD154 (1 mg i.v. on d. −1) prolongs heart allograft survival. The graft survival is compared to recipients containing memory T cells and treated with either CTLA4-Ig or anti-CD154 mAb alone.

Example 4. Treating Cancer with DLL1-Derived Multimers

This example illustrates methods of using a Notch-modulating peptide as described herein to treat cancer in a human adult.

An adult human subject who has been diagnosed with cancer is administered a therapeutically effective amount of a pharmaceutical compositions comprising a multimeric Notch-modulating peptide comprising at least four monomeric units connected by peptide linkers, wherein the monomeric units comprise: a mammalian Delta-like 1 (DLL1) protein DSL domain; and two or three mammalian DLL1 EGF domains. The pharmaceutical composition is administered by intravenous, intramuscular, or subcutaneous injection. The subject is evaluated for progression of the disease, as well as for the presence and/or severity of signs and symptoms associated with active disease, such as unintended weight loss, metastasis, tumor volume, etc. The subject is treated with repeated administrations until the subject is in remission and/or until one or more signs/symptoms of cancer are reduced, ameliorated, or eliminated.

Additionally, the DLL1-derived multimer may be co-administered with a monovalent fragment of Jagged comprising: a mammalian Jagged1 (Jag1) protein DSL domain; and two or three mammalian Jag1 EGF domains to further stimulate the patient's immune response to the cancer.

Example 5. Treating Graft-Versus-Host Disease GVHD with Jag1-Derived Multimers This example illustrates methods of using a Notch-modulating peptide as described herein to treat graft-versus-host disease (GVHD) in a human adult that has received an organ transplant.

An adult human subject who has received an organ transplant is administered a therapeutically effective amount of a pharmaceutical compositions comprising a multimeric Notch-modulating peptide comprising at least four monomeric units connected by peptide linkers, wherein the monomeric units comprise: a mammalian Jagged 1 (Jag1) protein DSL domain; and two or three mammalian Jag1 EGF domains. The pharmaceutical composition is administered by intravenous, intramuscular, or subcutaneous injection. The subject is evaluated for progression of the disease, as well as for the presence and/or severity of signs and symptoms associated with GVHD, such as ulcers, pain, fevers, rash, etc. The subject is treated with repeated administrations until the subject is in remission and/or until one or more signs/symptoms of GVHD are reduced, ameliorated, or eliminated.

Additionally, the Jag1-derived multimer may be co-administered with a monovalent fragment of Delta-like 1 (DLL1) comprising: a mammalian DLL1 DSL domain; and two or three mammalian DLL1 EGF domains to further inhibit the patient's immune response to the organ transplant.

Example 6. Expression of DLL1 Notch Ligand in Dendritic Cells is Essential for the Induction of Efficient Anti-Tumor Immune Responses Evidence argues that Notch system regulates peripheral T cells during antigen-specific responses and lineage commitment by providing instructive signals. Using genetic and pharmacological approaches, dendritic cells (DC) were investigated for being integral to the T cell anti-tumor immunity regulate T cell responses via varying expression of Notch ligands. Deletion of even one allele of Delta-like ligand (DLL) 1 in $CD11c^+$ cells resulted in remarkable acceleration of tumor growth and decreased survival of tumor bearing mice. This associated with significantly attenuated accumulation of tumor antigen specific IFN-γ-producing but not IL-4-producing cells in tumor tissue, decreased CD8 T cell activation and lower number of memory T cells. Numbers of tumor-infiltrating and splenic DC and DC phenotype were largely unchanged. In tumor bearing mice with deletion of Jagged (Jag)2 in DC, production of IL-4 but not IFN-γ by tumor infiltrating cells was decreased while no statistically significant accelerations of tumor growth or immune cell phenotype was observed. Treatment of wild type mice with a soluble DLL1 fragment interfering with Notch activation increased tumor growth. Data suggest that DLL1 expression renders DC the ability to induce Th1 anti-tumor responses and reveal molecular mechanisms of regulation of anti-tumor immunity by Notch system.

BACKGROUND

Signals delivered to naïve T cells by antigen-presenting cells (APC) along with the cytokine microenvironment play key roles in regulation of $CD4^+$ and $CD8^+$ cytotoxic T cells differentiation (1). Accumulating evidence suggests that the interaction between Notch ligands presented by APC and T cell Notch receptors might be important mediators of T cell differentiation (2-4). Notch, a transmembrane receptor, regulates a variety of processes in development and differentiation (5). The mammalian Notch family includes four cell-bound receptors, Notch1-4, and five cell-bound Notch ligands Delta-like (DLL)1, DLL3, DLL4, Jagged (Jag)1, and Jag2. Notch target genes are multiple and include transcriptional repressors that negatively regulate the expression of tissue-specific transcriptional activators, regulators of cell cycle, and anti-apoptotic genes (6, 7). In the immune system, Notch was implicated in enhancing $CD4^+$ T cell priming and governing mature T cell differentiation by providing instructive signal for the differentiation of T helper (Th) cells, follicular Th, and regulatory T cells (Treg) (8-14). One of the hypotheses also states that Notch promotes the generation of effector T cells by facilitating T cell activation and metabolic reprogramming rather than by specifying lineage choice or expression of master regulators at the initial steps of antigen encounter (15).

Data indicate that Notch can also regulate cytokine expression by CD8+ T cells (8, 16, 17). Contrasting roles for Notch have been proposed in the modulation of Th cell differentiation. Some evidence shows that Notch promotes Th1 cell differentiation and up-regulates T-bet and IFN-γ expression (18). Most gain-of-function studies indicate that delta-like ligands promote Th1 commitment of $CD4^+$ T cells (19, 20). Other evidence supports a prominent role for Notch in Th2 cell differentiation, which can directly transactivate Th2-promoting target genes 114 and Gata3 (9, 21). Although controversy exists, the bias is that Jagged ligands are associated with Th2-promoting Notch function (19, 22). Unlike other ligands, DLL3 is unable to activate Notch in cultured cells and seems to be a dedicated inhibitor of Notch signaling (23).

One study demonstrated that Notch enhances the magnitude, kinetics, and quality of primary immune responses and increases antigen sensitivity of naïve $CD4^+$ T cells. These effects are likely mediated via stimulation of PI3-kinase and mTOR signaling in T cells upon interaction of DLL4 expressed by dendritic cells (DC) and Notch on T cells (15). DC are integral to the differentiation of mature T cells. In addition to co-stimulatory molecules, they express and provide ligands for T cell Notch receptors. Reported experiments suggested that Notch ligand-specific signaling might specify Th1 or Th2 differentiation with different ligands supporting different polarization of Th cells (24-27). Regulation of IL17 and RORγt gene promoters and activation of Th17 differentiation has also been reported for Notch (11). In addition to influencing Th1, Th2 and Th17 differentiation, an immunosuppressive function of Notch was identified. Expression of Jagged ligands by APC or hematopoietic progenitors favored generation of suppressive T cells in vitro and regulatory (Treg) in vivo (28-30). Systemic blockage of Jag1 and 2 with specific antibodies improved anti-tumor T cell responses and overcame tumor-induced T cell tolerance suggesting the involvement of these ligands in mediating immunosuppression (31).

Strong evidence implicated Notch1 and 2 in the induction of anti-tumor immunity including induction of tumor-specific CTL and central memory T cells (15, 32-34). In previous investigations, it was found that Notch signaling and expression of Notch ligands in hematopoietic compartment are variable and could be significantly altered pharmacologically or by tumor derived factors suggesting that this could mediate tumor induced immunosuppression (35-37). The immunological correlates of the systemic therapeutic activation of Notch signaling and its efficacy in combination with oncogene-targeted treatment in a mouse lung cancer model was also investigated. DLL1-based Notch activating therapy could induce robust tumor antigen-specific T cell effector and memory responses, enhance T cell infiltration into the tumor, while decreasing Treg differentiation and tumor angiogenesis. This suggest an important role for DLL1-mediated Notch signaling in anti-tumor immunity. However, the specific roles of various Notch ligands and origin of the cells that provide ligand-mediated signal are yet to be revealed.

In the present example, using genetic and pharmacological approaches, the roles of DLL1 and Jag2 expression were evaluated in DCs in the regulation of T cell-mediated anti-tumor immunity and found that DLL1 but Jag2 expression is indispensable for the proper T cell activation, induction of tumor antigen specific responses and generation of memory T cells. By treating tumor bearing mice lacking DLL1 in $CD11c^+$ cells with Notch activating clustered DLL1, it was also demonstrated that genetic deficiency of DLL1 could be compensated in large part by pharmacological stimulation of DLL1/Notch signaling.

Materials and Methods

Cell Lines

Murine Lewis lung carcinoma (LLC) cell line was obtained from the American Type Culture Collection (Manassas, Va.). Murine MT5 pancreatic cells were a kind gift from Dr. Tuveson (Cold Spring Harbor Laboratory, Cold Spring Harbor, N.Y.). Low-passage (less than 10) cultures were used for the experiments.

Mice and Generation of Lineage Specific Knockouts

Male and female C57BL/6 mice and Balb/c (7 to 8-week-old) used at equal numbers were purchased from The Jackson Laboratory (Bar Harbor, Minn.).

C57BL/6 mice with foxed alleles for Dll1 genes were received from Dr. J. Lewis (Cancer Research UK, London, UK); Jag2 gene-targeted foxed mice were kindly provided by Dr. T. Gridley (Maine Medical Center, Scarborough, Minn.). Generation of $DLL1^{flox/flox}$ and $Jagged2^{flox/flox}$ conditional knockout mice and genotyping of floxed and deleted alleles was described previously (38-40). B6.Cg-Tg(Itgax-cre)1-1Reiz/J mice expressing Cre recombinase under CD11c (integrin-αX; CD11c-Cre) promoter were purchased from The Jackson Laboratory.

Mice bearing deletion of Dll1 or Jag2 in $CD11c^+$ cells were generated by mating syngeneic B6.Cg-Tg(Itgax-cre)1-1Reiz/J mice expressing Cre recombinase under CD11c promoter and $DLL1^{flox/flox}$ or $Jag2^{flox/flox}$ mice and then by crossing their progeny. In the resultant mice, $CD11c^+$ cells of with hetero- or homozygous allele deletion had genotype $Dll1^{flox/-}Cre^{+/-}$, $Jag2^{flox/-}Cre^{+/-}$, $Dll1^{-/-}Cre^{+/-}$ or $Jag2^{-/-}Cre^{+/-}$, respectively. Their littermates with "foxed" alleles but without Cre recombinase transgene served as respective controls in all animal experiments. The allele deletion was confirmed by genotyping and by the assessment of Notch ligand mRNA expression in flow sorted $CD11^+$ DC population from spleen by genomic and RT-PCR using sets of primers specific for foxed and deleted alleles and for ligand mRNA described previously (35, 38-40). The animals were housed in pathogen-free units at the Ohio State University School of Medicine, in compliance with the Institutional Animal Care and Use Committee (IACUC) regulations.

Expression Levels of Notch Ligands

RT-PCR was utilized to confirm deletion of Notch ligand genes in $CD11c^+$ cells. $CD11c^+$ cells were isolated from splenocytes by flow sorting, as described below. RNA was extracted with an RNeasy Mini kit and possible genomic DNA contamination was removed by on-column DNase digestion using the RNase-free DNase set (Qiagen; Valencia, Calif.). cDNA was synthesized using SuperScript III Reverse Transcriptase kit (Invitrogen, Grand Island, N.Y.) and used in PCR reactions with gene-specific primers, described previously (35). Amplification of endogenous β-actin was used as an internal control.

Tumor Model Experiments

To induce tumors, mice were inoculated subcutaneously (s.c.) in flank with $0.3\times10^6$ LLC or $10^6$ MT5 cells as described previously (36, 41, 42). Tumor volume was measured with calipers. For survival experiments, mice were observed until they reach exclusion criteria as determined by the IACUC protocol. To evaluate immunological correlatives, mice were sacrificed on days 17-18 and 14-15 for LLC and MT5 models, respectively.

Pharmacological Inhibition and Activation of DLL1 Signaling

Activation of Notch receptor proteolytic cleavage and signaling requires a multivalent interaction between Notch receptors and ligands, whereas soluble forms of ligands act as competitive Notch inhibitors (43). To produce a reagent for inhibition of DLL1 signaling, part of soluble extracellular domain of mouse DLL1 protein comprising the DSL, EGF1 and EGF2 domains with TEV and 6-His sequences was expressed in bacteria and isolated using Ni-column (Bio-Rad, Hercules, Calif.). The preparation was 90% pure as assessed by polyacrylamide gel electrophoresis with Coomassie R-250 staining. The ability of this reagent to inhibit Notch activity was confirmed in cell culture assay.

Tumor-bearing mice received soluble DLL1 fragment at doses of 1 mg/kg (25 μg per injection) of the protein in 100 μl of PBS intraperitoneally (i.p.) every other day. The control group received 100 μl of PBS instead of DLL1 fragment.

Multivalent form of DLL1 (clustered DLL1) was utilized to stimulated DLL1-mediated Notch activation in vivo at a dose of 0.2 mg/kg (5 μg per injection) of DLL1-Fc fusion protein i.p. every other day, as described previously (35, 36).

Immunological Assays

LLC cells have a defined antigenic peptide MUT1 (spontaneously mutated connexin 37), FEQNTAQP (SEQ ID NO:129) (44, 45). LLC tumor single cell suspension was prepared using Miltenyi Biotech (Auburn, Calif.) gentle MACS Dissociator and Tissue Dissociation kit according to the manufacturer's recommendations. Lymphocytes were than enriched by Lympholyte M (Cedarlane, Burlington, Canada) gradient centrifugation and used to quantify the cytokine producing cells: $5\times10^5$ cells per well were re-stimulated with 10 μM of MUT1 or control peptide for 48 hrs in the presence of mitomycin C treated syngeneic splenocytes and IFN-γ- or IL-4-producing cells were evaluated by dual ELISPOT assay (CTL, Shaker Heights, Ohio) according to the manufacturer's protocol. MUT1 peptide was synthesized by the American Peptide Company, Inc.

(Sunnyvale, Calif.). Alternatively, gradient centrifugation-enriched cells ($1.5\times10^5$ cells per well) were stimulated with Dynabeads Mouse T-Activator (anti-CD3, anti-CD28 antibodies coupled to beads; Life Technologies, Carlsbad, Calif.) at a bead-to-cell ratio of 1:1 and IFN-γ- or IL-4-producing cells were enumerated by ELISPOT assay. This analysis was performed on day 17-18 after initiation of LLC tumor growth.

Part of the tumor single cell suspension was used to evaluate tumor infiltration by immune lineages by flow cytometry (see below).

For evaluation of IFN-γ and IL-4 production by spleen and LN cells in LLC tumor bearing mice, $1.5\times10^5$ of combined splenocytes and draining LN cell population were stimulated with 10 μM of MUT1 or control peptide for 48 hrs and IFN-γ- and IL-4-producing cells were enumerated by ELISPOT assay, as above.

To evaluate the effect of Notch ligand gene knockout on T cell stimulatory activity of DC, allogeneic mixed lymphocyte reaction was used. DC were generated from bone marrow of wild type or knockout animals in the presence of GM-CSF and IL-4, as described earlier (41). T cells from allogeneic mice isolated by negative selection using T cell isolation columns (R&D Systems, Minneapolis, Minn.) were labeled with Cell Trace Violet dye (ThermoFisher Sci., Grand Island, N.Y.) and incubated for 5 days with bone-marrow derived DC in the presence of soluble anti-CD3.

Flow Cytometry and Sorting

Fluorochrome-labeled cell-surface marker or intracellular protein specific antibodies were obtained from BD Bioscience Pharmingen and eBioscience, Inc. (San Diego, Calif.). For staining of cell-surface markers, cells were incubated with the antibodies for 20 minutes on ice. For intracellular FoxP3, cells were first stained for lineage-specific markers and then permeabilized for 20 minutes with BD fixation/permeabilization kit and incubated with fluorochrome-labeled FoxP3-specific antibody. Matched fluorochrome-conjugated isotype IgG controls were used. Flow cytometry data were acquired using a FACS LSR II (BD Immunocytometry) and analyzed with FlowJo software (Tree Star, Ashland, Oreg.).

Flow sorting of $CD11c^+$ cells from splenocytes of wild type mice or animals with Notch gene deletion was performed using Aria IIu cell sorter (BD Immunocytometry). Nonviable cells were excluded by using 7-amino actinomycin D staining. Antigen negativity was defined as having the same fluorescent intensity as the isotype control.

Statistical Analysis

Data were analyzed using the GraphPad Prism 4.0 software (GraphPad Software Inc., San Diego, Calif.) and presented as mean±SEM. Comparisons between treatment and control groups were performed using one-way ANOVA followed by Dunnett's posttests. Comparisons between two groups were per-formed using two-tailed unpaired t tests. Survival curves were compared using Mantel-Haenszel log rank test. Values were considered statistically significant when p was less than 0.05.

Results

Deletion of Dll1 but not Jag2 in DC Remarkably Accelerates Tumor Growth and Decreases Animal Survival Mice with lineage specific Notch ligand knockout appeared normal. Phenotyping of immune cells population of lymphoid and myeloid lineages in thymus, spleen and lymph nodes by flow cytometry revealed no detectable differences between genetically modified and control CD11c-Cre, $DLL4^{flox/flox}$ or $Jag2^{lox/flox}$ mice demonstrating that these animals do not have major immune abnormalities and suggestive that possible alterations in tumor growth or immune responses in these mice could be attributed to the ablation of Notch ligands in DC.

Figure 26A:
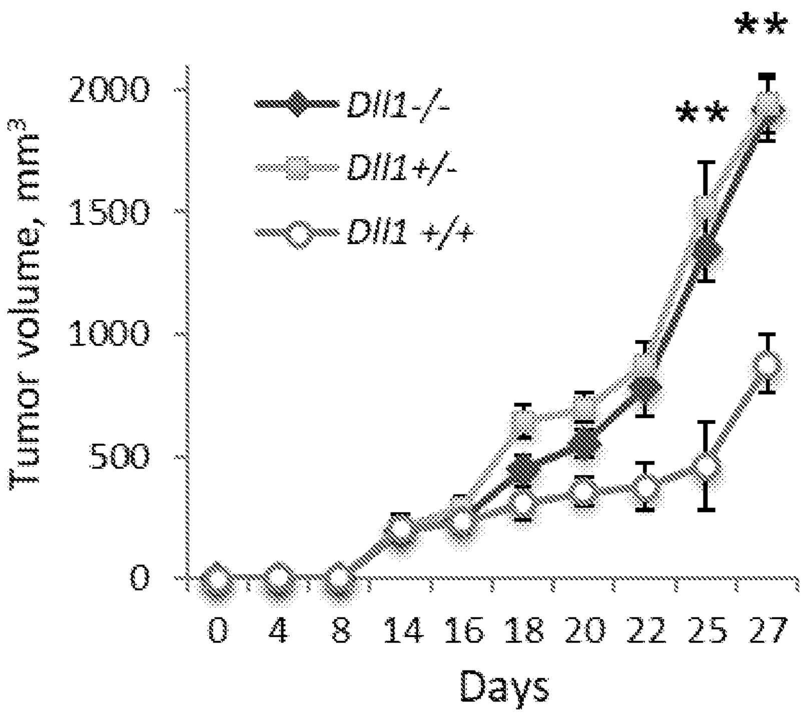
FIGS. 26A-26D. Genetic ablation of Dll1, but not Jag2, in $CD11c^+$ cells in mice results in significant acceleration of tumor growth decreased survival. LLC tumor growth (FIG. 26A) and survival curves (FIG. 26B) for mice with homo- or heterozygous deletion of Dll1 in $CD11c^+$ cells and wild type littermates.
Figure 26B:
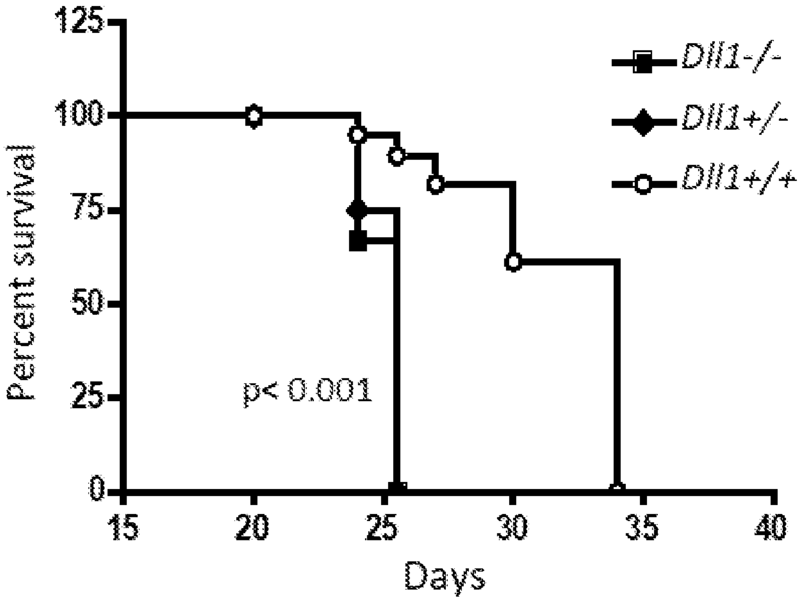
Figure 26C:
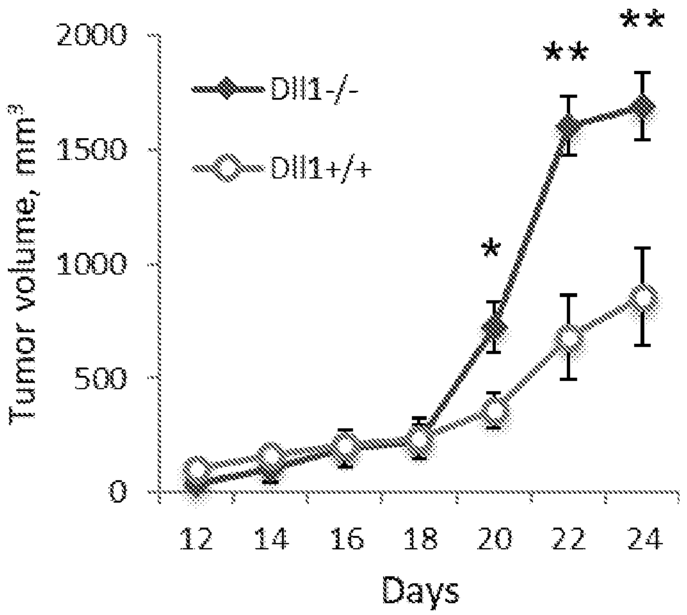

In tumor model experiments, mice with hetero- and homozygous deletion of Dll1 gene allele in $CD11c^+$ cells exhibited remarkably accelerated LLC tumor growth and significantly decreased survival compared to their wild type littermates (FIG. 26A, B). This effect was reproduced in MT5 tumor model (FIG. 26C) demonstrating the generality of the effect of Dll1 gene deletion. The fact that loss of even one Dll1 allele produces such significant aggravation clearly indicates the importance of DLL1 expression in DC for tumor rejection.

Figure 26D:
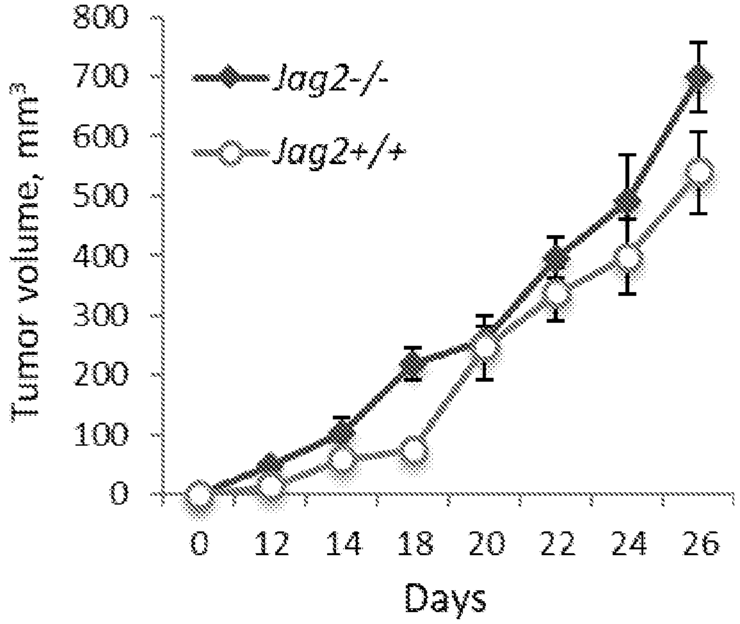

Contrasting to this, deletion of even two alleles of Jag2 did not result in major alteration in tumor growth in genetically modified mice (FIG. 26D). There was tendency toward increased tumor growth but not statistically significant suggesting that Jag2 presentation by DC does not play major role in anti-tumor responses and tumor rejection.

Figure 27A:
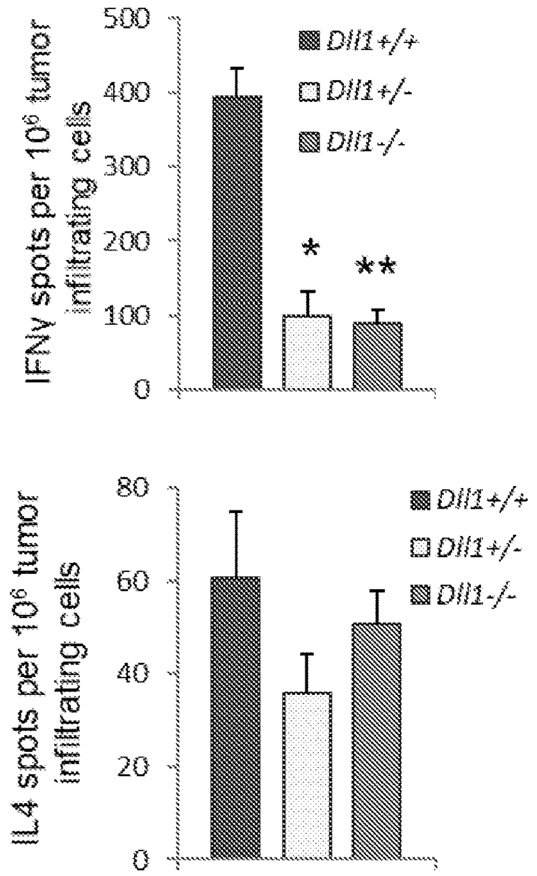
FIGS. 27A-27E. Mice with CD11c lineage-specific ablation of Dll1 show reduced IFN-γ producing cells and abrogated T cell proliferation. IFN-γ and IL-4-producing cells were enumerated by ELISPOT assay in LLC tumor-infiltrating lymphocytes (TILs) from mice with CD11c lineage-specific deletion of Dll1 (FIG. 27A, 27B) or Jag2 (FIG. 27C) and wild type littermates following re-stimulation with anti-CD3/CD28 labeled beads or with LLC tumor antigenic peptide MUT1 (FEQNTAQP (SEQ ID NO:134)) loaded on autologous splenocytes for 48 h (FIG. 27D).
Figure 27B:
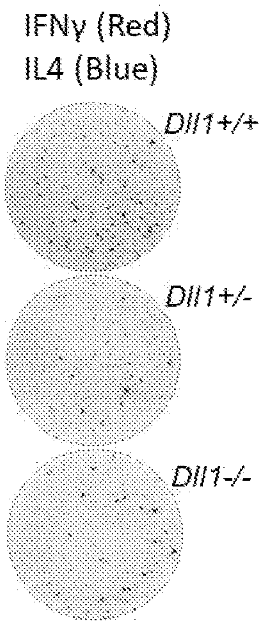
Figure 27C:
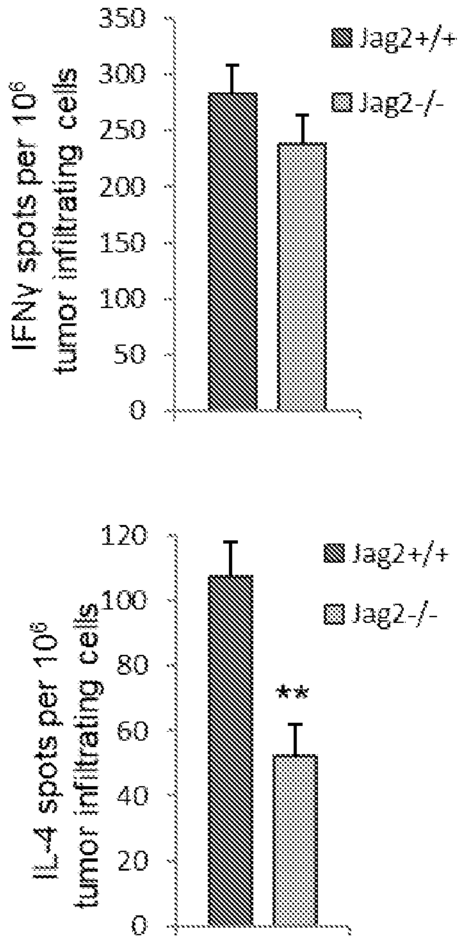
Figure 27D:
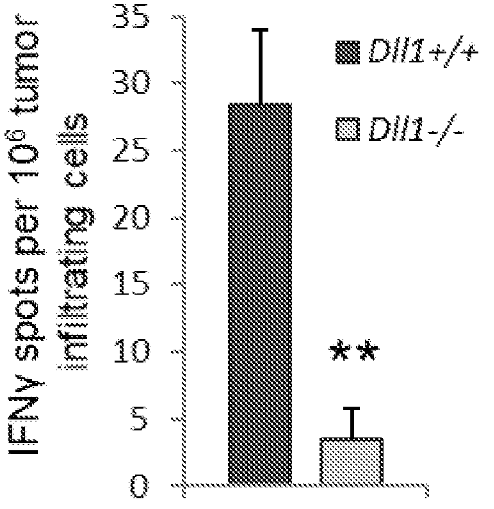
Figure 27E:
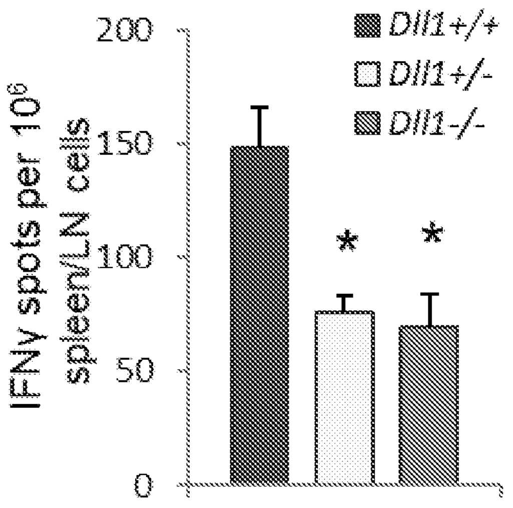

Impaired Anti-Tumor Immune Responses and Altered Th Cell Differentiation in Tumor Bearing Mice Lacking DLL1 but not Jag2 Expression in Dendritic Cells Evidence exists that Notch signaling plays an important role in regulating differentiation of naive $CD4^+$ T cells into distinct Th lineages and in $CD8^+$ T cell differentiation. It was found that genetic ablation of DLL1 signaling provided by DC significantly affected differentiation of Th cells and prevented eliciting Th1 type anti-tumor immune response and generation of cytotoxic T lymphocytes (CTL). Evaluation of IFN-γ and IL-4 producing tumor infiltrating cells by ELISPOT assay using stimulation with CD3/CD28 antibodies or LLC tumor antigen specific stimulus with MUT1 peptide revealed that in mice with hetero- and homozygous deletion of Dll1 in DC the numbers of IFN-γ secreting cells was markedly decreased, whereas the numbers of infiltrating IL-4-producing cells was not significantly altered (FIG. 27A-D). Similarly, reduction of IFN-γ secreting cells was found in the combined population of splenocytes and draining lymph node (LN) cells (FIG. 27E). These observations point to the significant role of DC expressed DLL1 for the induction of Th1 type anti-tumor responses.

Figure 29A:
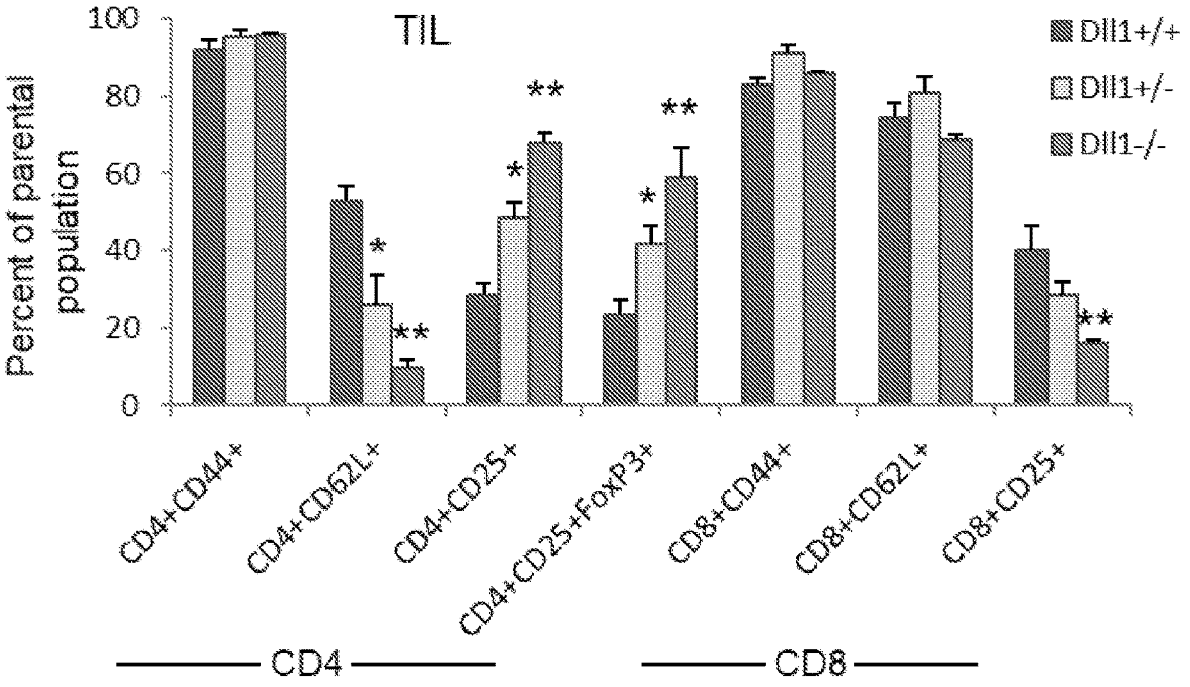
FIGS. 29A-29C. Tumor-bearing mice with CD11c lineage-specific deletion of Dll1 exhibit increased Treg and decreased effector T cell subsets. Lymphoid populations were evaluated by flow cytometry on day 17-18 after LLC tumor initiation in Dll1 knockout and wild type littermate mice. Percentage of indicated populations are shown in $CD4^+$ and $CD8^+$ subsets in the tumor infiltrate (TIL) from $Dll1^{-/-}$ and wild type littermates (FIG. 29A) with representative flow plots for CD4 versus CD25 and CD8 versus CD25 (FIG. 29B) and in spleens from the same mice (FIG. 29C). Mean±SEM, 5 mice per group, *$p<0.05$; **$p<0.01$.

Genetic interference with DLL1-mediated signaling had significant effect on $CD8^+$ T lymphocytes and resulted in strongly decreased activation of tumor infiltrating $CD8^+$ T cell; the proportion of $CD8^+$ T cells expressing CD25 activation marker was significantly lower in knockout mice than in wild type animals (FIG. 29A, B).

Deletion of Dll1 gene also resulted in significantly decreased generation of $CD4^+CD62L^+$ memory T cells as seen by their decreased number in tumor tissue and favored differentiation of FoxP3+ regulatory T cells (Treg). Most of tumor infiltrating CD4+CD25+ cells were also FoxP3 positive and their proportion was increased by about 2 folds in homozygous DC specific Dll1" knockout mice compared to wild type littermates (FIG. 29A, B).

The data strongly indicate that deletion of Dll1 in DC affects several important T cell differentiation and functional mechanisms and interferes with the generation of efficient anti-tumor immune responses. While differentiation of Th1 cells and CTL become suppressed, the abrogation of DLL1-mediated signaling supports shift toward Treg differentiation.

Figure 29B:
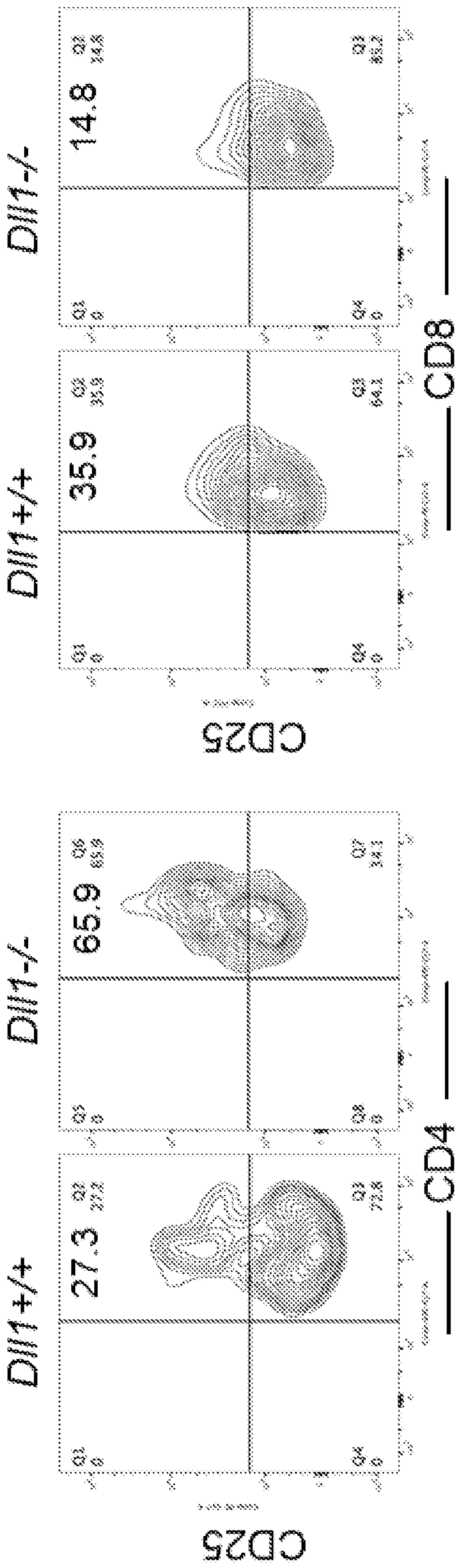
Figure 29C:
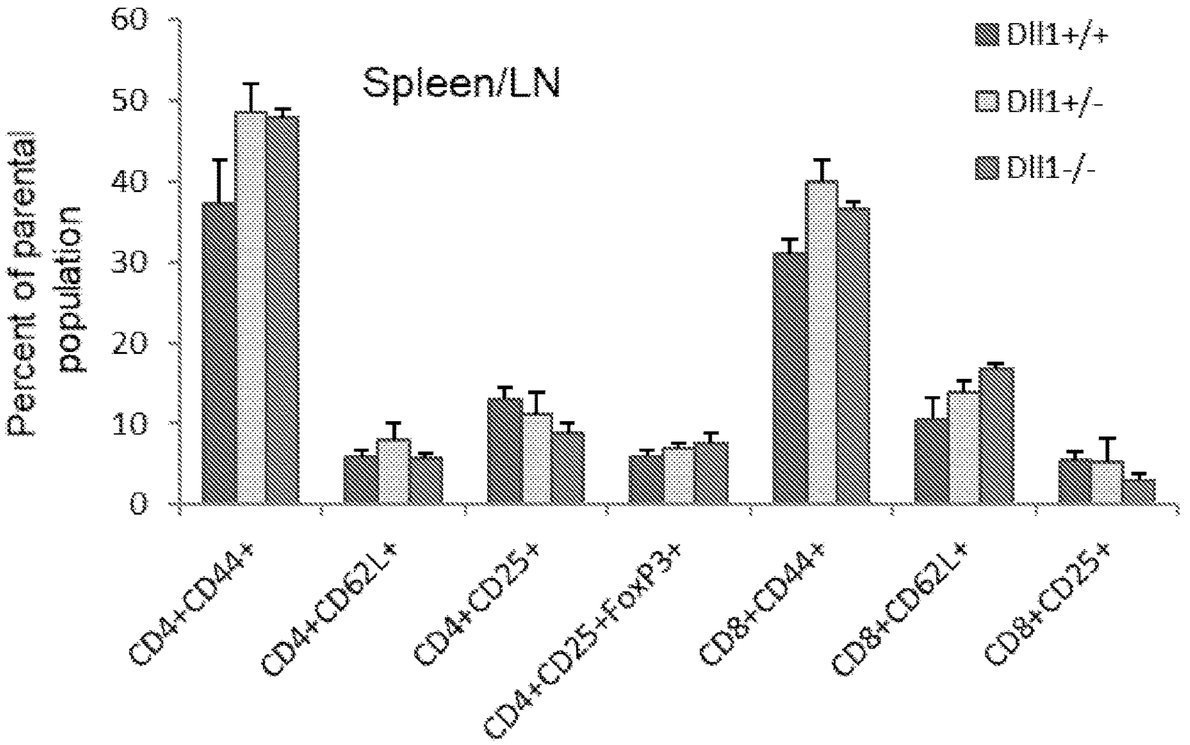

FIG. 29 demonstrates proportions of different immune cells lineages in tumor immune infiltrate and in combined spleen and draining LN cell population. The fact that are no significant differences in lymphoid compartment between wild type and knockout animals in spleen/LN cells compared to tumor immune infiltrate may suggest that the observed effects of Dll1 gene deletion have antigen-specific context rather than systemic.

Effects of Dll1 Deletion on Myeloid Compartment

Analysis of myeloid lineages in LLC tumor bearing mice revealed that the deletion of either one or two alleles of Dll1 did not alter the number or phenotype of $CD11c^+$ DC population nor affected their ability to infiltrate tumor tissue (FIG. 28). This clearly indicates that the observed alterations in T lymphoid compartment could be attributed to the aberrant expression of DLL1 in DC rather than to general DC deficiency in genetically modified animals.

Figure 28A:
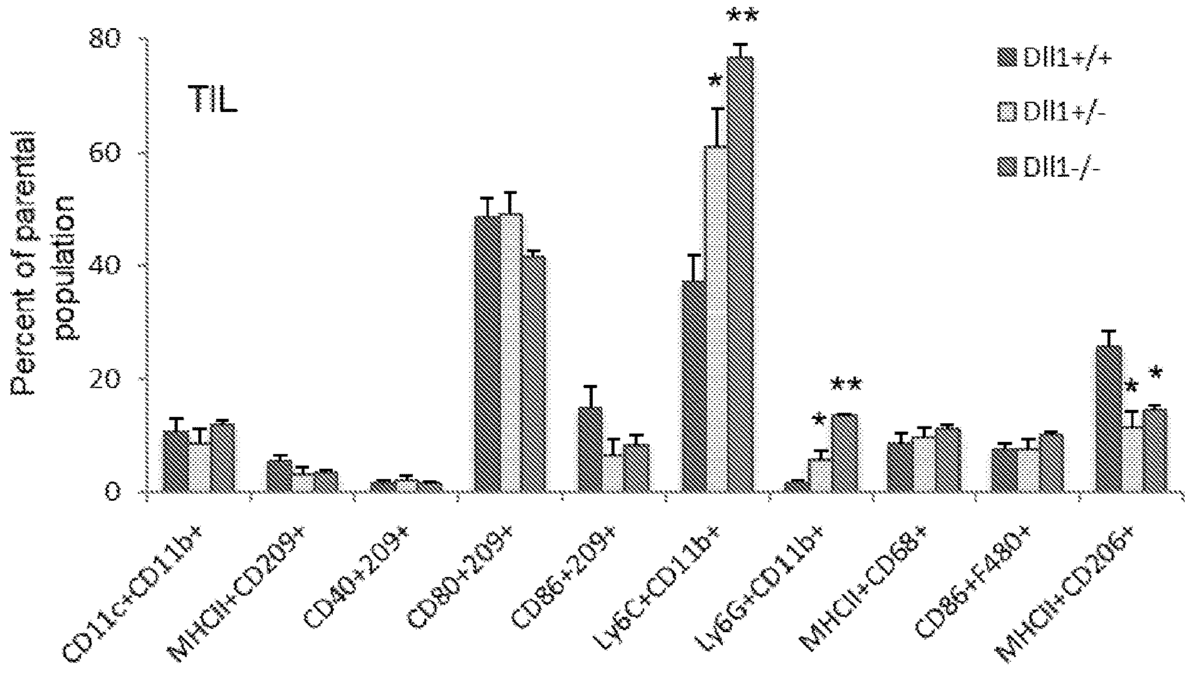
FIGS. 28A-28D. Tumor-bearing mice with CD11c lineage-specific deletion of Dll1 exhibit no change in dendritic cells but increased myeloid-derived suppressor cells. Myeloid populations were evaluated by flow cytometry on day 17-18 after LLC tumor initiation in Dll1 knockout and wild type littermate mice. Percentage of indicated populations are shown in the tumor infiltrate from Dll1 knockout and wild type littermates (FIG. 28A), along with total cell yields from the spleen and tumors (FIG. 28B), and representative flow plots for CD11b versus CD11c, Ly6C and Ly6G (FIG. 28C). Percentage of indicated populations are also shown in spleens from the same mice (FIG. 28D). Mean±SEM, 5-7 mice per group, *$p<0.05$; **$p<0.01$.
Figure 28B:
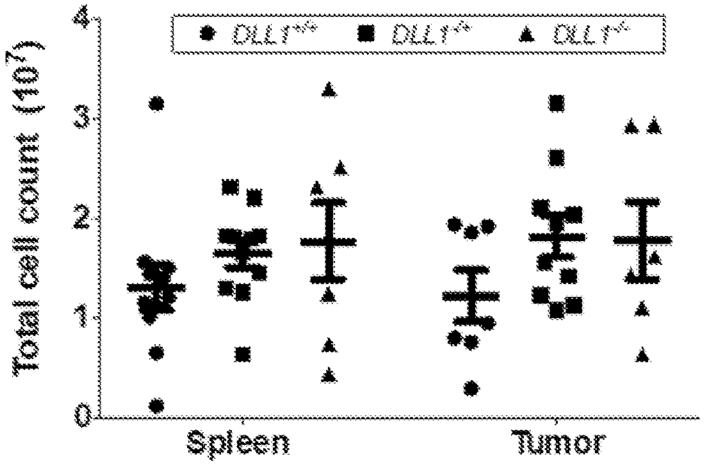
Figure 28C:
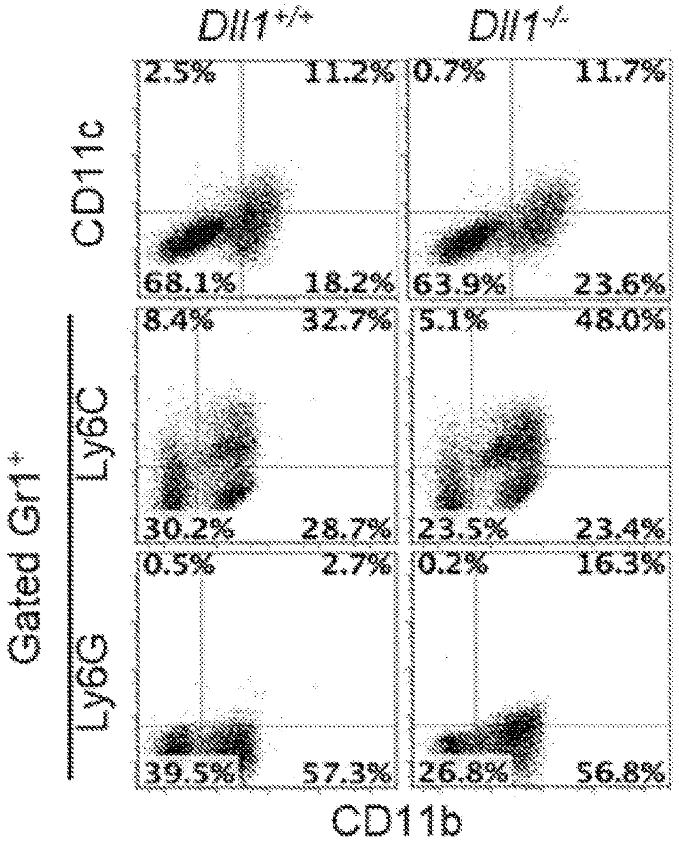
Figure 28D:
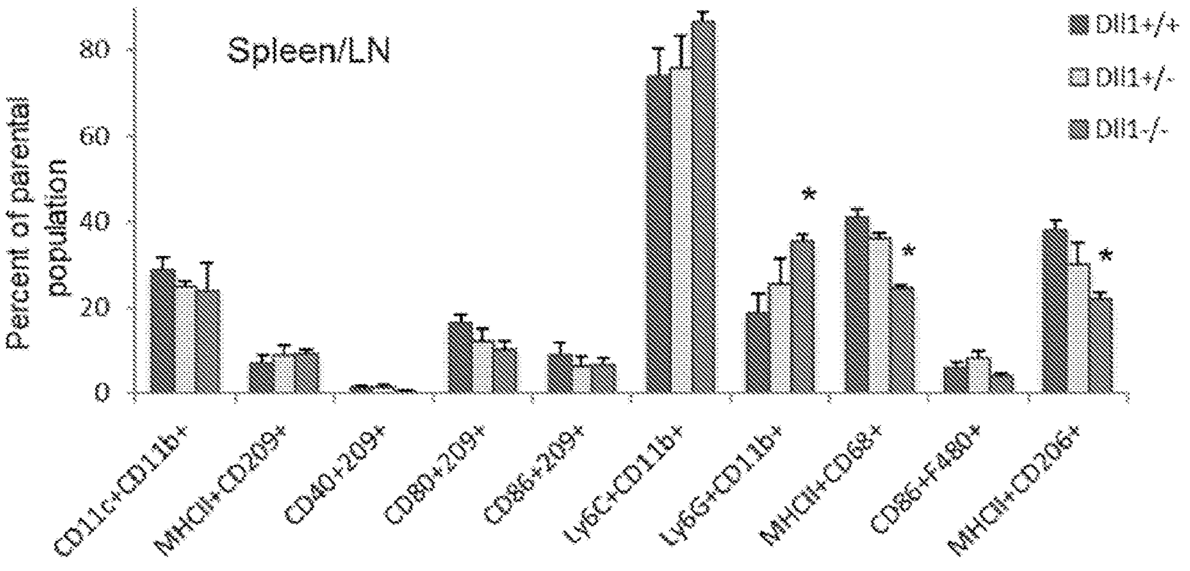

Obvious differences in myeloid lineages between tumor bearing Dll1' knockout and wild type mice include increased number of $Ly6G^+CD11b^+$ cells in combined splenic/LN population and significantly higher tumor infiltration with both $Ly6c^+CD11b^+$ and $Ly6G^+CD11b^+$ cells (FIG. 28C, D). There is also a decline in the proportions of $MHCII^+CD68^+$ M1 macrophages in splenic/LN population (FIG. 28D). Accumulation of these cell populations strongly depends on the tumor burden, and thus these effects are secondary to the variances in tumor burden in these mice.

Jag2 Deletion in DC Impairs Th2 but Th1 Responses in Tumor Bearing Mice

Contrasting to the remarkable effect of Dll1 deletion, knocking out Jag2 in DC did not have major effect on the induction of CTL responses; the number of tumor infiltrating IFN-γ-producing cells was not significantly altered. Interference with Jag2-mediated signaling, however, resulted in the decreased generation of IL-4-secreting cells consistent with the reported role of Jag2 in Th2 type differentiation (FIG. 27C).

Figure 30A:
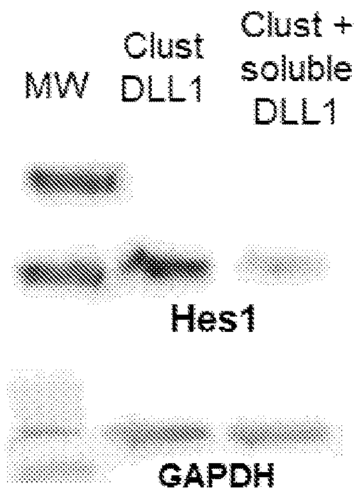
FIGS. 30A-30G. Monomeric soluble DLL1 ligand and genetic ablation of Dll1 in DC inhibits signaling and impairs T cell response.
Figure 30B:
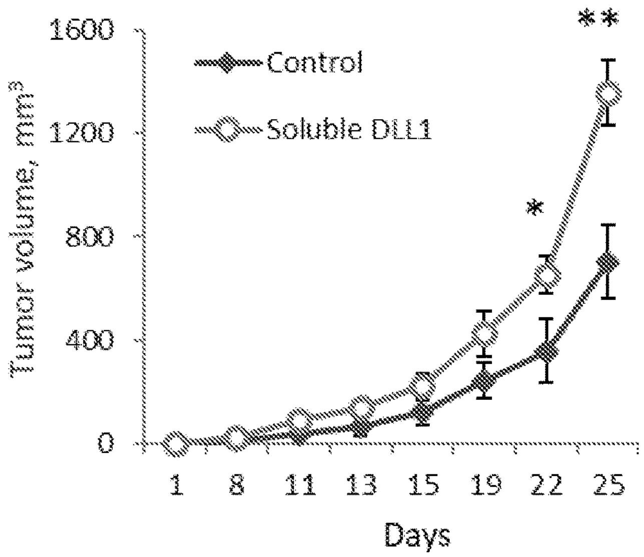
Figure 30C:
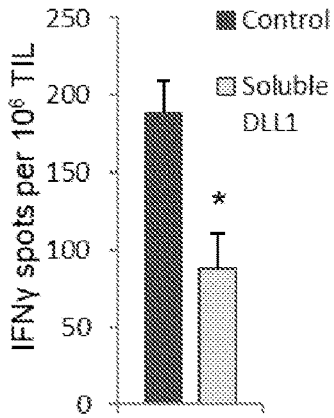
Figure 30D:
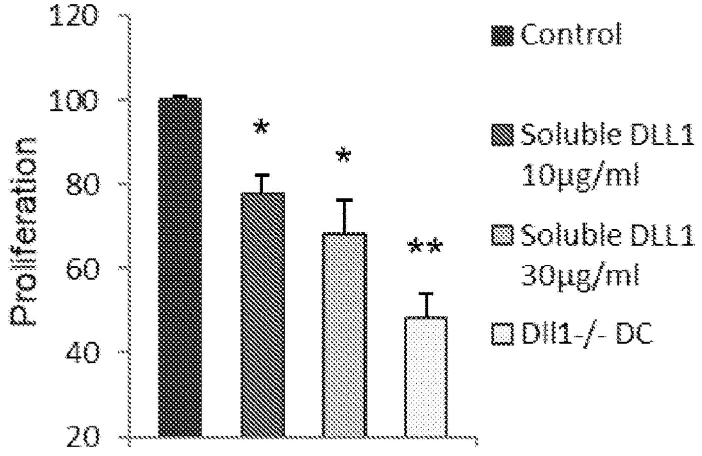

Pharmacological Interference with DLL1 Signaling Reproduces Effect of Genetic Deletion of Dll1 Gene in Tumor Model Activation of Notch receptor proteolytic cleavage and signaling requires a multivalent interaction with the ligands, whereas soluble forms of ligands inhibit Notch activation (43). To confirm the requirement for DLL1-mediated Notch signaling for the induction of anti-tumor responses, the monovalent fragment of DLL1 comprising DSL and two N-terminal EGF repeat domains was utilized as a competitive inhibitor of DLL1 signaling. Treatment of LLC tumor bearing mice with this compound significantly accelerated tumor growth similar to the genetic interference with Dll1 gene deletion (FIG. 30B). This inhibition corresponded to the attenuated T cell immune responses (FIG. 30C, D).

Figure 30E:
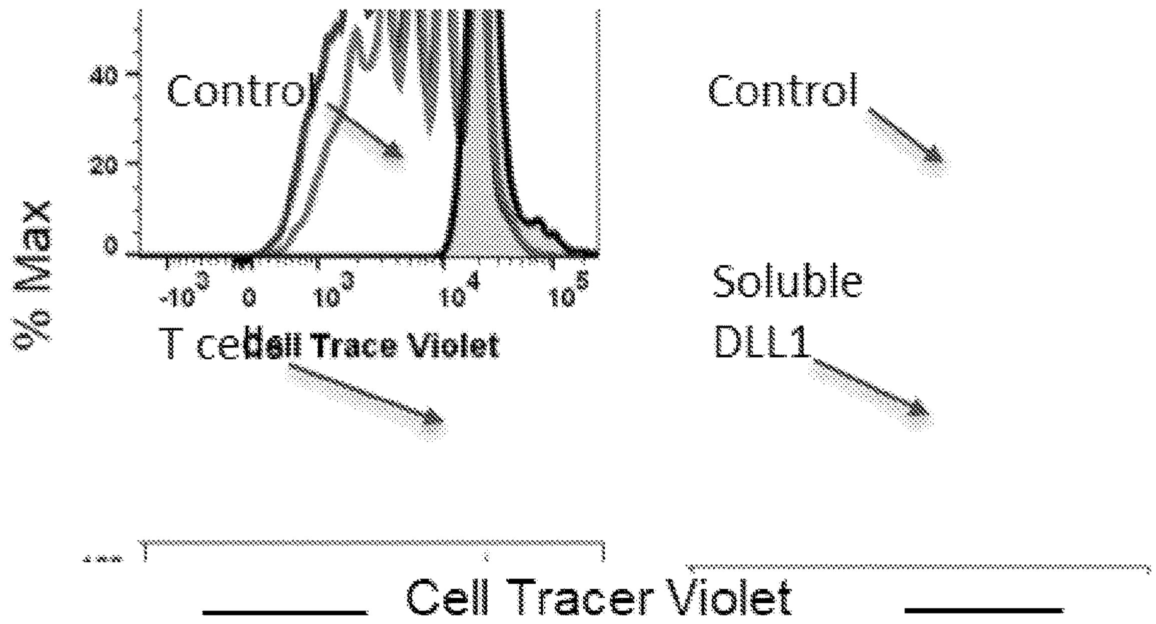
Figure 30F:
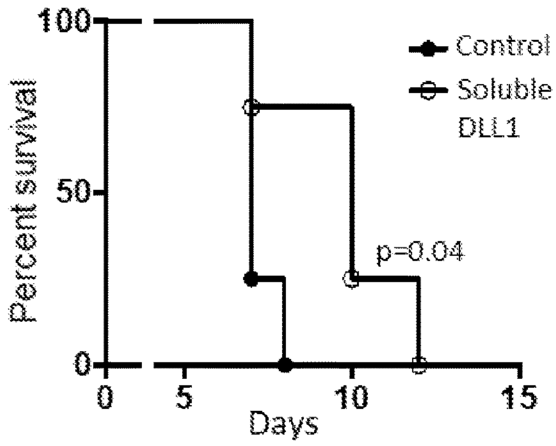
Figure 30G:
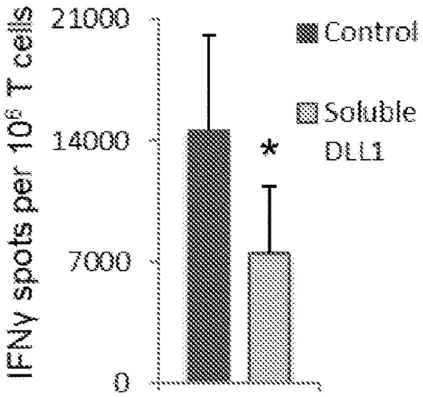

Genetic or Pharmacological Interference with DC DLL1-Mediated Signaling Impairs Allogeneic T Cell Proliferative Response In Vitro and In Vivo To substantiate the hypothesis that DLL1-mediated Notch signaling is important for the proper stimulation of T lymphocytes, the effect of DLL1 genetic or pharmacological blockage on the ability of DC to stimulate T cell proliferative function in allogenic mixed lymphocyte reaction (MLR) was evaluated. DC were generated from wild type or $Dll1^{-/-}$ knockout mouse bone marrow cells, as described previously (41) and incubated with allogeneic T cells labeled with fluorescent dye in the presence of soluble anti-CD3 antibody. In some samples with wild type DC, the soluble fragment of DLL1 protein was added to block DLL1-mediated signaling. Both pharmacological and genetic disruption of DLL1-Notch interaction in the MLR setting resulted in significant decrease of T cells proliferation assessed by the dye dilution (FIG. 30E, F, G), thus confirming the requirement for DLL1-Notch signaling for DC-induced T cell stimulation.

Figure 31A:
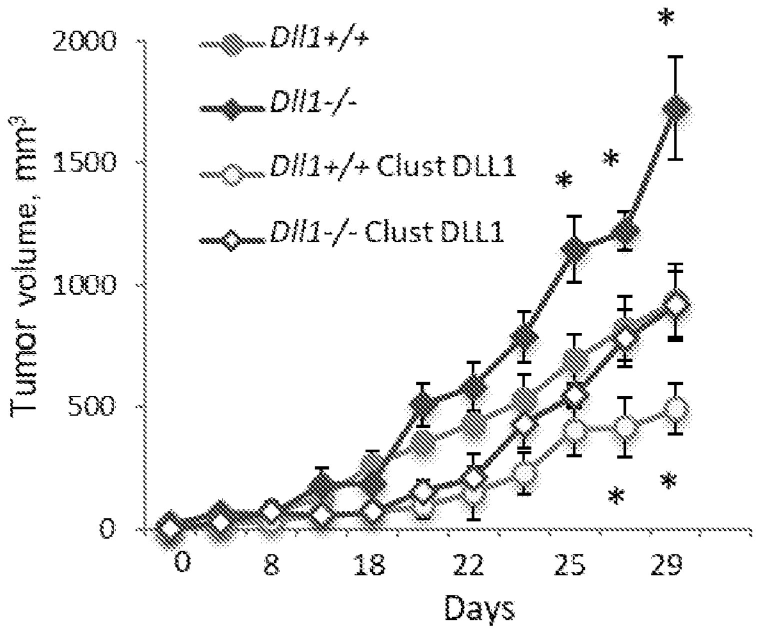
FIGS. 31A-31E. Enhancement of DLL1 signaling using multivalent clustered DLL1 overcomes the critical dendritic cell DLL1 deficiency to attenuate tumor growth and improve survival in mice. S. c. LLC tumor growth (FIG. 31A) and survival curves (FIG. 31B) and s.c. MT5 pancreatic tumor growth (FIG. 31C) in wild type mice and mice with homozygous deletion of Dll1 in dendritic cells (DC). Mice were treated with treated with multivalent DLL1, 0.2 mg/kg of DLL1-Fc fusion protein every 2 days.
Figure 31B:
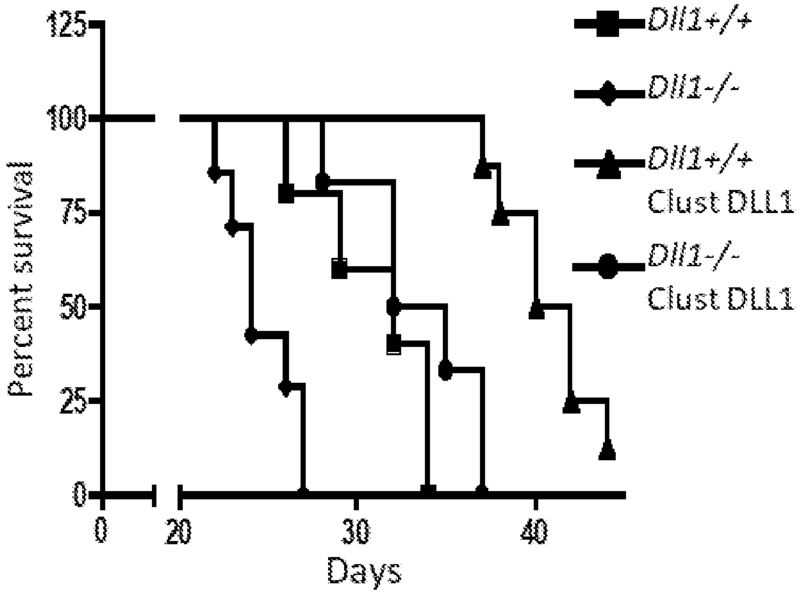
Figure 31C:
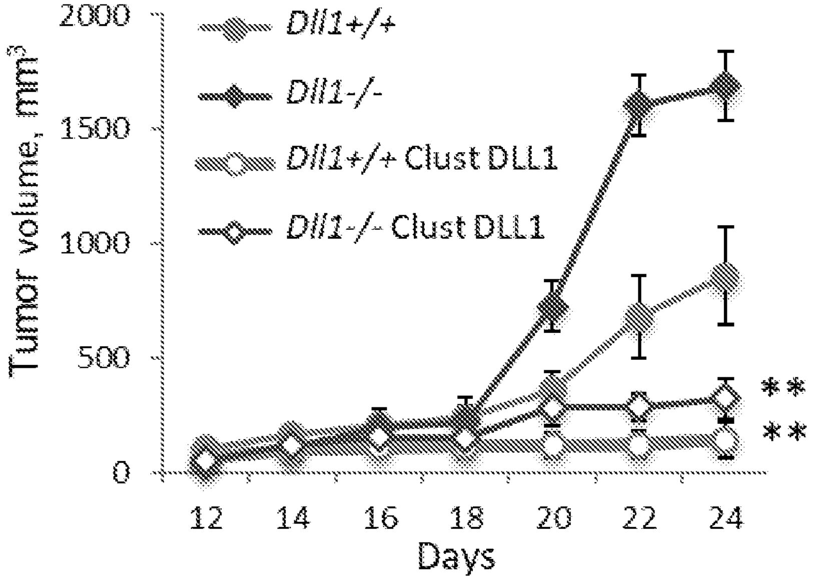
Figure 31D:
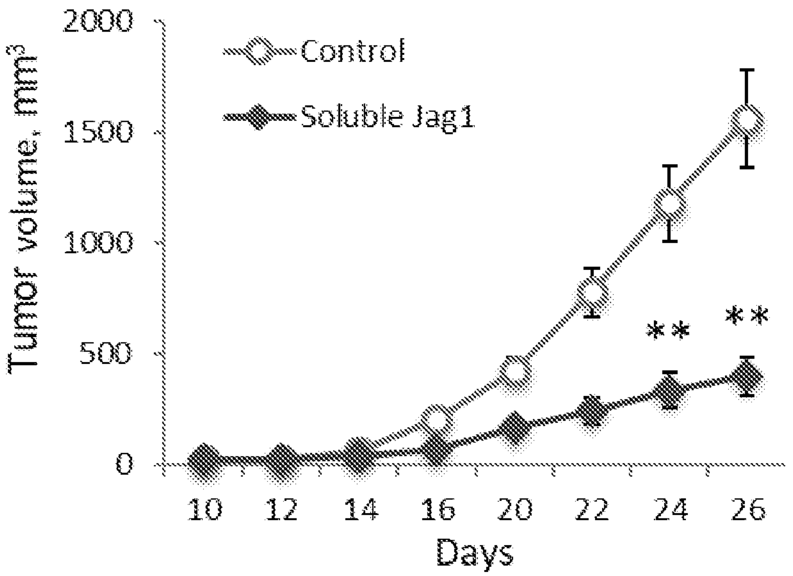
Figure 31E:
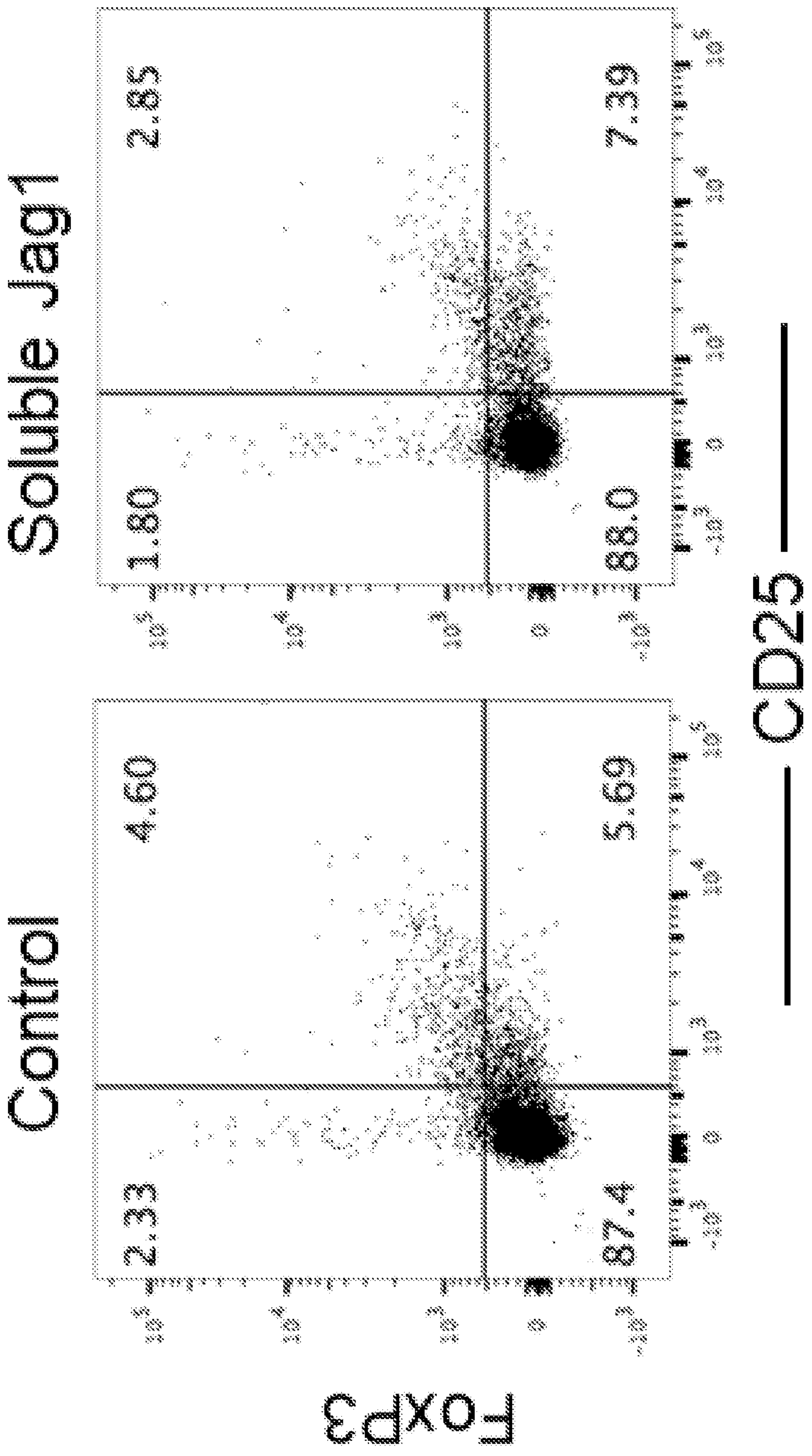

Interference with DLL1-mediated Notch activation using soluble fragment of DLL1 also had negative significant effect on the induction of alloreactive T cell responses in tumor-free host. Treatment of C57BL/6 mouse recipients of fully MHC-mismatched heterotopic Balb/c heart allografts with the monovalent DLL1 fragment around the time of transplantation significantly prolonged allograft survival compared to control treatment (FIG. 31A). The prolonged survival was associated with the decreased production of IFN-γ by donor-reactive $CD8^+$ T cells (FIG. 31B, C) without shift to IL-4 or IL-17 (82±7 vs. 84±8 IL-4 spots and 16±5 vs. 18±2 IL-17 spots per $10^6$ spleen cells for control and soluble DLL1 fragment treated groups, respectively). In this model, slightly reduced numbers of $FoxP3^+$ regulatory T cells in recipient spleen was also noticed (FIG. 31E), which is different from the tumor model and suggestive of the involvement of other potent factors driving Treg differentiation in tumor bearing host.

Pharmacological Enhancement of DLL1-Mediated Notch Signaling Reverses Genetic Insufficiency of DLL1 Signaling Therapeutic applications of Notch signaling modulating agents raise an important question of whether deficiency of DC ligand-mediated Notch activation could be reconstituted by pharmacological enhancement of DLL1/Notch interaction. To answer this question, a multivalent (clustered) form of DLL1 was utilized. Clustered DLL1 is a complex of DLL1-IgG Fc fusion proteins with biotinylated anti-Fc antibody and avidin, acting as an activator of Notch and it's in vivo application was described previously (35, 36).

In two different tumor models, LLC and MT5, clustered DLL1 was able to significantly attenuate tumor growth in both wild type and DLL1 deficient animals. These results clearly demonstrate that DLL1-based Notch activating therapeutics can enhance DLL1-mediated signaling and substitute in large part for inadequate presentation of DLL1 by dendritic cells needed for proper T cell stimulation and tumor rejection.

DISCUSSION

Interaction of dendritic cells with T lymphocytes is a key event that determines the type and strength of the induced immune response. Adequate presentation of antigen along with the other signals delivered by APC and secretion of the appropriate cytokines are needed for the eliciting strong anti-tumor immune responses including differentiation of Th1 cells and CTL. In the immune system, specific inflammatory responses up-regulate expression of either Delta-like or Jagged ligands in DC to guide activated $CD4^+$ T cells toward a specific type of T-helper commitment (18, 20). The current example demonstrates that in addition to the known T cell differentiation signals, interaction between Notch ligands presented by DC and Notch receptors on T cells provides Th polarization signal for lymphocytes and that presentation of DLL1 is indispensable for the induction of anti-tumor responses.

The Notch system is highly responsiveness to the modulation by Notch ligand. In the hematopoietic organs, the activation of downstream signaling may result in modulation of the expression of different Notch family receptors and ligands. Expression of Notch ligands in the hematopoietic compartment is variable (46-49). Previous results showed that their expression could be a target of immunosuppression in cancer (35-37). In particular, expression of delta-like ligands DLL1 and DLL4 was significantly down-regulated in tumor bearing hosts (35-37). Pharmacological or genetic enhancement of DLL1 mediated signaling attenuated tumor growth and strongly improved tumor antigen specific T cell responses (35, 36). At the same time, genetic abrogation or systemic blockage of DLL1/Notch interaction employed in the current study resulted in disease aggravation and impairment of anti-tumor immune responses. It is conceivable that the decreased presentation of DLL1 by DC plays an important role in mediating the observed impairment of anti-tumor immunity in tumor bearing host. Deficiency in DLL1 presentation by DC results in significant reduction of tumor antigen-specific CTL and their tumor infiltration, decrease in $CD8^+$ T cells activation and decreased differentiation of central memory $CD4^+CD62^+$ T cell population. These results show the requirement for the adequate expression DLL1 in DC for the induction of effector T cells.

Earlier studies demonstrated that Notch concurrently regulates Th1, Th2, and Th17 cell differentiation and can simultaneously orchestrate multiple T cell lineage programs. In this function, Notch activity is thought to be unbiased and not affected by the cytokine environment (50). Significant effort toward uncovering the roles of Notch signaling and Notch ligands in the eliciting various types of immune responses including previous and current results reveals that it is not just Notch activation but also the specific ligand-receptor interactions that determine the variant outcomes and T cell lineage commitment. These results together with earlier gain-of-function experiments suggest the instructive nature of DC-expressed ligand/T cell Notch receptor interaction in regulation of T lymphocyte commitment and that high expression of Delta-like ligands promotes Th1 type responses (19, 20).

Notch2 and Notch1 were identified as key Notch receptors for the eliciting anti-tumor responses, whereas recent studies showed that the activation of Notch1 could be the initial step of Notch activation in T cells by DC presented ligands followed by the significant up-regulation and engagement of Notch2 (15, 18). These investigations also revealed the involvement of Notch signaling in the regulation of T cell metabolic reprogramming and suggested that Notch might promote the generation of effector T cell lineages by "facilitating T cell activation, metabolic reprogramming, and IL-2 secretion upon antigen encounter" (15). It was also proposed that activation of Th cell Notch1 by DC expressed DLL4 was essential for fine tuning adaptive immune responses by influencing the sensitivity, magnitude, and quality of the initial $CD4^+$ T cell response. Given the confirmed roles of Notch1, Notch2, DLL4 in DC/T cell interaction along with the data on the involvement of DLL1 in this process, a multistep process of T cell lineage commitment is plausible. In this case, the initial DC DLL4/T cell Notch1 interaction supports T cell activation and metabolic reprogramming, enhance expression of Notch2 and potentially modulate expression of other Notch ligands. Subsequent engagement of DLL1 and Notch2 induces Th1 differentiation and CTL responses.

Together with the above data, these results point to the functional axis DLL1 and Notch1 and Notch2 as an essential element in DC/T cell interaction needed for the induction of effector T cell differentiation and T cell-mediated anti-tumor immunity.

Jag2 was previously implicated in the induction of Th2 type responses (22, 27, 49) and in the present example its deletion in DC did not result in any major changes in anti-tumor responses. Out of the measured immunological correlatives, deletion of Jag2 had negative effect on the number of IL-4 producing cells consistent with the role of Jag2 in supporting Th2 differentiation.

Data on the roles of different Notch ligands in regulation of T cell differentiation are summarized in FIG. 1. With both Notch1 and 2 receptors being involved, higher DLL1 and DLL4 expression by DC and other antigen presenting cells favors eliciting of Th1 type responses (4, 24, 25, 35, 36). Higher expression of Jag2 is linked to predominant Th2 and likely Th17 type responses, whereas high expression of Jag1 and decreased expression of delta-like ligands supports regulatory T cell commitment (4, 11, 22, 26, 27, 49, 51-53).

The current data herein demonstrates that therapeutic activation of Notch signaling by DLL1 can in large part reconstitute the deficient presentation of DLL1 by DC. The experiments with mono- and multivalent DLL1 demonstrate the power of Notch ligand-based reagents in regulation of specific types of immune responses.

REFERENCES CITED IN THIS EXAMPLE

1. Radtke F, MacDonald H R, Tacchini-Cottier F. Regulation of innate and adaptive immunity by Notch. Nat Rev Immunol 2013; 13: 427-37.
2. Yuan J S, Kousis P C, Suliman S, Visan I, Guidos C J. Functions of notch signaling in the immune system: consensus and controversies. Annu Rev Immunol 2010; 28: 343-65.
3. Osborne B A, Minter L M. Notch signalling during peripheral T-cell activation and differentiation. Nat Rev Immunol 2007; 7: 64-75.
4. Radtke F, Fasnacht N, Macdonald H R. Notch signaling in the immune system. Immunity 2010; 32: 14-27.
5. Fiuza U M, Arias A M. Cell and molecular biology of Notch. J Endocrinol 2007; 194: 459-74.
6. Kopan R, Ilagan M X. The canonical Notch signaling pathway: unfolding the activation mechanism. Cell 2009; 137: 216-33.
7. Bettelli E, Carrier Y, Gao W, et al. Reciprocal developmental pathways for the generation of pathogenic effector TH17 and regulatory T cells. Nature 2006; 441: 235-8.
8. Tsukumo S, Yasutomo K. Notch governing mature T cell differentiation. J Immunol 2004; 173: 7109-13.
9. Amsen D, Antov A, Jankovic D, et al. Direct regulation of Gata3 expression determines the T helper differentiation potential of Notch. Immunity 2007; 27: 89-99.
10. Auderset F, Schuster S, Fasnacht N, et al. Notch signaling regulates follicular helper T cell differentiation. J Immunol 2013; 191: 2344-50.
11. Keerthivasan S, Suleiman R, Lawlor R, et al. Notch signaling regulates mouse and human Th17 differentiation. J Immunol 2011; 187: 692-701.
12. Mukherjee S, Schaller M A, Neupane R, Kunkel S L, Lukacs N W. Regulation of T cell activation by Notch ligand, DLL4, promotes IL-17 production and Rorc activation. J Immunol 2009; 182: 7381-8.
13. Samon J B, Champhekar A, Minter L M, et al. Notch1 and TGFbeta1 cooperatively regulate Foxp3 expression and the maintenance of peripheral regulatory T cells. Blood 2008; 112: 1813-21.
14. Riella L V, Yang J, Chock S, et al. Jagged2-signaling promotes IL-6-dependent transplant rejection. Eur J Immunol 2013; 43: 1449-58.
15. Laky K, Evans S, Perez-Diez A, Fowlkes B J. Notch signaling regulates antigen sensitivity of naive CD4+ T cells by tuning co-stimulation. Immunity 2015; 42: 80-94.
16. Palaga T, Miele L, Golde T E, Osborne B A. TCR-mediated Notch signaling regulates proliferation and IFN-gamma production in peripheral T cells. J Immunol 2003; 171: 3019-24.

17. Sauma D, Ramirez A, Alvarez K, Rosemblatt M, Bono M R. Notch signalling regulates cytokine production by CD8+ and CD4+ T cells. Scand J Immunol 2012; 75: 389-400.
18. Maekawa Y, Tsukumo S, Chiba S, et al. Delta1-Notch3 interactions bias the functional differentiation of activated CD4+ T cells. Immunity 2003; 19: 549-59.
19. Amsen D, Antov A, Flavell R A. The different faces of Notch in T-helper-cell differentiation. Nat Rev Immunol 2009; 9: 116-24.
20. Amsen D, Blander J M, Lee G R, Tanigaki K, Honjo T, Flavell R A. Instruction of distinct CD4 T helper cell fates by different notch ligands on antigen-presenting cells. Cell 2004; 117: 515-26.
21. Tanigaki K, Tsuji M, Yamamoto N, et al. Regulation of alphabeta/gammadelta T cell lineage commitment and peripheral T cell responses by Notch/RBP-J signaling. Immunity 2004; 20: 611-22.
22. Krawczyk C M, Sun J, Pearce E J. Th2 differentiation is unaffected by Jagged2 expression on dendritic cells. J Immunol 2008; 180: 7931-7.
23. Ladi E, Nichols J T, Ge W, et al. The divergent DSL ligand Dll3 does not activate Notch signaling but cell autonomously attenuates signaling induced by other DSL ligands. J Cell Biol 2005; 170: 983-92.
24. Skokos D, Nussenzweig M C. CD8-DCs induce IL-12-independent Th1 differentiation through Delta 4 Notch-like ligand in response to bacterial LPS. J Exp Med 2007; 204: 1525-31.
25. Kassner N, Krueger M, Yagita H, et al. Cutting edge: Plasmacytoid dendritic cells induce IL-10 production in T cells via the Delta-like-4/Notch axis. J Immunol 2010; 184: 550-4.
26. Liotta F, Frosali F, Querci V, et al. Human immature myeloid dendritic cells trigger a TH2-polarizing program via Jagged-1/Notch interaction. J Allergy Clin Immunol 2008; 121: 1000-5 e8.
27. Sun J, Krawczyk C J, Pearce E J. Suppression of Th2 cell development by Notch ligands Delta1 and Delta4. J Immunol 2008; 180: 1655-61.
28. Vigouroux S, Yvon E, Wagner H J, et al. Induction of antigen-specific regulatory T cells following overexpression of a Notch ligand by human B lymphocytes. J Virol 2003; 77: 10872-80.
29. Yvon E S, Vigouroux S, Rousseau R F, et al. Overexpression of the Notch ligand, Jagged-1, induces alloantigen-specific human regulatory T cells. Blood 2003; 102: 3815-21.
30. Kared H, Adle-Biassette H, Fois E, et al. Jagged2-expressing hematopoietic progenitors promote regulatory T cell expansion in the periphery through notch signaling. Immunity 2006; 25: 823-34.
31. Sierra R A, Trillo-Tinoco J, Mohamed E, et al. Anti-Jagged Immunotherapy Inhibits MDSCs and Overcomes Tumor-Induced Tolerance. Cancer Res 2017; 77: 5628-38.
32. Auderset F, Schuster S, Coutaz M, et al. Redundant Notch1 and Notch2 signaling is necessary for IFNgamma secretion by T helper 1 cells during infection with *Leishmania major*. PLoS pathogens 2012; 8: e1002560.
33. Sierra R A, Thevenot P, Raber P L, et al. Rescue of notch-1 signaling in antigen-specific CD8+ T cells overcomes tumor-induced T-cell suppression and enhances immunotherapy in cancer. Cancer immunology research 2014; 2: 800-11.
34. Sugimoto K, Maekawa Y, Kitamura A, et al. Notch2 signaling is required for potent antitumor immunity in vivo. J Immunol 2010; 184: 4673-8.
35. Biktasova A K, Dudimah D F, Uzhachenko R V, et al. Multivalent Forms of the Notch Ligand DLL-1 Enhance Antitumor T-cell Immunity in Lung Cancer and Improve Efficacy of EGFR-Targeted Therapy. Cancer Res 2015; 75: 4728-41.
36. Huang Y, Lin L, Shanker A, et al. Resuscitating cancer immunosurveillance: selective stimulation of DLL1-Notch signaling in T cells rescues T-cell function and inhibits tumor growth. Cancer Res 2011; 71: 6122-31.
37. Thounaojam M C, Dudimah D F, Pellom S T, Jr., et al. Bortezomib enhances expression of effector molecules in anti-tumor CD8+T lymphocytes by promoting Notch-nuclear factor-kappaB crosstalk. Oncotarget 2015; 6: 32439-55.
38. Hozumi K, Negishi N, Suzuki D, et al. Delta-like 1 is necessary for the generation of marginal zone B cells but not T cells in vivo. Nat Immunol 2004; 5: 638-44.
39. Brooker R, Hozumi K, Lewis J. Notch ligands with contrasting functions: Jagged1 and Delta1 in the mouse inner ear. Development 2006; 133: 1277-86.
40. Xu J, Krebs L T, Gridley T. Generation of mice with a conditional null allele of the Jagged2 gene. Genesis 2010; 48: 390-3.
41. Novitskiy S V, Ryzhov S, Zaynagetdinov R, et al. Adenosine receptors in regulation of dendritic cell differentiation and function. Blood 2008; 112: 1822-31.
42. Mace T A, Shakya R, Pitarresi J R, et al. IL-6 and PD-L1 antibody blockade combination therapy reduces tumour progression in murine models of pancreatic cancer. Gut 2018; 67: 320-32.
43. Heinzel K, Benz C, Martins V C, Haidl I D, Bleul C C. Bone marrow-derived hemopoietic precursors commit to the T cell lineage only after arrival in the thymic microenvironment. J Immunol 2007; 178: 858-68.
44. Chen J Q, Xiu Q Y, Shen C, Yan Z M. [Treatment of spontaneous metastatic lung cancer with interleukin-12 gene-modified dendritic cells vaccine]. Ai Zheng 2002; 21: 1328-31.
45. Mandelboim O, Bar-Haim E, Vadai E, Fridkin M, Eisenbach L. Identification of shared tumor-associated antigen peptides between two spontaneous lung carcinomas. J Immunol 1997; 159: 6030-6.
46. Sauma D, Espejo P, Ramirez A, Fierro A, Rosemblatt M, Bono M R. Differential regulation of Notch ligands in dendritic cells upon interaction with T helper cells. Scand J Immunol 2011; 74: 62-70.
47. Matsushita S, Higashi T. Human Th17 cell clones and natural immune responses. Allergology international: official journal of the Japanese Society of Allergology 2008; 57: 135-40.
48. Krawczyk C, Pearce E, Borjian A, Young S, Mahbuba R. Regulation of dendritic cell function by Notch receptors and ligands. J Immunol 2012; 188.
49. Xiong Y, Lingrel J B, Wuthrich M, et al. Transcription Factor KLF2 in Dendritic Cells Downregulates Th2 Programming via the HIF-1alpha/Jagged2/Notch Axis. mBio 2016; 7.
50. Bailis W, Yashiro-Ohtani Y, Fang T C, et al. Notch simultaneously orchestrates multiple helper T cell programs independently of cytokine signals. Immunity 2013; 39: 148-59.
51. Mochizuki K, He S, Zhang Y. Notch and inflammatory T-cell response: new developments and challenges. Immunotherapy 2011; 3: 1353-66.

52. Wang Y, Xing F, Ye S, et al. Jagged-1 signaling suppresses the IL-6 and TGF-beta treatment-induced Th17 cell differentiation via the reduction of RORgammat/IL-17A/IL-17F/IL-23a/IL-12rb1. Scientific reports 2015; 5: 8234.
53. Cahill E F, Tobin L M, Carty F, Mahon B P, English K. Jagged-1 is required for the expansion of CD4+ CD25+ FoxP3+ regulatory T cells and tolerogenic dendritic cells by murine mesenchymal stromal cells. Stem cell research & therapy 2015; 6: 19.
54. D'Souza B, Meloty-Kapella L, Weinmaster G. Canonical and non-canonical Notch ligands. Current topics in developmental biology 2010; 92: 73-129.

Example 7. Analysis of Multimeric DLL1 Constructs

Figure 7:
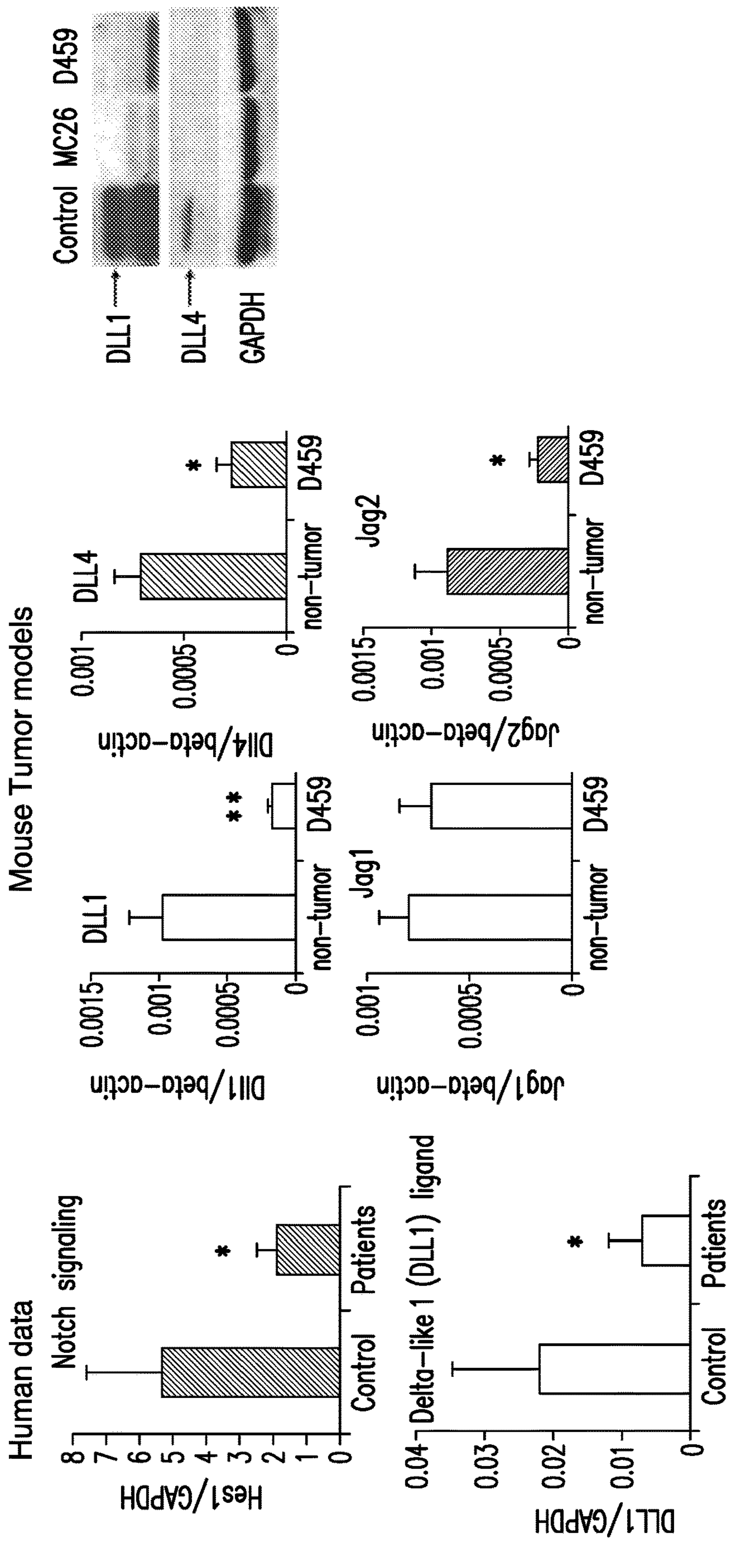
FIG. 7. Tumors alter Notch ligand expression in cancer patients and tumor-bearing animals. Left. Tumors attenuate Notch signaling in the bone marrow of cancer patients. Transcriptional levels of DLL1 and Hes1 in bone marrow of lung cancer patients and tumor-free donors were determined by quantitative RT-PCR (*, P<0.05, n=9 patients and 10 control individuals). Center. Quantitative RT-PCR analysis of Notch ligands in bone marrow cells from D459 fibrosarcoma tumor-bearing mice or non-tumor-bearing mice. Data were expressed as a relative ratio of target gene mRNA to housekeeping gene (b-actin) mRNA (*, P<0.05; **, P<0.01, 3 independent experiments). Data are Mean±SEM. Right. Expression of DLL1 and DLL4 in splenocytes of mice bearing colon sarcoma MC26 or D459 tumor or non-tumor-bearing mice (Control) assessed by Western blot.

As shown in FIG. 7, Notch ligand expression in hematopoietic compartment is altered in both cancer patients and tumor-bearing animals. Transcriptional levels of DLL1 and Hes1 in bone marrow of lung cancer patients and tumor-free individuals were determined by quantitative RT-PCR (*, $P<0.05$, n=9 patients and 10 control individuals) (Left panel). Levels of both DLL1 and Hes1 were suppressed. Similarly, RT-PCR analysis of Notch ligands in bone marrow cells from D459 fibrosarcoma tumor-bearing mice or non-tumor-bearing mice demonstrated a reduction in DLL1, DLL4 and Jag2 Notch ligands, whereas expression of Jag1 implicated in the induction of regulatory T cells (Treg) was not. Data were expressed as a relative ratio of target gene mRNA to housekeeping gene (b-actin) mRNA (*, $P<0.05$; **, $P<0.01$, 3 independent experiments). Expression of DLL1 and DLL4 in splenocytes of mice bearing colon sarcoma MC26 or D459 tumor or non-tumor-bearing mice (Control) assessed by Western blot also demonstrated a significant reduction in DLL1 and DLL4 in the tumor cells.

Figure 8:
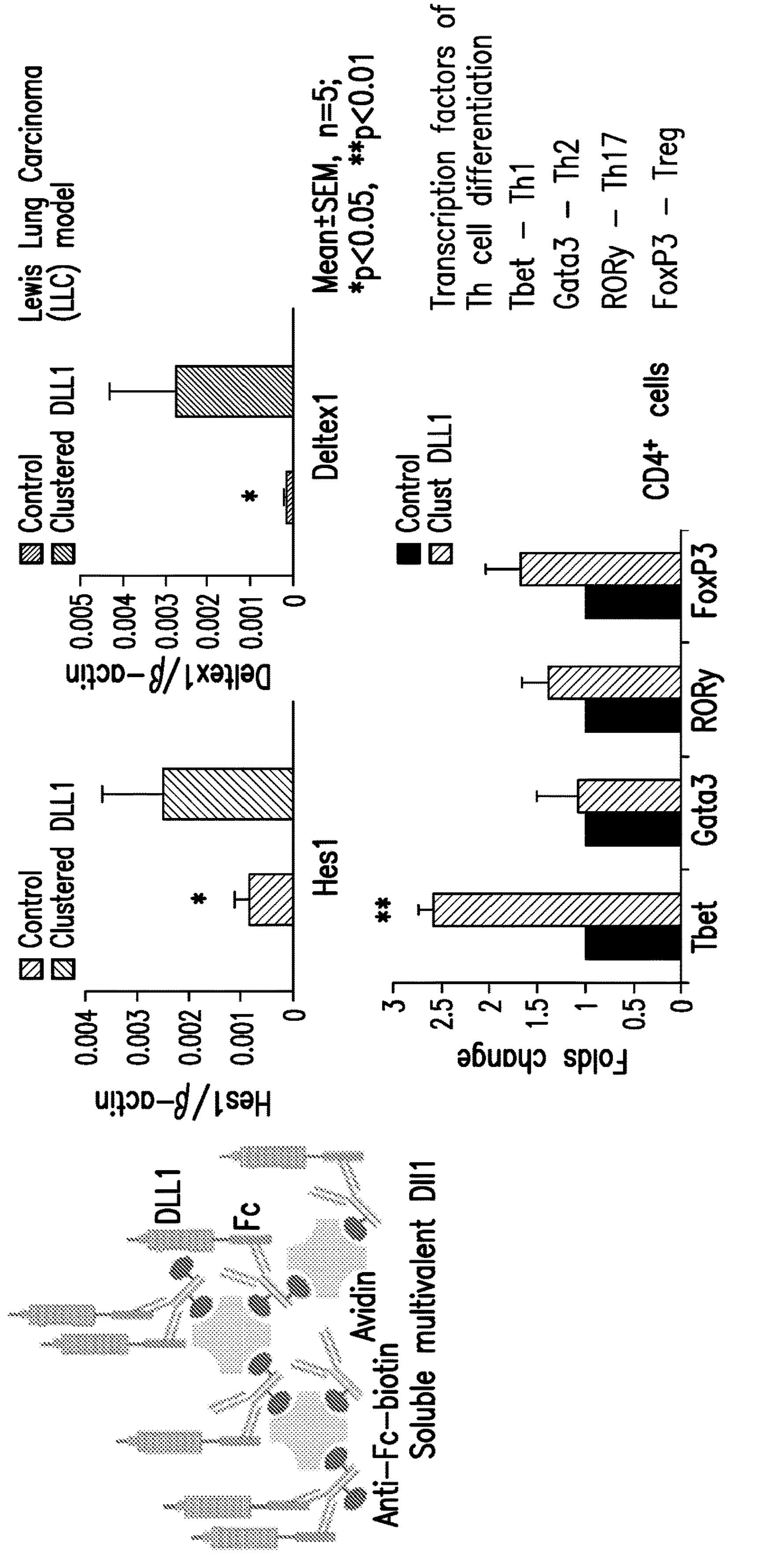
FIG. 8. Multivalent (clustered) DLL1 activates Notch and induces factors promoting Th1 type differentiation of T cells. Left. Scheme shows multivalent DLL1 complex consisting of DLL1-Fc, anti-Fc antibody and avidin capable to efficiently activate Notch signaling in vitro. Right. Treatment with soluble clustered DLL1 stimulates Notch signaling in bone marrow cells and improves T-cell immune response. Soluble clustered DLL1 treatment stimulates Notch signaling in bone marrow cells (*, P<0.05, n=5 mice per group). Data are Mean±SEM. Bottom. Expression of transcription factors regulating T cell differentiation assessed by qRT-PCR. Gene expression was evaluated in splenic $CD4^+$ cells; expressed as fold increase in clustered DLL1-treated mice over control clusters group. (**, P<0.01, n=5-7 mice per group). In both cases, mice bearing s. c. Lewis Lung Carcinoma (LLC) tumor were treated with clustered DLL1 or control clusters i.p. every 2 days for 10 days starting on day 3 after tumor inoculation. Mouse or human DLL1-Fc fusion protein is composed of the extracellular domain of mouse or human DLL1 and the Fc part of mouse IgG2A or human IgG1, respectively. To form DLL1 clusters, DLL1-Fc, biotinylated anti-IgG antibodies, and NeutrAvidin (Pierce, Rockford, Ill.) were mixed at a molar ratio of 1:4:10 in PBS, as described earlier. As a control in all applications, Fc fragment of mouse IgG2 (Sigma-Aldrich, St. Louis, Mo.) was used instead of DLL1-Fc. Mouse DLL1-Fc and biotinylated donkey anti-mouse IgG antibodies were from R&D Systems (Minneapolis, Minn.); human DLL1-Fc and biotinylated goat anti-human IgG antibodies—from Enzo Life Sciences, Inc. (Farmingdale, N.Y.). Tumor-bearing mice received clustered DLL1 at doses of 0.15 μg/kg (4 μg per injection) of DLL1-Fc protein in 100 μl of PBS intraperitoneally (i.p.) every other day. The control group received control clusters with Fc fragments instead of DLL1-Fc protein. Twice higher doses of clustered DLL1 were used in some experiments with similar results suggesting dose saturation of the clustered DLL1 effects.

As shown in FIG. 8, multivalent (clustered) DLL1 activates Notch and induces factors promoting Th1 type differentiation of T cells. Soluble multivalent DLL1 complex consisting of DLL1-Fc, anti-Fc antibody and avidin (clustered DLL1) efficiently activated Notch signaling (increase in Hes1 compared to control) in vitro. Similarly, in vivo treatment with soluble clustered DLL1 stimulates Notch signaling in bone marrow cells and improves T-cell immune response. This associated with the significant attenuation of tumor growth. Mice bearing s. c. D459 fibrosarcoma tumor were treated with clustered DLL1 or control clusters i.p. every 2 days for 10 days starting on day 3 after tumor inoculation). Tumor-bearing mice received clustered DLL1 at doses of 0.15 μg/kg (4 μg per injection) of DLL1-Fc protein in 100 μl of PBS intraperitoneally (i.p.) every other day. The control group received control clusters with Fc fragments instead of DLL1-Fc protein. Twice higher doses of clustered DLL1 were used in some experiments with similar results suggesting dose saturation of the clustered DLL1 effects. Soluble clustered DLL1 treatment stimulates Notch signaling in bone marrow cells (*, $P<0.05$, n=5 mice per group; mean±SEM). Expression of transcription factors regulating T cell differentiation was assessed by qRT-PCR. Gene expression was evaluated in splenic $CD4^+$ cells; expressed as fold increase in clustered DLL1-treated mice over control clusters group. Clustered DLL1 resulted in a 2-fold increase in Tbet, a factor associated with T cell differentiation to the Th1 phenotype (**, $P<0.01$, n=5-7 mice per group).

Figure 9:
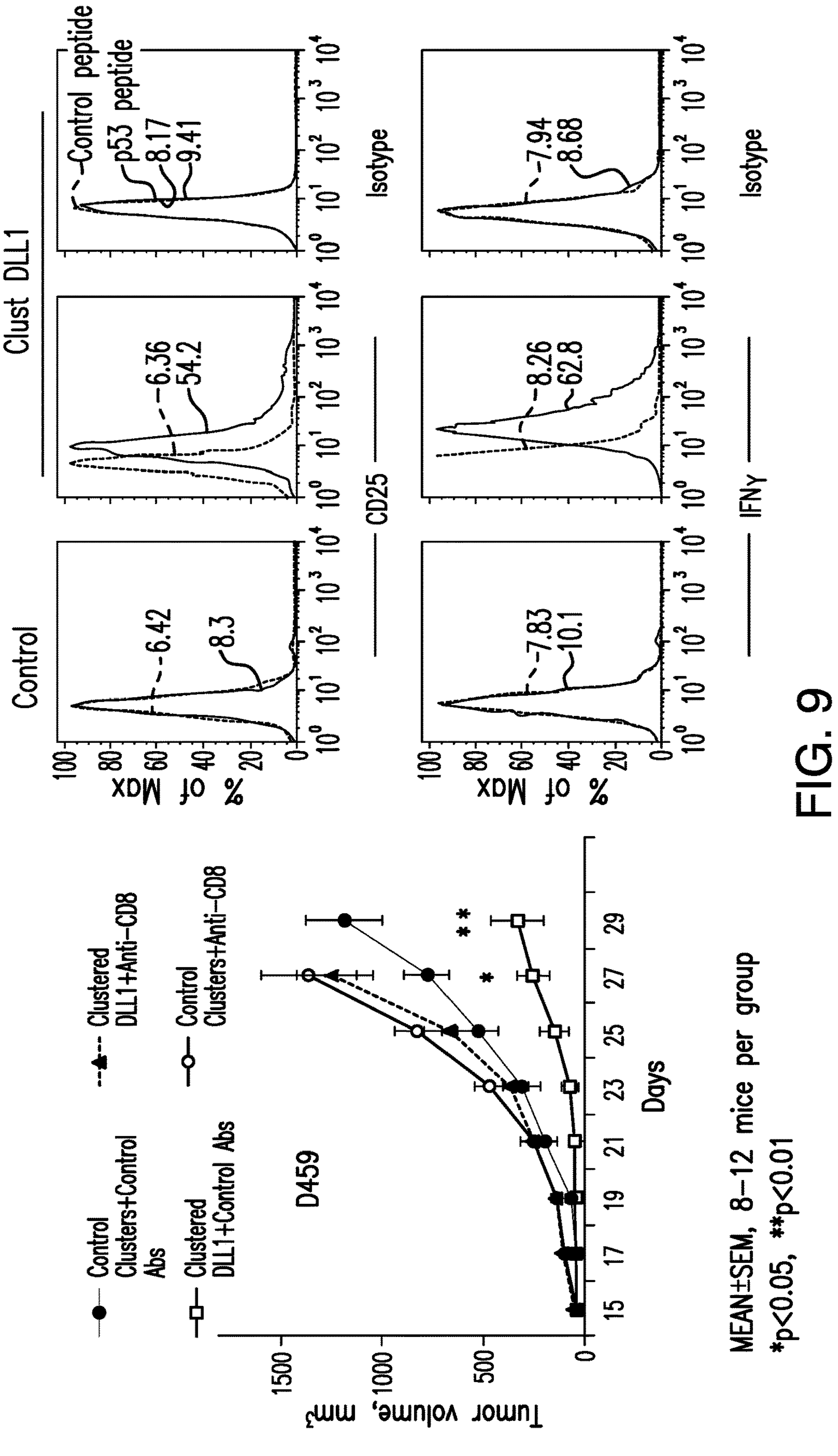
FIG. 9. Soluble clustered DLL1 significantly inhibits tumor growth in vivo in a T-cell-dependent manner and improves tumor antigen specific immune responses. Left. Tumor growth in clustered DLL1 treated or control mice without or with blockage of $CD8^+$ T cells by anti-CD8 antibody. Mice were inoculated s.c. with D459 cells. Treatment with clustered DLL1 at dose of 5 μg of DLL1-Fc protein i.p. every other day started on day 5 after tumor inoculation. Mice received non-specific IgG or anti-CD8 blocking antibody a day prior to tumor inoculation. Note that tumor inhibitory effect of clustered DLL1 is lost in mice that received anti-CD8 antibody. (**, P<0.01, n=8-12 mice per group). Data are mean±SEM. Right. Surface expression of activation marker CD25 and intracellular staining for IFN-γ in cultures of splenic CD8+ T cell isolated from the mice above on day 21 following re-stimulation in vitro with p53 D459 tumor antigenic or control peptide for 60 hrs. Numbers—MFI for control (blue) and cognate (red) peptide-stimulated cells. Representative histograms of total 4. D459 cells have a defined mutant p53 antigenic peptide (FYQLAKTCPVQL, aa 128-139; SEQ ID NO:157). Induction of antigen-specific responses in this model was characterized by evaluation of IFN-γ-producing T cells, as follows: splenocytes or LN cells from D459 tumor-bearing mice treated with clustered DLL1 or control clusters were stimulated with 10 μM of mutant p53 or control peptide for 60 hrs; IFN-γ intracellular staining was performed using Mouse Intracellular Cytokine Staining Kit (BD Pharmingen, San Jose, Calif.) according to manufacturer's recommendations. Data were acquired with FACSCalibur flow cytometer (BD Immunocytometry Systems, Franklin Lakes, N.J.). Gates were set on $CD8^+$ or $CD8^+CD44^+CD62L^+$ cells.

As shown in FIG. 9, soluble clustered DLL1 significantly inhibits tumor growth in vivo in a T-cell-dependent manner and improves tumor antigen specific immune responses. Mice were inoculated subcutaneously (s.c.) with D459 cells. Treatment with clustered DLL1 at dose of 5 μg of DLL1-Fc protein i.p. every other day started on day 5 after tumor inoculation. Mice received non-specific IgG or anti-CD8 blocking antibody a day prior to tumor inoculation. Clustered DLL1 resulted in a significant inhibitory effect on tumor growth. This tumor inhibitory effect was lost in mice that received anti-CD8 antibody. Surface expression of activation marker CD25 and intracellular staining for IFN-γ in cultures of splenic CD8+ T cells isolated from the mice was determined on day 21 following re-stimulation in vitro with p53 D459 tumor antigenic or control peptide (10 μM of mutant p53 or control peptide) for 60 hrs. Significantly higher levels of T cell activation marker CD25 and intracellular IFN-γ production were observed in the splenic and lymph node CD8+ T cells following re-challenge with D459 tumor antigenic mutant p53 peptide.

Figure 10:
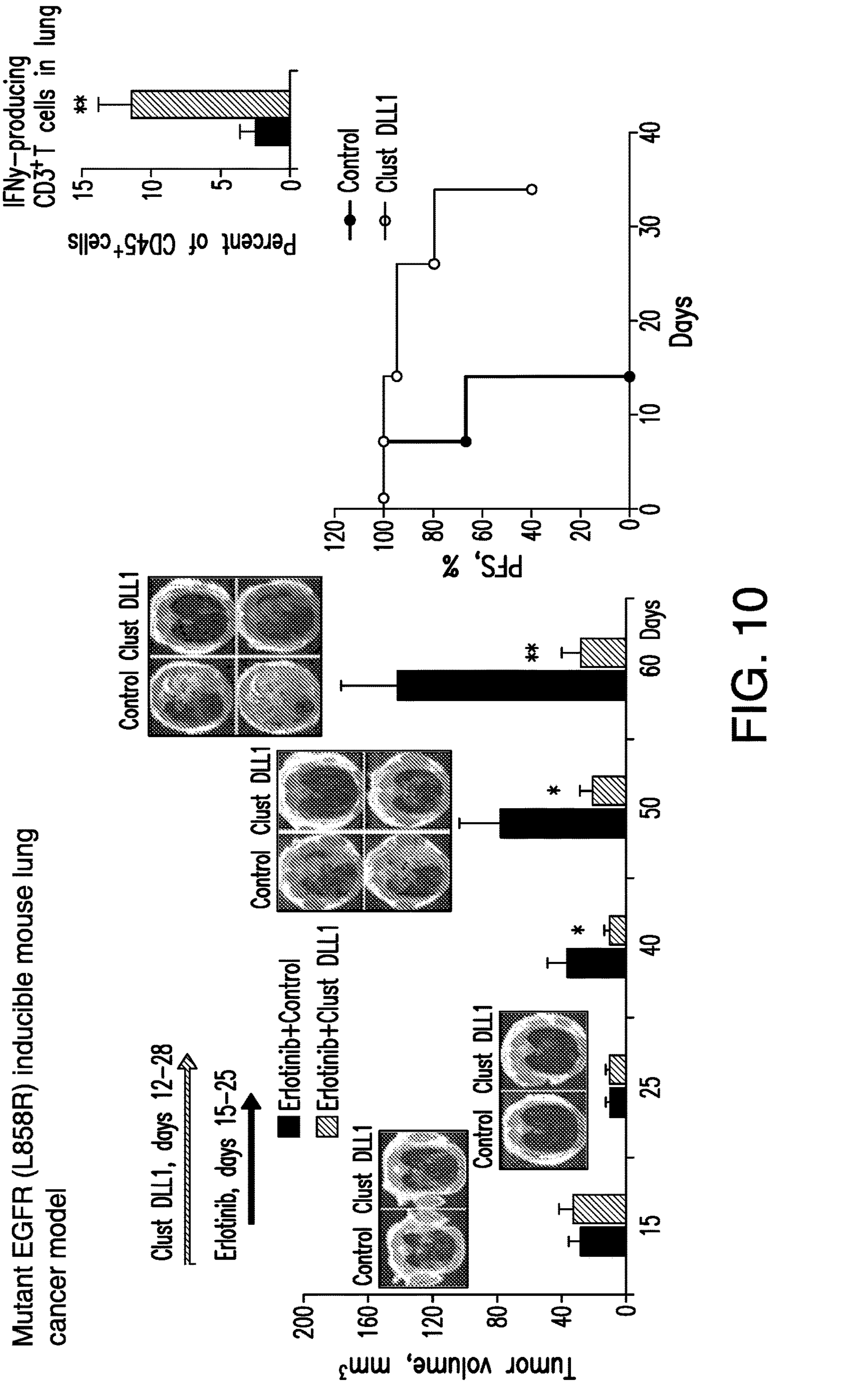
FIG. 10. Multivalent DLL1 significantly improves progression-free survival in combination with EGFR oncogene-targeted treatment in the EGFRL858R transgenic model. Transgenic EGFRL858R mice with induced lung tumors were treated with erlotinib in combination with clustered DLL1 or control clusters, as shown in (Left). Left. Lung tumor (white opacities) growth was evaluated by MRI and volume quantified. (Inserts) Representative MRI images at the corresponding time points. Center. Progression-free survival; recurrence was determined when tumor volume exceeded by 30% residual tumor volume after erlotinib treatment. Mean±SEM, 8 mice per group, *, P<0.05, , P<0.01. Right. Clustered DLL1 resulted in significant increase in the numbers of INFγ-producing cells infiltrating diseased lungs. Numbers of INFγ-producing cells in ling single cell suspension from the mice above were evaluated by intracellular cytokine staining within $CD3^+$ cell population. Mean±SEM, 8 mice per group, , P<0.01. In mutant EGFR inducible tumor model, mice were treated with clustered DLL1 or control clusters, as above, from day 12 to 28 after tumor induction by doxycycline, whereas erlotinib was given during days 15 to 25 daily at a dose of 50 mg/kg, i.p., as previously described (24).

As shown in FIG. 10, soluble, clustered (multivalent) DLL1 significantly improves progression-free survival in combination with EGFR oncogene-targeted treatment in the transgenic mouse model expressing human mutant EGF receptor EGFRL858R in lung epithelium. Transgenic EGFRL858R mice with induced lung tumors were treated with erlotinib in combination with clustered DLL1 or control clusters. In this mutant EGFR inducible tumor model, mice were treated with clustered DLL1 or control clusters, from day 12 to 28 after tumor induction by doxycycline, whereas erlotinib was given during days 15 to 25 daily at a dose of 50 mg/kg, i.p. Clustered DLL1 resulted in significant increase in the numbers of INFγ-producing cells infiltrating diseased lungs.

Figure 11:
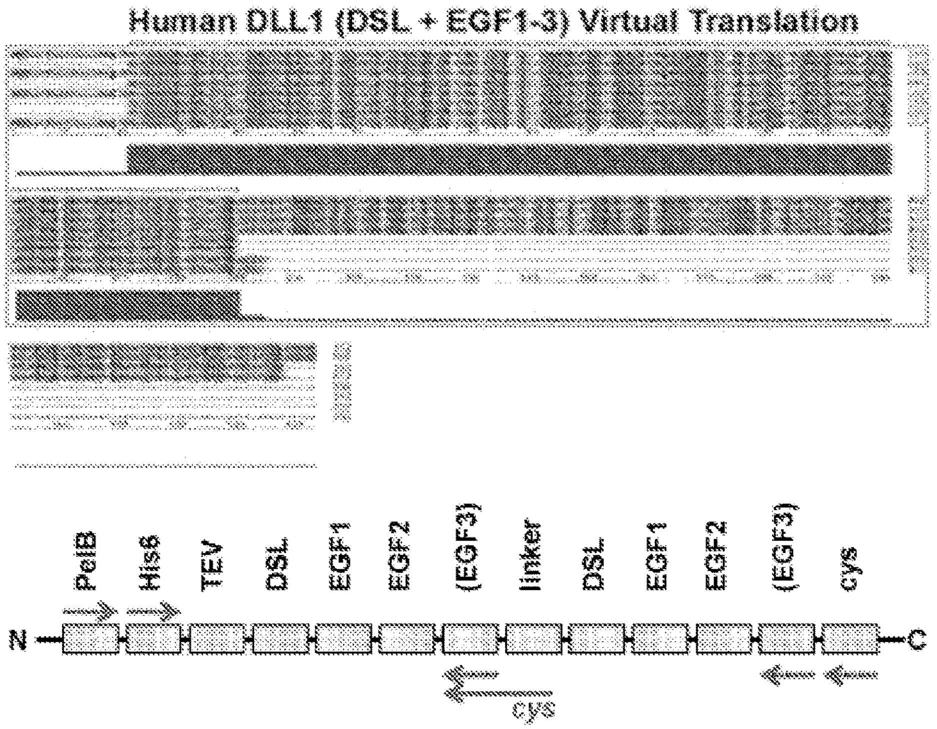
FIG. 11. Gene and primer design of DLL1 fragment monomers. Translated DNA sequences after virtual PCR shows various DLL1 ligand fragments with and without features including: PelB leader sequence, C-terminal cysteine, and tandem repeat. Virtual translations were performed for Human DLL1 [DSL+EGF1-2], Human DLL1 [DSL+EGF1-3] (top), Mouse DLL1 [DSL+EGF1-2], Mouse DLL1 [DSL+EGF1-3]. Primer annealing sites are shown (bottom) in relations to these various features and domains.

As shown in FIG. 11, the gene and primer design of DLL1 fragment monomers was investigated. Translated DNA sequences after virtual PCR shows various DLL1 ligand fragments with and without features including: PelB leader sequence, C-terminal cysteine, and tandem repeat. Virtual translations were performed for Human DLL1 [DSL+EGF1-2], Human DLL1 [DSL+EGF1-3] (top), Mouse DLL1 [DSL+EGF1-2], Mouse DLL1 [DSL+EGF1-3]. Primer annealing sites are shown (bottom) in relations to these various features and domains.

Figure 12:
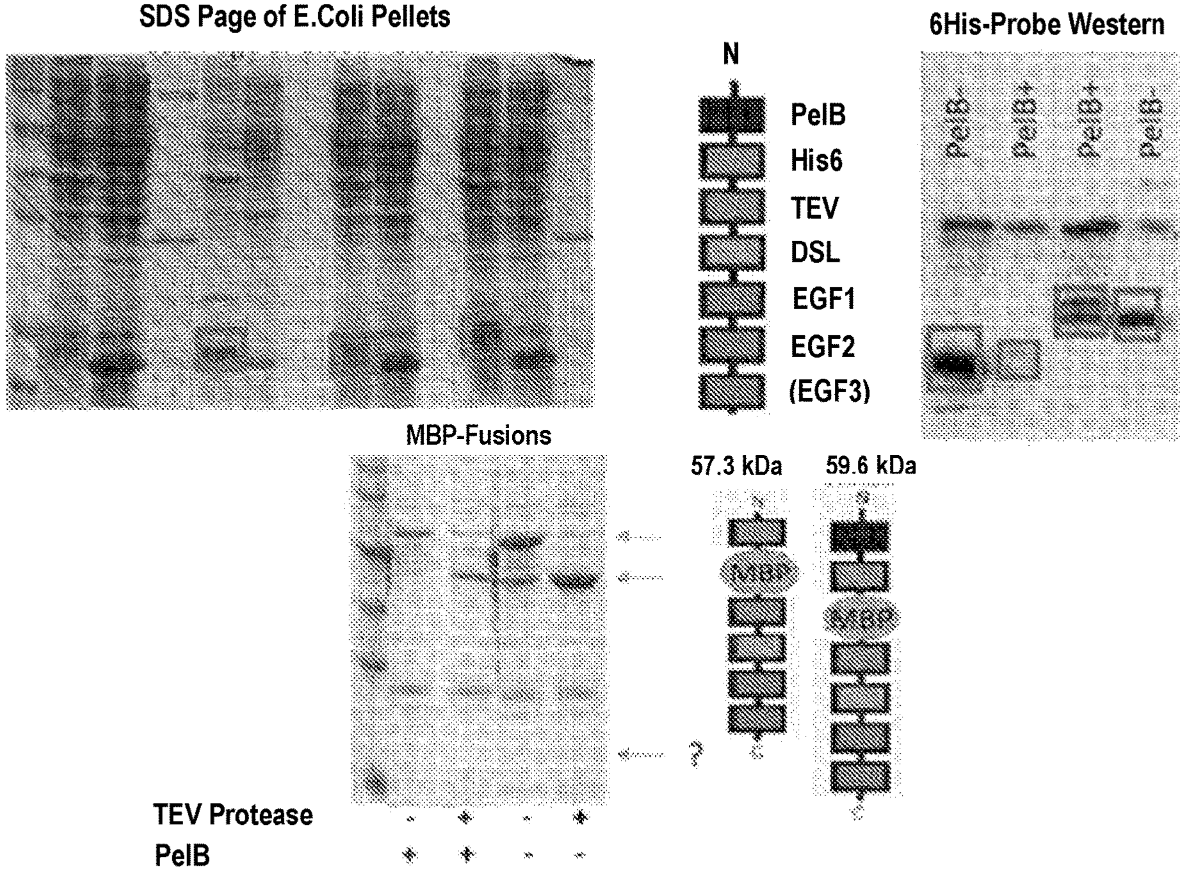
FIG. 12. Insoluble expression of DLL1 ligand fragments. (Top left) SDS-PAGE gel showing DLL1 ligands in the insoluble fraction. This was validated by His-Probe western blot that confirmed these areas of the gel were His-tagged DLL1 ligand (top right). Periplasmic expression by the inclusion of an N-terminal PelB leader sequence does not have any apparent effect on solubility. N-terminal maltose binding protein (MBP) fusions prevent inclusion body formation of DLL1 ligand but does not yield well folded protein and is insoluble after TEV cleavage from the MBP tag (bottom).

As shown in FIG. 12, the insoluble expression of DLL1 ligand fragments was investigated. SDS-PAGE gel showing DLL1 ligands in the insoluble fraction (Top left panel). This was validated by His-Probe western blot that confirmed these areas of the gel were His-tagged DLL1 ligand (top right panel). Periplasmic expression by the inclusion of an N-terminal PelB leader sequence does not have any apparent effect on solubility. N-terminal maltose binding protein (MBP) fusions prevent inclusion body formation of DLL1 ligand but does not yield well folded protein and is insoluble after TEV cleavage from the MBP tag (bottom panel).

Figure 13:
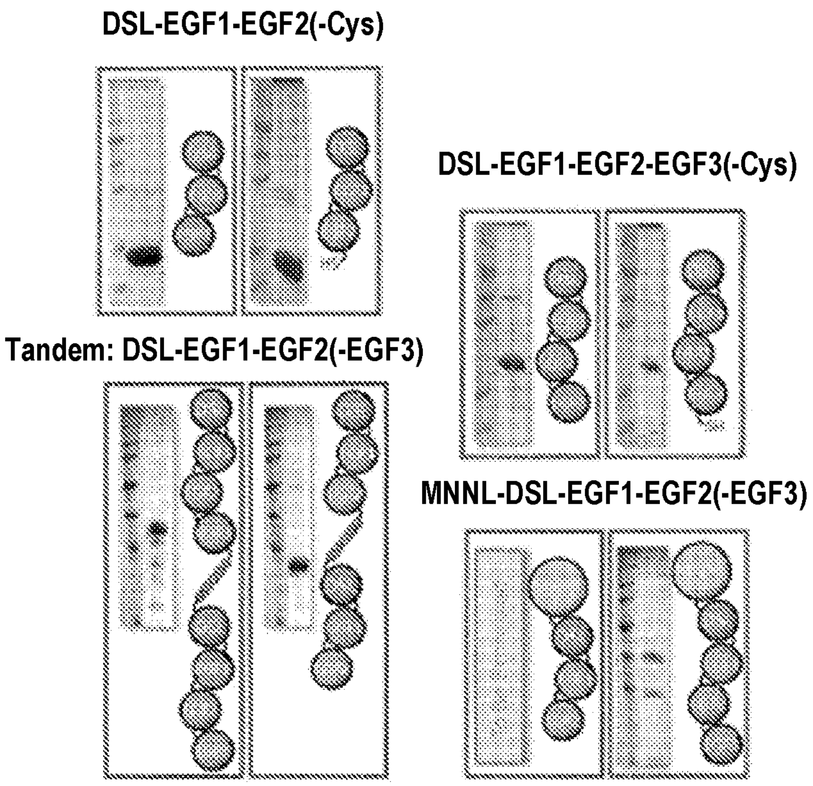
FIG. 13. SDS-PAGE and cartoon schematic of first generation soluble DLL1 constructs. On column refolding of insoluble cell lysate yielded soluble DLL1 ligands. These include DSL-EGF1-2(-Cys), DSL-EGF1-3(-Cys), Tandem DSL-EGF1-2(-3), and MNNL-DSL-EGF1-3.

As shown in FIG. 13, first generation soluble DLL1 constructs were developed. On column refolding of insoluble cell lysate yielded soluble DLL1 ligands. These include DSL-EGF1-2(-Cys), DSL-EGF1-3(-Cys), Tandem DSL-EGF1-2(-3), and MNNL-DSL-EGF1-3.

Figure 14:
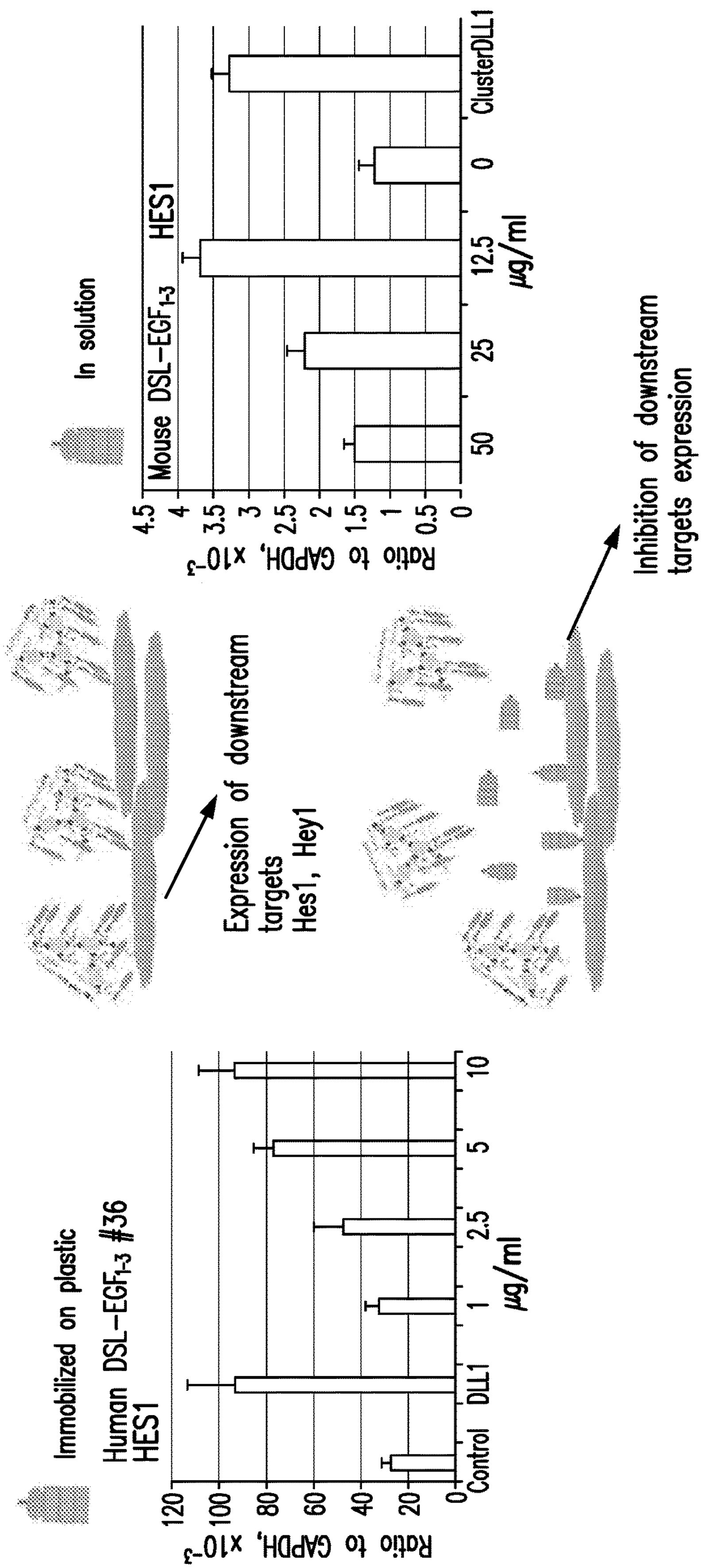
FIG. 14. Cell-based assay results with monomer fragments: Inhibition of Notch activation by soluble DLL1 peptide. Human H460 lung tumor cells expressing NOTCH or mouse 3T3-L1 cells were incubated with human or mouse clustered DLL1, respectively, for 16 hrs. Increasing concentrations of human or mouse DLL1 monovalent constructs were added to the cultures at the same time to compete with Notch activation by clustered DLL1. Downstream target Hes1 mRNA expression was assessed by qRT-PCR. Activation of Notch is decreased by monovalent DLL1 constructs in dose-dependent manner.

As shown in FIG. 14, DLL1 protein constructs comprising Notch binding domains activate Notch signaling in multimeric form while they inhibit signaling in monomeric form. Human H460 lung tumor cells expressing NOTCH or mouse 3T3-L1 cells were incubated with human or mouse clustered DLL1, respectively, for 16 hrs. Increasing concentrations of human or mouse DLL1 monovalent constructs were added to the cultures at the same time to compete with Notch activation by clustered DLL1. Downstream target Hes1 mRNA expression was assessed by qRT-PCR. Monovalent human DLL1 construct #36 comprising DSL and EGF repeats 1-3 inhibits clustered DLL1-mediated Notch activation in human H460 epithelial cells. Mouse monovalent DSL-EGF1-3 also decreased notch activation in a dose-dependent manner.

Figure 15:
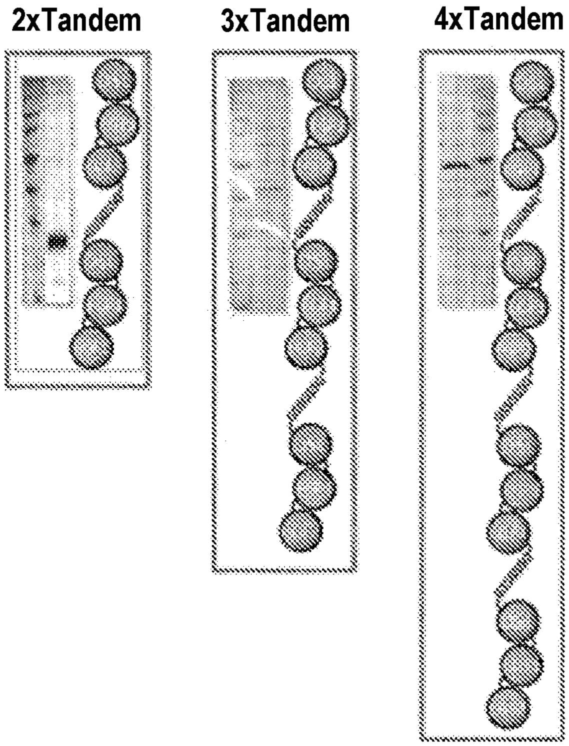
FIG. 15. SDS-PAGE and cartoon schematic of second generation soluble tandem DLL1 constructs. On column refolding of insoluble cell lysate yielded soluble DLL1 ligands with 2-4× tandem repeats. These include DLL1 Tandem 2× (also shown in FIG. 13), DLL1 Tandem 3×, and DLL1 Tandem 4×.

As shown in FIG. 15, second generation soluble tandem DLL1 constructs were developed. On column refolding of insoluble cell lysate yielded soluble DLL1 ligands with 2-4× tandem repeats. These include DLL1 Tandem 2× (also shown in FIG. 13), DLL1 Tandem 3×, and DLL1 Tandem 4×.

Figure 16:
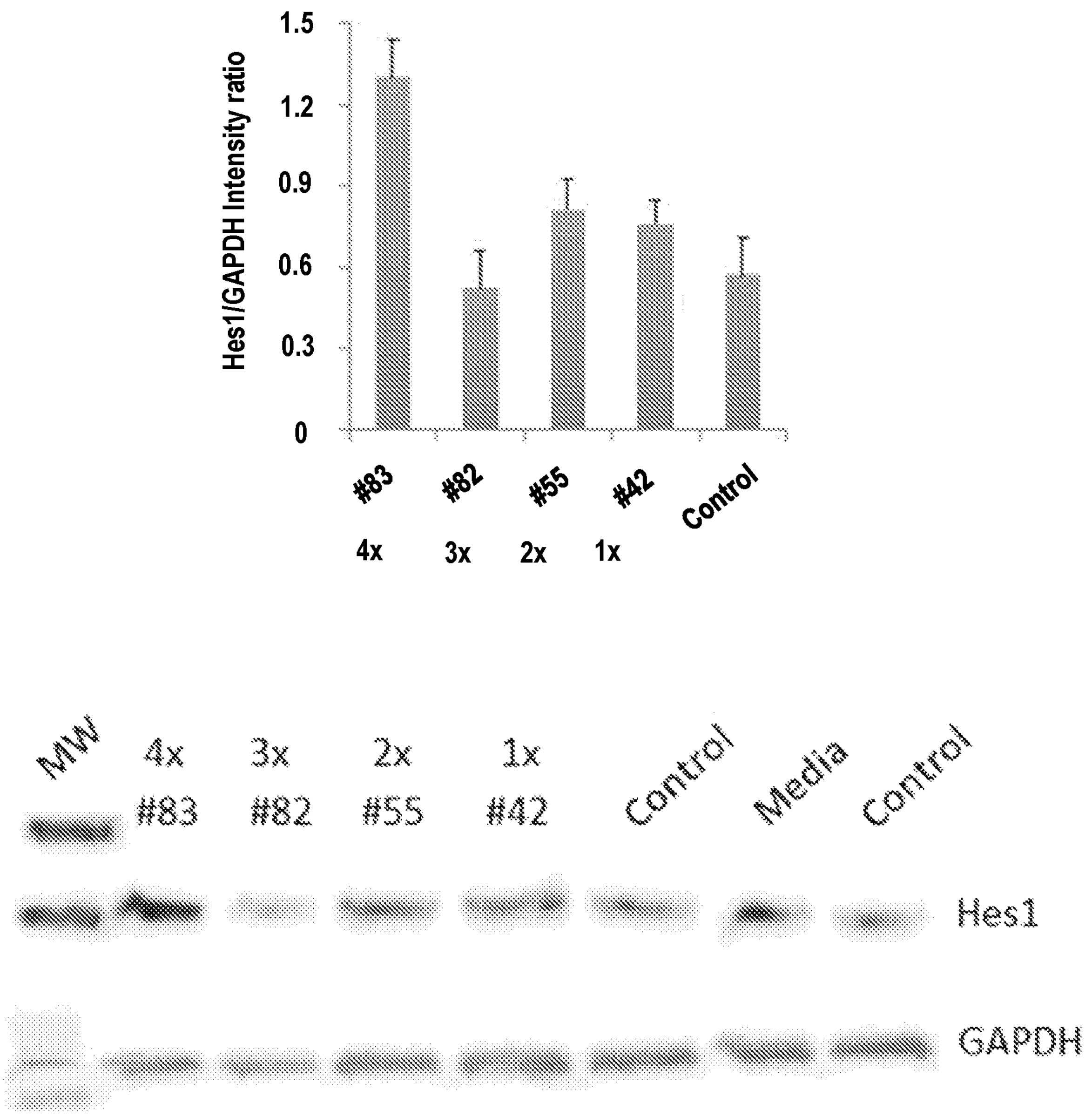
FIG. 16. DLL1 Tetramer (4×) Construct Demonstrates Enhanced Notch Activation. Mouse EL4 T cells were treated without or with DLL1 constructs at indicated concentrations for 24 hrs. Downstream target protein expression was assessed by Western blotting. The results demonstrate that four DSL-EGF12 repeats (tetramer) are required for effective Notch activation FIG. 17. DLL1 Tetramer (4×) Construct Demonstrates Enhanced Production of INFγ. Mouse splenocytes were stimulated with CD3/CD28 antibodies without or with increasing concentrations of DLL1 constructs. The number of INFγ producing cells was determined by ELISPOT (per $10^5$ cells). These results demonstrate that the 4× construct resulted in enhanced production of INFγ.

As shown in FIG. 16, the DLL1 tetramer (4×) construct demonstrates enhanced Notch activation in mouse EL4 T cell treated without or with DLL1 constructs for 24 hrs. Downstream target protein expression was assessed by Western blotting. The results demonstrate that four DSL-EGF12 repeats (tetramer) are required for effective Notch activation.

Figure 17:
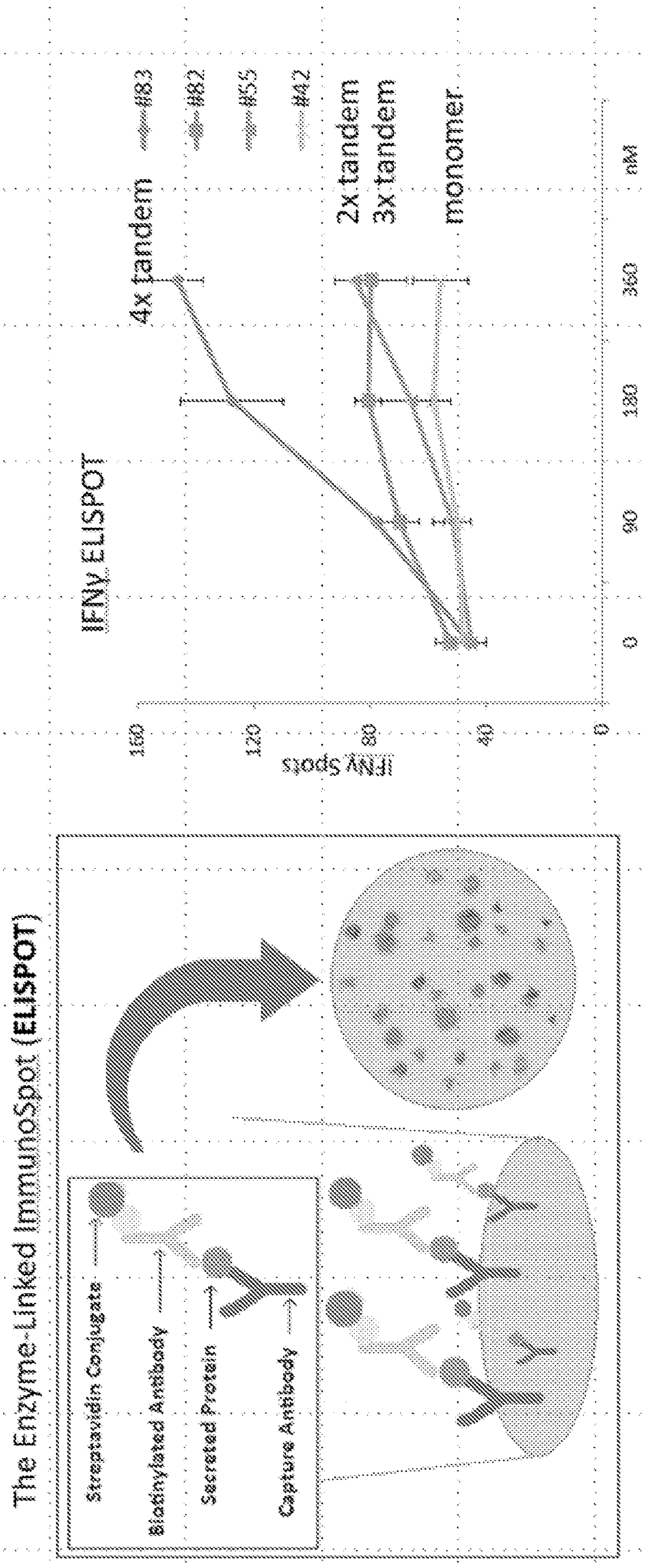

As shown in FIG. 17, the DLL1 tetramer (4×) construct not only enhanced Notch activation but also enhanced the production of INFγ in mouse splenocytes stimulated with CD3/CD28 antibodies without or with increasing concentrations of DLL1 constructs. The number of INFγ producing cells was determined by ELISPOT (per $10^5$ cells).

Figure 18:
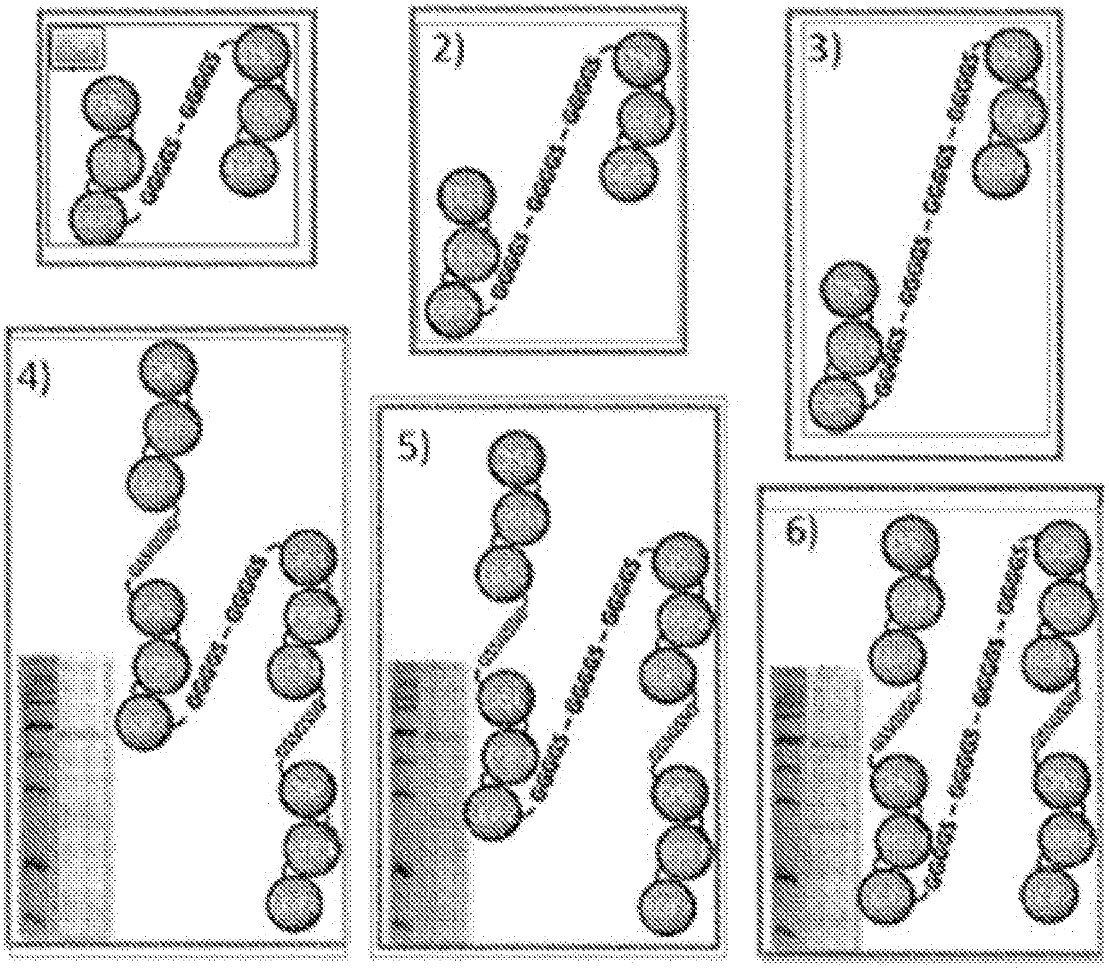
FIG. 18. SDS-PAGE and cartoon schematic of soluble tandem DLL1 linker variants. On column refolding of insoluble cell lysate yielded soluble DLL1 ligands with 2× and 4× tandem repeats. These include DLL1 Tandem 2× with $(G_4S)_2$, $(G_4S)_3$, and $(G_4S)_4$ linkers as well as DLL1 Tandem 4× with $(G_4S)_2$, $(G_4S)_3$, and $(G_4S)_4$ linkers.

As shown in FIG. 18, soluble tandem DLL1 linker variants were investigated. On column refolding of insoluble cell lysate yielded soluble DLL1 ligands with 2× and 4× tandem repeats. These include DLL1 Tandem 2× with $(G_4S)_2$, $(G_4S)_3$, and $(G_4S)_4$ linkers as well as DLL1 Tandem 4× with $(G_4S)_2$, $(G_4S)_3$, and $(G_4S)_4$ linkers.

Figure 19:
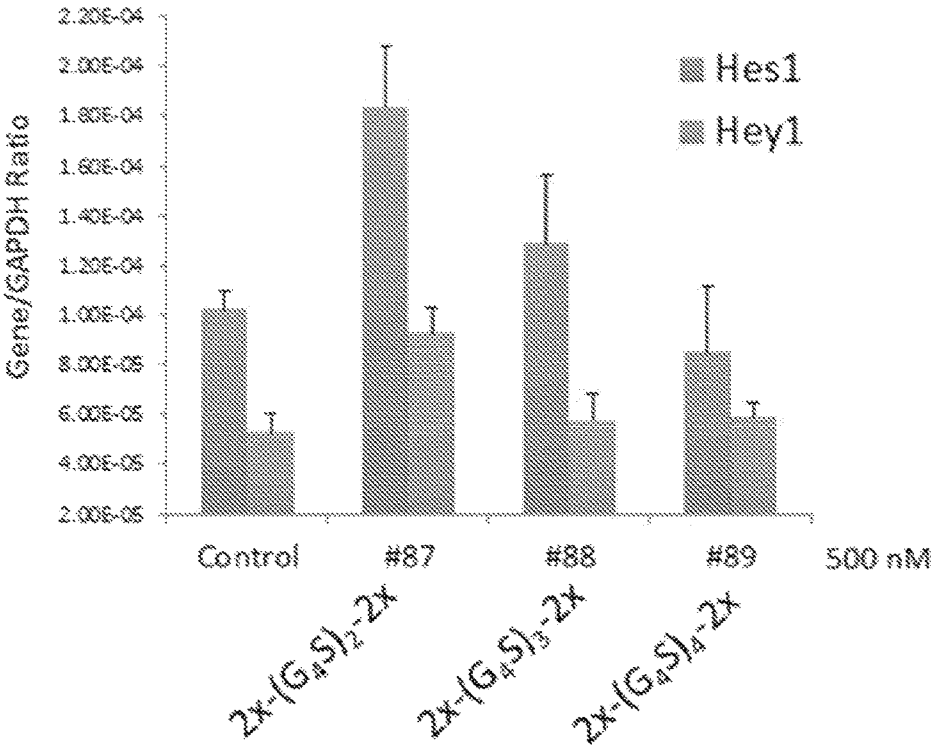
FIG. 19. Short Linker Tetramer (4×) Constructs Activate Notch Most Strongly Than Longer Linkers. Mouse EL4 T cells were treated without or with DLL1 constructs at indicated concentrations for 16 hrs. Downstream target Hes1 and Hey1 mRNA expression was assessed by qRT-PCR. Two different murine short linker 4× constructs (#83 and #87 shown below) resulted in more Hes1 and Hey1 activation that the longer linkers.

As shown in FIG. 19, short linker tetramer (4×) constructs unexpectedly activated Notch more strongly than longer linker. Mouse EL4 T cells were treated without or with DLL1 constructs at 500 nM concentrations for 16 hrs. Downstream target Hes1 and Hey1 mRNA expression was assessed by qRT-PCR. Two different murine short linker 4× constructs (#83 and #87) resulted in more Hes1 and Hey1 activation that the longer linkers (#88 and #89).

Figure 20:
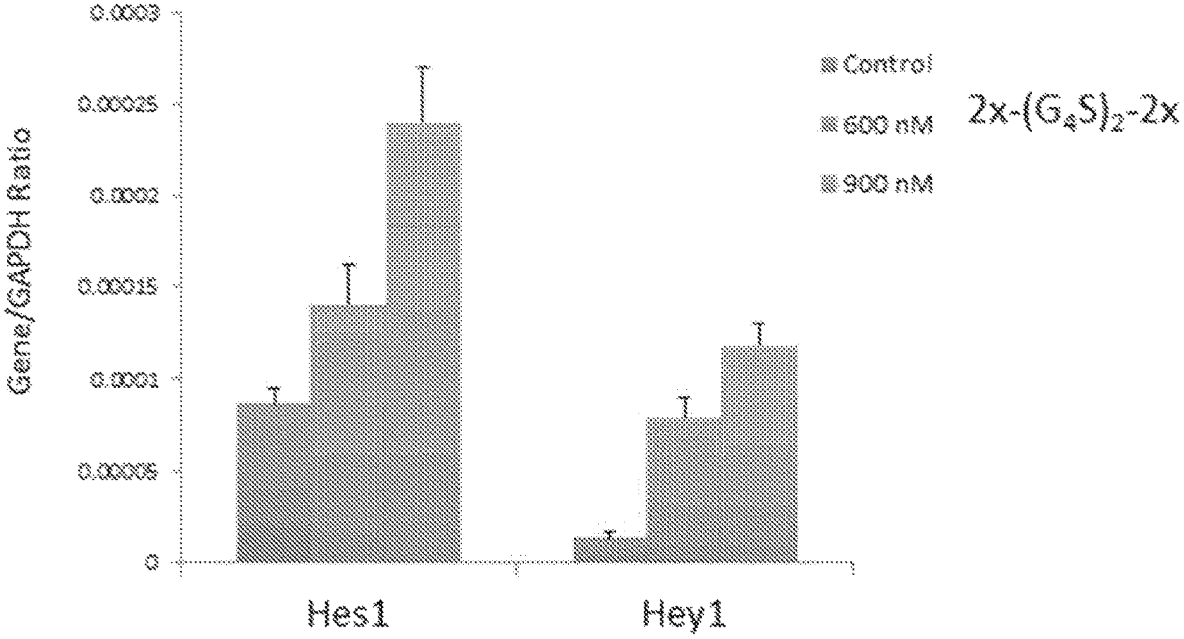
FIG. 20. Soluble DLL1 Short Linker Tetramer (4×) Construct Results in Concentration-Dependent Notch Activation. Mouse EL4 T cells were treated without or with DLL1 constructs at the indicated concentrations for 16 hrs. Downstream target Hes1 and Hey1 mRNA protein expression was assessed by qRT-PCR. Dose dependent increase of both target genes was observed. A consistent effect was observed between different batches of the construct.

As shown in FIG. 20, the soluble DLL1 short linker tetramer (4×) construct resulted in a concentration-dependent Notch activation. Mouse EL4 T cells were treated without or with the DLL1 construct at 600 and 900 nM concentrations for 16 hrs. Downstream target Hes1 and Hey1 mRNA protein expression was assessed by qRT-PCR. A dose dependent increase of both target genes was observed and a consistent effect was observed between different batches of the construct.

Figure 21:
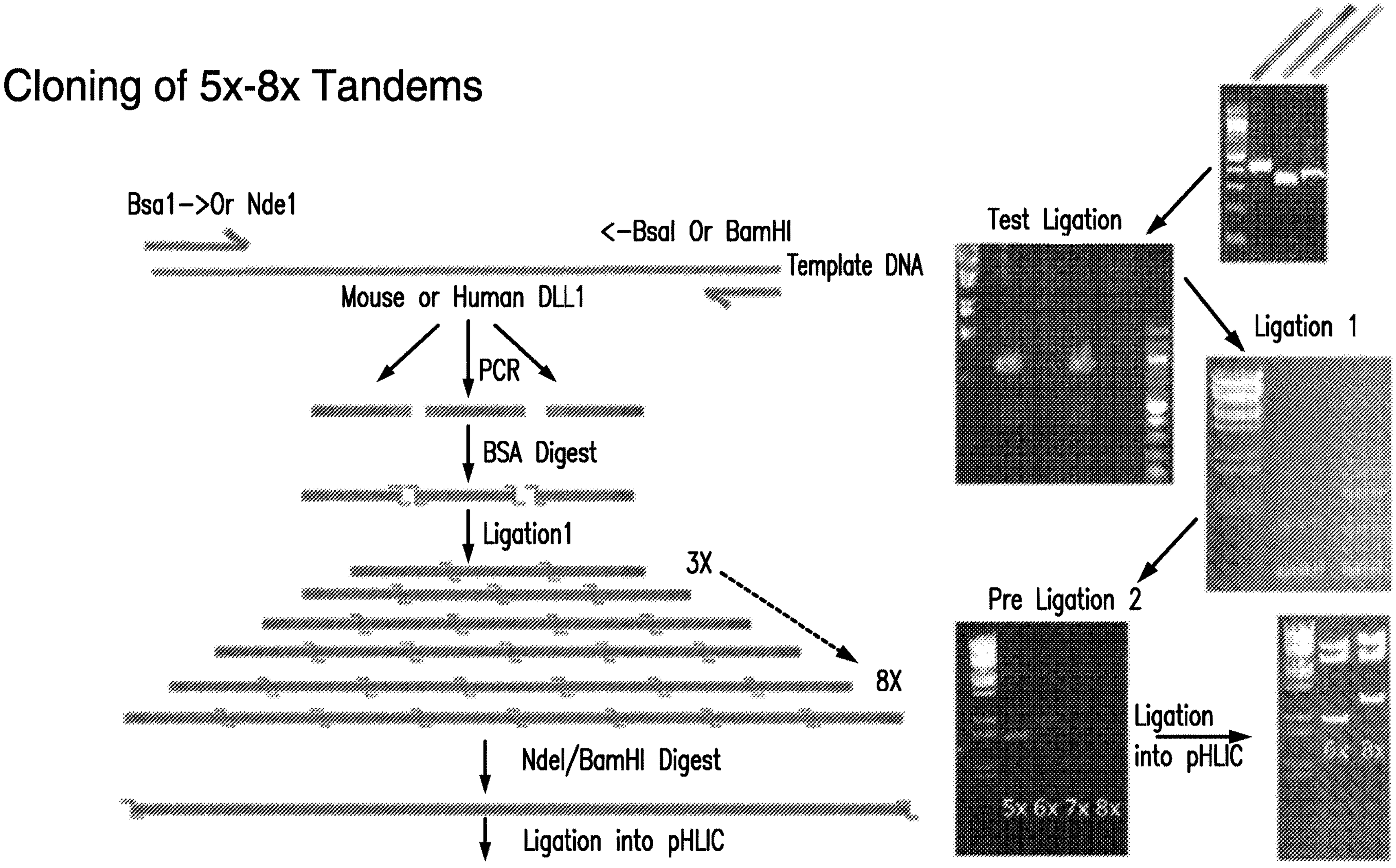
FIG. 21. Cloning scheme developed to produce larger (5-8×) tandem repeats of DLL1 ligand fragments. PCR products containing repeats of DLL1 ligands are ligated in a semi-controlled reaction and capped with NdeI and BamHI containing PCR fragments. Desired DNA lengths corresponding to proper gene size are extracted and ligated into expression vector.

As shown in FIG. 21, the cloning scheme was developed to produce larger (5-8×) tandem repeats of DLL1 ligand fragments. PCR products containing repeats of DLL1 ligands are ligated in a semi-controlled reaction and capped with NdeI and BamHI containing PCR fragments. Desired DNA lengths corresponding to proper gene size are extracted and ligated into expression vector.

Figure 22:
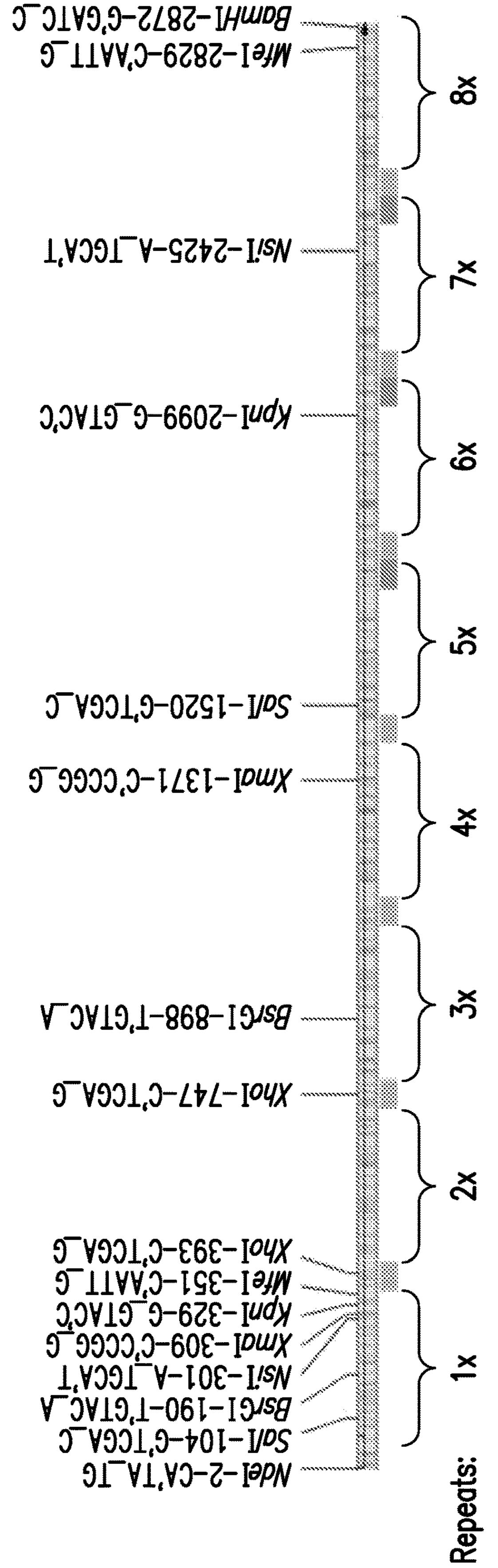
FIG. 22. Alternate construction of DLL1 repeats from a large 8× tandem repeat. Sets of restrictions sites located throughout the gene were designed to be used to create smaller fragments (i.e., 5-7× tandem repeats) from a single restriction digest and ligation reaction. Degenerate codon usage in the linker region (orange) can be used for entire gene sequencing. Degenerate codon usage in the C-terminal regions of repeats 5-7× (blue) can be used for gene alterations via PCR.

As shown in FIG. 22, tandem constructs have been made from 1× to 8×. FIG. 22 shows the schematic which includes restriction sites for easy 5×, 6×, and 7× cloning and gene manipulation.

Figure 23:
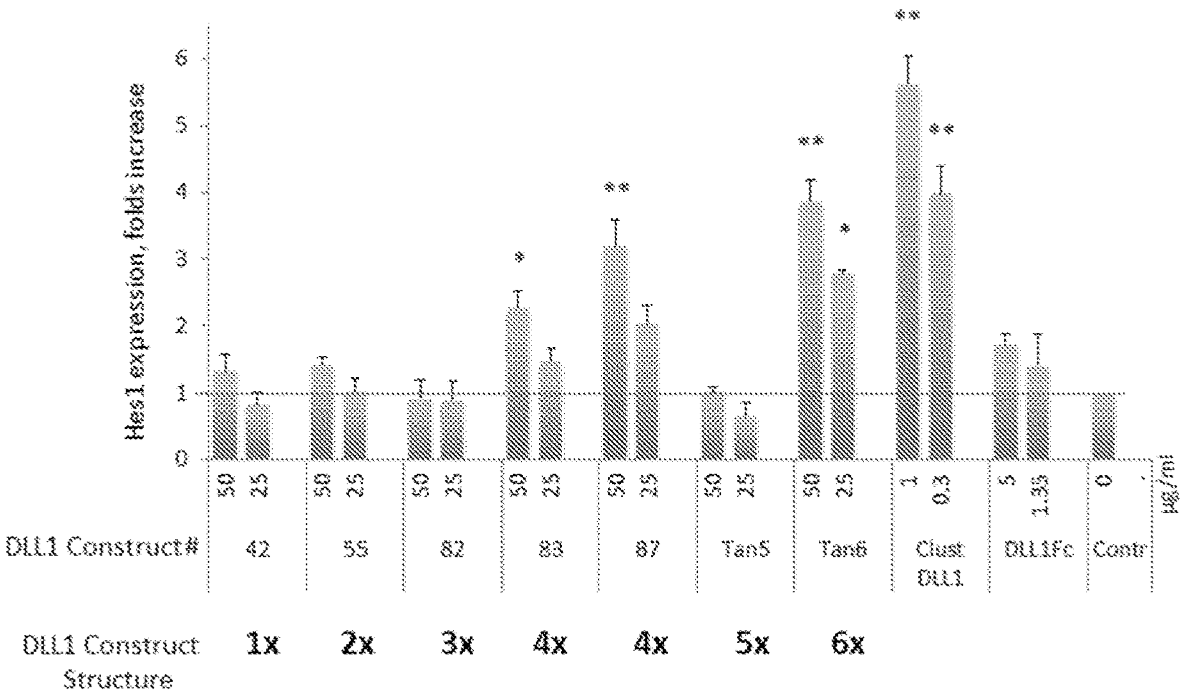
FIG. 23. Tetramer (4×) and Hexamer (6×) DLL1 Constructs Activate Notch. Mouse 3T3-L1 cells were stimulated for 6 hours with controls or with varying concentrations of different DLL1 constructs or clustered DLL1. Downstream target Hes 1 mRNA expression was assessed by qRT-PCR. These results demonstrate that the two tetramer constructs (labeled as 4× at the bottom) and hexamer construct (labeled as 6×) both resulted in significant up-regulation of Hes1 expression when compared to control or lower valency constructs. *$P<0.05$, ** $p<0.01$ FIG. 24. Tetramer (4×) and Hexamer (6×; Tan 6) DLL1 Constructs Demonstrate Concentration-Dependent Activation of Notch. Mouse 3T3 cells were stimulated for 12 hours with vehicle control or varying concentrations of tetramer and hexamer DLL1 constructs; vehicle—buffer for DLL1 constructs, PBS containing 0.5 mM DTT, 10% glycerol. Protein lysates were collected and Western blots were performed to visualize expression of the Notch downstream target Hes1. Vehicle was used as a negative control. Hes1 appears as a double band; β-actin is a loading control. These results demonstrate that the tetramer and hexamer constructs resulted in a concentration-dependent activation of Notch. Indicated amounts of the constructs were added into 1 ml of cell culture.

As shown in FIG. 23, multimeric DLL1 constructs are able to activate Notch. Longer tandem constructs (5× and 6×) were designed, expressed, purified, and tested. Mouse EL4 T cells were treated with DLL1 constructs, and assessed by qRT-PCR. The controls included vehicle (buffer) for DLL1 constructs and IgG clusters for Clustered DLL1.

Figure 24:
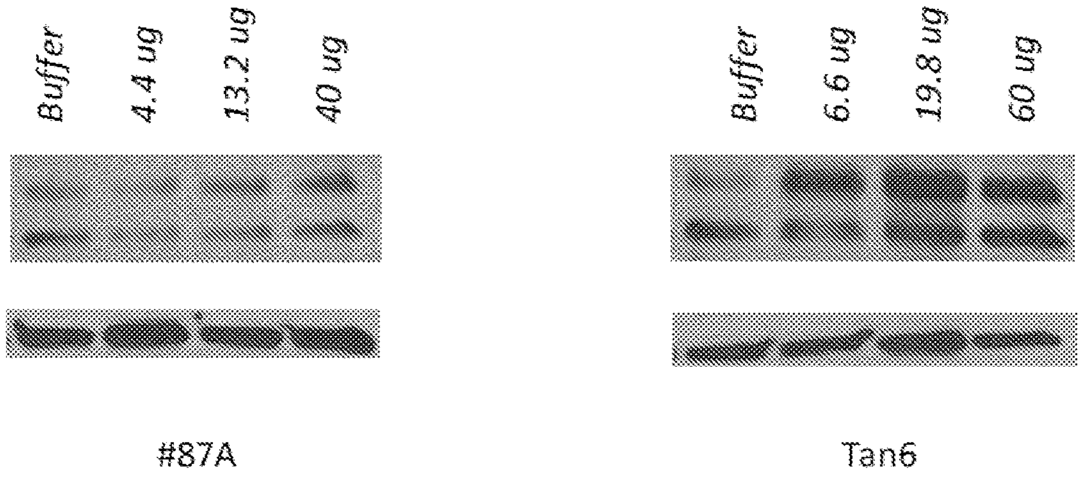

As shown in FIG. 24, 4× and 6×DLL1 constructs were compared for their ability to activate Notch. Mouse 3T3 cells were cultured in the presence of increasing amounts of DLL1 constructs for 12 hrs. Protein lysates were collected and Western blot was performed to visualize expression of Notch downstream target Hes1. Total volume of cell cultures 1 ml. Buffer (vehicle) was used for the constructs is a negative control. Hes1 appears as a double band; β-actin is a loading control. #87—4-mer with longer spacers; Tan 6—6-mer.

Figure 25:
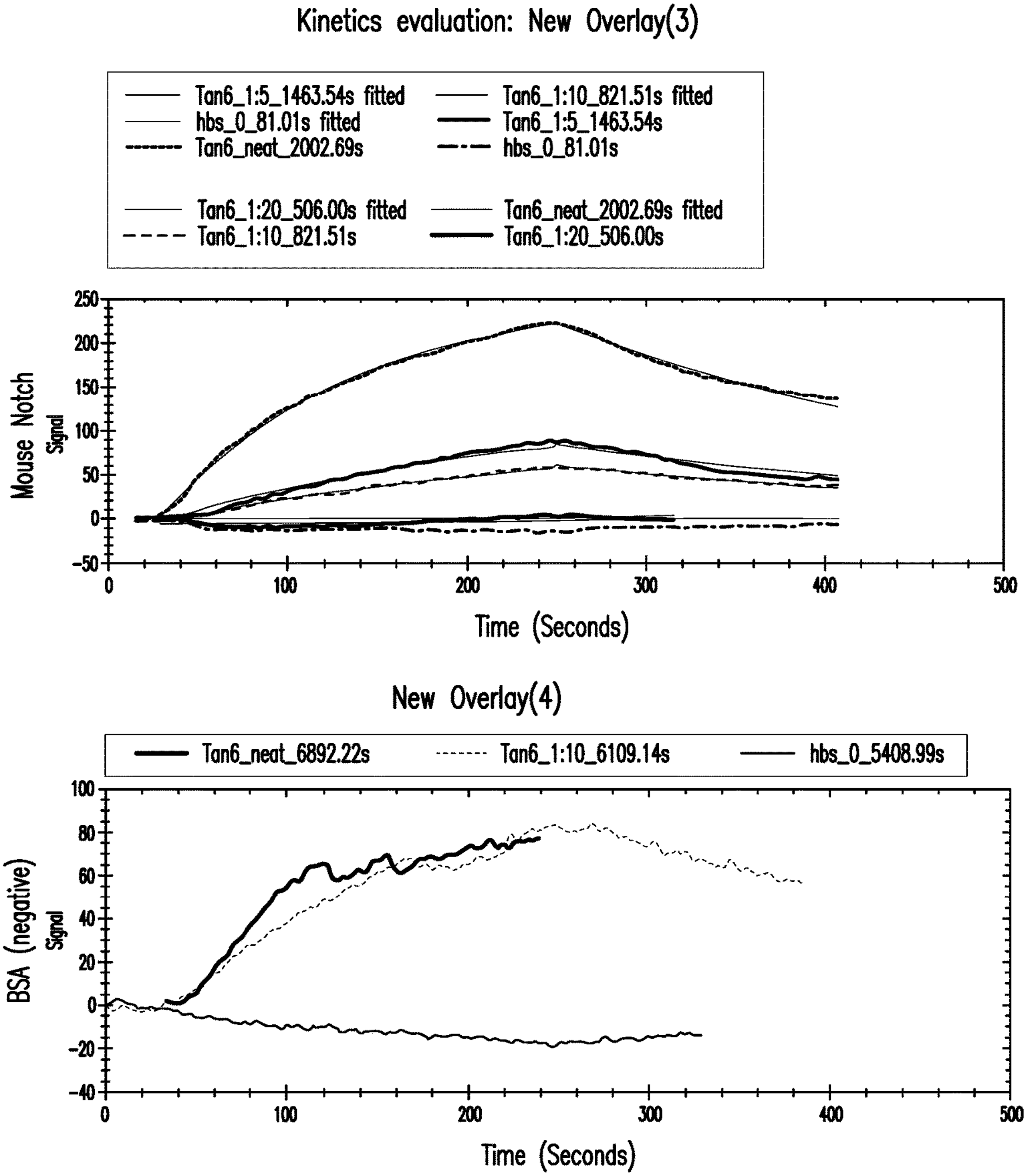
FIG. 25. Open surface plasmon resonance (SPR) binding experiments of DLL1 Tandem 6× against immobilized mouse full length notch extracellular domain (Top) and BSA negative control (bottom). DLL1 Tandem 6× was injected at concentrations of 2.2 μM, 0.45 μM, 0.22 μM, 0.11 μM, and 0 μM (HBS buffer only). Signal to noise of these binding experiments were 3 to 1.

As shown in FIG. 25, the Tan 6 construct binds to mNotch1ECD-Fc as shown by surface plasmon resonance. The top panel shows the binding and unbinding curves of the Tan 6 binding to mNotch1ECD-Fc at various concentrations of Tan 6. The apparent KD is 1.5 μM. The bottom panel shows binding of Tan 6 to BSA as a negative control. The signal:noise of binding to Notch1 versus BSA is about 3:1 at the same concentrations.

Materials and Methods

Cell Lines

Murine 3T3 and 3T3-L1 fibroblast, Lewis lung carcinoma (LLC) and EL4 lymphoma cell lines were obtained from the American Type Culture Collection; low-passage (less than 10) cultures were used for the experiments. Mouse splenocytes were obtained from spleens of C57BL/6 mice.

Evaluation of Functional Activity of DLL1 Constructs

Functional activity of DLL1 constructs was evaluated by their ability to induce Notch activation and modulate cytokine expression.

Evaluation of Notch activation. Notch activation was assessed by the expression of Notch down-stream targets Hes1 and Hey1 using quantitative real time PCR (qRT-PCR) and Western blot and accumulation of intracellular domain of Notch (ICD) by Western blot.

3T3 or LLC cells were plated at 0.5-2×$10^6$ per well in 12- or 6-well RNA, EL4 cells were seeded at 2-4×$10^6$ cells. DLL1 constructs were added to cells at varying doses in the same volume of the construct buffer (PBS, 10% glycerol, 5 mM DTT). Buffer added at the same volume was used as a negative control. For positive control, clustered DLL1 was titered at concentrations between 0 and 2 μg/ml (based on DLL1-Fc protein). When surface-bound constructs were used, they were absorbed on the plates by incubating their varying dilutions from 0.5 to 5 μg/ml in PBS in cell culture plate overnight at 4° C.; plates the were washed with PBS and 10% BSA solution in PBS was then added for additional 2 hrs at room temperature. Plates were washed with PBS and cells seeded. Cells were cultured for 6-12 hrs for qRT-PCR, 16 hrs for Western blot analyses and harvested.

RNA was extracted with an RNeasy Mini kit and possible genomic DNA contamination was removed by on-column DNase digestion using the RNase-free DNase set (Qiagen; Valencia, Calif.). cDNA was synthesized using SuperScript III Reverse Transcriptase kit (Invitrogen, Grand Island, N.Y.). cDNA, iQ SYBR green supermix (Bio-Rad, Hercules, Calif.) and gene-specific primers (Hes1 forward: GCC AAT TTG CCT TTC TCA TC (SEQ ID NO:135), Hes1 reverse AGC CAC TGG AAG GTG ACA CT (SEQ ID NO:136); Hey1 forward: CTC TCA GCC TTC CCC TTT TC (SEQ ID NO:137), Hey1 reverse: ATC TCT GTC CCC CAA GGT CT (SEQ ID NO:138) were used in 20 μl PCR reactions as recommended by the manufacturer and described previously[1]. Amplification of endogenous β-actin or GAPDH was used as internal controls.

For Western blot, cells were lysed in a lysis buffer containing 20 mM HEPES, 150 mM NaCl, 10% glycerol, 1% Triton X-100, 1 mM EGTA, and 1.5 mM MgCl2 with set of inhibitors, as described previously. Equal amounts of protein were mixed with SDS sample buffer and separated by 7.5 or 10% SDS-PAGE, and transferred to PVDF membrane (Amersham Biosciences, Piscataway, N.J.). The following antibodies were used for detection: Notch1 recognizing epitopes in intracellular domain (ICD) of Notch and Hes1 (Cell Signaling, MA).

Modulation of Cytokine Expression.

The ability of DLL1 constructs to modulate cytokine expression in splenocytes was evaluated by ELISPOT assay. Splenocytes from normal mice were seeded at $2.5\times10^5$ cells per well in IFN-γ ELISPOT plates (CTL, Shaker Heights, Ohio). Cells were stimulated with CD3/CD28 beads (Dynal). Varying doses of DLL1 constructs, clustered DLL1 or buffer control were added to cells, as described above. Splenocytes were cultured for 48 hrs and IFN-γ-producing cells were enumerated by ELISPOT assay according to the manufacturer's protocol.

Mice and Tumor Models

Female and male Balb/c, C57BL/6 mice (7 to 8-week-old) were purchased from The Jackson Laboratory. The animals were housed in pathogen-free units at the Vanderbilt University School of Medicine, in compliance with the Institutional Animal Care and Use Committee regulations. To induce tumor, mice were inoculated subcutaneously (s.c.) in flank with $0.3\times10^6$ D459 or LLC cells, as described previously[3,4]. Tumor volume was measured with calipers and tumor tissues were weighed at the endpoint of the experiments.

DLL1 clusters and treatment regimen. Mouse DLL1-Fc fusion protein is composed of the extracellular domain of mouse or human DLL1 and the Fc part of mouse IgG2A or human IgG1, respectively. To form DLL1 clusters, DLL1-Fc, biotinylated anti-IgG antibodies, and NeutrAvidin (Pierce, Rockford, Ill.) were mixed at a molar ratio of 1:4:10 in PBS, as described earlier[4,5]. As a control in all applications, Fc fragment of mouse IgG2 (Sigma-Aldrich, St. Louis, Mo.) was used instead of DLL1-Fc. Mouse DLL1-Fc and biotinylated donkey anti-mouse IgG antibodies were from R&D Systems (Minneapolis, Minn.).

Tumor-bearing mice received clustered DLL1 at doses of 0.15 μg/kg (4 μg per injection) of DLL1-Fc protein in 100 μl of PBS intraperitoneally (i.p.) every other day for 3 weeks. The control group received control clusters with Fc fragments instead of DLL1-Fc protein. Twice higher doses of clustered DLL1 were used in some experiments with similar results suggesting dose saturation of the clustered DLL1 effects.

Statistical Analysis

Data were analyzed using the GraphPad Prism 4.0 software (GraphPad Software Inc., San Diego, Calif.) and presented as mean±SEM. Comparisons between two groups were performed using two-tailed unpaired t tests. Values were considered statistically significant when P was less than 0.05.

REFERENCES CITED IN THIS EXAMPLE

1. Biktasova A K, Dudimah D F, Uzhachenko R V, Park K, Akhter A, Arasada R R, Evans J V, Novitskiy S V, Tchekneva E E, Carbone D P, Shanker A, Dikov M M. Multivalent Forms of the Notch Ligand DLL-1 Enhance Antitumor T-cell Immunity in Lung Cancer and Improve Efficacy of EGFR-Targeted Therapy. Cancer research. 2015; 75:4728-4741.
2. Atochina-Vasserman E N, Biktasova A, Abramova E, Cheng D S, Polosukhin V V, Tanjore H, Takahashi S, Sonoda H, Foye L, Venkov C, Ryzhov S V, Novitskiy S, Shlonimskaya N, Ikeda M, Blackwell T S, Lawson W E, Gow A J, Harris R C, Dikov M M, Tchekneva E E. Aquaporin 11 insufficiency modulates kidney susceptibility to oxidative stress. American journal of physiology Renal physiology. 2013; 304:F1295-1307.
3. Novitskiy S V, Ryzhov S, Zaynagetdinov R, Goldstein A E, Huang Y, Tikhomirov O Y, Blackburn M R, Biaggioni I, Carbone D P, Feoktistov I, Dikov M M. Adenosine receptors in regulation of dendritic cell differentiation and function. Blood. 2008; 112:1822-1831.
4. Huang Y, Lin L, Shanker A, Malhotra A, Yang L, Dikov M M, Carbone D P. Resuscitating cancer immunosurveillance: selective stimulation of DLL1-Notch signaling in T cells rescues T-cell function and inhibits tumor growth. Cancer research. 2011; 71:6122-6131.
5. Heinzel K, Benz C, Bleul C C. A silent chemokine receptor regulates steady-state leukocyte homing in vivo. Proceedings of the National Academy of Sciences of the United States of America. 2007; 104:8421-8426.

Example 8. Mouse Tandem Construct Gene Sequences

The tandem construct repeats were designed by reverse translation and *E. coli* codon optimization through GENEWIZ. Restriction sites were added on either end to transfer the gene from the delivered pUC plasmid into the expression vector pHLIC. In addition, KpnI, SalI, BsrGI, NsiI, XmaI, MfeI, and XhoI restriction sites were added once into the first DLL1 repeat as well as a second time throughout the gene. This allows for the generation of 1×, 2×, 3×, 4×, 5×, 6×, and 7× tandem repeat construct by a single digest and ligation. If this digestion proved problematic, unique degenerate codon sequences were used at the end of 5×, 6×, and 7× tandem repeats. Consequently, polymerase chain reaction steps could be used as an alternate way to generate these smaller fragments. Limitations in degenerate codon diversity prevented the addition of this feature to repeats 1×, 2×, 3×, and 4× tandem repeats which had previously been generated through PCR. The length and repetitiveness of this gene made it problematic to sequence longer gene constructs by traditional sanger sequencing methods. To overcome this problem, the linker region codons, coding for GSSGSSG, were randomized and could be used for sequencing primer annealing as well as unique sites to stitch together multiple sequencing reads. Similar strategies are used to clone and develop even larger constructs, for example, 9×, 10×, 11×, 12×, or more.

Sequences for mouse tandem constructs are found in the sequence section of the application at SEQ ID NO:121, SEQ ID NO:122, SEQ ID NO:123, SEQ ID NO:124, SEQ ID NO:125, SEQ ID NO:126, SEQ ID NO:127, and SEQ ID NO:128.

Example 9. Human Tandem Construct Gene Sequence

The tandem construct repeats were designed by reverse translation and *E. coli* codon optimization through GENEWIZ. Restriction sites were added on either end to transfer the gene from the delivered pUC plasmid into the expression vector pHLIC. In addition, KpnI, SalI, BsrGI, NsiI, XmaI, MfeI, and XhoI restriction sites were added once into the first DLL1 repeat as well as a second time throughout the gene. This allows for the generation of 1×, 2×, 3×, 4×, 5×, 6×, and 7× tandem repeat construct by a single digest and ligation. The length and repetitiveness of this gene made it problematic to sequence gene constructs by traditional sanger sequencing methods. To overcome this problem, the linker region codons, coding for GSSGSSG, were randomized and could be used for sequencing primer annealing as well as unique sites to stitch together multiple sequencing reads. Similar strategies are used to clone and develop even larger constructs, for example, 9×, 10×, 11×, 12×, or more.

Sequences for human tandem constructs are found in the sequence section of the application at SEQ ID NO:144, SEQ ID NO:145, SEQ ID NO:146, SEQ ID NO:147, SEQ ID NO:148, SEQ ID NO:149, and SEQ ID NO:150.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

Sequences

Nomenclature

Each name given to a DLL1 ligand describes its various features. This can be broken down into three categories which are separated in the name by a period. The first describes if the sequence is human (HuDLL1) or mouse (MuDLL1). The second indicates the presence of a Pel B leader sequence in the construct (by the presence of PelB-) and if the construct has two or three EGF domains (EFG12 vs EGF123). The third category indicates whether or not the DSL-EGF domains are repeated in tandem connected by a GSSGSSG linker (Tan), the construct contains a C-terminal cysteine for potential chemical conjugation (Cys), both (Tan/Cys) or neither. Some constructs also contain an N-terminal 6× histidine affinity tag followed directly by a TEV cleavage site.

Tandem Sequences (those having more than one repeat) have a number corresponding to the number of repeats in the given construct. For example: MuDLL1.DSL-EGF12.Tan 4 indicates there are four repeats of DLL1-EGF12 domains. For linker variants, the letters and numbers preceding the Tan indicate the type of Gly/Ser linker used.

Summary

Human Monomer Protein Sequences

1) HuDLL1.PelB-DSL-EGF123.Tan/Cys (SEQ ID NO:1)
2) HuDLL1.DSL-EGF123.Tan/Cys (SEQ ID NO:2)
3) HuDLL1.PelB-DSL-EGF12.Tan/Cys (SEQ ID NO:3)
4) HuDLL1. DSL-EGF12.Tan/Cys (SEQ ID NO:4)
5) HuDLL1.PelB-DSL-EGF123.Tan (SEQ ID NO:5)
6) HuDLL1. DSL-EGF123.Tan (NL 49) (SEQ ID NO:6)
7) HuDLL1.PelB-DSL-EGF12.Tan (SEQ ID NO:7)
8) HuDLL1.DSL-EGF12.Tan (NL 51) (SEQ ID NO:8)
9) HuDLL1.PelB-DSL-EGF123.Cys (SEQ ID NO:9)
10) HuDLL1.DSL-EGF123.Cys (NL 50) (SEQ ID NO:10)
11) HuDLL1.PelB-DSL-EGF12.Cys (SEQ ID NO:11)
12) HuDLL1.DSL-EGF12.Cys (NL 52) (SEQ ID NO:12)
13) HuDLL1.PelB-DSL-EGF123 (NL 35) (SEQ ID NO:13)
14) HuDLL1.DSL-EGF123 (NL 36) (SEQ ID NO:14)
15) HuDLL1.PelB-DSL-EGF12 (NL 38) (SEQ ID NO:15)
16) HuDLL1.DSL-EGF12 (NL 37) (SEQ ID NO:16)
17) HuDLL1.PelB-MNNL-DSL-EGF123 (NL 57) (SEQ ID NO:17)
18) HuDLL1.MNNL-DSL-EGF123 (SEQ ID NO:18)
19) HuDLL1.PelB-MNNL-DSL-EGF12 (NL 80) (SEQ ID NO:19)
20) HuDLL1.MNNL-DSL-EGF12 (SEQ ID NO:20)

Mouse Protein Sequences

1) MuDLL1.PelB-DSL-EGF123.Tan/Cys (SEQ ID NO:21)
2) MuDLL1.DSL-EGF123.Tan/Cys (SEQ ID NO:22)
3) MuDLL1.PelB-DSL-EGF12.Tan/Cys (SEQ ID NO:23)
4) MuDLL1.DSL-EGF12.Tan/Cys (SEQ ID NO:24)
5) MuDLL1.PelB-DSL-EGF123.Tan (SEQ ID NO:25)
6) MuDLL1.DSL-EGF123.Tan (NL 53) (SEQ ID NO:26)
7) MuDLL1.PelB-DSL-EGF12.Tan (SEQ ID NO:27)
8) MuDLL1.DSL-EGF12.Tan (NL 55)* (SEQ ID NO:28)
9) MuDLL1.PelB-DSL-EGF123.Cys (SEQ ID NO:29)
10) MuDLL1.DSL-EGF123.Cys (NL 54) (SEQ ID NO:30)
11) MuDLL1.PelB-DSL-EGF12.Cys (SEQ ID NO:31)
12) MuDLL1.DSL-EGF12.Cys (NL 56) (SEQ ID NO:32)
13) MuDLL1.PelB-DSL-EGF123 (NL 40) (SEQ ID NO:33)
14) MuDLL1.DSL-EGF123 (NL 39) (SEQ ID NO:34)
15) MuDLL1.PelB-DSL-EGF12 (NL 41) (SEQ ID NO:35)
16) MuDLL1.DSL-EGF12 (NL 42)* (SEQ ID NO:36)
17) MuDLL1.PelB-MNNL-DSL-EGF123 (NL 58) (SEQ ID NO:37)
18) MuDLL1.MNNL-DSL-EGF123 (SEQ ID NO:38)
19) MuDLL1.PelB-MNNL-DSL-EGF12 (SEQ ID NO:39)
20) MuDLL1.MNNL-DSL-EGF12 (SEQ ID NO:40)

Human Tandem Protein Sequences

1) HuDLL1. DSL-EGF12.Tan 3 (NL 94) (SEQ ID NO:41)
2) HuDLL1. DSL-EGF12.Tan 4 (NL 95) (SEQ ID NO:42)
3) HuDLL1. DSL-EGF12.Tan 5 (NL 96) (SEQ ID NO:43)

Mouse Tandem Protein Sequences

1) MuDLL1.DSL-EGF12.Tan 3 (NL 82)* (SEQ ID NO:44)
2) MuDLL1.DSL-EGF12.Tan 4 (NL 83)* (SEQ ID NO:45)
3) MuDLL1.DSL-EGF12.Tan 5 (NL 101) (SEQ ID NO:46)
4) MuDLL1.DSL-EGF12.Tan 6 (NL 99) (SEQ ID NO:47)
5) MuDLL1.DSL-EGF12.Tan 7 (NL 100) (SEQ ID NO:48)
6) MuDLL1.DSL-EGF12.Tan 8 (NL 98) (SEQ ID NO:49)

Mouse Linker Variant Protein Sequences

1) MuDLL1.DSL-EGF12.G4S2.Tan 2 (NL 84) (SEQ ID NO:50)
2) MuDLL1.DSL-EGF12.G4S3.Tan 2 (NL 85) (SEQ ID NO:51)
3) MuDLL1.DSL-EGF12.G4S4.Tan 2 (NL 86) (SEQ ID NO:52)
4) MuDLL1.DSL-EGF12.G4S2.Tan 4 (NL 87)* (SEQ ID NO:53)
5) MuDLL1.DSL-EGF12.G4S3.Tan 4 (NL 88)* (SEQ ID NO:54)
6) MuDLL1.DSL-EGF12.G4S4.Tan 4 (NL 89)* (SEQ ID NO:55)

EGF-Free Human Constructs—Protein Sequences

1) HuDLL1.PelB-MNNL-DSL (SEQ ID NO:56)
2) HuDLL1.PelB-MNNL (SEQ ID NO:57)
3) HuDLL1.DSL (SEQ ID NO:58)

EGF-Free Mouse Constructs—Protein Sequences

1) MuDLL1.PelB-MNNL-DSL (SEQ ID NO:59)
2) MuDLL1.PelB-MNNL (SEQ ID NO:60)
3) MuDLL1.DSL (SEQ ID NO:61)

FLAG-Tagged Constructs—Protein Sequences

1) MuDLL1.DSL-EGF12-FLAG (NL 92) (SEQ ID NO:62)
2) MuDLL1.DSL-EGF12.Tan 4-FLAG (NL 93) (SEQ ID NO:63)

Human Monomer Nucleic Acid Sequences

21) HuDLL1.PelB-DSL-EGF123.Tan/Cys (SEQ ID NO:64)
22) HuDLL1.DSL-EGF123.Tan/Cys (SEQ ID NO:65)
23) HuDLL1.PelB-DSL-EGF12.Tan/Cys (SEQ ID NO:66)
24) HuDLL1. DSL-EGF12.Tan/Cys (SEQ ID NO:67)
25) HuDLL1.PelB-DSL-EGF123.Tan (SEQ ID NO:68)
26) HuDLL1. DSL-EGF123.Tan (NL 49) (SEQ ID NO:69)
27) HuDLL1.PelB-DSL-EGF12.Tan (SEQ ID NO:70)
28) HuDLL1.DSL-EGF12.Tan (NL 51) (SEQ ID NO:71)
29) HuDLL1.PelB-DSL-EGF123.Cys (SEQ ID NO:72)
30) HuDLL1.DSL-EGF123.Cys (NL 50) (SEQ ID NO:73)
31) HuDLL1.PelB-DSL-EGF12.Cys (SEQ ID NO:74)
32) HuDLL1.DSL-EGF12.Cys (NL 52) (SEQ ID NO:75)
33) HuDLL1.PelB-DSL-EGF123 (NL 35) (SEQ ID NO:76)
34) HuDLL1.DSL-EGF123 (NL 36) (SEQ ID NO:77)
35) HuDLL1.PelB-DSL-EGF12 (NL 38) (SEQ ID NO:78)
36) HuDLL1.DSL-EGF12 (NL 37) (SEQ ID NO:79)
37) HuDLL1.PelB-MNNL-DSL-EGF123 (NL 57) (SEQ ID NO:80)
38) HuDLL1.MNNL-DSL-EGF123 (SEQ ID NO:81)
39) HuDLL1.PelB-MNNL-DSL-EGF12 (NL 80) (SEQ ID NO:82)
40) HuDLL1.MNNL-DSL-EGF12 (SEQ ID NO:83)

Mouse Nucleic Acid Sequences

21) MuDLL1.PelB-DSL-EGF123.Tan/Cys (SEQ ID NO:84)
22) MuDLL1.DSL-EGF123.Tan/Cys (SEQ ID NO:85)
23) MuDLL1.PelB-DSL-EGF12.Tan/Cys (SEQ ID NO:86)
24) MuDLL1.DSL-EGF12.Tan/Cys (SEQ ID NO:87)
25) MuDLL1.PelB-DSL-EGF123.Tan (SEQ ID NO:88)
26) MuDLL1.DSL-EGF123.Tan (NL 53) (SEQ ID NO:89)
27) MuDLL1.PelB-DSL-EGF12.Tan (SEQ ID NO:90)
28) MuDLL1.DSL-EGF12.Tan (NL 55)* (SEQ ID NO:91)
29) MuDLL1.PelB-DSL-EGF123.Cys (SEQ ID NO:92)
30) MuDLL1.DSL-EGF123.Cys (NL 54) (SEQ ID NO:93)
31) MuDLL1.PelB-DSL-EGF12.Cys (SEQ ID NO:94)
32) MuDLL1.DSL-EGF12.Cys (NL 56) (SEQ ID NO:95)
33) MuDLL1.PelB-DSL-EGF123 (NL 40) (SEQ ID NO:96)
34) MuDLL1.DSL-EGF123 (NL 39) (SEQ ID NO:97)
35) MuDLL1.PelB-DSL-EGF12 (NL 41) (SEQ ID NO:98)
36) MuDLL1.DSL-EGF12 (NL 42)* (SEQ ID NO:99)
37) MuDLL1.PelB-MNNL-DSL-EGF123 (NL 58) (SEQ ID NO:100)
38) MuDLL1.MNNL-DSL-EGF123 (SEQ ID NO:101)
39) MuDLL1.PelB-MNNL-DSL-EGF12 (SEQ ID NO:102)
40) MuDLL1.MNNL-DSL-EGF12 (SEQ ID NO:103)

Human Tandem Nucleic Acid Sequences

1) HuDLL1. DSL-EGF12.Tan 3 (NL 94) (SEQ ID NO:104)
2) HuDLL1. DSL-EGF12.Tan 4 (NL 95) (SEQ ID NO:105)
3) HuDLL1. DSL-EGF12.Tan 5 (NL 96) (SEQ ID NO:106)

Mouse Tandem Nucleic Acid Sequences

1) MuDLL1.DSL-EGF12.Tan 3 (NL 82)* (SEQ ID NO:107)
2) MuDLL1.DSL-EGF12.Tan 4 (NL 83)* (SEQ ID NO:108)
3) MuDLL1.DSL-EGF12.Tan 5 (NL 101) (SEQ ID NO:109)
4) MuDLL1.DSL-EGF12.Tan 6 (NL 99) (SEQ ID NO:110)
5) MuDLL1.DSL-EGF12.Tan 7 (NL 100) (SEQ ID NO:111)
6) MuDLL1.DSL-EGF12.Tan 8 (NL 98) (SEQ ID NO:112)

Mouse Linker Variant Nucleic Acid Sequences

1) MuDLL1.DSL-EGF12.G4S2.Tan 2 (NL 84) (SEQ ID NO:113)
2) MuDLL1.DSL-EGF12.G4S3.Tan 2 (NL 85) (SEQ ID NO:114)
3) MuDLL1.DSL-EGF12.G4S4.Tan 2 (NL 86) (SEQ ID NO:115)
4) MuDLL1.DSL-EGF12.G4S2.Tan 4 (NL 87)* (SEQ ID NO:116)
5) MuDLL1.DSL-EGF12.G4S3.Tan 4 (NL 88)* (SEQ ID NO:117)
6) MuDLL1.DSL-EGF12.G4S4.Tan 4 (NL 89)* (SEQ ID NO:118)

FLAG-Tagged Constructs—Nucleic Acid Sequences

1) MuDLL1.DSL-EGF12-FLAG (NL 92) (SEQ ID NO:119)
2) MuDLL1.DSL-EGF12.Tan 4-FLAG (NL 93) (SEQ ID NO:120)

Sequences

Human Monomer Sequences

1) HuDLL1.PelB-DSL-EGF123.Tan/Cys (SEQ ID NO: 1)

MKYLLPTAAAGLLLLAAQPAMAA HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

-continued

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGC

DNA (SEQ ID NO: 64):

CATATG

AAGTATCTCTTGCCTACTGCCGCGGCAGGGCTTTTACTTCTCGCAGCTCAGCCTGCAATGGCAGCT

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTTTGCAATCAAGACCTGAACT

ATTGTACTCATCACAAGCCGTGTAAAAACGGAGCCACGTGTACGAACACAGGTCAAGGATCATATACGT

GCTCGTGTCGCCCCGGTTACACCGGTGCTACTTGCGAATTG

*GGGTCCTCAGGATCTAGTGG*

ATTCGTATGCGATGAACATTATTACGGAGAAGGCTGTAGTGTTTTCTGTAGGCCTAGAGACGATGCTTTC

GGGCATTTTACGTGCGGCGAGAGAGGCGAGAAAGTGTGTAATCCTGGGTGGAAAGGGCCCTATTGTAC

AGAACCAATATGCCTTCCAGGTTGCGACGAGCAACACGGTTTTTGTGACAAACCCGGCGAATGTAAATG

CCGGGTCGGGTGGCAGGGCCGATATTGCGACGAATGCATCCGTTATCCCGGATGTCTGCATGGTACTTG

CCAGCAACCTTGGCAGTGTAACTGCCAAGAAGGATGGGGGGGTCTATTTTGCAATCAAGATCTGAATTA

TTGCACACACCACAAACCGTGCAAAAACGGTGCTACATGTACGAATACCGGTCAGGGTAGCTATACCTG

CAGTTGCAGACCTGGATACACAGGCGCGACCTGTGAGCTA

GGT AGC AGC GGC TGT TAA

GGATCC

2) HuDLL1.DSL-EGF123.Tan/Cys (SEQ ID NO: 2)

HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHPCKNGATCTNTGQGSYTCSCRPGYGATCEL

GSSGC

-continued

DNA (SEQ ID NO:65):
CATATG

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTTTGCAATCAAGACCTGAACT

ATTGTACTCATCACAAGCCGTGTAAAAACGGAGCCACGTGTACGAACACAGGTCAAGGATCATATACGT

GCTCGTGTCGCCCCGGTTACACCGGTGCTACTTGCGAATTG

*GGGTCCTCAGGATCTAGTGG*

ATTCGTATGCGATGAACATTATTACGGAGAAGGCTGTAGTGTTTTCTGTAGGCCTAGAGACGATGCTTTC

GGGCATTTTACGTGCGGCGAGAGAGGCGAGAAAGTGTGTAATCCTGGGTGGAAAGGGCCCTATTGTAC

AGAACCAATATGCCTTCCAGGTTGCGACGAGCAACACGGTTTTTGTGACAAACCCGGCGAATGTAAATG

CCGGGTCGGGTGGCAGGGCCGATATTGCGACGAATGCATCCGTTATCCCGGATGTCTGCATGGTACTTG

CCAGCAACCTTGGCAGTGTAACTGCCAAGAAGGATGGGGGGGTCTATTTTGCAATCAAGATCTGAATTA

TTGCACACACCACAAACCGTGCAAAAACGGTGCTACATGTACGAATACCGGTCAGGGTAGCTATACCTG

CAGTTGCAGACCTGGATACACAGGCGCGACCTGTGAGCTA

GGT AGC AGC GGC TGT TAA
GGATCC

3) HuDLL1.PelB-DSL-EGF12.Tan/Cys (SEQ ID NO: 3)

MKYLLPTAAAGLLLLAAQPAMAA HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

GSSGC

DNA (SEQ ID NO: 66):
CATATG

AAGTATCTCTTGCCTACTGCCGCGGCAGGGCTTTTACTTCTCGCAGCTCAGCCTGCAATGGCAGCT

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

-continued

*GGGTCCTCAGGATCTAGTGGA*

TTCGTATGCGATGAACATTATTACGGAGAAGGCTGTAGTGTTTTCTGTAGGCCTAGAGACGATGCTTTCG

GGCATTTTACGTGCGGCGAGAGAGGCGAGAAAGTGTGTAATCCTGGGTGGAAAGGGCCCTATTGTACA

GAACCAATATGCCTTCCAGGTTGCGACGAGCAACACGGTTTTTGTGACAAACCCGGCGAATGTAAATGC

CGGGTCGGGTGGCAGGGCCGATATTGCGACGAATGCATCCGTTATCCCGGATGTCTGCATGGTACTTGC

CAGCAACCTTGGCAGTGTAACTGCCAAGAAGGATGGGGGGGTCTATTTTGCAATCAA

GGT AGC AGC GGC TGT TAA

GGATCC

4) HuDLL1.DSL-EGF12.Tan/Cys (SEQ ID NO: 4)

HHHHHH GGENLYFQG

VFCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

GSSGC

DNA (SEQ ID NO: 67):

CATATG

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

*GGGTCCTCAGGATCTAGTGGA*

TTCGTATGCGATGAACATTATTACGGAGAAGGCTGTAGTGTTTTCTGTAGGCCTAGAGACGATGCTTTCG

GGCATTTTACGTGCGGCGAGAGAGGCGAGAAAGTGTGTAATCCTGGGTGGAAAGGGCCCTATTGTACA

GAACCAATATGCCTTCCAGGTTGCGACGAGCAACACGGTTTTTGTGACAAACCCGGCGAATGTAAATGC

CGGGTCGGGTGGCAGGGCCGATATTGCGACGAATGCATCCGTTATCCCGGATGTCTGCATGGTACTTGC

CAGCAACCTTGGCAGTGTAACTGCCAAGAAGGATGGGGGGGTCTATTTTGCAATCAA

GGT AGC AGC GGC TGT TAA

5) HuDLL1.PelB-DSL-EGF123.Tan (SEQ ID NO: 5)

MKYLLPTAAAGLLLLAAQPAMAA HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

-continued

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

DNA (SEQ ID NO: 68):

CATATG

AAGTATCTCTTGCCTACTGCCGCGGCAGGGCTTTTACTTCTCGCAGCTCAGCCTGCAATGGCAGCT

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTTTGCAATCAAGACCTGAACT

ATTGTACTCATCACAAGCCGTGTAAAAACGGAGCCACGTGTACGAACACAGGTCAAGGATCATATACGT

GCTCGTGTCGCCCCGGTTACACCGGTGCTACTTGCGAATTG

*GGGTCCTCAGGATCTAGTGG*

ATTCGTATGCGATGAACATTATTACGGAGAAGGCTGTAGTGTTTTCTGTAGGCCTAGAGACGATGCTTTC

GGGCATTTTACGTGCGGCGAGAGAGGCGAGAAAGTGTGTAATCCTGGGTGGAAAGGGCCCTATTGTAC

AGAACCAATATGCCTTCCAGGTTGCGACGAGCAACACGGTTTTTGTGACAAACCCGGCGAATGTAAATG

CCGGGTCGGGTGGCAGGGCCGATATTGCGACGAATGCATCCGTTATCCCGGATGTCTGCATGGTACTTG

CCAGCAACCTTGGCAGTGTAACTGCCAAGAAGGATGGGGGGGTCTATTTTGCAATCAAGATCTGAATTA

TTGCACACACCACAAACCGTGCAAAAACGGTGCTACATGTACGAATACCGGTCAGGGTAGCTATACCTG

CAGTTGCAGACCTGGATACACAGGCGCGACCTGTGAGCTA TAA

6) HuCLL1.DSL-EGF123.Tan (SEQ ID NO: 6)

HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

DNA (SEQ ID NO: 69):

CATATG

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

-continued

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTTTGCAATCAAGACCTGAACT

ATTGTACTCATCACAAGCCGTGTAAAAACGGAGCCACGTGTACGAACACAGGTCAAGGATCATATACGT

GCTCGTGTCGCCCCGGTTACACCGGTGCTACTTGCGAATTG

*GGGTCCTCAGGATCTAGTGG*

ATTCGTATGCGATGAACATTATTACGGAGAAGGCTGTAGTGTTTTCTGTAGGCCTAGAGACGATGCTTTC

GGGCATTTTACGTGCGGCGAGAGAGGCGAGAAAGTGTGTAATCCTGGGTGGAAAGGGCCCTATTGTAC

AGAACCAATATGCCTTCCAGGTTGCGACGAGCAACACGGTTTTTGTGACAAACCCGGCGAATGTAAATG

CCGGGTCGGGTGGCAGGGCCGATATTGCGACGAATGCATCCGTTATCCCGGATGTCTGCATGGTACTTG

CCAGCAACCTTGGCAGTGTAACTGCCAAGAAGGATGGGGGGGTCTATTTTGCAATCAAGATCTGAATTA

TTGCACACACCACAAACCGTGCAAAAACGGTGCTACATGTACGAATACCGGTCAGGGTAGCTATACCTG

CAGTTGCAGACCTGGATACACAGGCGCGACCTGTGAGCTA TAA

GGATCC

7) HuDLL1.PelB-DSL-EGF12.Tan (SEQ ID NO: 7)

MKYLLPTAAAGLLLLAAQPAMAA HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ
DNA (SEQ ID NO: 70):

CATATG

AAGTATCTCTTGCCTACTGCCGCGGCAGGGCTTTTACTTCTCGCAGCTCAGCCTGCAATGGCAGCT

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

*GGGTCCTCAGGATCTAGTGGA*

TTCGTATGCGATGAACATTATTACGGAGAAGGCTGTAGTGTTTTCTGTAGGCCTAGAGACGATGCTTTCG

GGCATTTTACGTGCGGCGAGAGAGGCGAGAAAGTGTGTAATCCTGGGTGGAAAGGGCCCTATTGTACA

GAACCAATATGCCTTCCAGGTTGCGACGAGCAACACGGTTTTTGTGACAAACCCGGCGAATGTAAATGC

-continued

CGGGTCGGGTGGCAGGGCCGATATTGCGACGAATGCATCCGTTATCCCGGATGTCTGCATGGTACTTGC

CAGCAACCTTGGCAGTGTAACTGCCAAGAAGGATGGGGGGGTCTATTTTGCAATCAA TAA

8) HuDLL1.DSL-EGF12.Tan (SEQ ID NO: 8)

HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DNA (SEQ ID NO: 71):

CATATG

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

*GGGTCCTCAGGATCTAGTGGA*

TTCGTATGCGATGAACATTATTACGGAGAAGGCTGTAGTGTTTTCTGTAGGCCTAGAGACGATGCTTTCG

GGCATTTTACGTGCGGCGAGAGAGGCGAGAAAGTGTGTAATCCTGGGTGGAAAGGGCCCTATTGTACA

GAACCAATATGCCTTCCAGGTTGCGACGAGCAACACGGTTTTTGTGACAAACCCGGCGAATGTAAATGC

CGGGTCGGGTGGCAGGGCCGATATTGCGACGAATGCATCCGTTATCCCGGATGTCTGCATGGTACTTGC

CAGCAACCTTGGCAGTGTAACTGCCAAGAAGGATGGGGGGGTCTATTTTGCAATCAA TAA

GGATCC

9) HuDLL1.PelB-DSL-EGF123.Cys (SEQ ID NO: 9)

MKYLLPTAAAGLLLLAAQPAMAA HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGC

DNA (SEQ ID NO: 72):

CATATG

AAGTATCTCTTGCCTACTGCCGCGGCAGGGCTTTTACTTCTCGCAGCTCAGCCTGCAATGGCAGCT

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

-continued

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTTTGCAATCAAGACCTGAACT

ATTGTACTCATCACAAGCCGTGTAAAAACGGAGCCACGTGTACGAACACAGGTCAAGGATCATATACGT

GCTCGTGTCGCCCCGGTTACACCGGTGCTACTTGCGAATTG

GGT AGC AGC GGC TGT TAA

GGATCC

10) HuDLL1.DSL-EGF123.Cys (SEQ ID NO: 10)

HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGC

DNA (SEQ ID NO: 73):

CATATG

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTTTGCAATCAAGACCTGAACT

ATTGTACTCATCACAAGCCGTGTAAAAACGGAGCCACGTGTACGAACACAGGTCAAGGATCATATACGT

GCTCGTGTCGCCCCGGTTACACCGGTGCTACTTGCGAATTG

GGT AGC AGC GGC TGT TAA

GGATCC

11) HuDLL1.PelB-DSL-EGF12.Cys (SEQ ID NO: 11)

MKYLLPTAAAGLLLLAAQPAMAA HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

GSSGC

DNA (SEQ ID NO: 74):

CATATG

AAGTATCTCTTGCCTACTGCCGCGGCAGGGCTTTTACTTCTCGCAGCTCAGCCTGCAATGGCAGCT

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

-continued

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

GGT AGC AGC GGC TGT TAA

GGATCC

12) HuDLL1.DSL-EGF12.Cys (SEQ ID NO: 12)

HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

GSSGC

DNA (SEQ ID NO: 75):

CATATG

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

GGT AGC AGC GGC TGT TAA

GGATCC

13) HuDLL1.PelB-DSL-EGF123

(SEQ ID NO: 13)

MKYLLPTAAAGLLLLAAQPAMAA HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

DNA (SEQ ID NO: 76):

CATATG

AAGTATCTCTTGCCTACTGCCGCGGCAGGGCTTTTACTTCTCGCAGCTCAGCCTGCAATGGCAGCT

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTTTGCAATCAAGACCTGAACT

-continued

ATTGTACTCATCACAAGCCGTGTAAAAACGGAGCCACGTGTACGAACACAGGTCAAGGATCATATACGT

GCTCGTGTCGCCCCGGTTACACCGGTGCTACTTGCGAATTG TAA

GGATCC

14) HuDLL1.DSL-EGF123

(SEQ ID NO: 14)

HHHHHH

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

DNA (SEQ ID NO: 77):

CATATG

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTTTGCAATCAAGACCTGAACT

ATTGTACTCATCACAAGCCGTGTAAAAACGGAGCCACGTGTACGAACACAGGTCAAGGATCATATACGT

GCTCGTGTCGCCCCGGTTACACCGGTGCTACTTGCGAATTG TAA

GGATCC

15) HuDLL1.PelB-DSL-EGF12

(SEQ ID NO: 15)

MKYLLPTAAAGLLLLAAQPAMAAHHHHHHGGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DNA (SEQ ID NO: 78):

CATATG

AAGTATCTCTTGCCTACTGCCGCGGCAGGGCTTTTACTTCTCGCAGCTCAGCCTGCAATGGCAGCT

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG TAA

GGATCC

16) HuDLL1.DSL-EGF12

(SEQ ID NO: 16)

HHHHHHGGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

-continued

DNA (SEQ ID NO: 79):

CATATG

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG TAA

GGATCC

17) HuDLL1.PelB-MNNL-DSL-EGF123

(SEQ ID NO: 17)

MKYLLPTAAAGLLLLAAQPAMA A HHHHHH GGENLYFQG

QVWSSGVFELKLQEFVNKKGLLGNRNCCRGGAGPPPCARTFFRVCLKHYQASVSPEPPCTYGSAVTPVLG

VDSFSLPDGGGADSAFSNPIRFPFGFTWPGTFSLIIEALHTDSPDDLATENPERLISRLATQRHLTVGEEWSQD

LHSSGRTDLKYSYRFVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

DNA (SEQ ID NO: 80):

CATATGA

AATATCTTCTCCCCACAGCCGCTGCAGGACTTCTGTTATTGGCCGCACAACCCGCGATGGCTGCA

CATCACCATCACCATCAC

GGGGGAGAGAATCTTTACTTCCAGGGC

CAAGTGTGGAGCTCTGGAGTATTCGAGTTGAAACTACAAGAATTCGTTAACAAGAAAGGCTTGCTGGGA

AATCGTAATTGCTGTCGGGGTGGAGCGGGACCGCCCCCTTGCGCTTGTCGCACTTTCTTTCGTGTGTGTT

TAAAGCACTATCAGGCTAGTGTATCTCCTGAGCCGCCTTGCACCTATGGAAGTGCCGTAACCCCGGTTCT

GGGGGTAGACTCGTTTAGTCTCCCCGATGGTGGCGGGGCGGATTCTGCTTTTTCCAATCCAATCAGATTT

CCGTTCGGGTTTACATGGCCAGGGACTTTTAGCTTAATAATCGAGGCCTTGCACACTGATAGCCCAGACG

ATCTAGCAACGGAAAATCCCGAAAGATTAATTTCACGACTCGCAACCCAGAGGCATTTAACGGTCGGAG

AGGAATGGTCCCAGGACCTTCACTCGAGTGGGAGGACCGACTTGAAGTACTCATATAGGTTTGTTTGCG

ACGAACATTATTACGGCGAAGGTTGTTCGGTCTTTTGCCGGCCGCGAGATGACGCCTTCGGTCATTTTAC

CTGTGGCGAACGCGGCGAGAAGGTGTGTAACCCTGGGTGGAAAGGTCCCTATTGTACAGAACCGATAT

GCCTACCAGGTTGTGATGAACAACACGGGTTCTGCGACAAGCCAGGAGAGTGCAAGTGCCGTGTCGGC

TGGCAGGGGCGATATTGTGATGAGTGCATTAGATACCCAGGTTGTCTCCATGGAACTTGCCAACAGCCT

TGGCAGTGTAACTGCCAAGAGGGTTGGGGCGGACTATTCTGCAAC

CAAGATCTAAACTACTGTACACATCACAAACCTTGTAAAAATGGTGCGACGTGTACAAACACAGGCCAA

GGCTCATACACGTGCTCCTGTCGGCCAGGTTACACGGGGGCGACTTGCGAACTGTAA

GGATCC

18) HuDLL1.MNNL-DSL-EGF123

(SEQ ID NO: 18)

HHHHHH GGENLYFQG

QVWSSGVFELKLQEFVNKKGLLGNRNCCRGGAGPPPCACRTFFRVCLKHYQASVSPEPPCTYGSAVTPVLG

VDSFSLPDGGGADSAFSNPIRFPFGFTWPGTFSLIIEALHTDSPDDLATENPERLISRLATQRHLTVGEEWSQD

-continued

LHSSGRTDLKYSYRFVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

DNA (SEQ ID NO: 81):

CATATGA

CATCACCATCACCATCAC

GGGGGAGAGAATCTTTACTTCCAGGGC

CAAGTGTGGAGCTCTGGAGTATTCGAGTTGAAACTACAAGAATTCGTTAACAAGAAAGGCTTGCTGGGA

AATCGTAATTGCTGTCGGGGTGGAGCGGGACCGCCCCCTTGCGCTTGTCGCACTTTCTTTCGTGTGTGTT

TAAAGCACTATCAGGCTAGTGTATCTCCTGAGCCGCCTTGCACCTATGGAAGTGCCGTAACCCCGGTTCT

GGGGGTAGACTCGTTTAGTCTCCCCGATGGTGGCGGGGCGGATTCTGCTTTTTCCAATCCAATCAGATTT

CCGTTCGGGTTTACATGGCCAGGGACTTTTAGCTTAATAATCGAGGCCTTGCACACTGATAGCCCAGACG

ATCTAGCAACGGAAAATCCCGAAAGATTAATTTCACGACTCGCAACCCAGAGGCATTTAACGGTCGGAG

AGGAATGGTCCCAGGACCTTCACTCGAGTGGGAGGACCGACTTGAAGTACTCATATAGGTTTGTTTGCG

ACGAACATTATTACGGCGAAGGTTGTTCGGTCTTTTGCCGGCCGCGAGATGACGCCTTCGGTCATTTTAC

CTGTGGCGAACGCGGCGAGAAGGTGTGTAACCCTGGGTGGAAAGGTCCCTATTGTACAGAACCGATAT

GCCTACCAGGTTGTGATGAACAACACGGGTTCTGCGACAAGCCAGGAGAGTGCAAGTGCCGTGTCGGC

TGGCAGGGGCGATATTGTGATGAGTGCATTAGATACCCAGGTTGTCTCCATGGAACTTGCCAACAGCCT

TGGCAGTGTAACTGCCAAGAGGGTTGGGGCGGACTATTCTGCAAC

CAAGATCTAAACTACTGTACACATCACAAACCTTGTAAAAATGGTGCGACGTGTACAAACACAGGCCAA

GGCTCATACACGTGCTCCTGTCGGCCAGGTTACACGGGGGCGACTTGCGAACTGTAA

GGATCC

19) HuDLL1.PelB-MNNL-DSL-EGF12

(SEQ ID NO: 19)

MKYLLPTAAAGLLLLAAQPAMA A HHHHHH GGENLYFQG

QVWSSGVFELKLQEFVNKKGLLGNRNCCRGGAGPPPCACRTFFRVCLKHYQASVSPEPPCTYGSAVTPVLG

VDSFSLPDGGGADSAFSNPIREPFGFTWPGTFSLIIEALHTDSPRDDLATENPERLISRLATQRHLTVGEEWSQD

LHSSGRTDLKYSYR FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCN

DNA (SEQ ID NO: 82):

CATATGA

AATATCTTCTCCCCACAGCCGCTGCAGGACTTCTGTTATTGGCCGCACAACCCGCGATGGCTGCA

CATCACCATCACCATCAC

GGGGGAGAGAATCTTTACTTCCAGGGC

CAAGTGTGGAGCTCTGGAGTATTCGAGTTGAAACTACAAGAATTCGTTAACAAGAAAGGCTTGCTGGGA

AATCGTAATTGCTGTCGGGGTGGAGCGGGACCGCCCCCTTGCGCTTGTCGCACTTTCTTTCGTGTGTGTT

TAAAGCACTATCAGGCTAGTGTATCTCCTGAGCCGCCTTGCACCTATGGAAGTGCCGTAACCCCGGTTCT

GGGGGTAGACTCGTTTAGTCTCCCCGATGGTGGCGGGGCGGATTCTGCTTTTTCCAATCCAATCAGATTT

CCGTTCGGGTTTACATGGCCAGGGACTTTTAGCTTAATAATCGAGGCCTTGCACACTGATAGCCCAGACG

ATCTAGCAACGGAAAATCCCGAAAGATTAATTTCACGACTCGCAACCCAGAGGCATTTAACGGTCGGAG

-continued

AGGAATGGTCCCAGGACCTTCACTCGAGTGGGAGGACCGACTTGAAGTACTCATATAGGTTTGTTTGCG

ACGAACATTATTACGGCGAAGGTTGTTCGGTCTTTTGCCGGCCGCGAGATGACGCCTTCGGTCATTTTAC

CTGTGGCGAACGCGGCGAGAAGGTGTGTAACCCTGGGTGGAAAGGTCCCTATTGTACAGAACCGATAT

GCCTACCAGGTTGTGATGAACAACACGGGTTCTGCGACAAGCCAGGAGAGTGCAAGTGCCGTGTCGGC

TGGCAGGGGCGATATTGTGATGAGTGCATTAGATACCCAGGTTGTCTCCATGGAACTTGCCAACAGCCT

TGGCAGTGTAACTGCCAAGAGGGTTGGGGCGGACTATTCTGCAAC TAA

GGATCC

20) HuDLL1.MNNL-DSL-EGF12

(SEQ ID NO: 20)

HHHHHH GGENLYFQG

QVWWSSGVFELKLQEFVNKKGLLGNRNCCRGGAGPPCACRTFFRVCLKHYQASVSPEPPCTVGSAVTPVLG

VDSFSLPDGGGADSAFSNPIRFPFGFTWPGTFSLIIEALHTDSPDDLATENPERLISRLATQRHLTVGEEWSQD

LHSSGRTDLKYSYRFVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCN

DNA (SEQ ID NO: 83):

CATATGA

CATCACCATCACCATCAC

GGGGGAGAGAATCTTTACTTCCAGGGC

CAAGTGTGGAGCTCTGGAGTATTCGAGTTGAAACTACAAGAATTCGTTAACAAGAAAGGCTTGCTGGGA

AATCGTAATTGCTGTCGGGGTGGAGCGGGACCGCCCCCTTGCGCTTGTCGCACTTTCTTTCGTGTGTGTT

TAAAGCACTATCAGGCTAGTGTATCTCCTGAGCCGCCTTGCACCTATGGAAGTGCCGTAACCCCGGTTCT

GGGGGTAGACTCGTTTAGTCTCCCCGATGGTGGCGGGGCGGATTCTGCTTTTTCCAATCCAATCAGATTT

CCGTTCGGGTTTACATGGCCAGGGACTTTTAGCTTAATAATCGAGGCCTTGCACACTGATAGCCCAGACG

ATCTAGCAACGGAAAATCCCGAAAGATTAATTTCACGACTCGCAACCCAGAGGCATTTAACGGTCGGAG

AGGAATGGTCCCAGGACCTTCACTCGAGTGGGAGGACCGACTTGAAGTACTCATATAGGTTTGTTTGCG

ACGAACATTATTACGGCGAAGGTTGTTCGGTCTTTTGCCGGCCGCGAGATGACGCCTTCGGTCATTTTAC

CTGTGGCGAACGCGGCGAGAAGGTGTGTAACCCTGGGTGGAAAGGTCCCTATTGTACAGAACCGATAT

GCCTACCAGGTTGTGATGAACAACACGGGTTCTGCGACAAGCCAGGAGAGTGCAAGTGCCGTGTCGGC

TGGCAGGGGCGATATTGTGATGAGTGCATTAGATACCCAGGTTGTCTCCATGGAACTTGCCAACAGCCT

TGGCAGTGTAACTGCCAAGAGGGTTGGGGCGGACTATTCTGCAAC TAA

GGATCC

Mouse Protein Sequences

1) MuDLL1.PelB-DSL-EGF123.Tan/Cys (SEQ ID NO: 21)

MKYLLPTAAAGLLLLAAQPAMAA HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

-continued

DLNYCTHHKPCRNGATCTNTGQGSYTCSCRPGYTGANCEL

GSSGC
DNA (SEQ ID NO: 84):
CATATG

AAGTATCTCTTGCCCACGGCCGCTGCAGGGTTGCTGTTGCTTGCGGCACAGCCGGCTATGGCAGCT

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCCTATTCTGCAATCAGGACTTGAATT

ACTGTACTCACCATAAACCTTGTAGGAACGGAGCAACTTGTACAAACACAGGTCAAGGTTCATACACAT

GCAGCTGTCGTCCCGGTTACACTGGCGCAAATTGCGAGCTG

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAGGATCTCAAC

TATTGCACGCATCATAAACCATGTCGCAACGGTGCAACCTGTACTAATACGGGCCAAGGTAGTTATACCT

GTTCCTGTCGGCCTGGATACACAGGAGCTAACTGTGAATTA

GGT AGC AGC GGC TGT TAA
GGATCC

2) MuDLL1.DSL-EGF123.Tan/Cys (SEQ ID NO: 22)

HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL

GSSGC
DNA (SEQ ID NO: 85):
CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

-continued

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCCTATTCTGCAATCAGGACTTGAATT

ACTGTACTCACCATAAACCTTGTAGGAACGGAGCAACTTGTACAAACACAGGTCAAGGTTCATACACAT

GCAGCTGTCGTCCCGGTTACACTGGCGCAAATTGCGAGCTG

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAGGATCTCAAC

TATTGCACGCATCATAAACCATGTCGCAACGGTGCAACCTGTACTAATACGGGCCAAGGTAGTTATACCT

GTTCCTGTCGGCCTGGATACACAGGAGCTAACTGTGAATTA

GGT AGC AGC GGC TGT TAA

GGATCC

3)MuDLL1.PelB-DSL-EGF12.Tan/Cys (SEQ ID NO: 23)

MKYLLPTAAAGLLLLAAQPAMAA HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGC

DNA (SEQ ID NO: 86):

CATATG

AAGTATCTCTTGCCCACGGCCGCTGCAGGGTTGCTGTTGCTTGCGGCACAGCCGGCTATGGCAGCT

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

-continued

TGTCAGCAACCCTGGCAGTGCAATTGTCAGGAAGGATGGGGTGGACTTTTTTGTAATCAG

GGT AGC AGC GGC TGT TAA

4) MuDLL1. DSL-EGF12.Tan/Cys (SEQ ID NO: 24)

HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGH FTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGC

DNA (SEQ ID NO: 87):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG

GGT AGC AGC GGC TGT TAA

5) MuDLL1.PelB-DSL-EGF123.Tan (SEQ ID NO: 25)

MKYLLPTAAAGLLLLAAQPAMAA HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL

GSSGSSG

FVCDEHYYGEGCSVFCRPRDDAFGHFTCGDRGEKMCDPGWKGQYC

TDPICLPGCDDQHGYCDKPGECKCRVGWQGRYCD

-continued

ECIRYPGCLHGTCQQPWQCNCQEGWGGLFCNQ

DLNYCTHHKPCRNGATCTNTGQGSYTCSCRPGYTGANCEL
DNA (SEQ ID NO: 88):
CATATG

AAGTATCTCTTGCCCACGGCCGCTGCAGGGTTGCTGTTGCTTGCGGCACAGCCGGCTATGGCAGCT

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCCTATTCTGCAATCAGGACTTGAATT

ACTGTACTCACCATAAACCTTGTAGGAACGGAGCAACTTGTACAAACACAGGTCAAGGTTCATACACAT

GCAGCTGTCGTCCCGGTTACACTGGCGCAAATTGCGAGCTG

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAGGATCTCAAC

TATTGCACGCATCATAAACCATGTCGCAACGGTGCAACCTGTACTAATACGGGCCAAGGTAGTTATACCT

GTTCCTGTCGGCCTGGATACACAGGAGCTAACTGTGAATTA TAA
GGATCC

6) MuDLL1. DSL-EGF123.Tan (SEQ ID NO: 26)

HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL
DNA (SEQ ID NO: 89):
CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

-continued

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCCTATTCTGCAATCAGGACTTGAATT

ACTGTACTCACCATAAACCTTGTAGGAACGGAGCAACTTGTACAAACACAGGTCAAGGTTCATACACAT

GCAGCTGTCGTCCCGGTTACACTGGCGCAAATTGCGAGCTG

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAGGATCTCAAC

TATTGCACGCATCATAAACCATGTCGCAACGGTGCAACCTGTACTAATACGGGCCAAGGTAGTTATACCT

GTTCCTGTCGGCCTGGATACACAGGAGCTAACTGTGAATTA TAA

GGATCC

7) MuDLL1.PelB-DSL-EGF12.Tan (SEQ ID NO: 27)

MKYLLPTAAAGLLLLAAQPAMAA HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 90):

CATATG

AAGTATCTCTTGCCCACGGCCGCTGCAGGGTTGCTGTTGCTTGCGGCACAGCCGGCTATGGCAGCT

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

-continued

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG TAA

GGATCC

8) MuDLL1.DSL-EGF12.Tan (SEQ ID NO: 28)

HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 91):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG TAA

GGATCC

9) MuDLL1.PelB-DSL-EGF123.Cys (SEQ ID NO: 29)

MKYLLPTAAAGLLLLAAQPAMAA HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL

GSSGC

DNA (SEQ ID NO: 92):

CATATG

AAGTATCTCTTGCCCACGGCCGCTGCAGGGTTGCTGTTGCTTGCGGCACAGCCGGCTATGGCAGCT

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

-continued

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCCTATTCTGCAATCAGGACTTGAATT

ACTGTACTCACCATAAACCTTGTAGGAACGGAGCAACTTGTACAAACACAGGTCAAGGTTCATACACAT

GCAGCTGTCGTCCCGGTTACACTGGCGCAAATTGCGAGCTG

GGT AGC AGC GGC TGT TAA

GGATCC

10) MuDLL1.DSL-EGF123.Cys (SEQ ID NO: 30)

HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL

GSSGC

DNA (SEQ ID NO: 93):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCCTATTCTGCAATCAGGACTTGAATT

ACTGTACTCACCATAAACCTTGTAGGAACGGAGCAACTTGTACAAACACAGGTCAAGGTTCATACACAT

GCAGCTGTCGTCCCGGTTACACTGGCGCAAATTGCGAGCTG

GGT AGC AGC GGC TGT TAA

GGATCC

11) MuDLL1.PelB-DSL-EGF12.Cys (SEQ ID NO: 31)

MKYLLPTAAAGLLLLAAQPAMAA HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGC

DNA (SEQ ID NO: 94):

CATATG

AAGTATCTCTTGCCCACGGCCGCTGCAGGGTTGCTGTTGCTTGCGGCACAGCCGGCTATGGCAGCT

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

-continued

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

GGT AGC AGC GGC TGT TAA

GGATCC

12) MuDLL1.DSL-EGF12.Cys (SEQ ID NO: 32)

HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGC

DNA (SEQ ID NO: 95):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

GGT AGC AGC GGC TGT TAA

GGATCC

13) MuDLL1.PelB-DSL-EGF123

(SEQ ID NO: 33)

MKYLLPTAAAGLLLLAAQPAMAA HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL

DNA (SEQ ID NO: 96):

CATATG

AAGTATCTCTTGCCCACGGCCGCTGCAGGGTTGCTGTTGCTTGCGGCACAGCCGGCTATGGCAGCT

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

-continued

GCCAGCAACCTTGGCAATGTAACTGTCAAGAAGGATGGGGAGGCCTATTCTGCAATCAGGACTTGAATT

ACTGTACTCACCATAAACCTTGTAGGAACGGAGCAACTTGTACAAACACAGGTCAAGGTTCATACACAT

GCAGCTGTCGTCCCGGTTACACTGGCGCAAATTGCGAGCTG TAA

14) MuDLL1.DSL-EGF123

(SEQ ID NO: 34)

HHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL

DNA (SEQ ID NO: 97):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCCTATTCTGCAATCAGGACTTGAATT

ACTGTACTCACCATAAACCTTGTAGGAACGGAGCAACTTGTACAAACACAGGTCAAGGTTCATACACAT

GCAGCTGTCGTCCCGGTTACACTGGCGCAAATTGCGAGCTG TAA

GGATCC

15) MuDLL1.PelB-DSL-EGF12

(SEQ ID NO: 35)

MKYLLPTAAAGLLLLAAQPAMAA HHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 98):

CATATG

AAGTATCTCTTGCCCACGGCCGCTGCAGGGTTGCTGTTGCTTGCGGCACAGCCGGCTATGGCAGCT

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

-continued

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA TAA

GGATCC

16) MuDLL1.DSL-EGF12

(SEQ ID NO: 36)

HHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 99):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGTTATTCTGCAACCAA TAA

GGATCC

17) MuDLL1.PeIB-MNNL-DSL-EGF123

(SEQ ID NO: 37)

MKYLLPTAAAGLLLLAAQPAMAA HHHHHH GGENLYFQG

QVWSSGVFELKLQEFVNKKGLGNRNCCRGGSGPPCACRTFFRVCLKHYQASVSPEPPCTYGSAVTPVLGVD

SFSLPDGAGIDPAFSNPIRFPFGFTWPGTFSLIIEALHTDSPDDLATENPERLISRLTTQRHLTVGEEWSQDLHS

SGRTDLRYSYRFVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL

DNA (SEQ ID NO: 100):

CATATG

AAATACTTGCTACCAACCGCAGCGGCAGGCTTACTTTTGTTAGCAGCGCAACCTGCGATGGCGGCC

CATCACCATCACCATCAC

GGTGGCGAGAATCTGTATTTCCAGGGA

CAAGTGTGGAGCTCAGGTGTCTTCGAACTTAAGTTGCAAGAATTCGTAAATAAGAAAGGACTATTGGGA

AACCGGAACTGCTGTCGTGGCGGTTCGGGCCCACCGTGCGCTTGCAGGACATTCTTTCGGGTTTGTCTG

AAGCACTATCAGGCCTCCGTCAGCCCGGAACCGCCCTGTACTTATGGTAGTGCCGTGACACCCGTTCTGG

GTGTCGATAGTTTCTCGCTCCCCGATGGTGCCGGTATTGATCCTGCTTTCAGCAACCCCATCCGTTTTCCT

TTCGGGTTTACATGGCCTGGCACCTTTTCTCTTATAATTGAGGCACTCCACACGGACAGTCCAGACGATT

TGGCTACTGAGAACCCGGAAAGGCTCATATCACGATTAACGACTCAACGTCATCTCACAGTGGGGGAAG

AGTGGAGTCAGGACCTGCATTCCTCTGGAAGAACGGACTTAAGATATTCGTATCGCTTCGTATGCGACG

AGCATTACTATGGGGAGGGCTGTTCCGTTTTTTGCAGACCGAGAGATGACGCTTTTGGTCACTTTACTTG

TGGAGACAGGGGGGAAAAAATGTGCGACCCCGGGTGGAAGGGCCAGTACTGTACTGACCCTATATGTT

TACCAGGATGTGATGATCAACATGGATACTGCGATAAGCCAGGCGAGTGCAAATGTCGGGTAGGGTGG

-continued

CAAGGCCGCTACTGTGATGAATGCATCCGATATCCAGGATGCCTACATGGGACCTGTCAACAGCCCTGG

CAATGTAATTGCCAGGAGGGATGGGGGGGCCTTTTTTGCAAT

CAGGATCTAAACTATTGTACGCACCACAAACCGTGCAGGAACGGTGCAACATGTACCAATACAGGGCAA

GGGTCATACACGTGTTCTTGCCGACCTGGATACACCGGTGCTAATTGCGAACTATAA

GGATCC

18) MuDLL1.MNNL-DSL-EGF123

(SEQ ID NO: 38)

HHHHH GGENLYFQG

QVWSSGVFELKLQEFVNKKGLLGNRNCCRGGSGPPCACRTFFRVCLKHYQASVSPEPPCTYGSAVTPVLGVD

SFSLPDGAGIDPAFSNPIRFPFGFTWPGTFSLIIEALHTDSPDDLATENPERLISRLTTQRHLTVGEEWSQDLHS

SGRTDLRYSYRFVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DLNYCTHHKPCRNGATCTNTGQGSYTCSCRPGYTGANCEL

DNA (SEQ ID NO: 101):

CATATG

CATCACCATCACCATCAC

GGTGGCGAGAATCTGTATTTCCAGGGA

CAAGTGTGGAGCTCAGGTGTCTTCGAACTTAAGTTGCAAGAATTCGTAAATAAGAAAGGACTATTGGGA

AACCGGAACTGCTGTCGTGGCGGTTCGGGCCCACCGTGCGCTTGCAGGACATTCTTTCGGGTTTGTCTG

AAGCACTATCAGGCCTCCGTCAGCCCGGAACCGCCCTGTACTTATGGTAGTGCCGTGACACCCGTTCTGG

GTGTCGATAGTTTCTCGCTCCCCGATGGTGCCGGTATTGATCCTGCTTTCAGCAACCCCATCCGTTTTCCT

TTCGGGTTTACATGGCCTGGCACCTTTTCTCTTATAATTGAGGCACTCCACACGGACAGTCCAGACGATT

TGGCTACTGAGAACCCGGAAAGGCTCATATCACGATTAACGACTCAACGTCATCTCACAGTGGGGGAAG

AGTGGAGTCAGGACCTGCATTCCTCTGGAAGAACGGACTTAAGATATTCGTATCGCTTCGTATGCGACG

AGCATTACTATGGGGAGGGCTGTTCCGTTTTTTGCAGACCGAGAGATGACGCTTTTGGTCACTTTACTTG

TGGAGACAGGGGGGAAAAAATGTGCGACCCCGGGTGGAAGGGCCAGTACTGTACTGACCCTATATGTT

TACCAGGATGTGATGATCAACATGGATACTGCGATAAGCCAGGCGAGTGCAAATGTCGGGTAGGGTGG

CAAGGCCGCTACTGTGATGAATGCATCCGATATCCAGGATGCCTACATGGGACCTGTCAACAGCCCTGG

CAATGTAATTGCCAGGAGGGATGGGGGGGCCTTTTTTGCAAT

CAGGATCTAAACTATTGTACGCACCACAAACCGTGCAGGAACGGTGCAACATGTACCAATACAGGGCAA

GGGTCATACACGTGTTCTTGCCGACCTGGATACACCGGTGCTAATTGCGAACTA TAA

GGATCC

19) MuDLL1.PelB-MNNL-DSL-EGF12

(SEQ ID NO: 39)

MKYLLPTAAAGLLLLAAQPAMAA HHHHHH GGENLYFQG

QVWSSGVFELKLQEFVNKKGLLGNRNCCRGGSGPPCACRTFFRVCLKHYQASVSPEPPCTYGSAVTPVLGVD

SFSLPDGAGIDPAFSNPIRFPFGFTWPGTFSLIIEALHTDSPDDLATENPERLISRLTTQRHLTVGEEWSQDLHS

-continued

SGRTDLRYSYR FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCN

DNA (SEQ ID NO: 102):

CATATG

AAATACTTGCTACCAACCGCAGCGGCAGGCTTACTTTTGTTAGCAGCGCAACCTGCGATGGCGGCC

CATCACCATCACCATCAC

GGTGGCGAGAATCTGTATTTCCAGGGA

CAAGTGTGGAGCTCAGGTGTCTTCGAACTTAAGTTGCAAGAATTCGTAAATAAGAAAGGACTATTGGGA

AACCGGAACTGCTGTCGTGGCGGTTCGGGCCCACCGTGCGCTTGCAGGACATTCTTTCGGGTTTGTCTG

AAGCACTATCAGGCCTCCGTCAGCCCGGAACCGCCCTGTACTTATGGTAGTGCCGTGACACCCGTTCTGG

GTGTCGATAGTTTCTCGCTCCCCGATGGTGCCGGTATTGATCCTGCTTTCAGCAACCCCATCCGTTTTCCT

TTCGGGTTTACATGGCCTGGCACCTTTTCTCTTATAATTGAGGCACTCCACACGGACAGTCCAGACGATT

TGGCTACTGAGAACCCGGAAAGGCTCATATCACGATTAACGACTCAACGTCATCTCACAGTGGGGGAAG

AGTGGAGTCAGGACCTGCATTCCTCTGGAAGAACGGACTTAAGATATTCGTATCGCTTCGTATGCGACG

AGCATTACTATGGGGAGGGCTGTTCCGTTTTTTGCAGACCGAGAGATGACGCTTTTGGTCACTTTACTTG

TGGAGACAGGGGGGAAAAAATGTGCGACCCCGGGTGGAAGGGCCAGTACTGTACTGACCCTATATGTT

TACCAGGATGTGATGATCAACATGGATACTGCGATAAGCCAGGCGAGTGCAAATGTCGGGTAGGGTGG

CAAGGCCGCTACTGTGATGAATGCATCCGATATCCAGGATGCCTACATGGGACCTGTCAACAGCCCTGG

CAATGTAATTGCCAGGAGGGATGGGGGGGCCTTTTTTGCAAT TAA

GGATCC

20) MuDLL1.MNNL-DSL-EGF12

(SEQ ID NO: 40)

HHHHHH GGENLYFQG

QVWSSGVFELKLQEFVNKKGLLGNRNCCRGGSGPPCACRTFFRVCLKHYQASVSPEPPCTYGSAVTPVLGVD

SFSLPDGAGIDPAFSNPIRFPFGFTWPGTFSLIIEALHTDSPDDLATENPERLISRLTTQRHLTVGEEWSQDLHS

SGRTDLRYSYR FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCN

DNA (SEQ ID NO: 103):

CATATG

CATCACCATCACCATCAC

GGTGGCGAGAATCTGTATTTCCAGGGA

CAAGTGTGGAGCTCAGGTGTCTTCGAACTTAAGTTGCAAGAATTCGTAAATAAGAAAGGACTATTGGGA

AACCGGAACTGCTGTCGTGGCGGTTCGGGCCCACCGTGCGCTTGCAGGACATTCTTTCGGGTTTGTCTG

AAGCACTATCAGGCCTCCGTCAGCCCGGAACCGCCCTGTACTTATGGTAGTGCCGTGACACCCGTTCTGG

GTGTCGATAGTTTCTCGCTCCCCGATGGTGCCGGTATTGATCCTGCTTTCAGCAACCCCATCCGTTTTCCT

TTCGGGTTTACATGGCCTGGCACCTTTTCTCTTATAATTGAGGCACTCCACACGGACAGTCCAGACGATT

TGGCTACTGAGAACCCGGAAAGGCTCATATCACGATTAACGACTCAACGTCATCTCACAGTGGGGGAAG

AGTGGAGTCAGGACCTGCATTCCTCTGGAAGAACGGACTTAAGATATTCGTATCGCTTCGTATGCGACG

AGCATTACTATGGGGAGGGCTGTTCCGTTTTTTGCAGACCGAGAGATGACGCTTTTGGTCACTTTACTTG

TGGAGACAGGGGGGAAAAAATGTGCGACCCCGGGTGGAAGGGCCAGTACTGTACTGACCCTATATGTT

-continued

TACCAGGATGTGATGATCAACATGGATACTGCGATAAGCCAGGCGAGTGCAAATGTCGGGTAGGGTGG

CAAGGCCGCTACTGTGATGAATGCATCCGATATCCAGGATGCCTACATGGGACCTGTCAACAGCCCTGG

CAATGTAATTGCCAGGAGGGATGGGGGGGCCTTTTTTGCAAT TAA

GGATCC

Human Tandem Sequences
1) HuDLL1. DSL-EGF12.Tan3

(SEQ ID NO: 41)

MAA HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL
DNA (SEQ ID NO: 104):
CATATG

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

*GGGTCCTCAGGATCTAGTGGA*

TTTGTCTGTGACGAGCATTACTATGGTGAAGGGTGCTCTGTGTTTTGTAGGCCAAGGGACGATGCGTTC

GGACATTTTACCTGCGGGGAACGAG GTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

*GGGTCCTCAGGATCTAGTGGA*

TTCGTATGCGATGAACATTATTACGGAGAAGGCTGTAGTGTTTTCTGTAGGCCTAGAGACGATGCTTTCG

GGCATTTTACGTGCGGCGAGAGAGGCGAGAAAGTGTGTAATCCTGGGTGGAAAGGGCCCTATTGTACA

-continued

GAACCAATATGCCTTCCAGGTTGCGACGAGCAACACGGTTTTTGTGACAAACCCGGCGAATGTAAATGC

CGGGTCGGGTGGCAGGGCCGATATTGCGACGAATGCATCCGTTATCCCGGATGTCTGCATGGTACTTGC

CAGCAACCTTGGCAGTGTAACTGCCAAGAAGGATGGGGGGGTCTATTTTGCAATCAA TAA

GGATCC

2) HuDLL1. DSL-EGF12.Tan4

(SEQ ID NO: 42)

MAA HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

DNA (SEQ ID NO: 105):

CATATG

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

*GGGTCCTCAGGATCTAGTGGA*

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

-continued

*GGGTCCTCAGGATCTAGTGGA*

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

*GGGTCCTCAGGATCTAGTGGA*

TTCGTATGCGATGAACATTATTACGGAGAAGGCTGTAGTGTTTTCTGTAGGCCTAGAGACGATGCTTTCG

GGCATTTTACGTGCGGCGAGAGAGGCGAGAAAGTGTGTAATCCTGGGTGGAAAGGGCCCTATTGTACA

GAACCAATATGCCTTCCAGGTTGCGACGAGCAACACGGTTTTTGTGACAAACCCGGCGAATGTAAATGC

CGGGTCGGGTGGCAGGGCCGATATTGCGACGAATGCATCCGTTATCCCGGATGTCTGCATGGTACTTGC

CAGCAACCTTGGCAGTGTAACTGCCAAGAAGGATGGGGGGGTCTATTTTGCAATCAA TAA

GGATCC

3) HuDLL1. DSL-EGF12.Tan5

(SEQ ID NO: 43)

MAA HHHHHH GGENLYFQG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

FVCDEHYYGEGCSVFCRPRDDAFGHFTCGERGEKVCNPGWKGPYCT

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL

GSSGSSG

FVCDEHYYGEGCSVFCRPR DDAFGHFTCGERGEKVCNPGWKGPYCT

-continued

EPICLPGCDEQHGFCDKPGECKCRVGWQGRYCD

ECIRYPGCLHGTCQQPWQCNCQEGWGGLFCNQ

DLNYCTHHKPCKNGATCTNTGQGSYTCSCRPGYTGATCEL
DNA (SEQ ID NO: 106):
CATATG

CATCACCATCACCATCAC

GGTGGCGAGAATCTATACTTCCAGGGC

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

*GGGTCCTCAGGATCTAGTGGA*

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

*GGGTCCTCAGGATCTAGTGGA*

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

*GGGTCCTCAGGATCTAGTGGA*

TTTGTCTGTGACGAGCATTACTATGGTGAAGGGTGCTCTGTGTTTTGTAGGCCAAGGGACGATGCGTTC

GGACATTTTACCTGCGGGGAACGAGGTGAGAAGGTTTGCAACCCGGGGTGGAAGGGACCCTACTGCAC

TGAACCAATTTGCTTACCAGGGTGTGATGAGCAACACGGATTCTGCGATAAGCCGGGCGAATGTAAGTG

TCGGGTAGGCTGGCAAGGCCGCTACTGCGATGAGTGTATACGTTACCCAGGATGTTTACACGGAACATG

TCAGCAACCGTGGCAGTGTAATTGCCAAGAAGGGTGGGGAGGGTTGTTCTGTAACCAG

*GGGTCCTCAGGATCTAGTGGA*

TTCGTATGCGATGAACATTATTACGGAGAAGGCTGTAGTGTTTTCTGTAGGCCTAGAGACGATGCTTTCG

GGCATTTTACGTGCGGCGAGAGAGGCGAGAAAGTGTGTAATCCTGGGTGGAAAGGGCCCTATTGTACA

GAACCAATATGCCTTCCAGGTTGCGACGAGCAACACGGTTTTTGTGACAAACCCGGCGAATGTAAATGC

CGGGTCGGGTGGCAGGGCCGATATTGCGACGAATGCATCCGTTATCCCGGATGTCTGCATGGTACTTGC

CAGCAACCTTGGCAGTGTAACTGCCAAGAAGGATGGGGGGGTCTATTTTGCAATCAA TAA

CGATCC

Mouse Tandem Sequences
1) MuDLL1. DSL-EGF12.Tan3

(SEQ ID NO: 44)

MAAHHHHHH GGENLYFQG

FVCDEHYYGEGCSVFCRPRDDAFGHFTCGDRGEKMCDPGWKGQYC

-continued

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 107):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG TAA

GGATCC

2) MuDLL1. DSL-EGF12.Tan4

(SEQ ID NO: 45)

MAAHHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

-continued

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNQEGWGGLFCNQ

DNA (SEQ ID NO: 108):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG TAA

GGATCC

3) MuDLL1. DSL-EGF12.Tan5

(SEQ ID NO: 46)

MAAHHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

-continued

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ
DNA (SEQ ID NO: 109):
CATATGGCCGCACATCATCATCACCACCATGGTGGTGAAAACCTGTATTTTCAGGGCTTTGTGTGCGATG

AGCATTATTACGGTGAAGGCTGTAGCGTGTTTTGTCGACCGCGTGATGACGCATTTGGCCATTTTACCTG

CGGTGACCGCGGCGAGAAAATGTGCGATCCGGGCTGGAAAGGTCAGTATTGTACAGACCCTATTTGTCT

GCCGGGCTGTGACGATCAGCACGGCTACTGTGACAAGCCGGGCGAATGTAAATGTCGCGTTGGCTGGC

AGGGTCGCTATTGTGATGAATGCATCCGCTACCCGGGTTGCTTACATGG CACATGCCAACAGCCTTGGC

AATGTAATTGTCAGGAAGGCTGGGGAGGTTTATTTTGTAATCAAGGCAGTTCAGGGTCTAGTGGTTTTG

TGTGCGACGAACATTACTACGGCGAGGGCTGCAGCGTGTTCTGTCGACCTCGTGACGACGCTTTTGGCC

ACTTCACCTGCGGCGATCGCGGCGAGAAGATGTGCGATCCTGGCTGGAAAGGCCAGTACTGCACAGAT

CCGATTTGCCTGCCGGGCTGTGATGACCAACATGGCTATTGTGATAAGCCGGGCGAGTGTAAGTGCCGT

GTTGGTTGGCAAGGCCGCTATTGCGATGAGTGCATCCGTTATCCTGGCTGTCTGCATGGCACTTGTCAGC

AACCGTGGCAATGCAACTGCCAAGAGGGTTGGGGTGGGTTGTTCTGCAATCAGGGATCTTCGGGGTCC

TCTGGTTTTGTGTGTGACGAACACTATTACGGCGAGGGCTGCAGTGTGTTCTGCCGCCCTCGTGACGAC

GCCTTCGGTCATTTCACCTGTGGCGATCGTGGCGAAAAGATGTGTGATCCTGGTTGGAAGGGTCAATAC

TGTACCGACCCGATCTGTCTGCCTGGCTGCGACGACCAGCATGGTTACTGTGACAAACCGGGCGAGTGT

AAATGCCGTGTTGGTTGGCAAGGCCGCTACTGTGATGAGTGCATTCGCTATCCTGGTTGCCTGCACGGT

ACCTGCCAGCAACCTTGGCAATGCAACTGCCAGGAAGGTTGGGGGGGCCTGTTCTGCAACCAGGGTAG

CTCTGGCTCATCCGGGTTCGTTTGCGACGAGCATTATTACGGCGAAGGCTGTAGTGTTTTCTGCCGTCCT

CGTGACGACGCATTTGGCCATTTCACCTGTGGTGACCGCGGCGAAAAAATGTGTGACCCTGGCTGGAAG

GGCCAATATTGCACTGATCCGATTTGTCTGCCGGGTTGTGACGATCAACACGGCTACTGCGATAAGCCG

GGCGAATGTAAGTGCCGTGTGGGTTGGCAAGGCCGCTATTGTGATGAATGCATTCGCTATCCGGGCTGT

CTGCACGGCACTTGCCAGCAGCCGTGGCAATGTAATTGCCAAGAAGGTTGGGGCGGACTCTTTTGTAAC

CAAGGATCATCAGGTAGTAGCGGCTTTGTTTGTGACGAGCACTACTATGGTGAAGGCTGCAGCGTTTTT

TGTCGTCCGCGCGATGATGCCTTTGGTCATTTCACCTGTGGCGACCGCGGCGAGAAAATGTGCGATCCT

-continued

GGTTGGAAAGGCCAGTATTGCACCGATCCGATCTGCCTGCCGGGCTGCGACGATCAACACGGCTATTGT

GACAAACCGGGTGAATGCAAATGTCGTGTGGGTTGGCAGGGCCGCTACTGCGATGAGTGTATTCGTTA

TCCTGGTTGCCTGCATGGCACATGTCAACAGCCGTGGCAGTGCAATTGTCAGGAAGGTTGGGGCGGCCT

GTTCTGCAACCAGTAAGGATCC

4) MuDLL1. DSL-EGF12.Tan6

(SEQ ID NO: 47)

MAAHHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 110):

CATATGGCCGCACATCATCATCACCACCATGGTGGTGAAAACCTGTATTTTCAGGGCTTTGTGTGCGATG

AGCATTATTACGGTGAAGGCTGTAGCGTGTTTTGTCGACCGCGTGATGACGCATTTGGCCATTTTACCTG

CGGTGACCGCGGCGAGAAAATGTGCGATCCGGGCTGGAAAGGTCAGTATTGTACAGATCCTATCTGCCT

GCCGGGTTGTGACGATCAACACGGTTATTGCGACAAGCCGGGTGAATGCAAGTGTCGTGTGGGCTGGC

AGGGCCGTTATTGTGACGAATGTATTCGCTATCCGGGTTGCTTACACGGCACATGTCAACAGCCGTGGC

AGTGTAATTGCCAGGAAGGTTGGGGAGGTTTATTTTGTAATCAAGGTTCTTCCGGATCGAGTGGCTTCG

TGTGTGACGAGCACTACTATGGCGAGGGTTGTAGCGTTTTCTGTCGCCCGCGCGACGACGCTTTTGGCC

ACTTTACCTGTGGCGATCGCGGTGAGAAAATGTGTGATCCTGGTTGGAAGGGCCAGTACTGCACAGACC

CGATTTGTCTGCCGGGTTGCGATGATCAGCATGGCTACTGCGACAAACCGGGTGAATGCAAATGTCGTG

TGGGCTGGCAGGGCCGCTATTGCGACGAGTGTATTCGCTACCCGGGTTGCTTACATGGCACATGCCAAC

AGCCTTGGCAATGTAATTGTCAGGAAGGCTGGGGAGGTTTATTTTGTAATCAAGGCAGTTCAGGGTCTA

GTGGTTTTGTGTGCGACGAACATTACTACGGCGAGGGCTGCAGCGTGTTCTGTCGACCTCGTGACGACG

-continued

CTTTTGGCCACTTCACCTGCGGCGATCGCGGCGAGAAGATGTGCGATCCTGGCTGGAAAGGCCAGTACT

GCACAGATCCGATTTGCCTGCCGGGCTGTGATGACCAACATGGCTATTGTGATAAGCCGGGCGAGTGTA

AGTGCCGTGTTGGTTGGCAAGGCCGCTATTGCGATGAGTGCATCCGTTATCCTGGCTGTCTGCATGGCA

CTTGTCAGCAACCGTGGCAATGCAACTGCCAAGAGGGTTGGGGTGGGTTGTTCTGCAATCAGGGATCTT

CGGGGTCCTCTGGTTTTGTGTGTGACGAACACTATTACGGCGAGGGCTGCAGTGTGTTCTGCCGCCCTC

GTGACGACGCCTTCGGTCATTTCACCTGTGGCGATCGTGGCGAAAAGATGTGTGATCCTGGTTGGAAGG

GTCAATACTGTACCGACCCGATCTGTCTGCCTGGCTGCGACGACCAGCATGGTTACTGTGACAAACCGG

GCGAGTGTAAATGCCGTGTTGGTTGGCAAGGCCGCTACTGTGATGAGTGCATTCGCTATCCTGGTTGCC

TGCACGGTACCTGCCAGCAACCTTGGCAATGCAACTGCCAGGAAGGTTGGGGGGGCCTGTTCTGCAACC

AGGGTAGCTCTGGCTCATCCGGGTTCGTTTGCGACGAGCATTATTACGGCGAAGGCTGTAGTGTTTTCT

GCCGTCCTCGTGACGACGCATTTGGCCATTTCACCTGTGGTGACCGCGGCGAAAAAATGTGTGACCCTG

GCTGGAAGGGCCAATATTGCACTGATCCGATTTGTCTGCCGGGTTGTGACGATCAACACGGCTACTGCG

ATAAGCCGGGCGAATGTAAGTGCCGTGTGGGTTGGCAAGGCCGCTATTGTGATGAATGCATTCGCTATC

CGGGCTGTCTGCACGGCACTTGCCAGCAGCCGTGGCAATGTAATTGCCAAGAAGGTTGGGGCGGACTC

TTTTGTAACCAAGGATCATCAGGTAGTAGCGGCTTTGTTTGTGACGAGCACTACTATGGTGAAGGCTGC

AGCGTTTTTTGTCGTCCGCGCGATGATGCCTTTGGTCATTTCACCTGTGGCGACCGCGGCGAGAAAATGT

GCGATCCTGGTTGGAAAGGCCAGTATTGCACCGATCCGATCTGCCTGCCGGGCTGCGACGATCAACACG

GCTATTGTGACAAACCGGGTGAATGCAAATGTCGTGTGGGTTGGCAGGGCCGCTACTGCGATGAGTGT

ATTCGTTATCCTGGTTGCCTGCATGGCACATGTCAACAGCCGTGGCAGTGCAATTGTCAGGAAGGTTGG

GGCGGCCTGTTCTGCAACCAGTAAGGATCC

5) MuDLL1. DSL-EGF12.Tan7

(SEQ ID NO: 48)

MAAHHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

-continued

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 111):

CATATGGCCGCACATCATCATCACCACCATGGTGGTGAAAACCTGTATTTTCAGGGCTTTGTGTGCGATG

AGCATTATTACGGTGAAGGCTGTAGCGTGTTTTGTCGACCGCGTGATGACGCATTTGGCCATTTTACCTG

CGGTGACCGCGGCGAGAAAATGTGCGATCCGGGCTGGAAAGGTCAGTATTGTACAGACCCTATTTGTCT

GCCGGGCTGTGACGATCAGCACGGCTACTGTGACAAGCCGGGCGAATGTAAATGTCGCGTTGGCTGGC

AGGGTCGCTATTGTGATGAATGCATCCGCTACCCGGGCTGCCTGCACGGTACCTGTCAGCAGCCGTGGC

AATGCAATTGTCAAGAGGGCTGGGGAGGTTTATTTTGTAATCAAGGCTCGAGTGGAAGCTCAGGCTTTG

TGTGTGATGAGCATTATTACGGCGAAGGCTGCAGCGTTTTCTGTCGCCCGCGCGATGACGCATTTGGCC

ACTTCACATGTGGCGATCGCGGCGAAAAGATGTGCGACCCTGGCTGGAAAGGCCAATATTGTACAGATC

CTATCTGCCTGCCGGGTTGTGACGATCAACACGGTTATTGCGACAAGCCGGGTGAATGCAAGTGTCGTG

TGGGCTGGCAGGGCCGTTATTGTGACGAATGTATTCGCTATCCGGGTTGCTTACACGGCACATGTCAAC

AGCCGTGGCAGTGTAATTGCCAGGAAGGTTGGGGAGGTTTATTTTGTAATCAAGGTTCTTCCGGATCGA

GTGGCTTCGTGTGTGACGAGCACTACTATGGCGAGGGTTGTAGCGTTTTCTGTCGCCCGCGCGACGACG

CTTTTGGCCACTTTACCTGTGGCGATCGCGGTGAGAAAATGTGTGATCCTGGTTGGAAGGGCCAGTACT

GCACAGACCCGATTTGTCTGCCGGGTTGCGATGATCAGCATGGCTACTGCGACAAACCGGGTGAATGCA

AATGTCGTGTGGGCTGGCAGGGCCGCTATTGCGACGAGTGTATTCGCTACCCGGGTTGCTTACATGGCA

CATGCCAACAGCCTTGGCAATGTAATTGTCAGGAAGGCTGGGGAGGTTTATTTTGTAATCAAGGCAGTT

CAGGGTCTAGTGGTTTTGTGTGCGACGAACATTACTACGGCGAGGGCTGCAGCGTGTTCTGTCGACCTC

GTGACGACGCTTTTGGCCACTTCACCTGCGGCGATCGCGGCGAGAAGATGTGCGATCCTGGCTGGAAA

GGCCAGTACTGCACAGATCCGATTTGCCTGCCGGGCTGTGATGACCAACATGGCTATTGTGATAAGCCG

GGCGAGTGTAAGTGCCGTGTTGGTTGGCAAGGCCGCTATTGCGATGAGTGCATCCGTTATCCTGGCTGT

CTGCATGGCACTTGTCAGCAACCGTGGCAATGCAACTGCCAAGAGGGTTGGGGTGGGTTGTTCTGCAAT

CAGGGATCTTCGGGGTCCTCTGGTTTTGTGTGTGACGAACACTATTACGGCGAGGGCTGCAGTGTGTTC

TGCCGCCCTCGTGACGACGCCTTCGGTCATTTCACCTGTGGCGATCGTGGCGAAAAGATGTGTGATCCT

GGTTGGAAGGGTCAATACTGTACCGACCCGATCTGTCTGCCTGGCTGCGACGACCAGCATGGTTACTGT

GACAAACCGGGCGAGTGTAAATGCCGTGTTGGTTGGCAAGGCCGCTACTGTGATGAGTGCATTCGCTAT

CCTGGTTGCCTGCACGGTACCTGCCAGCAACCTTGGCAATGCAACTGCCAGGAAGGTTGGGGGGGCCT

GTTCTGCAACCAGGGTAGCTCTGGCTCATCCGGGTTCGTTTGCGACGAGCATTATTACGGCGAAGGCTG

TAGTGTTTTCTGCCGTCCTCGTGACGACGCATTTGGCCATTTCACCTGTGGTGACCGCGGCGAAAAAATG

TGTGACCCTGGCTGGAAGGGCCAATATTGCACTGATCCGATTTGTCTGCCGGGTTGTGACGATCAACAC

GGCTACTGCGATAAGCCGGGCGAATGTAAGTGCCGTGTGGGTTGGCAAGGCCGCTATTGTGATGAATG

CATTCGCTATCCGGGCTGTCTGCACGGCACTTGCCAGCAGCCGTGGCAATGTAATTGCCAAGAAGGTTG

GGGCGGACTCTTTTGTAACCAAGGATCATCAGGTAGTAGCGGCTTTGTTTGTGACGAGCACTACTATGG

TGAAGGCTGCAGCGTTTTTTGTCGTCCGCGCGATGATGCCTTTGGTCATTTCACCTGTGGCGACCGCGGC

-continued

GAGAAAATGTGCGATCCTGGTTGGAAAGGCCAGTATTGCACCGATCCGATCTGCCTGCCGGGCTGCGAC

GATCAACACGGCTATTGTGACAAACCGGGTGAATGCAAATGTCGTGTGGGTTGGCAGGGCCGCTACTG

CGATGAGTGTATTCGTTATCCTGGTTGCCTGCATGGCACATGTCAACAGCCGTGGCAGTGCAATTGTCA

GGAAGGTTGGGGCGGCCTGTTCTGCAACCAGTAAGGATCC

6) MuDLL1. DSL-EGF12.Tan8

(SEQ ID NO: 49)

MAAHHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 112):

CATATGGCCGCACATCATCATCACCACCATGGTGGTGAAAACCTGTATTTTCAGGGCTTTGTGTGCGATG

AGCATTATTACGGTGAAGGCTGTAGCGTGTTTTGTCGACCGCGTGATGACGCATTTGGCCATTTTACCTG

CGGTGACCGCGGCGAGAAAATGTGCGATCCGGGCTGGAAAGGTCAGTATTGTACAGACCCTATTTGTCT

GCCGGGCTGTGACGATCAGCACGGCTACTGTGACAAGCCGGGCGAATGTAAATGTCGCGTTGGCTGGC

-continued

AGGGTCGCTATTGTGATGAATGCATCCGCTACCCGGGCTGCCTGCACGGTACCTGTCAGCAGCCGTGGC

AATGCAATTGTCAAGAGGGCTGGGGAGGTTTATTTTGTAATCAAGGCTCGAGCGGTTCATCGGGATTTG

TTTGCGATGAACACTATTATGGTGAAGGTTGTAGTGTGTTTTGCCGCCCGCGCGACGACGCTTTTGGTCA

TTTTACATGCGGCGATCGCGGTGAAAAAATGTGCGATCCGGGTTGGAAGGGCCAGTACTGTACCGATCC

GATTTGTCTGCCGGGTTGCGATGATCAGCATGGCTATTGTGACAAGCCGGGTGAGTGCAAGTGTCGTGT

GGGTTGGCAGGGCCGCTACTGTGACGAGTGCATTCGCTATCCGGGCTGTTTACACGGCACCTGTCAGCA

GCCGTGGCAATGTAATTGTCAAGAAGGCTGGGGAGGTTTATTTTGTAATCAAGGCTCGAGTGGAAGCTC

AGGCTTTGTGTGTGATGAGCATTATTACGGCGAAGGCTGCAGCGTTTTCTGTCGCCCGCGCGATGACGC

ATTTGGCCACTTCACATGTGGCGATCGCGGCGAAAAGATGTGCGACCCTGGCTGGAAAGGCCAATATTG

TACAGATCCTATCTGCCTGCCGGGTTGTGACGATCAACACGGTTATTGCGACAAGCCGGGTGAATGCAA

GTGTCGTGTGGGCTGGCAGGGCCGTTATTGTGACGAATGTATTCGCTATCCGGGTTGCTTACACGGCAC

ATGTCAACAGCCGTGGCAGTGTAATTGCCAGGAAGGTTGGGGAGGTTTATTTTGTAATCAAGGTTCTTC

CGGATCGAGTGGCTTCGTGTGTGACGAGCACTACTATGGCGAGGGTTGTAGCGTTTTCTGTCGCCCGCG

CGACGACGCTTTTGGCCACTTTACCTGTGGCGATCGCGGTGAGAAAATGTGTGATCCTGGTTGGAAGGG

CCAGTACTGCACAGACCCGATTTGTCTGCCGGGTTGCGATGATCAGCATGGCTACTGCGACAAACCGGG

TGAATGCAAATGTCGTGTGGGCTGGCAGGGCCGCTATTGCGACGAGTGTATTCGCTACCCGGGTTGCTT

ACATGGCACATGCCAACAGCCTTGGCAATGTAATTGTCAGGAAGGCTGGGGAGGTTTATTTTGTAATCA

AGGCAGTTCAGGGTCTAGTGGTTTTGTGTGCGACGAACATTACTACGGCGAGGGCTGCAGCGTGTTCTG

TCGACCTCGTGACGACGCTTTTGGCCACTTCACCTGCGGCGATCGCGGCGAGAAGATGTGCGATCCTGG

CTGGAAAGGCCAGTACTGCACAGATCCGATTTGCCTGCCGGGCTGTGATGACCAACATGGCTATTGTGA

TAAGCCGGGCGAGTGTAAGTGCCGTGTTGGTTGGCAAGGCCGCTATTGCGATGAGTGCATCCGTTATCC

TGGCTGTCTGCATGGCACTTGTCAGCAACCGTGGCAATGCAACTGCCAAGAGGGTTGGGGTGGGTTGTT

CTGCAATCAGGGATCTTCGGGGTCCTCTGGTTTTGTGTGTGACGAACACTATTACGGCGAGGGCTGCAG

TGTGTTCTGCCGCCCTCGTGACGACGCCTTCGGTCATTTCACCTGTGGCGATCGTGGCGAAAAGATGTGT

GATCCTGGTTGGAAGGGTCAATACTGTACCGACCCGATCTGTCTGCCTGGCTGCGACGACCAGCATGGT

TACTGTGACAAACCGGGCGAGTGTAAATGCCGTGTTGGTTGGCAAGGCCGCTACTGTGATGAGTGCATT

CGCTATCCTGGTTGCCTGCACGGTACCTGCCAGCAACCTTGGCAATGCAACTGCCAGGAAGGTTGGGGG

GGCCTGTTCTGCAACCAGGGTAGCTCTGGCTCATCCGGGTTCGTTTGCGACGAGCATTATTACGGCGAA

GGCTGTAGTGTTTTCTGCCGTCCTCGTGACGACGCATTTGGCCATTTCACCTGTGGTGACCGCGGCGAAA

AAATGTGTGACCCTGGCTGGAAGGGCCAATATTGCACTGATCCGATTTGTCTGCCGGGTTGTGACGATC

AACACGGCTACTGCGATAAGCCGGGCGAATGTAAGTGCCGTGTGGGTTGGCAAGGCCGCTATTGTGAT

GAATGCATTCGCTATCCGGGCTGTCTGCACGGCACTTGCCAGCAGCCGTGGCAATGTAATTGCCAAGAA

GGTTGGGGCGGACTCTTTTGTAACCAAGGATCATCAGGTAGTAGCGGCTTTGTTTGTGACGAGCACTAC

TATGGTGAAGGCTGCAGCGTTTTTTGTCGTCCGCGCGATGATGCCTTTGGTCATTTCACCTGTGGCGACC

GCG GCGAGAAAATGTGCGATCCTGGTTGGAAAGGCCAGTATTGCACCGATCCGATCTGCCTGCCGGGC

-continued

TGCGACGATCAACACGGCTATTGTGACAAACCGGGTGAATGCAAATGTCGTGTGGGTTGGCAGGGCCG

CTACTGCGATGAGTGTATTCGTTATCCTGGTTGCCTGCATGGCACATGTCAACAGCCGTGGCAGTGCAAT

TGTCAGGAAGGTTGGGGCGGCCTGTTCTGCAACCAGTAAGGATCC

Mouse Linker Variant Sequences

1) MuDLL1. DSL-EGF12.G452.Tan2

(SEQ ID NO: 50)

MAAHHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GGGGSGGGGS

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 113):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGC GGA GGa GGC TCT GGC GGA GGT GGC TCT*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG TAA

GGATCC

2) MuDLL1. DSL-EGF12.G453.Tan2

(SEQ ID NO: 51)

MAAHHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GGGGSGGGGSGGGGS

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 114):

CATATG

CATCACCATCACCATCAC

GGTGGGGAGAATCTCTATTTCCAGGGG

-continued

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGC GGA GGa GGC TCT GGC GGA GGT GGC TCT GGC GGA GGT GGC TCa*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG TAA

GGATCC

3) MuDLL1. DSL-EGF12.G454.Tan2

(SEQ ID NO: 52)

MAAHHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GGGGSGGGGSGGGGSGGGGS

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 115):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGC GGA GGa GGC TCT GGC GGA GGT GGC TCT GGC GGA GGT GGC agC GGC GGA GGT GGa*

*TCa*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG TAA

GGATCC

4) MuDLL1. DSL-EGF12.G452.Tan4

(SEQ ID NO: 53)

MAAHHHHHH GGENLYFQG

FVCDEHYYGEGCSVFCRPRDDAFGHFTCGDRGEKMCDPGWKGQYC

-continued

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GGGGSGGGGS

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 116):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGC GGA GGa GGC TCT GGC GGA GGT GGC TCT*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

-continued

TGTCAGCAACCCTGGCAGTGCAATTGTCAGGAAGGATGGGGTGGACTTTTTTGTAATCAG TAA

GGATCC

5) MuDLL1. DSL-EGF12.G453.Tan4

(SEQ ID NO: 54)

MAAHHHHHH GGENLYFQG

FVCDEHYYGEGCSVFCRPRDDAFGHFTCGDRGEKMCDPGWKGQYC

TDPICLPGCDDQHGYCDKPG ECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GGGGSGGGGSGGGGS

FVCDEHYYGEGCSVFCRPRDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPG ECKCRVGWQGRYCD

ECIRYPGCLHGTCQQPWQCNCQEGWGGLFCNQ

DNA (SEQ ID NO: 117):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGC GGA GGa GGC TCT GGC GGA GGT GGC TCT GGC GGA GGT GGC TCa*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG

*GGCTCGTCTGGCTCCTCGGGG*

-continued

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG TAA

GGATCC

6) MuDLL1.DSL-EGF12.G454.Tan4

(SEQ ID NO: 55)

MAAHHHHHH GGENLYFQG

FVCDEHYYGEGCSVFCRPRDDAFGHFTCGDRGEKMCDPGWKGQYC

TDPICLPGCDDQHGYCDKPGECKCRVGWQGRYCD

ECIRYPGCL GTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGG LFCNQ

GGGGSGGGGSGGGGSGGGGS

FVCDEHYYGEGCSVFCRPRDDAFGHFTCGDRGEKMCDPGWKGQYC

TDPICLPGCDDQHGYCDKPGECKCRVGWQGRYCD

EC RYPGCLHGTCQQPWQCNCQEGWGGLFCNQ

GSSGSSG

FVCDEHYYGEGCSVFCRPRDDAFGHFTCGDRGEKMCDPGWKGQYC

TDPICLPGCDDQHGYCDKPGECKCRVGWQGRYCD

ECIRYPGCLHGTCQQPWQCNCQEGWGGLFCNQ

DNA (SEQ ID NO: 118):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGC GGA GGa GGC TCT GGC GGA GGT GGC TCT GGC GGA GGT GGC agC GGC GGA GGT GGa*

*TCa*

-continued

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG TAA

GGATCC

EGF-Free Human Constructs

1) HuDLL1.PelB-MNNL-DSL (SEQ ID NO: 56)

MKYLLPTAAAGLLLLAAQPAMA A HHHHHH GGENLYFQG

QVWSSGVFELKLQEFVNKKGLLGNRNCCRGGAGPPPCACRTFFRVCLKHYQASVSPEPPCTYGSAVTPVLG

VDSFSLPDGGGADSAFSNPIRFPFGFTWPGTFSLIIEALHTDSPDDLATENPERLISRLATQRHLTVGEEWSQD

LHSSGRTDLKYSYR FVCDEHYYGEGCSVFCRPRDDAFGHFTCGERGEKVCNPGWKGPYCT

2) HuDLL1.PelB-MNNL (SEQ ID NO: 57)

MKYLLPTAAAGLLLLAAQPAMA A HHHHHH GGENLYFQG

QVWSSGVFELKLQEFVNKKGLLGNRNCCRGGAGPPPCACRTFFRVCLKHYQASVSPEPPCTYGSAVTPVLG

VDSFSLPDGGGADSAFSNPIRFPFGFTWPGTFSLIIEALHTDSPDDLATENPERLISRLATQRHLTVGEEWSQD

LHSSGRTDLKYSYR

3) HuDLL1.DSL (SEQ ID NO: 58)

HHHHHH GGENLYFQG

FVCDEHYYGEGCSVFCRPRDDAFGHFTCGERGEKVCNPGWKGPYCT

EGF-Free Mouse Constructs

1) MuDLL1.PelB-MNNL-DSL (SEQ ID NO: 59)

MKYLLPTAAAGLLLLAAQPAMA A HHHHHH GGENLYFQG

QVWSSGVFELKLQEFVNKKGLLGNRNCCRGGSGPPCACRTFFRVCLKHYQASVSPEPPCTYGSAVTPVLGVD

SFSLPDGAGIDPAFSNPIRFPFGFTWPGTFSLIIEALHTDSPDDLATENPERLISRLTTQRHLTVGEEWSQDLHS

SGRTDLRYSYR FVCDEHYYGEGCSVFCRPRDDAFGHFTCGDRGEKMCDPGWKGQYC

2) MuDLL1.PeIB-MNNL (SEQ ID NO: 60)

MKYLLPTAAAGLLLLAAQPAMA A HHHHHH GGENLYFQG

QVWSSGVFELKLQEFVNKKGLLGNRNCCRGGSGPPCACRTFFRVCLKHYQASVSPEPPCTYGSAVTPVLGVD

SFSLPDGAGIDPAFSNPIRFPFGFTWPGTFSLIIEALHTDSPDDLATENPERLISRLTTQRHLTVGEEWSQDLHS

SGRTDLRYSYR

3) MuDLL1.DSL (SEQ ID NO:61)

HHHHH GGENLYFQG

FVCDEHYYGEGCSVFCRPRDDAFGHFTCGDRGEKMCDPGWKGQYC

FLAG-Tagged Constructs

1) MuDLL1.DSL-EGF12-FLAG

-continued (SEQ ID NO: 62)

MAAHHHHHHGGENLYFQGFVCDEHYYGEGCSVFCRPRDDAFGHFTCGDRGEKMCDPGWKGQYCTDPIC

LPGCDDQHGYCDKPGECKCRVGWQGRYCDECIRYPGCLHGTCQQPWQCNCQEGWGGLFCNQGSSGDY

KDDDDK

DNA (SEQ ID NO: 119):
CATATGGCASCTCATCACCATCACCATCACGGTGGGGAGAATCTCTATTTCCAGGGGTTCGTATGTGACG

AACACTATTACGGAGAGGGGTGCAGTGTCTTCTGCCGTCCGAGAGACGATGCCTTTGGTCACTTTACSTG

TGGAGACAGAGGCGAAAAAATGTGTGATCCAGGATGGAAGGGGCAGTACTGCACAGATCCGATATGCT

TACCGGGTTGCGATGACCAACATGGTTACTGTGATAAGCCGGGGGAATGCAAGTGCAGGGTGGGGTG

GCAAGGAAGGTATTGCGATGAATGCATCCGATATCCAGGCTGTCTACACGGAACTTGTCAGCAACCCTG

GCAGTGCAATTGTCAGGAAGGATGGGGTGGACTTTTTTGTAATCAG GGT AGC AGC GGC GAC TAC

AAG GAT GAC GAC GAT AAG TAAGGATCC

2) MuDLL1.DSL-EGF12.Tan4-FLAG (SEQ ID NO: 63)

MAAHHHHHHGGENLYFQGFVCDEHYYGEGCSVFCRPRDDAFGHFTCGDRGEKMCDPGWKGQYCTDPIC

LPGCDDQHGYCDKPGECKCRVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQGSSGDYKDDDDK

DNA (SEQ ID NO: 120):

CATATG

CATCACCATCACCATCAC

GGTGGGGAGAATCTCTATTTCCAGGGG

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTCGTATGTGACGAACACTATTACGGAGAGGGGTGCAGTGTCTTCTGCCGTCCGAGAGACGATGCCTTT

GGTCACTTTACGTGTGGAGACAGAGGCGAAAAAATGTGTGATCCAGGATGGAAAGGACAGTATTGTAC

GGACCCCATTTGCCTTCCTGGCTGCGATGACCAACACGGGTATTGTGACAAACCCGGCGAGTGCAAGTG

TCGTGTTGGGTGGCAAGGGCGATACTGCGACGAGTGCATAAGATACCCTGGTTGCCTGCACGGGACCT

GCCAGCAACCTTGGCAATGTAACTGTCAAGAAGGATGGGGAGGCTTATTCTGCAACCAA

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

-continued

TGTCAGCAACCCTGGCAGTGCAATTGTCAGGAAGGATGGGGTGGACTTTTTTGTAATCAG

*GGCTCGTCTGGCTCCTCGGGG*

TTTGTATGCGACGAACATTATTACGGCGAGGGGTGCTCAGTTTTTTGTCGGCCACGCGATGACGCGTTC

GGTCATTTTACCTGCGGCGATCGAGGCGAGAAAATGTGTGATCCAGGATGGAAGGGGCAGTACTGCAC

AGATCCGATATGCTTACCGGGTTGCGATGACCAACATGGTTACTGTGATAAGCCGGGGGAATGCAAGT

GCAGGGTGGGGTGGCAAGGAAGGTATTGCGATGAATGCATCCGATATCCAGGCTGTCTACACGGAACT

TGTCAGCAACCCTGGCAGTGCAATTGTCAGGAAGGATGGGGTGGACTTTTTTGTAATCAG GGT AGC

AGC GGC GAC TAC AAG GAT GAC GAC GAT AAG TAAGGATCC
For sequences SEQ ID NO: 121 to SEQ ID NO: 128 below
Species: Mouse
Codon bias: *E. coli*
Functional Unit: DSL-EGF1-EGF2
Linker: GSSGSSG
Format: NdeI-His6-TEV-(DLL 1 -Linker)$_7$-DLL1 -BamHI
8x DNA Sequence (SEQ ID NO: 121)

CATATG GCCGCA CATCATCATCACCACCAT GGTGGT GAA AAC CTG TAT TTT CAG GGC

TTTGTGTGCGATGAGCATTATTACGGTGAAGGCTGTAGCGTGTTTTGTCGACCGCGTGATGACGCATTT

GGCCATTTTACCTGCGGTGACCGCGGCGAGAAAATGTGCGATCCGGGCTGGAAAGGTCAGTATTGTAC

AGACCCTATTTGTCTGCCGGGCTGTGACGATCAGCACGGCTACTGTGACAAGCCGGGCGAATGTAAATG

TCGCGTTGGCTGGCAGGGTCGCTATTGTGATGAATGCATCCGCTACCCGGGCTGCCTGCACGGTACCTG

TCAGCAGCCGTGGCAATGCAATTGTCAAGAGGGCTGGGG

A GGT TTA TTT TGT AAT CAA

*GGc TCG AGC GGT TCA TCG GGA*

TTTGTTTGCGATGAACACTATTATGGTGAAGGTTGTAGTGTGTTTTGCCGCCCGCGCGACGACGCTTTTG

GTCATTTTACATGCGGCGATCGCGGTGAAAAAATGTGCGATCCGGGTTGGAAGGGCCAGTACTGTACC

GATCCGATTTGTCTGCCGGGTTGCGATGATCAGCATGGCTATTGTGACAAGCCGGGTGAGTGCAAGTGT

CGTGTGGGTTGGCAGGGCCGCTACTGTGACGAGTGCATTCGCTATCCGGGCTGTTTACACGGCACCTGT

CAGCAGCCGTGGCAATGTAATTGTCAAGAAGGCTGGGG

A GGT TTA TTT TGT AAT CAA

*GGc TCG AGT GGA AGC TCA GGC*

TTTGTGTGTGATGAGCATTATTACGGCGAAGGCTGCAGCGTTTTCTGTCGCCCGCGCGATGACGCATTTG

GCCACTTCACATGTGGCGATCGCGGCGAAAAGATGTGCGACCCTGGCTGGAAAGGCCAATATTGtACAG

ATCCTATCTGCCTGCCGGGTTGTGACGATCAACACGGTTATTGCGACAAGCCGGGTGAATGCAAGTGTC

GTGTGGGCTGGCAGGGCCGTTATTGTGACGAATGTATTCGCTATCCGGGTTGCTTACACGGCACATGTC

AACAGCCGTGGCAGTGTAATTGCCAGGAAGGTTGGGG

A GGT TTA TTT TGT AAT CAA

*GGT TCT TCC GGA TCG AGT GGC*

TTCGTGTGTGACGAGCACTACTATGGCGAGGGTTGTAGCGTTTTCTGTCGCCCGCGCGACGACGCTTTT

GGCCACTTTACCTGTGGCGATCGCGGTGAGAAAATGTGTGATCCTGGTTGGAAGGGCCAGTACTGCACA

GACCCGATTTGTCTGCCGGGTTGCGATGATCAGCATGGCTACTGCGACAAACCGGGTGAATGCAAATGT

CGTGTGGGCTGGCAGGGCCGCTATTGCGACGAGTGTATTCGCTACCCGGGTTGCTTACATGGCACATGC

CAACAGCCTTGGCAATGTAATTGTCAGGAAGGCTGGGG

A GGT TTA TTT TGT AAT CAA

*GGC AGT TCA GGG TCT AGT GGT*

-continued

TTTGTGTGCGACGAACATTACTACGGCGAGGGCTGCAGCGTGTTCTGTCGACCTCGTGACGACGCTTTT

GGCCACTTCACCTGCGGCGATCGCGGCGAGAAGATGTGCGATCCTGGCTGGAAAGGCCAGTACTGCAC

AGATCCGATTTGCCTGCCGGGCTGTGATGACCAACATGGCTATTGTGATAAGCCGGGCGAGTGTAAGTG

CCGTGTTGGTTGGCAAGGCCGCTATTGCGATGAGTGCATCCGTTATCCTGGCTGTCTGCATGGCACTTGT

CAGCAACCGTGGCAATGCAACTGCCAAGAGGGTTGGGG

T GGG TTG TTC TGC AAT CAG

*GGA TCT TCG GGG TCC TCT GGT*

TTTGTGTGTGACGAACACTATTACGGCGAGGGCTGCAGTGTGTTCTGCCGCCCTCGTGACGACGCCTTC

GGTCATTTCACCTGTGGCGATCGTGGCGAAAAGATGTGTGATCCTGGTTGGAAGGGTCAATACTGTACC

GACCCGATCTGTCTGCCTGGCTGCGACGACCAGCATGGTTACTGTGACAAACCGGGCGAGTGTAAATGC

CGTGTTGGTTGGCAAGGCCGCTACTGTGATGAGTGCATTCGCTATCCTGGTTGCCTGCACGGTACCTGCC

AGCAACCTTGGCAATGCAACTGCCAGGAAGGTTGGGG

G GGC CTG TTC TGC AAC CAG

*GGT AGC TCT GGC TCA TCC GGG*

TTCGTTTGCGACGAGCATTATTACGGCGAAGGCTGTAGTGTTTTCTGCCGTCCTCGTGACGACGCATTTG

GCCATTTCACCTGTGGTGACCGCGGCGAAAAAATGTGTGACCCTGGCTGGAAGGGCCAATATTGCACTG

ATCCGATTTGTCTGCCGGGTTGTGACGATCAACACGGCTACTGCGATAAGCCGGGCGAATGTAAGTGCC

GTGTGGGTTGGCAAGGCCGCTATTGTGATGAATGCATTCGCTATCCGGGCTGTCTGCACGGCACTTGCC

AGCAGCCGTGGCAATGTAATTGCCAAGAAGGTTGGGG

C GGA CTc TTT TGT AAC CAA

*GGA TCA TCA GGT AGT AGC GGC*

TTTGTTTGTGACGAGCACTACTATGGTGAAGGCTGCAGCGTTTTTTGTCGTCCGCGCGATGATGCCTTTG

GTCATTTCACCTGTGGCGACCGCGGCGAGAAAATGTGCGATCCTGGTTGGAAAGGCCAGTATTGCACCG

ATCCGATCTGCCTGCCGGGCTGCGACGATCAACACGGCTATTGTGACAAACCGGGTGAATGCAAATGTC

GTGTGGGTTGGCAGGGCCGCTACTGCGATGAGTGTATTCGTTATCCTGGTTGCCTGCATGGCACATGTC

AACAGCCGTGGCAGTGCAATTGTCAGGAAGGTTGGGGCGGCCTGTTCTGCAACCAGTAA GGATCC

Restriction sites: Kpnl, SaIl, BsrGI, Nsil, Xmal, Mfel, Xhol are to be used for the construction of shorter repeat DLL1 constructs. Double cut plasmids can be produced from a single digest.
Purified digest can be ligated to create a smaller DLL1 repeat from this gene.
Bold sequences have degenerate codons located at the end of each DLL1 repeat. This can be used for potential future PCR modification.
*Italicized sequences* have degenerate codons and are located in the linker. This can be used for unique sequencing primer location.
8x Protein Sequence (SEQ ID NO: 122)

MAAHHHHHH GGENLYFQG

FVCDEHYYGEGCSVFCRPRDDAFGHFTCGDRGEKMCDPGWKGQYCTDPICLPGCDDQHGYCDKPGECKC

RVGWQGRYCDECI RYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

-continued

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

7x DNA Sequence (SEQ ID NO: 123)

CATATG GCCGCA CATCATCATCACCACCAT GGTGGT GAA AAC CTG TAT TTT CAG GGC

TTTGTGTGCGATGAGCATTATTACGGTGAAGGCTGTAGCGTGTTTTGTCGACCGCGTGATGACGCATTT

GGCCATTTTACCTGCGGTGACCGCGGCGAGAAAATGTGCGATCCGGGCTGGAAAGGTCAGTATTGTAC

AGACCCTATTTGTCTGCCGGGCTGTGACGATCAGCACGGCTACTGTGACAAGCCGGGCGAATGTAAATG

TCGCGTTGGCTGGCAGGGTCGCTATTGTGATGAATGCATCCGCTACCCGGGCTGCCTGCACGGTACCTG

TCAGCAGCCGTGGCAATGCAATTGTCAAGAGGGCTGGGG

A GGT TTA TTT TGT AAT CAA

*GGc TCG AGT GGA AGC TCA GGC*

TTTGTGTGTGATGAGCATTATTACGGCGAAGGCTGCAGCGTTTTCTGTCGCCCGCGCGATGACGCATTTG

GCCACTTCACATGTGGCGATCGCGGCGAAAAGATGTGCGACCCTGGCTGGAAAGGCCAATATTGtACAG

ATCCTATCTGCCTGCCGGGTTGTGACGATCAACACGGTTATTGCGACAAGCCGGGTGAATGCAAGTGTC

GTGTGGGCTGGCAGGGCCGTTATTGTGACGAATGTATTCGCTATCCGGGTTGCTTACACGGCACATGTC

AACAGCCGTGGCAGTGTAATTGCCAGGAAGGTTGGGG

A GGT TTA TTT TGT AAT CAA

*GGT TCT TCC GGA TCG AGT GGC*

TTCGTGTGTGACGAGCACTACTATGGCGAGGGTTGTAGCGTTTTCTGTCGCCCGCGCGACGACGCTTTT

GGCCACTTTACCTGTGGCGATCGCGGTGAGAAAATGTGTGATCCTGGTTGGAAGGGCCAGTACTGCACA

GACCCGATTTGTCTGCCGGGTTGCGATGATCAGCATGGCTACTGCGACAAACCGGGTGAATGCAAATGT

CGTGTGGGCTGGCAGGGCCGCTATTGCGACGAGTGTATTCGCTACCCGGGTTGCTTACATGGCACATGC

CAACAGCCTTGGCAATGTAATTGTCAGGAAGGCTGGGG

A GGT TTA TTT TGT AAT CAA

*GGC AGT TCA GGG TCT AGT GGT*

TTTGTGTGCGACGAACATTACTACGGCGAGGGCTGCAGCGTGTTCTGTCGACCTCGTGACGACGCTTTT

GGCCACTTCACCTGCGGCGATCGCGGCGAGAAGATGTGCGATCCTGGCTGGAAAGGCCAGTACTGCAC

AGATCCGATTTGCCTGCCGGGCTGTGATGACCAACATGGCTATTGTGATAAGCCGGGCGAGTGTAAGTG

-continued

CCGTGTTGGTTGGCAAGGCCGCTATTGCGATGAGTGCATCCGTTATCCTGGCTGTCTGCATGGCACTTGT

CAGCAACCGTGGCAATGCAACTGCCAAGAGGGTTGGGG

T GGG TTG TTC TGC AAT CAG

*GGA TCT TCG GGG TCC TCT GGT*

TTTGTGTGTGACGAACACTATTACGGCGAGGGCTGCAGTGTGTTCTGCCGCCCTCGTGACGACGCCTTC

GGTCATTTCACCTGTGGCGATCGTGGCGAAAAGATGTGTGATCCTGGTTGGAAGGGTCAATACTGTACC

GACCCGATCTGTCTGCCTGGCTGCGACGACCAGCATGGTTACTGTGACAAACCGGGCGAGTGTAAATGC

CGTGTTGGTTGGCAAGGCCGCTACTGTGATGAGTGCATTCGCTATCCTGGTTGCCTGCACGGTACCTGCC

AGCAACCTTGGCAATGCAACTGCCAGGAAGGTTGGGG

G GGC CTG TTC TGC AAC CAG

*GGT AGC TCT GGC TCA TCC GGG*

TTCGTTTGCGACGAGCATTATTACGGCGAAGGCTGTAGTGTTTTCTGCCGTCCTCGTGACGACGCATTTG

GCCATTTCACCTGTGGTGACCGCGGCGAAAAAATGTGTGACCCTGGCTGGAAGGGCCAATATTGCACTG

ATCCGATTTGTCTGCCGGGTTGTGACGATCAACACGGCTACTGCGATAAGCCGGGCGAATGTAAGTGCC

GTGTGGGTTGGCAAGGCCGCTATTGTGATGAATGCATTCGCTATCCGGGCTGTCTGCACGGCACTTGCC

AGCAGCCGTGGCAATGTAATTGCCAAGAAGGTTGGGG

C GGA CTc TTT TGT AAC CAA

*GGA TCA TCA GGT AGT AGC GGC*

TTTGTTTGTGACGAGCACTACTATGGTGAAGGCTGCAGCGTTTTTTGTCGTCCGCGCGATGATGCCTTTG

GTCATTTCACCTGTGGCGACCGCGGCGAGAAAATGTGCGATCCTGGTTGGAAAGGCCAGTATTGCACCG

ATCCGATCTGCCTGCCGGGCTGCGACGATCAACACGGCTATTGTGACAAACCGGGTGAATGCAAATGTC

GTGTGGGTTGGCAGGGCCGCTACTGCGATGAGTGTATTCGTTATCCTGGTTGCCTGCATGGCACATGTC

AACAGCCGTGGCAGTGCAATTGTCAGGAAGGTTGGGGCGGCCTGTTCTGCAACCAGTAA GGATCC

7x Protein Sequence (SEQ ID NO: 124)

MAAHHHHHH GGENLYFQG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGH FTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGH FTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

-continued

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

6x DNA Sequence (SEQ ID NO: 125)

CATATG GCCGCA CATCATCATCACCACCAT GGTGGT GAA AAC CTG TAT TTT CAG GGC

TTTGTGTGCGATGAGCATTATTACGGTGAAGGCTGTAGCGTGTTTTGTCGACCGCGTGATGACGCATTT

GGCCATTTTACCTGCGGTGACCGCGGCGAGAAAATGTGCGATCCGGGCTGGAAAGGTCAGTATTGTAC

AGATCCTATCTGCCTGCCGGGTTGTGACGATCAACACGGTTATTGCGACAAGCCGGGTGAATGCAAGTG

TCGTGTGGGCTGGCAGGGCCGTTATTGTGACGAATGTATTCGCTATCCGGGTTGCTTACACGGCACATG

TCAACAGCCGTGGCAGTGTAATTGCCAGGAAGGTTGGGG

A GGT TTA TTT TGT AAT CAA

*GGT TCT TCC GGA TCG AGT GGC*

TTCGTGTGTGACGAGCACTACTATGGCGAGGGTTGTAGCGTTTTCTGTCGCCCGCGCGACGACGCTTTT

GGCCACTTTACCTGTGGCGATCGCGGTGAGAAAATGTGTGATCCTGGTTGGAAGGGCCAGTACTGCACA

GACCCGATTTGTCTGCCGGGTTGCGATGATCAGCATGGCTACTGCGACAAACCGGGTGAATGCAAATGT

CGTGTGGGCTGGCAGGGCCGCTATTGCGACGAGTGTATTCGCTACCCGGGTTGCTTACATGGCACATGC

CAACAGCCTTGGCAATGTAATTGTCAGGAAGGCTGGGG

A GGT TTA TTT TGT AAT CAA

*GGC AGT TCA GGG TCT AGT GGT*

TTTGTGTGCGACGAACATTACTACGGCGAGGGCTGCAGCGTGTTCTGTCGACCTCGTGACGACGCTTTT

GGCCACTTCACCTGCGGCGATCGCGGCGAGAAGATGTGCGATCCTGGCTGGAAAGGCCAGTACTGCAC

AGATCCGATTTGCCTGCCGGGCTGTGATGACCAACATGGCTATTGTGATAAGCCGGGCGAGTGTAAGTG

CCGTGTTGGTTGGCAAGGCCGCTATTGCGATGAGTGCATCCGTTATCCTGGCTGTCTGCATGGCACTTGT

CAGCAACCGTGGCAATGCAACTGCCAAGAGGGTTGGGG

T GGG TTG TTC TGC AAT CAG

*GGA TCT TCG GGG TCC TCT GGT*

TTTGTGTGTGACGAACACTATTACGGCGAGGGCTGCAGTGTGTTCTGCCGCCCTCGTGACGACGCCTTC

GGTCATTTCACCTGTGGCGATCGTGGCGAAAAGATGTGTGATCCTGGTTGGAAGGGTCAATACTGTACC

GACCCGATCTGTCTGCCTGGCTGCGACGACCAGCATGGTTACTGTGACAAACCGGGCGAGTGTAAATGC

CGTGTTGGTTGGCAAGGCCGCTACTGTGATGAGTGCATTCGCTATCCTGGTTGCCTGCACGGTACCTGCC

AGCAACCTTGGCAATGCAACTGCCAGGAAGGTTGGGG

G GGC CTG TTC TGC AAC CAG

*GGT AGC TCT GGC TCA TCC GGG*

TTCGTTTGCGACGAGCATTATTACGGCGAAGGCTGTAGTGTTTTCTGCCGTCCTCGTGACGACGCATTTG

GCCATTTCACCTGTGGTGACCGCGGCGAAAAAATGTGTGACCCTGGCTGGAAGGGCCAATATTGCACTG

ATCCGATTTGTCTGCCGGGTTGTGACGATCAACACGGCTACTGCGATAAGCCGGGCGAATGTAAGTGCC

-continued

GTGTGGGTTGGCAAGGCCGCTATTGTGATGAATGCATTCGCTATCCGGGCTGTCTGCACGGCACTTGCC

AGCAGCCGTGGCAATGTAATTGCCAAGAAGGTTGGGG

C GGA CTc TTT TGT AAC CAA

*GGA TCA TCA GGT AGT AGC GGC*

TTTGTTTGTGACGAGCACTACTATGGTGAAGGCTGCAGCGTTTTTTGTCGTCCGCGCGATGATGCCTTTG

GTCATTTCACCTGTGGCGACCGCGGCGAGAAAATGTGCGATCCTGGTTGGAAAGGCCAGTATTGCACCG

ATCCGATCTGCCTGCCGGGCTGCGACGATCAACACGGCTATTGTGACAAACCGGGTGAATGCAAATGTC

GTGTGGGTTGGCAGGGCCGCTACTGCGATGAGTGTATTCGTTATCCTGGTTGCCTGCATGGCACATGTC

AACAGCCGTGGCAGTGCAATTGTCAGGAAGGTTGGGGCGGCCTGTTCTGCAACCAGTAA GGATCC

6x Protein Sequence (SEQ ID NO: 126)

MAAHHHHHH GGENLYFQG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCG DRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGH FTCGDRGEKMCDPGWKGQYCTDPICLPGCDDQHGYCDKPGECKC

RVGWQGRYCDECIRYPGCLHGTCQQPWQCNCQEGWGGLFCNQ

5x DNA Sequence (SEQ ID NO: 127)

CATATG GCCGCA CATCATCATCACCACCAT GGTGGT GAA AAC CTG TAT TTT CAG GGC

TTTGTGTGCGATGAGCATTATTACGGTGAAGGCTGTAGCGTGTTTTGTCGACCGCGTGATGACGCATTT

GGCCATTTTACCTGCGGTGACCGCGGCGAGAAAATGTGCGATCCGGGCTGGAAAGGTCAGTATTGTAC

AGACCCTATTTGTCTGCCGGGCTGTGACGATCAGCACGGCTACTGTGACAAGCCGGGCGAATGTAAATG

TCGCGTTGGCTGGCAGGGTCGCTATTGTGATGAATGCATCCGCTACCCGGGTTGCTTACATGGCACATG

CCAACAGCCTTGGCAATGTAATTGTCAGGAAGGCTGGGG

A GGT TTA TTT TGT AAT CAA

*GGC AGT TCA GGG TCT AGT GGT*

TTTGTGTGCGACGAACATTACTACGGCGAGGGCTGCAGCGTGTTCTGTCGACCTCGTGACGACGCTTTT

GGCCACTTCACCTGCGGCGATCGCGGCGAGAAGATGTGCGATCCTGGCTGGAAAGGCCAGTACTGCAC

AGATCCGATTTGCCTGCCGGGCTGTGATGACCAACATGGCTATTGTGATAAGCCGGGCGAGTGTAAGTG

-continued

CCGTGTTGGTTGGCAAGGCCGCTATTGCGATGAGTGCATCCGTTATCCTGGCTGTCTGCATGGCACTTGT

CAGCAACCGTGGCAATGCAACTGCCAAGAGGGTTGGGG

T GGG TTG TTC TGC AAT CAG

*GGA TCT TCG GGG TCC TCT GGT*

TTTGTGTGTGACGAACACTATTACGGCGAGGGCTGCAGTGTGTTCTGCCGCCCTCGTGACGACGCCTTC

GGTCATTTCACCTGTGGCGATCGTGGCGAAAAGATGTGTGATCCTGGTTGGAAGGGTCAATACTGTACC

GACCCGATCTGTCTGCCTGGCTGCGACGACCAGCATGGTTACTGTGACAAACCGGGCGAGTGTAAATGC

CGTGTTGGTTGGCAAGGCCGCTACTGTGATGAGTGCATTCGCTATCCTGGTTGCCTGCACGGTACCTGCC

AGCAACCTTGGCAATGCAACTGCCAGGAAGGTTGGGG

G GGC CTG TTC TGC AAC CAG

*GGT AGC TCT GGC TCA TCC GGG*

TTCGTTTGCGACGAGCATTATTACGGCGAAGGCTGTAGTGTTTTCTGCCGTCCTCGTGACGACGCATTTG

GCCATTTCACCTGTGGTGACCGCGGCGAAAAAATGTGTGACCCTGGCTGGAAGGGCCAATATTGCACTG

ATCCGATTTGTCTGCCGGGTTGTGACGATCAACACGGCTACTGCGATAAGCCGGGCGAATGTAAGTGCC

GTGTGGGTTGGCAAGGCCGCTATTGTGATGAATGCATTCGCTATCCGGGCTGTCTGCACGGCACTTGCC

AGCAGCCGTGGCAATGTAATTGCCAAGAAGGTTGGGG

C GGA CTc TTT TGT AAC CAA

*GGA TCA TCA GGT AGT AGC GGC*

TTTGTTTGTGACGAGCACTACTATGGTGAAGGCTGCAGCGTTTTTTGTCGTCCGCGCGATGATGCCTTTG

GTCATTTCACCTGTGGCGACCGCGGCGAGAAAATGTGCGATCCTGGTTGGAAAGGCCAGTATTGCACCG

ATCCGATCTGCCTGCCGGGCTGCGACGATCAACACGGCTATTGTGACAAACCGGGTGAATGCAAATGTC

GTGTGGGTTGGCAGGGCCGCTACTGCGATGAGTGTATTCGTTATCCTGGTTGCCTGCATGGCACATGTC

AACAGCCGTGGCAGTGCAATTGTCAGGAAGGTTGGGGCGGCCTGTTCTGCAACCAGTAA GGATCC

5x Protein Sequence (SEQ ID NO: 128)

MAAHHHHHH GGENLYFQG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

-continued

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ

GSSGSSG

FVCDEHYYGEGCSVFCRPRDDAFGHFTCGDRGEKMCDPGWKGQYCTDPICLPGCDDQHGYCDKPGECKC

RVGWQGRYCDECIRYPGCLHGTCQQPWQCNCQEGWGGLFCNQ
For sequences SEQ ID NO: 144 to SEQ ID NO: 150 below
Species: Human
Codon bias: *E. coli*
Functional Unit: DSL-EGF1-EGF2
Linker: GSSGSSG
Format: Ndel-His6-TEV-(DLL1-Linker)7-DLL1-BamHI
Raw Sequence (SEQ ID NO: 144):
CATATG GCAGCT CATCACCATCACCATCAC GGTGGC GAG AAT CTA TAC UC CAG GGC

TTT GTC TGT GAC GAG CAT TAC TAT GGT GAA GGG TGC TCT GTG TTT TGT AGG CCA AGG GAC

GAT GCG TTC GGA CAT TAC ACC TGC GGG GAA CGA GGT GAG AAG GTT TGC AAC CCT GGG TGG

AAG GGA CCC TAC TGC ACT GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAG

TGT ATA CGT TAC CCA GGA TGT TTA CAC GGA ACA TGT CAG CAA CCG TGG CAG TGT AAT TGC

CAA GAA GGG TGG GGA GGG TTG TTC TGT AAC CAG

GGG TCC TCA GGA TCT AGT GGA

8x DNA Sequence (SEQ ID NO: 145)

CATATG GCAGCT CATCACCATCACCATCAC GGTGGC GAG AAT CTA TAC TTC CAG GGC

TTT GTC TGT GAC GAG CAT TAC TAT GGT GAA GGG TGC TCT GTG TTT TGT CGA CCA AGG GAC

GAT GCG TTC GGA CAT TTT ACC TGC GGG GAA CGA GGT GAG AAG GTT TGC AAC CCT GGG TGG

AAG GGA CCC TAC TGT ACA GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAA

TGC ATC CGT TAC CCG GGA TGT TTA CAC GGT ACC TGT CAG CAA CCG TGG CAG TGC AAT TGC

CAA GAA GGG TGG GGA GGG TTG TTC TGT AAC CAG

GGC TCG AGC GGT TCA TCG GGA

TTT GTC TGT GAC GAG CAT TAC TAT GGT GAA GGG TGC TCT GTG TTT TGT AGG CCA AGG GAC

GAT GCG TTC GGA CAT TTT ACC TGC GGG GAA CGA GGT GAG AAG GTT TGC AAC CCT GGG TGG

AAG GGA CCC TAC TGC ACT GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAG

TGT ATA CGT TAC CCA GGA TGT TTA CAC GGA ACA TGT CAG CAA CCG TGG CAG TGT AAT TGC

CAA GAA GGG TGG GGA GGG TTG TTC TGT AAC CAG

GGC TCG AGC GGA AGC TCA GGC

TTT GTC TGT GAC GAG CAT TAC TAT GGT GAA GGG TGC TCT GTG UT TGT AGG CCA AGG GAC

GAT GCG TTC GGA CAT TTT ACC TGC GGG GAA CGA GGT GAG AAG GTT TGC AAC CCT GGG TGG

AAG GGA CCC TAC TGT ACA GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAG

TGT ATA CGT TAC CCA GGA TGT TTA CAC GGA ACA TGT CAG CAA CCG TGG CAG TGT AAT TGC

CAA GAA GGG TGG GGA GGG TTG TTC TGT AAC CAG

GGT TCT TCC GGA TCG AGT GGC

TTT GTC TGT GAC GAG CAT TAC TAT GGT GAA GGG TGC TCT GTG TTT TGT AGG CCA AGG GAC

-continued

GAT GCG TTC GGA CAT TTT ACC TGC GGG GAA CGA GGT GAG AAG GTT TGC AAC CCT GGG TGG

AAG GGA CCC TAC TGC ACT GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAG

TGT ATA CGT TAC CCG GGA TGT TTA CAC GGA ACA TGT CAG CAA CCG TGG CAG TGT AAT TGC

CAA GAA GGG TGG GGA GGG TTG TTC TGT AAC CAG

GGC AGT TCA GGG TCT AGT GGT

TTT GTC TGT GAC GAG CAT TAC TAT GGT GAA GGG TGC TCT GTG UT TGT CGA CCA AGG GAC

GAT GCG TTC GGA CAT TTT ACC TGC GGG GAA CGA GGT GAG AAG GTT TGC AAC CCT GGG TGG

AAG GGA CCC TAC TGC ACT GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAG

TGT ATA CGT TAC CCA GGA TGT TTA CAC GGA ACA TGT CAG CAA CCG TGG CAG TGT AAT TGC

CAA GAA GGG TGG GGA GGG TTG TTC TGT AAC CAG

GGA TCT TCG GGG TCC TCT GGT

TTT GTC TGT GAC GAG CAT TAC TAT GGT GAA GGG TGC TCT GTG TTT TGT AGG CCA AGG GAC

GAT GCG TTC GGA CAT TTT ACC TGC GGG GAA CGA GGT GAG AAG GTT TGC AAC CCT GGG TGG

AAG GGA CCC TAC TGC ACT GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAG

TGT ATA CGT TAC CCA GGA TGT TTA CAC GGT ACC TGT CAG CAA CCG TGG CAG TGT AAT TGC

CAA GAA GGG TGG GGA GGG TTG TTC TGT AAC CAG

GGT AGC TCT GGC TCA TCC GGG

TTT GTC TGT GAC GAG CAT TAC TAT GGT GAA GGG TGC TCT GTG TTT TGT AGG CCA AGG GAC

GAT GCG TTC GGA CAT TTT ACC TGC GGG GAA CGA GGT GAG AAG GTT TGC AAC CCT GGG TGG

AAG GGA CCC TAC TGC ACT GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAA

TGC ATC CGT TAC CCA GGA TGT TTA CAC GGA ACA TGT CAG CAA CCG TGG CAG TGT AAT TGC

CAA GAA GGG TGG GGA GGG TTG TTC TGT AAC CAG

GGA TCA TCA GGT AGT AGC GGC

TTT GTC TGT GAC GAG CAT TAC TAT GGT GAA GGG TGC TCT GTG UT TGT AGG CCA AGG GAC

GAT GCG TTC GGA CAT TTT ACC TGC GGG GAA CGA GGT GAG AAG GTT TGC AAC CCT GGG TGG

AAG GGA CCC TAC TGC ACT GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAG

TGT ATA CGT TAC CCA GGA TGT TTA CAC GGA ACA TGT CAG CAA CCG TGG CAG TGC AAT TGC

CAA GAA GGG TGG GGA GGG TTG TTC TGT AAC CAG TAA GGATCC

Restriction sites: Kpnl, Sall, BsrGI, Nsil, Xmal, Mfel, Xhol are to be used for the construction of shorter repeat DLL1 constructs. Double cut plasmids can be produced from a single digest. Purified digest can be ligated to create a smaller DLL1 repeat from this gene.
Bold sequences have degenerate codons located at the end of each DLL1 repeat. This can be used for potential future PCR modification.
*Italicized sequences* have degenerate codons and are located in the linker. This can be used for unique sequencing primer location.
8x Protein Sequence (SEQ ID NO: 146)

MAAHHHHHHGGENLYFQGFVCDEHYYGEGCSVFCRPRDDAFGHFTCGERGEKVCNPGWK

GPYCTEPICLPGCDEQHGFCDKPGECKCRVGWQGRYCDECIRYPGCLHGTCQQPWQCNCQEGWGGLFCN

Q

-continued

GSSGSSG

FVCDEHYYGEGCSVFCRPRDDAFGHFTCGERGEKVCNPGWKGP

YCTEPICLPGCDEQHGFCDKPGECKCRVGWQGRYCDECIRYPGCLHGTCQQPWQCNCQEGWGGLFCNQ

GSSGSSG

FVCDEHYYGEGCSVFCRPRDDAFGHFTCGERGEKVCNPGWKGPYC

TEPICLPGCDEQHGFCDKPGECKCRVGWQGRYCDECIRYPGCLHGTCQQPWQCNCQEGWGGLFCNQ

GSSGSSG

FVCDEHYYGEGCSVFCRPRDDAFGHFTCGERGEKVCNPGWKGPYCTE

PICLPGCDEQHGFCDKPGECKCRVGWQGRYCDECIRYPGCLHGTCQQPWQCNCQEGWGGLFCNQ

GSSGSSG

FVCDEHYYGEGCSVFCRPRDDAFGHFTCGERGEKVCNPGWKGPYCTEPI

CLPGCDEQHGFCDKPGECKCRVGWQGRYCDECIRYPGCLHGTCQQPWQCNCQEGWGGLFCNQ

GSSGSSG

FVCDEHYYGEGCSVFCRPRDDAFGHFTCGERGEKVCNPGWKGPYCTEPICL

PGCDEQHGFCDKPGECKCRVGWQGRYCDECIRYPGCLHGTCQQPWQCNCQEGWGGLFCNQ

GSSGSSG

FVCDEHYYGEGCSVFCRPRDDAFGHFTCGERGEKVCNPGWKGPYCTEPICLPG

CDEQHGFCDKPGECKCRVGWQGRYCDECIRYPGCLHGTCQQPWQCNCQEGWGGLFCNQ

GSSGSSG

FVCDEHYYGEGCSVFCRPRDDAFGHFTCGERGEKVCNPGWKGPYCTEPICLPGCD

EQHGFCDKPGECKCRVGWQGRYCDECIRYPGCLHGTCQQPWQCNCQEGWGGLFCNQ

4x DNA Sequence (SEQ ID NO: 147)

CATATG GCAGCT CATCACCATCACCATCAC GGTGGC GAG AAT CTA TAC TTC CAG GGC

TTT GTC TGT GAC GAG CAT TAC TAT GGT GAA GGG TGC TCT GTG TTT TGT AGG CCA AGG GAC

GAT GCG TTC GGA CAT TTT ACC TGC GGG GAA CGA GGT GAG AAG GTT TGC AAC CCT GGG TGG

AAG GGA CCC TAC TGC ACT GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAG

TGT ATA CGT TAC CCA GGA TGT TTA CAC GGA ACA TGT CAG CAA CCG TGG CAG TGT AAT TGC

CAA GAA GGG TGG GGA GGG TTG UC TGT AAC CAG

GGG TCC TCA GGA TCT AGT GGA

CATATG GCAGCT CATCACCATCACCATCAC GGTGGC GAG AAT CTA TAC UC CAG GGC

TTT GTC TGT GAC GAG CAT TAC TAT GGT GAA GGG TGC TCT GTG TTT TGT AGG CCA AGG GAC

GAT GCG TTC GGA CAT TTT ACC TGC GGG GAA CGA GGT GAG AAG GTT TGC AAC CCT GGG TGG

AAG GGA CCC TAC TGC ACT GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAG

TGT ATA CGT TAC CCA GGA TGT TTA CAC GGA ACA TGT CAG CAA CCG TGG CAG TGT AAT TGC

CAA GAA GGG TGG GGA GGG TTG UC TGT AAC CAG

GGG TCC TCA GGA TCT AGT GGA

CATATG GCAGCT CATCACCATCACCATCAC GGTGGC GAG AAT CTA TAC UC CAG GGC

TTT GTC TGT GAC GAG CAT TAC TAT GGT GAA GGG TGC TCT GTG TTT TGT AGG CCA AGG GAC

GAT GCG TTC GGA CAT TTT ACC TGC GGG GAA CGA GGT GAG AAG GTT TGC AAC CCT GGG TGG

-continued

AAG GGA CCC TAC TGC ACT GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAG

TGT ATA CGT TAC CCA GGA TGT TTA CAC GGA ACA TGT CAG CAA CCG TGG CAG TGT AAT TGC

CAA GAA GGG TGG GGA GGG TTG UC TGT AAC CAG

GGG TCC TCA GGA TCT AGT GGA

CATATG GCAGCT CATCACCATCACCATCAC GGTGGC GAG AAT CTA TAC TTC CAG GGC

TTT GTC TGT GAC GAG CAT TAC TAT GGT GAA GGG TGC TCT GTG TTT TGT AGG CCA AGG GAC

GAT GCG TTC GGA CAT TTT ACC TGC GGG GAA CGA GGT GAG AAG GTT TGC AAC CCT GGG TGG

AAG GGA CCC TAC TGC ACT GAA CCA ATT TGC TTA CCA GGG TGT GAT GAG CAA CAC GGA TTC

TGC GAT AAG CCG GGC GAA TGT AAG TGT CGG GTA GGC TGG CAA GGC CGC TAC TGC GAT GAG

TGT ATA CGT TAC CCA GGA TGT TTA CAC GGA ACA TGT CAG CAA CCG TGG CAG TGT AAT TGC

CAA GAA GGG TGG GGA GGG TTG TTC TGT AAC CAG TAA GGATCC

4x Protein Sequence (SEQ ID NO: 148)

MAAHHHHHH GGENLYFQG FVCDEHYYGEGCSVFCRPRDDAFGHFTCGERGEKVCNPGWK

GPYCTEPICLPGCDEQHGFCDKPGECKCRVGWQGRYCDECIRYPGCLHGTCQQPWQCNCQEGWGGLFCN

Q

GSSGSSG

FVCDEHYYGEGCSVFCRPRDDAFGHFTCGERGEKVCNPGWKGP

YCTEPICLPGCDEQHGFCDKPGECKCRVGWQGRYCDECIRYPGCLHGTCQQPWQCNCQEGWGGLFCNQ

GSSGSSG

FVCDEHYYGEGCSVFCRPRDDAFGHFTCGERGEKVCNPGWKGPYC

TEPICLPGCDEQHGFCDKPGECKCRVGWQGRYCDECIRYPGCLHGTCQQPWQCNCQEGWGGLFCNQ

GSSGSSG

FVCDEHYYGEGCSVFCRPRDDAFGHFTCGERGEKVCNPGWKGPYCTE

PICLPGCDEQHGFCDKPGECKCRVGWQGRYCDECIRYPGCLHGTCQQPWQCNCQEGWGGLFCNQ

1x DNA Sequence (SEQ ID NO: 149)

CATATG GCAGCT CATCACCATCACCATCAC GGTGGC GAG AAT CTA TAC TTC CAG GGC

TTT GTC TGT GAC GAG CAT TAC TAT GGT GAA GGG TGC TCT GTG UT TGT AGG CCA AGG GAC

GAT GCG TTC GGA CAT TTT ACC TGC GGG GAA CGA GGT GAG AAG GTT TGC AAC CCT GGG TGG

AAG GGA CCC TAC TGC ACT GAA CCA ATT TGC TTA CCA GGG TGT GAT GAG CAA CAC GGA UC

TGC GAT AAG CCG GGC GAA TGT AAG TGT CGG GTA GGC TGG CAA GGC CGC TAC TGC GAT GAG

TGT ATA CGT TAC CCA GGA TGT TTA CAC GGA ACA TGT CAG CAA CCG TGG CAG TGT AAT TGC

CAA GAA GGG TGG GGA GGG TTG UC TGT AAC CAG

GGG TCC TCA GGA TCT AGT GGA

1x Protein Sequence (SEQ ID NO: 150)

MAAHHHHHH GGENLYFQGFVCDEHYYGEGCSVFCRPRDDAFGHFTCGERGEKVCNPGWK

GPYCTEPICLPGCDEQHGFCDKPGECKCRVGWQGRYCDECIRYPGCLHGTCQQPWQCNCQEGWGGLFCN

Q

Q61483|DLL1_MOUSE Delta-like protein 1

(SEQ ID NO: 151)

MGRRSALALAVVSALLCQVWSSGVFELKLQEFVNKKGLLGNRNCCRGGSGPPCACRTFFR

VCLKHYQASVSPEPPCTYGSAVTPVLGVDSFSLPDGAGIDPAFSNPIRFPFGFTWPGTFS

LIIEALHTDSPDDLATENPERLISRLTTQRHLTVGEEWSQDLHSSGRTDLRYSYRFVCDE

-continued

HYYGEGCSVFCRPRDDAFGHFTCGDRGEKMCDPGWKGQYCTDPICLPGCDDQHGYCDKPG

ECKCRVGWQGRYCDECIRYPGCLHGTCQQPWQCNCQEGWGGLFCNQDLNYCTHHKPCRNG

ATCTNTGQGSYTCSCRPGYTGANCELEVDECAPSPCKNGASCTDLEDSFSCTCPPGFYGK

VCELSAMTCADGPCFNGGRCSDNPDGGYTCHCPLGFSGFNCEKKMDLCGSSPCSNGAKCV

DLGNSYLCRCQAGFSGRYCEDNVDDCASSPCANGGTCRDSVN DFSCTCPPGYTGKNCSAP

VSRCEHAPCHNGATCHQRGQRYMCECAQGYGGPNCQFLLPEPPPGPMVVDLSERHMESQG

GPFPWVAVCAGVVLVLLLLLGCAAVVVCVRLKLQKHCIPPPEPCGGETETMNNLANCCIREK

DVSVSIIGATQIKNTNKKADFHGDHGAEKSSFKVRYPTVDYNLVRDLKGDEATVRDTHSK

RDTKCQSQSSAGEEKIAPTLRGGEIPDRKRPESVYSTSKDTKYQSVYVLSAEKDECVIAT

EV
>sp|O005481DLL1_HUMAN Delta-like protein 1

(SEQ ID NO: 152)

MGSRCALALAVLSALLCQVWSSGVFELKLQEFVNKKGLLGNRNCCRGGAGPPPCACRTFF

RVCLKHYQASVSPEPPCTYGSAVTPVLGVDSFSLPDGGGADSAFSNPIRFPFGFTWPGTF

SLIIEALHTDSPDDLATENPERLISRLATQRHLTVGEEWSQDLHSSGRTDLKYSYRFVCD

EHYYGEGCSVFCRPRDDAFGHFTCGERGEKVCNPGWKGPYCTEPICLPGCDEQHGFCDKP

GECKCRVGWQGRYCDECIRYPGCLHGTCQQPWQCNCQEGWGGLFCNQDLNYCTHHKPCKN

GATCTNTGQGSYTCSCRPGYTGATCELGIDECDPSPCKNGGSCTDLENSYSCTCPPGFYG

KICELSAMTCADGPCFNGGRCSDSPDGGYSCRCPVGYSGFNCEKKIDYCSSSPCSNGAKC

VDLGDAYLCRCQAGFSGRHCDDNVDDCASSPCANGGTCRDGVNDFSCTCPPGYTGRNCSA

PVSRCEHAPCHNGATCHERGHRYVCECARGYGGPNCQFLLPELPPGPAVVDLTEKLEGQG

GPFPWVAVCAGVILVLMLLLGCAAVVVCVRLRLQKHRPPADPCRGETETMNNLANCQREK

DISVSIIGATQIKNTNKKADFHGDHSADKNGFKARYPAVDYNLVQDLKGDDTAVRDAHSK

RDTKCQPQGSSGEEKGTPTTLRGGEASERKRPDSGCSTSKDTKYQSVYVISEEKDECVIA

TEV
DSL domain from human DLL1

(SEQ ID NO: 153)

>sp|O0048|177-221
FVCDEHYYGEGCSVFCRPRDDAFGHFTCGERGEKVCNPGWKGPYC
EGF1 domain from human DLL1

(SEQ ID NO: 154)

>sp|O00548|226-254
CLPGCDEQHGFCDKPGECKCRVGWQGRYC
EGF2 domain from human DLL1

(SEQ ID NO: 155)

>sp|O00548|257-285
CIRYPGCLHGTCQQPWQCNCQEGWGGLFC
EGF3 domain from human DLL1

(SEQ ID NO: 156)

>sp|O00548|292-325
CTHHKPCKNGATCTNTGQGSYTCSCRPGYTGATC

---

What is claimed is:

1. A Notch-modulating peptide comprising at least four monomeric units connected by peptide linkers in a single genetically-encoded peptide, the monomeric units comprising:

(a) a mammalian DSL domain; and (b) two or three mammalian EGF domains, wherein the two or three mammalian EGF domains independently comprise a sequence selected from SEQ ID NO: 154, SEQ ID NO: 155, SEQ ID NO: 156, or a sequence that is at least 90% identical to SEQ ID NO: 154, SEQ ID NO: 155, or SEQ ID NO: 156;

wherein the peptide linkers comprise the amino acid sequence GGGGS (SEQ ID NO: 132) or GSSGSSG (SEQ ID NO: 133);

wherein the mammalian DSL domain comprises SEQ ID NO: 153, or a sequence that is at least 90% identical to SEQ ID NO: 153.

2. The Notch-modulating peptide of claim 1, wherein the mammalian DSL and EGF domains are human DSL and EGF domains.

3. The Notch-modulating peptide of claim 1, wherein the monomeric unit comprises no more than two EGF domains.

4. The Notch-modulating peptide of claim 1, wherein the monomeric unit comprises three EGF domains.

5. The Notch-modulating peptide of claim 1, wherein the DSL domain and EGF domains are derived from Delta-like (DLL) family protein or Jagged family proteins.

6. The Notch-modulating peptide of claim 1, wherein the DSL domain and EGF domains are derived from DLL1, DLL3, or DLL4.

7. The Notch-modulating peptide of claim 1, wherein the DSL domain and EGF domains are derived from Jagged 1 or Jagged 2.

8. The Notch-modulating peptide of claim 1, wherein the peptide linkers comprise 10 or fewer amino acids.

9. The Notch-modulating peptide of claim 1, wherein the peptide linkers comprise a BirA tag sequence.

10. The Notch-modulating peptide of claim 1, wherein the monomeric units further comprise a module at the N-terminus of Notch ligands (MNNL) domain.

11. The Notch-modulating peptide of claim 1, wherein the peptide is a tetramer.

12. The Notch-modulating peptide of claim 1, wherein the peptide is a pentamer.

13. The Notch-modulating peptide of claim 1, wherein the peptide is a hexamer.

14. The Notch-modulating peptide of claim 1, wherein the peptide is a septamer.

15. The Notch-modulating peptide of claim 1, wherein the peptide is an octamer.

16. The Notch-modulating peptide of claim 1, wherein the peptide activates Notch signaling.

17. A method of treating cancer in a subject, comprising administering a therapeutically effective amount of the Notch-modulating peptide of claim 1 to a subject in need thereof, wherein the cancer is selected from lung cancer, melanoma, head and neck cancer, bladder cancer, colon cancer, lymphoma, non-Hodgkin's lymphoma, stomach cancer, cervical cancer, liver cancer, or skin cancer.

18. A method of suppressing the immune system of a subject, comprising administering a therapeutically effective amount of the Notch-modulating peptide of claim 1 to a subject in need thereof.

* * * * *